(12) United States Patent
Becker et al.

(10) Patent No.: US 9,315,860 B2
(45) Date of Patent: Apr. 19, 2016

(54) CONJUGATES OF NUCLEOTIDES AND METHOD FOR THE APPLICATION THEREOF

(75) Inventors: Claus Becker, Ötigheim (DE); Dmitry Cherkasov, Marburg (DE)

(73) Assignee: GENOVOXX GMBH, Luebeck (DE)

( * ) Notice: Subject to any disclaimer, the term of this patent is extended or adjusted under 35 U.S.C. 154(b) by 366 days.

(21) Appl. No.: 13/504,394

(22) PCT Filed: Oct. 26, 2010

(86) PCT No.: PCT/EP2010/006523
§ 371 (c)(1),
(2), (4) Date: Jan. 22, 2013

(87) PCT Pub. No.: WO2011/050938
PCT Pub. Date: May 5, 2011

(65) Prior Publication Data
US 2013/0171631 A1    Jul. 4, 2013

(30) Foreign Application Priority Data
Oct. 26, 2009   (DE) .......................... 10 2009 050 640

(51) Int. Cl.
*C12Q 1/68* (2006.01)
(52) U.S. Cl.
CPC .............. *C12Q 1/6853* (2013.01); *C12Q 1/686* (2013.01); *C12Q 1/6806* (2013.01)

(58) Field of Classification Search
None
See application file for complete search history.

(56) References Cited

U.S. PATENT DOCUMENTS

2010/0029494 A1 * 2/2010 Cherkasov et al. ................ 506/9
2010/0093992 A1 * 4/2010 Cherkasov et al. .......... 536/28.5

FOREIGN PATENT DOCUMENTS

| DE | 10356837 A1 | 6/2005 |
|---|---|---|
| DE | 102004009704 A1 | 9/2005 |
| WO | 2005/044836 A2 | 5/2005 |
| WO | 2006/097320 A2 | 9/2006 |
| WO | 2008/043426 A2 | 4/2008 |
| WO | 2011/050938 A1 | 5/2011 |

* cited by examiner

*Primary Examiner* — James Martinell
(74) *Attorney, Agent, or Firm* — McDermott Will & Emery LLP

(57) ABSTRACT

The invention relates to a novel method for enzymatically marking nucleic acid chains (target sequences) by using nucleotide conjugates. Said nucleotide conjugates are capable of binding specifically to the target sequence under reaction conditions and of being incorporated in the complementary growing strand by means of a polymerase. The nucleic acid chains marked with such conjugates can be bound to the solid phase. The marking can be carried out in parallel with the enzymatic amplification of target sequences.

51 Claims, 32 Drawing Sheets

Nuc macromolecule

1) Nuc component
2) Linker component
3) Target domain of the nuc macromolecule
4) Anchor domain of the nuc macromolecule
5) Signaldomain of the nuc macromolecule

Fig. 2
Basic structure of the nuc macromolecule
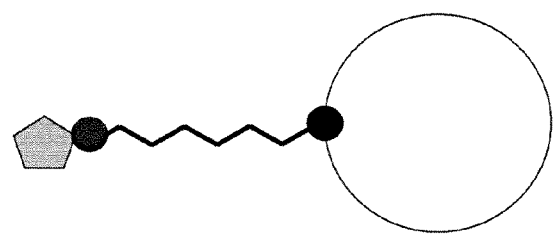
Legend
 Nuc component
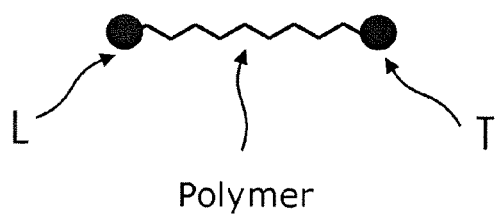
Linker component with
Coupling unit (L)
Polymer
coupling unit (T)
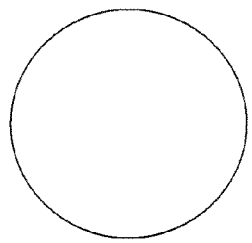 Markercomponent Primer-Template-complex 6) Primer
7) Template (target sequence)
8) Anchor domain of the primer
9) Signal domain of the primer

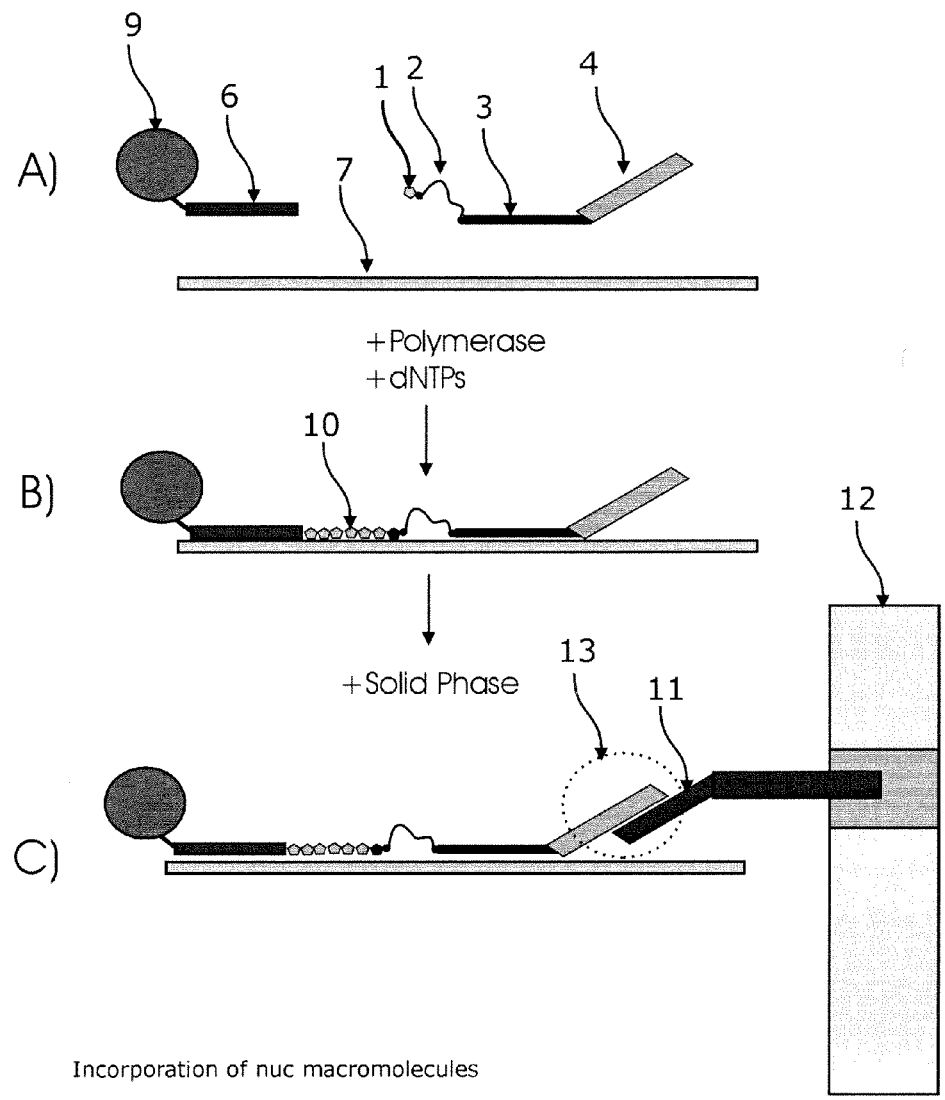

Fig. 6

Incorporation of nuc macromolecules

1) Nuc compoent
2) Linker compoent
3) Target domain of the nuc macromolecule
4) Anchor domain of the nuc macromolecule
6) Primer
7) Template (target sequence)
9) Signal domain of the primer
10) non labeled nucleotides (incorporiert)
11) Binding partner of the anchor domain
12) solid Phase 1 (e.g. Lateral flow test strip with immobilized binding partners)
13) Binding between Anchor domain and binding partner on the solid phase

Fig. 7
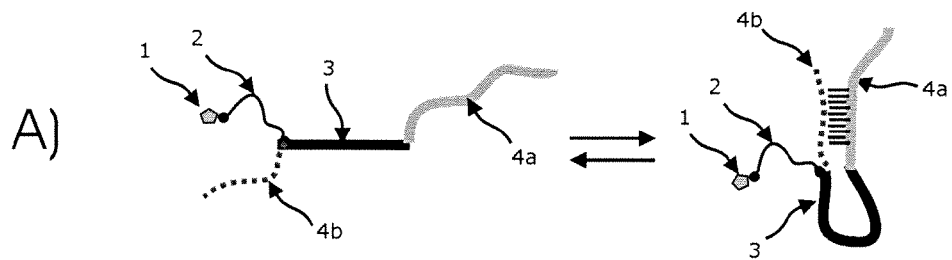
Labeling of target sequence with a nuc macromolecule with an antogonist to the anchor domain
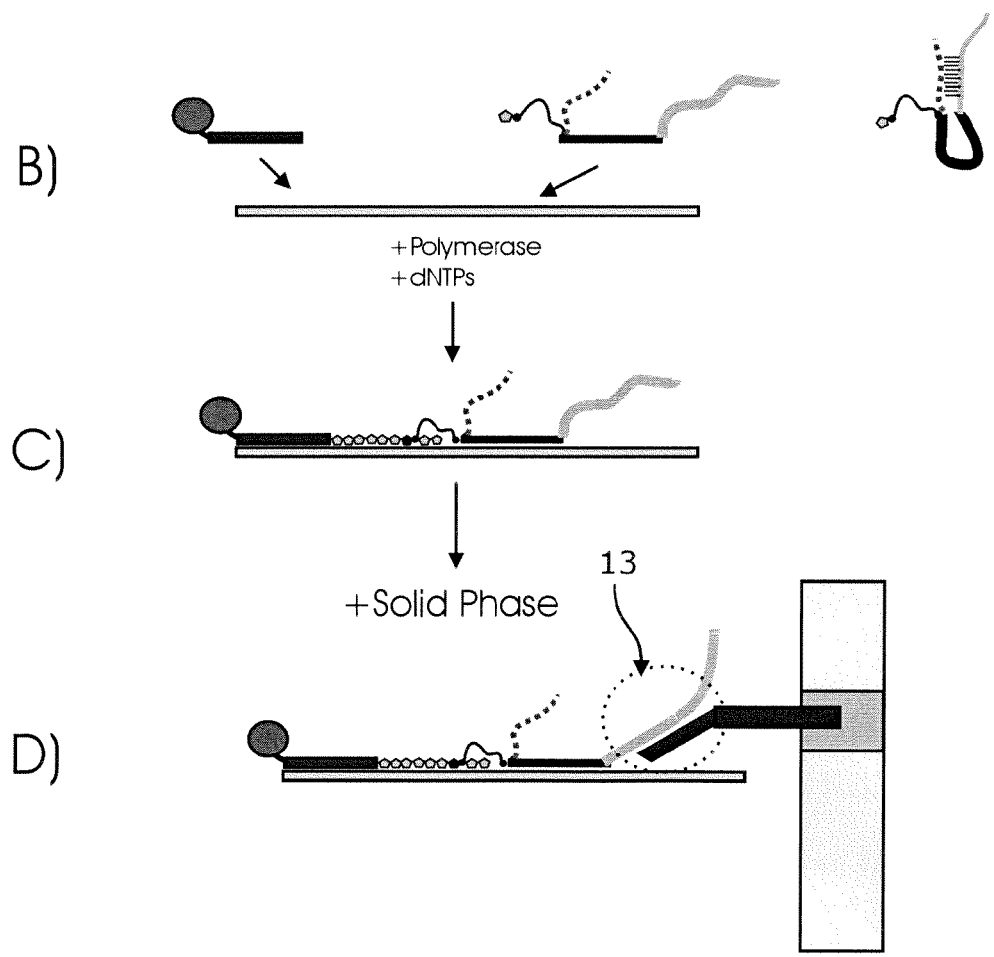

Fig. 9
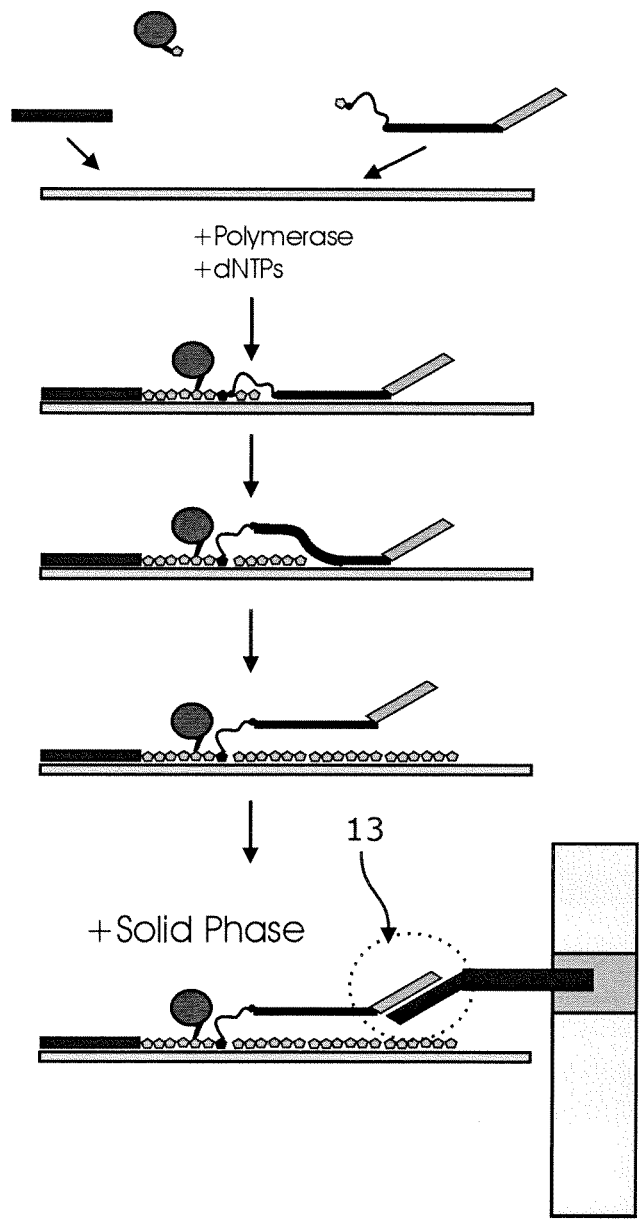
Legende
 Markiertes Nukleotid

Exonuclease degradation of the target domain of the nuc macromolecule

Fig. 11
A) No target sequence present
B) Target sequence present
binding as double strand
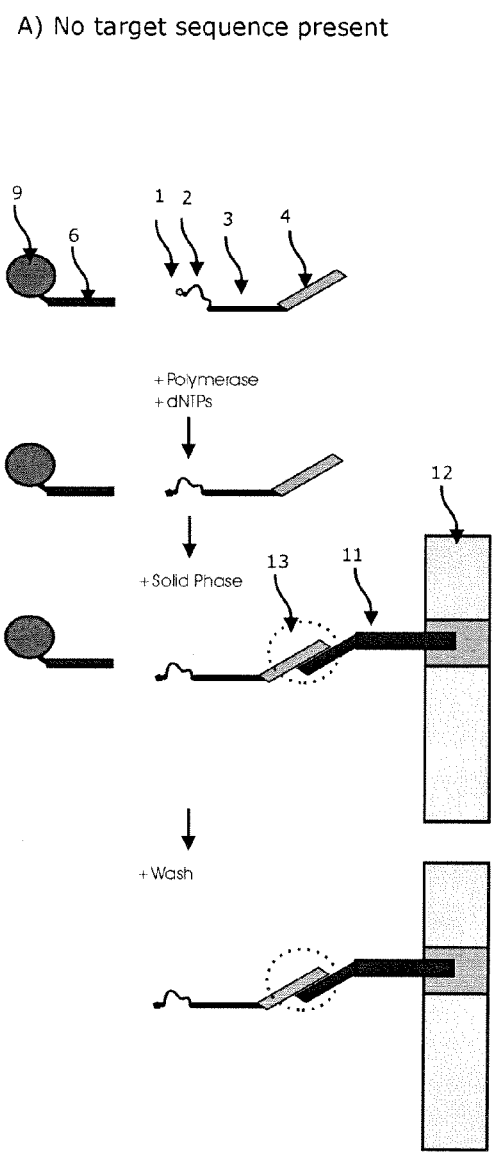
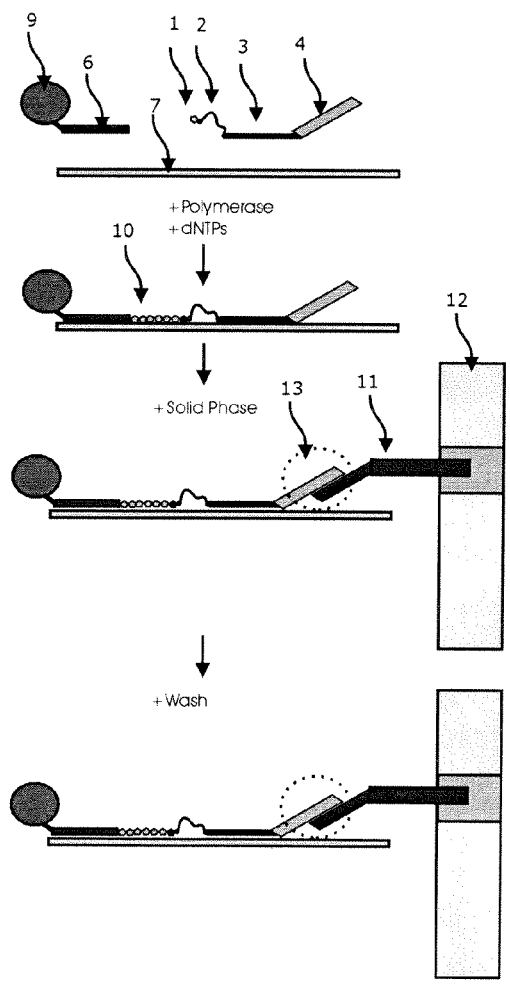

Fig. 12
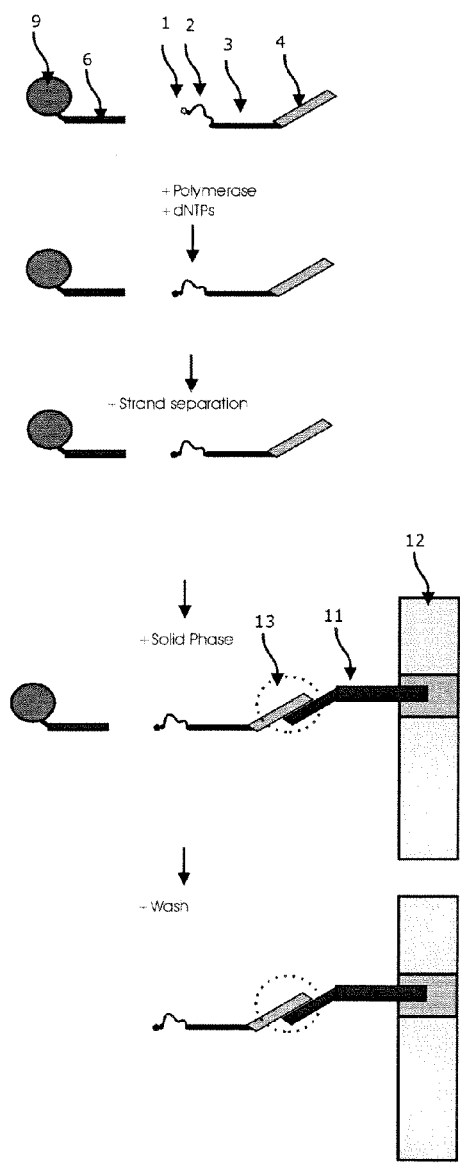
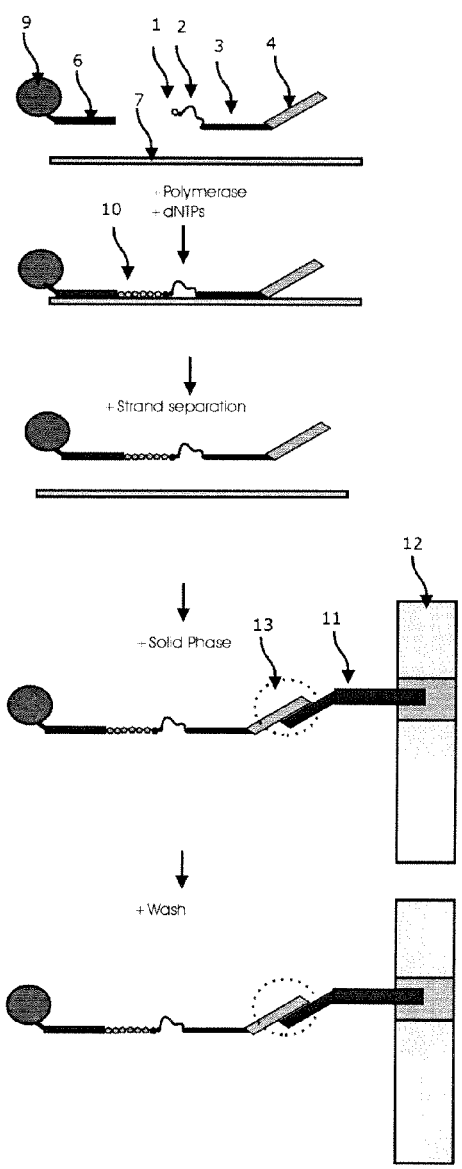

Fig. 13

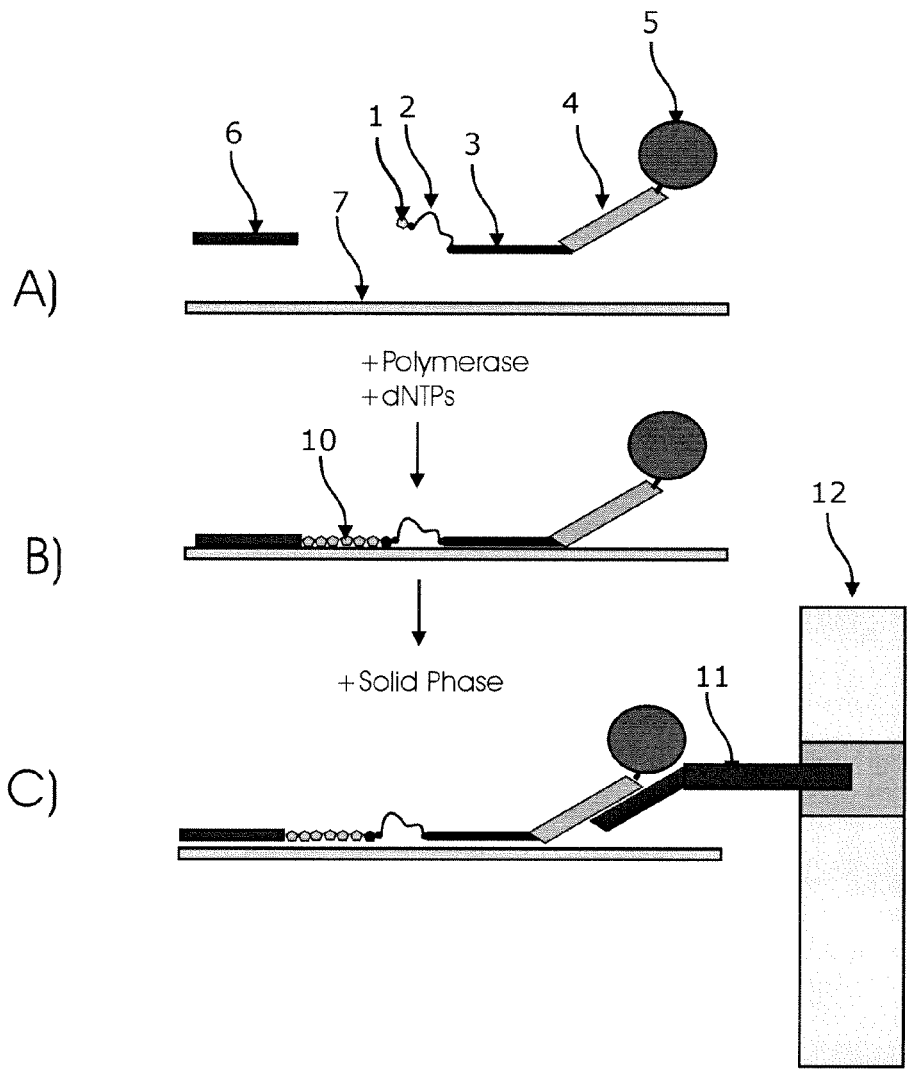

Incorporation of nuc macromolecules

1) Nuc compoent
2) Linker compoent
3) Target domain of the nuc macromolecule
4) Anchor domain of the nuc macromolecule
5) Signal domain of the nuc macromolecule
6) Primer
7) Template (target sequence)
10) non labeled nucleotides (incorporiert)
11) Binding partner of the anchor domain
12) solid Phase 1 (e.g. Lateral flow test strip with immobilized binding partners)

Fig. 14

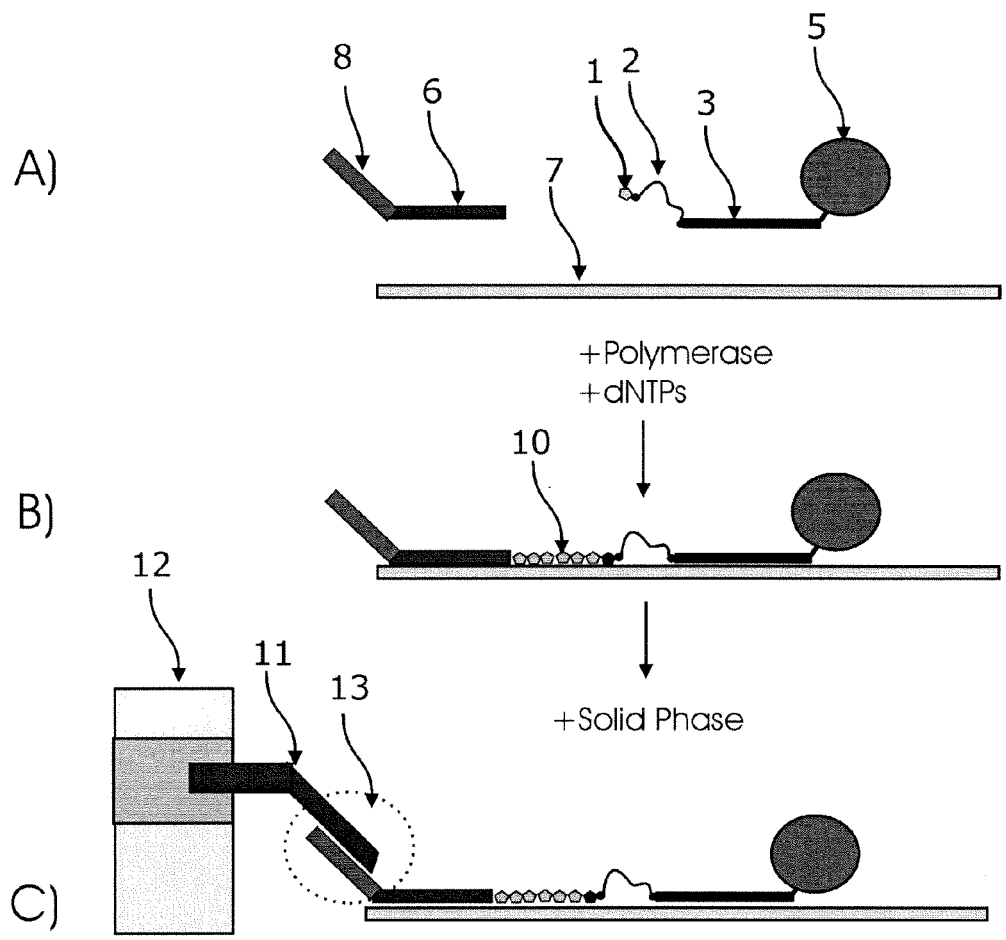

Incorporation of nuc macromolecules

1) Nuc compoent
2) Linker compoent
3) Target domain of the nuc macromolecule
4) Signal domain of the nuc macromolecule
6) Primer
7) Template (target sequence)
8) Anchor domain of the primer
10) non labeled nucleotides (incorporiert)
11) Binding partner of the anchor domain
12) solid Phase 1 (e.g. Lateral flow test strip with immobilized binding partners)
13) Binding between Anchor domain and binding partner on the solid phase

Fig. 15

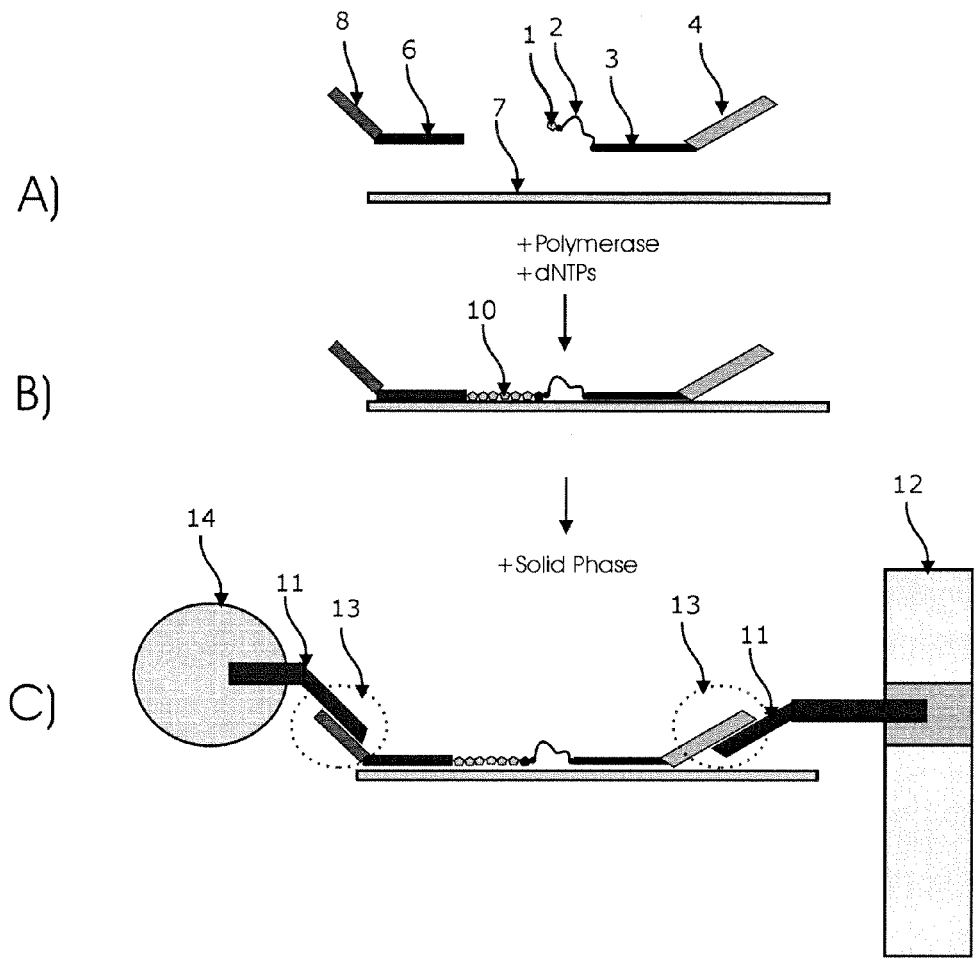

Incorporation of nuc macromolecules

1) Nuc compoent
2) Linker compoent
3) Target domain of the nuc macromolecule
4) Anchor domain of the nuc macromolecule
6) Primer
7) Template (target sequence)
8) Signal domain of the primer
10) non labeled nucleotides (incorporiert)
11) Binding partner of the anchor domain
12) solid Phase 1 (e.g. Lateral flow test strip with immobilized binding partners)
13) Binding between Anchor domain and binding partner on the solid phase
14) solid phase 2 ( e.g. Microparticles or nanoparticles)

Selection of the target sequence through the target domain, incorporation and addressable binding to the solid phase Parallel amplification and labeling of the target sequence Binding to the solid phase via anchor domain Parallel amplification and labeling of the target sequences Parallel amplification and labeling of the target sequences Fig. 22
A)
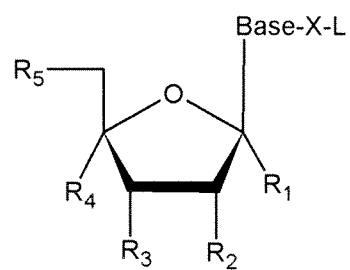
B)
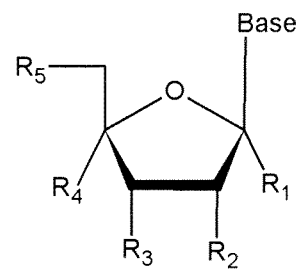

Fig. 24
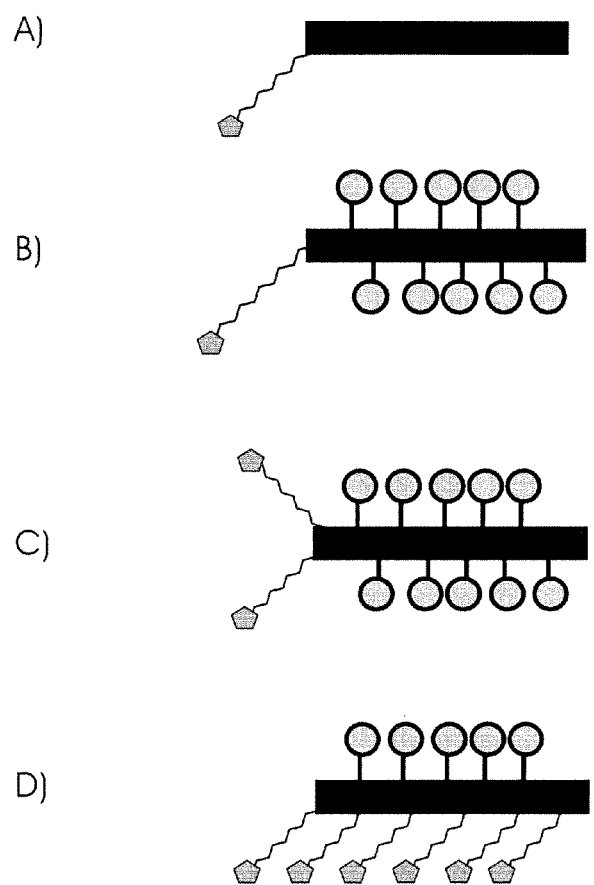
Legend:
     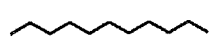          
Nuc component    Linker component    Core component    Marker unit with a linker Legend:

| Nuc component | Linker component | Signal-giving marker unit | Nucleic acid with a signal-giving marker unit |

CONJUGATES OF NUCLEOTIDES AND METHOD FOR THE APPLICATION THEREOF

RELATED APPLICATIONS

This application is the U.S. National Phase under 35 U.S.C. §317 of International Application No. PCT/EP2010/006523, filed on Oct. 26, 2010, which in turn claims the benefit of German Application DE 10 2009 050 640.3, filed on Oct. 26, 2009, the disclosures of which Applications are incorporated by reference herein.

DESCRIPTION OF THE INVENTION

INTRODUCTION

SEQUENCE LISTING

The instant application contains a Sequence Listing which has been submitted in ASCII format via EFS-Web and is hereby incorporated by reference in its entirety. Said ASCII copy, created on Jan. 15, 2013, is named Sequence Listing 076030-0014. txt and is 5.92 kilo bytes in size.

1.1 STATE OF THE ART AND OBJECTS OF THE INVENTION

Often, analysis of nucleic acid chains is used for a detection of a specific sequence of an organism, such as pathogens in clinical material. This sequence is often referred to as the target sequence. Often, such target sequences are present not as isolated form, but embedded in a sample matrix, the material. Patient samples, food, or a part of an organism can represent material of interest. The objective of this analysis is therefore testing for the presence of the target sequence in such material. Usually, an extraction of nucleic acids and amplification are carried out during such an analysis.

A person skilled in the area will be aware of many methods of isolation and amplification of specific fragments of nucleic acids from an organism. Methods are also known which allow direct detection of nucleic acids from material without prior isolation of the nucleic acids. The control of a successful and specific amplification of a target sequence is usually achieved via the hybridization of a fluorescent-labeled probe (e.g. Real-time PCR) or other hybridization methods, e.g. via a microarray, or by sequencing.

On the one hand, these methods have well-known advantages; on the other hand, there are significant drawbacks, including, among others, the requirement of expensive equipment or facilities which are reserved only for specialized laboratories. The development of analytical techniques for field analysis struggles with the limitations of current methods of detection.

The object of this application is to eliminate this bottleneck and provide components and methods that allow an expert to quickly detect a specific target sequence under simple conditions (without the use of real-time PCR apparatus or sequencing equipment).

A further object of the present invention is the providing of nucleotide conjugates which retain their substrate properties for polymerases.

A further object of the invention is to provide methods for labeling nucleic acids with nucleotide conjugates modified in accordance with this invention. Such modified nucleotides are nuc macromolecules with new structures of the marker component and new functions (FIG. 3).

The nucleotide structures represent new variants of nuc macromolecules with basic structure described in the applications Cherkasov et al WO2005044836, Cherkasov et al WO2006097320, Cherkasov et al WO2008043426, Cherkasov et al DE 10356837, Cherkasov et al DE 102004009704 (FIG. 2).

Surprisingly, these structures, in combination with other assay components, enable a new type of labeling efficiency and labeling specificity as well as new ways of detection in a multiplex analysis. The present invention discloses such an advantageous combination for a labeling reaction of target sequences (e.g. primers, modified primers, target sequence, etc.) (FIG. 4), so that new assays can be developed for the nucleic acid analysis. The inventive method allows a greater variety of molecules to be bound to the nucleic acid chains in a sequence-specific manner. Therefore, methods in the field of nucleic acid analysis can benefit from this invention.

1.2 BRIEF DESCRIPTION OF OBJECTS OF THE INVENTION

The subject of this application comprises methods for the detection of one or more nucleic acid chains (one or more target sequences), wherein a conjugate comprising at least one nucleotide triphosphate and an oligonucleotide is used, wherein the oligonucleotide can bind to the target sequence in a sequence-specific manner and the nucleotide triphosphate can be incorporated into the growing strand by a polymerase.

The subject of this application comprises methods for the detection of one or more nucleic acid chains (one or more target sequences), wherein modified nucleotides (nuc macromolecules, FIG. 1) with one of the following structures are used:

(Nuc-linker)$_n$-marker wherein:

Nuc is a nucleotide (nuc component)

Linker is a linker component wherein the linker links the nuc component to a macromolecular marker component Marker is a marker component which comprises at least one nucleic acid sequence, called the "target domain," e.g. an oligonucleotide, which is completely or partially complementary to the target sequence (n) is a positive integer from 1 to 1000

Such a nuc macromolecule is capable of sequence-specific binding to the target sequence in accordance with its complementary properties. The binding of the "target domain" to the target sequence enhances the yield of a specific labeling reaction of the complementary strands of the target sequence because the nuc component of the bound nuc macromolecule is preferentially incorporated by a polymerase.

The inventive nuc macromolecules are different from the natural nucleotides in several aspects:

In one advantageous embodiment of the invention, nuc macromolecules comprising at least an oligonucleotide moiety are used. According to the invention, this oligonucleotide part can bind complementarily at one position of the target sequence (template) to form a double strand. Such an oligonucleotide part is called "the target domain" and is abbreviated as "T domain" (FIG. 1).

In another advantageous embodiment of the invention, nuc macromolecules comprising at least one target domain and at least one anchor domain (abbreviated as "A-domain") are used (FIG. 1). A nuc macromolecule can be bound to a solid phase via such an anchor domain. Examples of an anchor domain are biotin and oligonucleotides. A nuc macromolecule can be bound to the solid phase via biotin or an oligonucleotide when this solid phase carries a streptavidin or a complementary oligonucleotide.

In another advantageous embodiment of the invention, nuc macromolecules comprising at least one target domain and at least one signal domain (abbreviated as "S-domain") are used (FIG. 1). A nuc macromolecule can be distinctively detected via such a signal domain. Fluorescent dyes represent examples of signal domains.

According to the inventive method, a labeling reaction, for example, can be carried out as follows (FIG. 5A): Providing of at least one target sequence (a nucleic acid template), at least one primer, at least one polymerase and at least one kind of the above mentioned nuc macromolecules and incubating under conditions which allow for an enzymatic incorporation of the nuc component of the nuc macromolecule into the growing strand by a polymerase. The complementary strand of the target sequence is labeled through the specific binding of the nuc macromolecules to the target sequence. The enzymatic coupling of such a nuc macromolecule in the growing nucleic acid strand leads to the formation of a bond between the extended strand and different domains of a nuc macromolecule.

In one embodiment of the present application, nuc macromolecules can be used which comprise at least one domain (target domain) which is able to bind sequence-specifically to the target sequence and at least one other domain (anchor domain) that can bind to a binding partner on a solid phase. By the enzymatic incorporation of such a nuc macromolecule, the anchor domain is also bound to the nucleic acid chain in a sequence-specific manner. Thus, during incubation of the labeled nucleic acid chains with a solid phase which includes at least one binding partner for the anchor domain, labeled nucleic acid chains can bind specifically to the solid phase.

As shown above, a nuc macromolecule can comprise structures that are complementary to the target sequence. Therefore, it is advantageous to perform an incorporation reaction under conditions which allow binding of these components to a complementary position in the template. Thereby, a selective labeling of selected target sequences can be achieved.

In an advantageous embodiment, nuc macromolecules can be used together with natural nucleotides (e.g. dNTPs or NTPs) in the same reaction. The invented nuc macromolecules and corresponding dNTPs, which are complementary to the template, compete with each other for their incorporation by the polymerase at the 3' terminus of the growing complementary strand. A nuc macromolecule being specifically bound to the target sequence via target domain outcompetes free nucleotides in the solution: it can be preferentially incorporated by the polymerase. Thus, the target sequence can be specifically labeled with nuc macromolecules even in the presence of natural dNTPs.

The incorporation of nuc macromolecules occurs preferentially in the vicinity of their binding site on the template. Sequence regions that are far away from this site or other sequences occurring in sample sequences ("non-target sequences") are not labeled. In an advantageous embodiment of the invention, the "non-target-sequences" remain unlabeled. This can be due to the lack of binding or only weak binding of nuc macromolecules to those "non-target sequences": complementary growing strands of such non-target sequences are extended with dNTPs and are only weakly or not labeled with nuc macromolecules.

The extended nucleic acid strand can gain affinity properties of the anchor domain of the nuc macromolecule due to the specific, predetermined composition of the nuc macromolecules. In analysis, a solid phase can be provided that comprises a suitable binding partner for the anchor domain of a nuc macromolecule. After the labeling reaction, the labeled target sequences are incubated with a solid phase with a binding partner (e.g. oligonucleotide-oligonucleotide-pair or biotin-streptavidin-pair or antibody-hapten-pair), which results in the binding of the extended strand to this binding partner (FIG. 6).

There are particularly advantageous embodiments in which a plurality of different templates with specific primers is provided and nuc macromolecules with corresponding oligonucleotide parts (target domains) that are specific to each template and specific anchor domains are provided. This allows for a sequence-specific incorporation of nuc macromolecules into the complementary strands of respectively specific target sequences and a subsequent selective binding to the solid phase by using different and distinct anchor domains. Particularly advantageous embodiments describe specific binding partners for anchor domains which are immobilized on a solid phase in an addressable array. This allows for a specific distribution of extended nucleic acid on the solid phase on the basis of their sequence composition.

The binding properties of the anchor domain to the binding partner can be optimized. For example, the anchor domains are designed in such a way that they do not include complementary sites to target sequence. Further, their binding strength and specificity can be optimized independently of the target sequence.

Another subject of the application is methods for the enzymatic synthesis of nucleic acid chains and components for applying these methods in accordance with the invention using nuc macromolecules for the labeling reaction.

Still another subject of the application is compositions of individual components which allow selective labeling of target sequences with nuc macromolecules.

The present invention offers several advantages for the development of methods for detection of nucleic acid chains.

BRIEF DESCRIPTION OF THE DRAWINGS

FIG. 2 provides a depiction of the nuc-macromolecular structure and its components.

FIG. 5B depicts a labelling reaction in which the target domain of a nuc macromolecule binds to a hybridization probe (Z) prior to or during the reaction instead of binding to a target sequence.

FIG. 6A, FIG. 6B and FIG. 6C provide examples of a labeling method for a target sequence or its equivalents with a subsequent binding to the solid phase. The following components are provided (FIG. 6A): one type of nuc macromolecules (1-4) with a target domain and an anchor domain, a single-stranded target sequence (7), one primer labeled with a signal domain (6 and 9), a DNA polymerase, and further nucleotides such as dNTPs. These components are incubated under conditions that allow the polymerase to incorporate dNTPs and nuc macromolecules into the growing strand (FIG. 6B). A solid phase 12 (FIG. 6C) which provides a binding partner 11 (FIG. 6C) for the anchor domain is provided.

FIG. 7A, FIG. 7B, FIG. 7C and FIG. 7D provide an example of a labeling method for a target sequence or its equivalents with a subsequent binding to the solid phase. The following components are provided: one type of nuc macromolecules 1-4 (FIG. 7A and FIG. 7B) with a target domain, an anchor domain (4a in FIG. 7A), and an antagonist of the anchor domain 4b (FIG. 7A). Further components such as single-stranded target sequence, one primer labeled with a signal domain, a DNA polymerase, and further nucleotides such as dNTPs (FIG. 7B) are provided. FIG. 7C shows the polymerase incorporatating the dNTPs and nuc macromolecules into the growing strand. FIG. 7D shows the labeled target sequence binding to the solid phase via the anchor domain of the incorporated nuc-macromolecule. (13) depicts the specific binding event between the anchor domain of the nucleotide conjugate/or primer/or oligonucleotide probe and the corresponding binding partner attached to the solid phase.

FIG. 9 shows a further example of a labeling method for a target sequence or its equivalents with a subsequent binding to the solid phase. The incorporated nucleotide conjugate comprises an anchor domain and other modified nucleotides comprise a detectable label.

FIG. 11A and FIG. 11B demonstrates a possible design for a reaction to test a particular solution for presence of a target sequence. Reaction (A): in absence of the target sequence there is no detectable signal on the solid phase. Reaction (B): in presence of the target sequence (7), the target sequence with the newly synthesized complementary strand is attached directly to the solid phase. The incorporated nucleotide conjugate comprises an anchor domain (4) and extended primer comprises a detectable signal domain (9).

FIG. 12A demonstrates a possible design for a reaction to test a particular solution for presence of a target sequence. Reaction (A): in absence of the target sequence there is no detectable signal on the solid phase. Reaction (B): in presence of the target sequence (7), the newly synthesized strand with the newly synthesized complementary strand is specifically attached (13) to the solid phase. In the process illustrated in FIG. 12B, a separation of the double strand is included. The incorporated nucleotide conjugate comprises an anchor domain (4) and extended primer comprises a detectable signal domain (9).

FIG. 13A shows an example of a labeling method for a target sequence or its equivalents with a subsequent binding to the solid phase. The reaction components are incubated under conditions that allow the polymerase to incorporate dNTPs and nuc-macromolecules into the growing strand (FIG. 13B). A solid phase (12) which comprises a binding partner (11) for the anchor domain is provided in FIG. 13C. The incorporated nucleotide conjugate comprises an anchor domain (4) and a detectable signal domain (5).

FIG. 14A provides a further example of a labeling method for a target sequence or its equivalents with a subsequent binding to the solid phase. The following components are provided: one type of nuc macromolecule with a nuc- component (1) and linker (2) and a target domain (3) and a signal domain (5), a single-stranded target sequence (7), a primer (6) with an anchor domain (8), a DNA polymerase, and further nucleotides such as dNTPs. These components are incubated under conditions that allow the polymerase to incorporate dNTPs and nuc-macromolecules into the growing strand (10) (FIG. 14B). A solid phase (12) which comprises a binding partner (11) for the anchor domain of the primer is provided in FIG. 14C.

FIG. 15 shows a further example of a labeling method for a target sequence or its equivalents with a subsequent binding to the solid phase. The following components are shown in FIG. 15A, FIG. 15B and FIG. 15C: one type of nuc macromolecule with a nuc-component (1) with a target domain (3), linker (2) and the anchor domain-1 (4), a single-stranded target sequence (7), a primer (6) with the anchor domain-2 (8), a DNA polymerase, and further nucleotides such as dNTPs. These components are incubated under conditions that allow the polymerase to incorporate dNTPs and nuc-macromolecules into the growing strand (10)(FIG. 15B). The first solid phase (solid phase-1) (12) which comprises a binding partner (11) for the anchor domain-1 of the nuc-macromolecule is provided, as well as the second solid phase (solid phase-2) (14) which comprises a binding partner for the anchor domain-2 of the primer is provided. (13) depicts the specific binding event between the anchor domain of the nucleotide conjugate/or primer/or oligonucleotide probe and the corresponding binding partner attached to the solid phase.

FIG. 18, FIG. 19, FIG. 20 and FIG. 21 A-D of each depict a schematic design for a combination of amplification of the target sequence and sequence specific labeling reaction thereof. Incorporation of nucleotide conjugates comprising a nuc-component (1), linker (2), at least one target domain (3) which can be hybridized to the single stranded target sequence (the target domain binds to the target sequence downstream from the 3' side of a corresponding primer) and anchor domain (4). The incorporation occurs during amplification. FIG. 19D shows binding via an anchor domain to a solid phase (12). (1), (2) and (4) depict regions of selective binding/signal; (3) depicts a region of no binding/signal.

FIG. 22A and FIG. 22B depict macromolecular nucleotide compounds of the invention wherein R1 -R5, X and L are various substituents as defined herein.

FIG. 24A, FIG. 24B, FIG. 24C and FIG. 24D shows that, generally, several marker units may be combined into one signal domain, then in one embodiment these units are bound to a framework, the core component of the marker.

FIG. 25B shows a nucleic acid chain used as a framework within the marker component of the nucleotide conjugate, the core component of the marker, to which individual marker units are bound.

Figure 1:
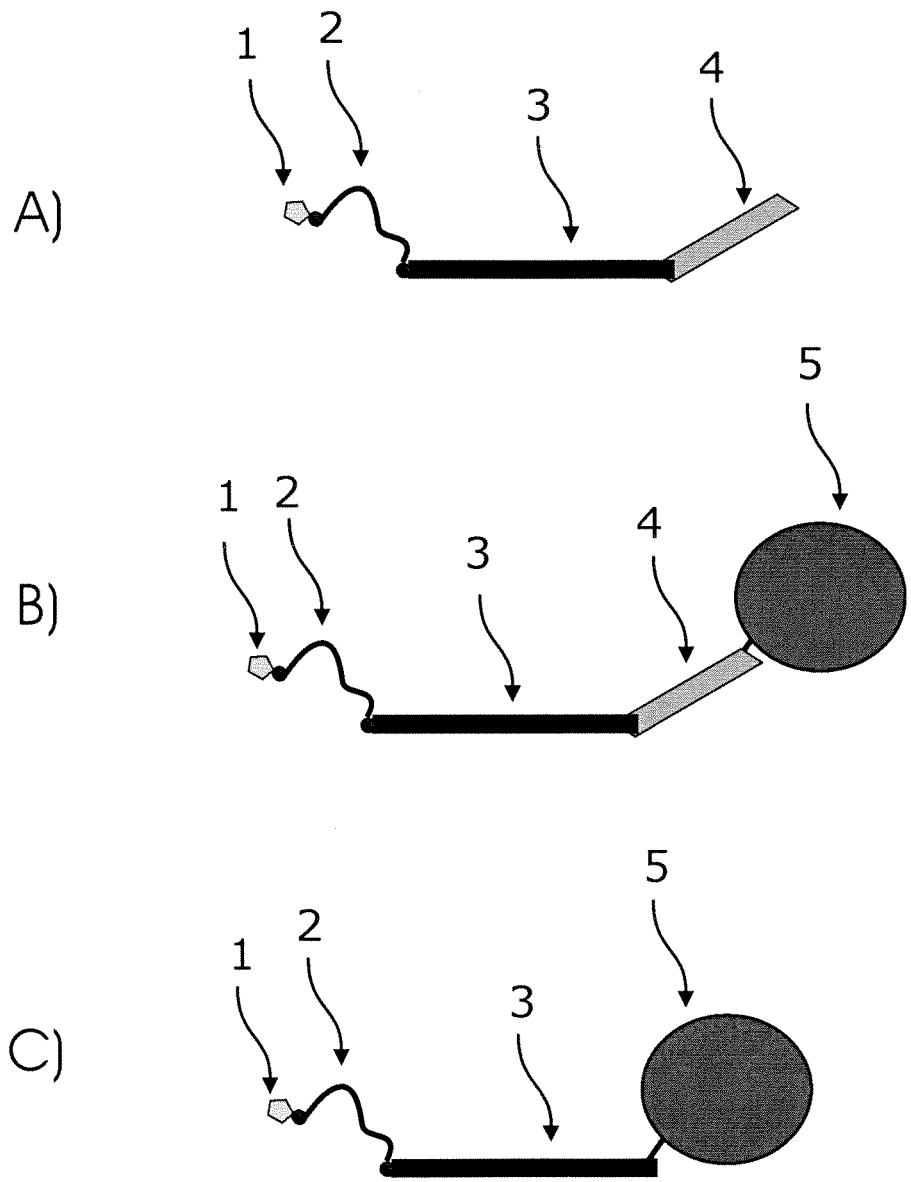
FIG. 1A, FIG. 1B and FIG. 1C depict the structure of the nuc-macromolecule, showing a nuc-component (1), a linker component (2), a target domain (3), an anchor domain (a moiety capable of specific binding to a solid phase) (4) and a signal carrying domain (5).

An advantage of this embodiment is that the binding properties of the anchor domain can be optimized independently of the target sequence and adapted to a particular method of detection. The conditions under which the specific binding between the anchor domain and the solid phase can occur can be made much more robust without losing sensitivity and specificity of binding.

Another advantage is that the same enzymes can be used for the labeling as for the amplification.

Another advantage is that, in contrast to conventionally labeled nucleotides, such as dUTP-biotin or dUTP-digoxigenin or dye labeled nucleotides, a target-sequence directed-incorporation is strongly favored due to the presence of the target domain.

Another advantage is that a plurality of differently constructed nuc macromolecules can be simultaneously used for specific detection of a target sequence

DETAILED DESCRIPTION OF THE INVENTION 1.3 TERMS AND DEFINITIONS

The structure of nuc macromolecules and their structural elements will be discussed below. The content of the section:
1.3.1 Macromolecular compound
1.3.2 Low molecular weight compound
1.3.3 A nuc macromolecule
1.3.3.1 Nuc component
1.3.3.1.1 Variations on phosphate
1.3.3.1.2 Variations on the base
1.3.3.1.3 Variations on sugar
1.3.3.1.4 Coupling of NT and Linker
1.3.3.1.5 Number of coupled nucleic components
1.3.3.2 Linker component
1.3.3.2.1 Linker constituents
1.3.3.2.2 Linker length
1.3.3.2.3 Left-coupling in a nuc macromolecule
1.3.3.3 Marker component 1.3.3.3.1 Target domain
1.3.3.3.2 Anchor domain of a nuc macromolecule and the combination with the solid phase
1.3.3.3.3 Signal domain (functions and composition)
1.3.3.3.3.1 Structure of signal-emitting or signal-mediating units of the signal domain
1.3.3.3.3.1.1 Structures with low molecular weight
1.3.3.3.3.1.2 Structures with a high mass (macromolecules)
1.3.3.3.4 Core component of the marker
1.3.3.3.5 Coupling of marker units or domains
1.3.3.3.6 Coupling between linker and marker
1.3.3.3.7 The ratio of nuc components in a nuc macromolecule
1.3.3.3.8 The ratio of marker units in a nuc macromolecule
1.3.3.4 Substrate properties of nuc macromolecules
1.3.4 Low Molecular Weight Marker
1.3.5. Conventionally modified nucleotide
1.3.6. Enzymes (polymerases)
1.3.7. Cleavable linker
1.3.8 DNA
1.3.9 RNA
13.10 PNA
1.3.11 LNA
1.3.12 Nucleotides
1.3.12.1 dNTP
1.3.12.2 NTP
1.3.12.3 abbreviation "NT"
1.3.13 NAC nucleic acid chain. DNA or RNA, PNA, LNA
1.3.14 Whole sequence
1.3.15 NACF
1.3.16 Primer binding site
1.3.17 Reference sequence
1.3.18 Tm—melting temperature
1.3.19 Sterical hindrance
1.3.20 Solid phase for analysis
1.3.21 Target sequence
1.3.22 Primer
1.3.23 Hybridization probe
1.3.24 Amplification methods
1.3.25 Detection methods
1.3.26 Further enzymes
1.3.1 Macromolecular Compound—a molecule or complex of molecules or a nanocrystal or nanoparticle, which has a molecular weight between 2 kDa and 20 kDa, 2 kDa and 50 kDa, 2 kDa and 100 kDa, 100 kDa and 200 kDa, 200 kDa and 1000 kDa or 1 MDa and 100 MDa or 100 MDa and 100 Gda. Examples of macromolecular compounds are nucleic acids, e.g. oligonucleotides with a length of more than 10 nucleotides, polynucleotides, polypeptides, proteins or enzymes, quantum dots, polymers like PEG, Mowiol, dextran, polyacrylate, nanogold particles and complexes comprising several macromolecules.

1.3.2 Low-Molecular Compound—a molecule or a molecule complex, which has a mass smaller than 2000 Da (2 kDa), e.g. biotin, natural nucleotides, dATP, dUTP, many dyes, like Cy3, rhodamine, fluorescein and conventionally modified nucleotides, like biotin-16-dUTP.

1.3.3 A Nuc-Macromolecule within the meaning of this application is a chemical structure (a nucleotide analog or a nucleotide conjugate), which comprises one or more nuc-components, one or more linker components, and at least a marker component, (FIGS. 1 to 3):

(Nuc-Linker)$_n$-Marker wherein:
Nuc is a nuc-component
Linker is a linker component Marker is a marker component n is a positive integer from 1 to 10000

Nuc is a nucleotide or a nucleoside monomer (a nuc component)

Linker has a composition which is not restricted as long as substrate properties of the nucleotides are not lost. Its length ranges between 5 and 10000 chain atoms.

Marker is a marker component, which can comprises one or several domains. For example a target domain, anchor domain, signal domain.

n is a positive interger from 1 to 10000, wherein (n) can be an average number.

In a further embodiment, the linker component comprises a coupling unit (L) for coupling the linker to the nuc-component, a hydrophilic, water soluble polymer and a coupling unit (T) for coupling the linker to the marker component. In this preferred embodiment, a nuc-macromolecule has the following structure, FIG. 1 or 2:

(Nuc-L-Polymer-T)$_n$-Marker wherein:

Nuc is a nucleotide monomer or a nucleoside monomer (nuc-component)

Linker comprises a coupling unit (L), a hydrophilic polymer and a coupling unit (T), wherein (L) is a part of the linker which connects the nuc and the linker-moiety (coupling unit L), and (T) is a part of the linker which connects the linker-moiety and the marker (coupling unit T).

Polymer is a part of the linker, which is hydrophilic, water soluble polymer with an average length between 5 and 100000 atoms.

(Coupling uni L, Polymer, coupling unit T are combined in this applications as a linker component).

Marker is a marker component, which can comprises one or several domains, for example a target domain, an achor domain, a signal domain.

n is a positive integer from 1 to 10000, wherein (n) can represent an average number.

Examples for the synthesis of nuc macromolecules are presented in the applications: Cherkasov et al WO 2005044836, Cherkasov et al WO2006097320, Cherkasov et al WO 2008043426, Cherkasov et al DE 10356837, Cherkasov et al DE 102004009704.

1.3.3.1 Nuc Component

Nuc component is a substrate for nucleotide or nucleoside accepting enzyme. A nuc-component can represent a nucleotide as well as a nucleoside. In the following, nucleotides will be described as example for both classes of the substances. Nucleosides can be converted into a nucleotide form with corresponding enzymes or via chemical methods.

In one embodiment, the nuc-component is a nucleotide monomer or a nucleoside monomer, which is coupled to the linker component. In principle, all conventional nucleotide variants that are suitable as a substrate for nucleotide-accepting enzymes can serve as nuc-component of the nuc-macromolecule so that naturally occurring nucleotides as well as modified nucleotides (nucleotide analogs) can be considered for the nuc-component. Modified nucleotides comprise base-, sugar- or phosphate-modified nucleotide analogs. Many examples are known to the person skilled in the art ("Nucleoside Triphosphates and their Analogs", Morteza Vaghefi, 2005, ISBN 1-57444-498-0; "Deoxynucleoside analogs in cancer therapy" Godefridus J. Peters, 2006, ISBN 1-58829-327-0; "Chemistry of nucleosides and nucleotides" Leroy B. Townsend, 1991, ISBN 0-306-43646-9; "Advanced organic chemistry of nucleic acids", 1994, Shabarova, ISBN 3-527-29021-4; "Nucleotide Analogs" Scheit, 1980, ISBN 0-471-04854-2; "Nucleoside and Nucleic Acid Chemistry", Kisakürek 2000, "Anti-HIV Nucleosides" Mitsuya, 1997, "Nucleoside Analogs in cancer therapy", Cheson, 1997). further examples for modifications of the nucleotides will also be cited in the text.

The nuc-component preferentially comprises a base part (base), a sugar part (sugar) and optionally a phosphate part (phosphate). Base, sugar and phosphate can be modified, i.e. the basic structure resembles the natural occurring nucleotides, but comprises e.g. additional chemical groups. Examples for combinations of different nucleotide components are known to the person skilled in the art. Such nuc-components can be used in a variety of enzymatic and chemical reactions (G. Wright et al. Pharmac. Ther. 1990, v. 47, p. 447-).

In a preferred embodiment, the nuc component is a substrate for DNA polymerase. In a another preferred embodiment, the nuc component is a substrate for RNA polymerase. Variations of the nucleotides, which allow for such substrate properties, can be used as nuc components. For example, substrates for nucleotide accepting enzymes, which lack a part of a conventional nucleotide, e.g. acyclic nucleotide analoga, can be used as nuc components, too.

1.3.3.1.1 Variations of the Phosphate

In one embodiment the nuc-component is a nucleoside. In another embodiment the nuc-component represents a nucleoside-monophosphate. In another embodiment the nuc-component represents a nucleoside-diphosphate. In another embodiment the nuc-component is a nucleoside-triphosphate. Still higher numbers of phosphate groups in a nucleotide (e.g. tetraphosphate, pentaphosphate etc.) can be used.

The said phosphate modifications can be located at the 5'-position of the sugar, like nucleoside-triphosphates, or also at other positions of the sugar part of the nucleotide, e.g. at the 3'-position.

Optionally, the phosphate part of the nucleotide can comprise modifications, in one embodiment such modifications comprising a linker, for example (D. Jameson et al. Methods in Enzymology 1997, v. 278, p. 363-, A. Draganescu et al. J. Biol. Chem. 2000v. 275, p. 4555-). In another embodiment of the invention, the phosphate part of the nuc-component comprises thiotriphosphate derivates (Burges et al. PNAS 1978 v. 75, p. 4798-).

In another embodiment of the invention, the phosphate part of the nuc-component comprises protected phosphate groups (e.g. phosphoroamidites).

In one embodiment, the phosphate part represents a linkage between the nuc-component and the linker component of the nuc-macromolecule.

1.3.3.1.2 Variations of the Base

The nuc-component can be natural nucleotide or nucleoside occurring in the nucleic acids in nature or their analogs, preferentially participating at the Watson-Crick base-pairing, e.g. adenine, guanine, thymine, cytosine, uracil, inosine or modified bases like 7-deazaadenine, 7-deazaguanine, 6-thioadenine (as referred above). Optionally, the base comprises modifications. In one embodiment, such modifications comprise for example a linker, e.g. amino-propargyl-linker or amino-allyl-linker. Further examples of linkers are known (Ward et al. U.S. Pat. No. 4,711,955, G. Wright et al. Pharmac. Ther. 1990, v. 47, p. 447-, Hobbs et al. U.S. Pat. No. 5,047,519 or other linkers e.g. Kievan U.S. Pat. No. 4,828, 979, Seela U.S. Pat. No. 6,211,158, U.S. Pat. No. 4,804,748, EP 0286028, Hanna M. Method in Enzymology 1996 v. 274, p. 403, Zhu et al. NAR 1994 v. 22 p. 3418, Jameson et al. Method in Enzymology, 1997, v. 278, p. 363-, Held et al. Nucleic acid research, 2002, v. 30 p. 3857-, Held et al. Nucleosides, nucleotides & nucleic acids, 2003, v. 22, p. 391, Short U.S. Pat. No. 6,579,704, Odedra WO 0192284). In one embodiment, a linker coupled to the base represents a connection part between the nuc-component and the linker component of the nuc-macromolecule. Further modifications of the base are described for example in the catalogue of Trilink Biotechnologies, Inc. San Diego, USA, and are presented in "Nucleoside triphosphates and their analogs", Morteza Vaghefi, 2005 ISBN 1-57444-498-0.

1.3.3.1.3 Variations of the Sugar

Different variations of the sugar part of the nucleotides, which are used e.g. in the diagnostics, therapy or research, are known to the person skilled in the art. Such variations comprise ribose, 2'-deoxyribose or 2',3'-dideoxyribose. Optionally, the sugar part comprises modifications (M. Metzker et al. Nucleic Acid Research 1994, v. 22, p. 4259-, Tsien WO 91/06678). In one embodiment, such modifications comprise for example a linker. The modifying group can be optionally be reversibly coupled to the sugar part (Hovinen et al. J. Chem. Soc. Prking Trans. 1994, s. 211-, Canard U.S. Pat. No. 5,798,210, Kwiatkowski U.S. Pat. No. 6,255,475, Kwiatkowski WO 01/25247, Ju et al. U.S. Pat. No. 6,664,079, Fahnestock et al. WO 91066678, Cheeseman U.S. Pat. No. 5,302,509, Parce et al. WO 0050642, Milton et al. WO 2004018493, Milton et al. 2004018497).

In one embodiment, the linker coupled to the sugar part represents the connection between the nuc-component and the linker component of the nuc-macromolecules.

In another embodiment, the sugar part comprises for example the following modifications: optionally the 3'-OH-Group or the 2'-OH-Group can be substituted by the following atoms or groups: halogen atoms, hydrogen atoms, amino- or mercapto- or azido groups (Beabealashvilli et al. Biochem Biophys Acta 1986, v. 868, p. 136-, Yuzhanov et al. FEBS Lett. 1992 v. 306, p. 185-).

In another embodiment, the nuc-component comprises acyclic nucleotide or nucleoside modifications (A. Holy Current Pharmaceutical Design 2003 v. 9, p. 2567-, G. Wright et al. Pharmac. Ther. 1990, v. 47, p. 447-). In another embodiment, the sugar part comprises a double bond.

In this application, the following abbreviations will be used for 2'-deoxynucleotides: dUTP for 2'-deoxyuridine-triphosphate, dCTP for 2'-deoxycytidine-triphosphate, dATP for 2'-deoxyadenosine-triphosphate, dGTP for 2'-deoxyguanosine-triphosphate.

1.3.3.1.4 Linking of the Nuc Component and Linker

The nuc-component is linked to the linker at a coupling position. This coupling position of the linker on the nuc-component can be located on the base, on the sugar (e.g. ribose or deoxyribose) or on the phosphate part.

The linkage between the linker component and the nuc-component is preferentially covalent.

If the coupling position is on the base, then the following positions are preferable: position 4 or 5 for pyrimidine bases and positions 6,7,8 for purine bases. (Ward et al. U.S. Pat. No. 4,711,955, G. Wright et al. Pharmac. Ther. 1990, V. 47, S. 447-, Hobbs et al. U.S. Pat. No. 5,047,519 or other linker e.g. Kievan U.S. Pat. No. 4,828,979, Seela U.S. Pat. No. 6,211,158, U.S. Pat. No. 4,804,748, EP 0286028, Hanna M. Method in Enzymology 1996 v. 274, S. 403, Zhu et al. NAR 1994 v. 22 S. 3418, Jameson et al. Method in Enzymology, 1997, v. 278, S. 363-, Held et al. Nucleic acid research, 2002, v. 30 3857-, Held et al. Nucleosides, nucleotides & nucleic acids, 2003, v. 22, S. 391, Short U.S. Pat. No. 6,579,704, Odedra WO 0192284). Further examples for modifications on the base are represented in "Nucleoside triphosphates and their analogs", Morteza Vaghefi, 2005 ISBN 1-57444-498-0; On sugar, positions 2', 3', 4' or 5' can serve as coupling positions. The coupling to the phosphate groups can proceed for example via alpha, beta, or gamma phosphate groups. Examples for coupling positions on the base are described in Short WO 9949082, Balasubramanian WO 03048387, Tcherkassov WO 02088382 (also see commercially available nucleotides e.g. from Amersham or Roche), on the ribose in Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Parce WO 0050642, on phosphate groups in Jameson et al. Method in Enzymology, 1997, v. 278, p. 363.

The location of the coupling position depends on the area of application of the nuc-macromolecules. For example, coupling positions on the sugar or on the base are preferable in cases where the marker is intended to stay coupled to the nucleic acid strand. The coupling to the gamma or beta phosphate groups can be used for example in cases where the marker has to be separated during the incorporation of the nuc-macromolecule.

The linking between the nuc-component and the linker component results for example via a coupling unit (L) that is a part of the linker component.

In one embodiment, the linkage between the nuc-component and the linker is stable, e.g. resistant to temperatures up to 130° C., pH-ranges from 1 to 14 and/or resistant to hydrolytical enzymes (e.g. proteases or esterases). In another embodiment of the invention, this linkage between the nuc-component and the linker component is cleavable under mild conditions.

This cleavable linkage allows removal of the linker components and the marker components. This can be advantageous for example for methods of sequencing by synthesis, like pyrosequencing, BASS (base addition sequencing schema) (Canard et al. U.S. Pat. No. 5,798,210, Rasolonjatovo Nucleosides & Nucleotides 1999, v. 18, p. 1021, Metzker et al. NAR 1994, v. 22, p. 4259, Welch et al. Nucleosides & Nucleotides 1999, v. 18, p. 19, Milton et al. WO 2004018493, Odedra at al. WO 0192284) or single molecule sequencing Tcherkassov WO 02088382. The choice of the cleavable linkage is not restricted insofar as it remains stable under conditions of enzymatic reaction, does not result in irreversible damage of the enzyme (e.g. polymerase) and is cleavable under mild conditions. "Mild conditions" is understood to mean conditions that do not result in damage of nucleic acid-primer complexes wherein, for example, the pH-range is preferentially between 3 and 11 and the temperature is between 0° C. and the temperature value (x). This temperature value (x) is dependent upon the Tm of the nucleic acid—primer complex (where Tm is the melting temperature) and is calculated for example as Tm (nucleic acid primer complex) minus 5° C. (e.g. Tm is 47° C., then the (x)-value is 42° C.; ester, thioester, acetales, phosphoester, disulfide linkages and photolabile compounds are suitable as cleavable linkages under these conditions).

Preferentially, the said cleavable linkage comprises chemical or enzymatic cleavable linkages or photolabile compounds. Ester, thioester, tartrate, disulfide and acetal linkages are preferred as examples of chemical cleavable groups (Short WO 9949082, "Chemistry of protein conjugation and crosslinking" Shan S. Wong 1993 CRC Press Inc., Herman et al. Method in Enzymology 1990 v. 184 p. 584, Lomant et al. J. Mol. Biol. 1976 v. 104 243, "Chemistry of carboxylic acid and esters" S. Patai 1969 Interscience Publ., Pierce Catalog). Examples for photolabile compounds are described in Rothschild WO 9531429, "Protective groups in organic synthesis" 1991 John Wiley & Sons, Inc., V. Pillai Synthesis 1980 p. 1, V.

Pillai Org. Photochem. 1987 v. 9 p. 225, Dissertation "Neue photolabile Schutzgruppen für die lichtgesteuerte Oligonucleotidsynthese" H. Giegrich, 1996, Konstanz, Dissertation "Neue photolabile Schutzgruppen für die lichtgesteuerte Oligonucleotidsynthese" S. M. Bühler, 1999, Konstanz).

1.3.3.1.5 Number of the Linked Nuc-Components

In one embodiment of the invention, only one nuc-component is coupled per nuc-macromolecule. In another embodiment of the invention, several nuc-components are coupled per nuc-macromolecule. If several nuc-components are coupled, they can be identical or different, whereas the average number of the nuc-components per nuc-macromolecule can range for example from 2 to 5, 5 to 10, 10 to 25, 25 to 50, 50 to 100, 100 to 250, 250 to 500, 500 to 1000, 1000 to 100000.

1.3.3.2 Linker Component

The function of the linker is to link a nuc component and a marker component in such a way that substrate properties of the nuc component are retained for nucleotide accepting enzymes even after the coupling of a macromolecular marker.

The terms "linker" and "linker component" will be used synonymously in this application and comprise the whole structural part of the nuc-macromolecule between the nuc-component and the marker component. The exact composition of the linker is not limited and can vary. In one embodiment, the linker is preferentially hydrophilic.

1.3.3.2.1 Linker Length

An average linker length ranges between 2 to 5, 5 to 10, 10 to 20, 20 to 30, 30 to 40, 40 to 50, 50 to 60, 60 to 70, 70 to 80, 80 to 90, 90 to 100, 50 to 100, 100 to 200, 200 to 500, 500 to 1000, 1000 to 2000, 2000 to 10000, 10000 to 100000 atoms (chain atoms), so that an average linker length amounts to between 2 to 5, 5 to 10, 10 to 20, 20 to 30, 30 to 40, 40 to 50, 50 to 60, 60 to 70, 70 to 80, 80 to 90, 90 to 100, 50 to 100, 100 to 200, 200 to 500, 500 to 1000, 1000 to 2000, 2000 to 10000, 10000 to 100000 angstroms (measured on a molecule potentially stretched-out as much as possible).

If a nuc-macromolecule comprises several linker components, these linker components can be of the same or different lengths relative to each other.

Some parts of the linkers can comprise rigid areas and other parts can comprise flexible areas.

1.3.3.2.2 Short Linker

In a preferred embodiment, nuc-macromolecules have a short linker. Its length comprises the ranges between 2 and 50 chain atoms. Such linkers can carry functional groups, as for example amino, carboxy, mercapto, hydroxy groups, alkyn-, isothiocyanat-, aldehyd- or azid-group. Such group can be provided in reactive form such as NHS-ester for carboxy group. Further molecules can be coupled to these groups. In one embodiment, cross-linker are bound to the short linker so that resulting nuc component can be further reacted with other substances such as macromolecular linker component or marker component. Examples of short linkers coupled to the nucleotides are known to the person skilled in the art ("Nucleoside triphosphates and their analogs", Morteza Vaghefi, 2005 ISBN 1-57444-498-0, Ward et al. U.S. Pat. No. 4,711,955, G. Wright et al. Pharmac. Ther. 1990, V. 47, S. 447-, Hobbs et al. U.S. Pat. No. 5,047,519 or other linker e.g. Klevan U.S. Pat. No. 4,828,979, Seela U.S. Pat. No. 6,211, 158, U.S. Pat. No. 4,804,748, EP 0286028, Hanna M. Method in Enzymology 1996 v. 274, S. 403, Zhu et al. NAR 1994 v. 22 S. 3418, Jameson et al. Method in Enzymology, 1997, v. 278, S. 3865-, Held et al. Nucleic acid research, 2002, v. 30 3857-, Held et al. Nucleosides, nucleotides & nucleic acids, 2003, v. 22, S. 391, Short U.S. Pat. No. 6,579,704, Odedra WO 0192284). The linker can contain one or several units of polymers, as for example amino acids, sugars, PEG units or carboxylic acids. The coupling unit (L) of a long linker can serve as further examples of short linkers (see below). Examples for cross-linker are known to an expert ("Chemistry of protein conjugation and crosslinking" Shan S. Wong 1993). Many cross-linker are commercially available, e.g. from Invitrogen (Lifescience Technologies, Pierce Biotech, Iris-Biotech). Examples of coupling of different substances to macromolecules such as oligonucleotides are also known (Y. Singh et al Chem. Soc. Rev. 2010, 39, 2054-). It should be obvious to an expert that the linker between the nuc component and the marker component can be assembled in several chemical steps.

1.3.3.2.3 Langer Linker

In another preferred embodiment of the invention, a long linker having a length of more than 50 chain atoms is used. The linker component has has in its structure, for example, the following components:

1) coupling unit (L)
2) hydrophilic or water soluble polymer
3) coupling unit (T)

The subdivision of the linker in separate parts is purely functional and should serve merely for better understanding of the structure. Depending on the approach, particular structures can be considered as one functional part or as another.

The coupling unit (L) has the function of linking the linker component and the nuc-component. Short, non-branched compounds from 1 to 20 atoms in length are preferred. The particular structure of the coupling unit (L) depends on the coupling position of the linker to the nucleotide and on the particular polymer of the linker. Several examples of coupling units (L) are shown in examples 1 to 33 of this application. Many conventionally modified nucleotides comprise a short linker; these short linkers are further examples of coupling units (L), e.g. short linker on the base: Short WO 9949082, Balasubramanian WO 03048387, Tcherkassov WO 02088382 (see also commercially available nucleotides from e.g. Amersham or Roche), short linker on the ribose as described in Herrlein et al. Helvetica Chimica Acta, 1994, v. 77, p. 586, Jameson et al. Method in Enzymology, 1997, v. 278, p. 363, Canard U.S. Pat. No. 5,798,210, Kwiatkowski U.S. Pat. No. 6,255,475, Kwiatkowski WO 01/25247, Ju et al. U.S. Pat. No. 6,664,079, Parce WO 0050642, and short linker on phosphate groups as described in Jameson et al. Method in Enzymology, 1997, v. 278, p. 363. Still further examples for the coupling unit (L) are presented in the following:

$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$, $R_6$—O—CO—$R_7$, $R_6$—CO—S—$R_7$, $R_6$—S—CO—$R_7$, $R_6$—P(O)$_2$—$R_7$, $R_6$—(CH$_2$)$_n$—$R_7$, $R_6$—(CH$_2$)$_n$—$R_7$, $R_6$-A-(CH$_2$)$_n$—$R_7$, $R_6$—(CH$_2$)$_n$—B—$R_7$, $R_6$—(CH═CH—)$_n$—$R_7$, $R_6$-(A-CH═CH—)$_n$—$R_7$, $R_6$—(CH═CH—B—)$_n$—$R_7$, $R_6$-A-CH═CH—(CH$_2$—)$_n$—$R_7$, $R_6$—(—CH═CH—CH$_2$)$_n$—B—$R_7$, $R_6$—(—CH═CH—CH$_2$—CH$_2$)$_n$—B—$R_7$, $R_6$—(C≡C—)$_n$—$R_7$, $R_6$-(A-C≡C—)$_n$—$R_7$, $R_6$—(C≡C—B—)$_n$—$R_7$, $R_6$-A-C≡C—(CH$_2$—)$_n$—$R_7$, $R_6$—(—C≡C—CH$_2$)$_n$—B—$R_7$, $R_6$—(—C≡C—CH$_2$—CH$_2$)$_n$—B—$R_7$, where $R_6$ is the nuc-component; $R_7$ is a polymer; A and B comprises the following structural elements: —NH—, —O—, —S—, —SS—, —CO—NH—, —NH—CO—, —CO—O—, —O—CO—, —CO—S—, —S—CO—, —P(O)$_2$—, —Si—, —(CH$_2$)$_n$—, a photolabile group; (n) is a number from 1 to 5

The coupling unit L is covalently linked to the nuc-component on the one side. On its other side further parts of the linker, for example, a hydrophilic polymer or directly the coupling unit (T) or directly the marker can be bound.

In the following, the coupling of the polymer, as a part of the linker is explained as example. The character of the linkage with the polymer depends on the kind of polymer. In a preferred embodiment, the ends of the polymer comprises reactive groups, for example NH2 (amino), OH (hydroxy), SH (mercapto), COOH (carboxy), CHO (aldehyde), acrylic, maleimide, or halogen groups, or alkyn-, Isothiocyanat- or Azid-Group. Such groups can be provided as a reactive form, e.g. NHS-ester for carboxy-group. Such polymers are commercially available (e.g. Fluka, Iris-Biotech, Nanocs inc, Pierce Biotech). Some examples for the coupling of polymers to the coupling unit are shown in the examples.

In a preferred embodiment, the water-soluble polymer represents the major part of the linker component. It is a polymer, preferentially hydrophilic, consisting of the same or different monomers.

Examples of suitable polymers are polyethylene-glycol (PEG), polyamides (e.g. polypeptides), polysaccharides and their derivates, dextran and its derivates, polyphosphates, polyacetates, poly(alkyleneglycols), copolymers with ethylenglycol and propyleneglycol, poly(olefinic alcohols), poly(vinylpyrrolidones), poly(hydroxyalkylmethacrylamides), poly(hydroxyalkylmethacrylates), poly(x-hydroxy acids), polyacrylic acid and their derivates, poly-acrylamide and its derivates, poly(vinylalcohol), polylactic acid, polyglycolic acid, poly(epsilon-caprolactones), poly(beta-hydroxybutyrates), poly(beta-hydroxyvalerate), polydioxanones, poly(ethylene terephthalates), poly(malic acid), poly(tartronic acid), poly(ortho esters), polyanhydrides, polycyanoacrylates, poly(phosphoesters), polyphosphazenes, hyaluronidate, and polysulfones.

In one embodiment, the polymer-part comprises branched polymers. In an other embodiment, the polymer-part comprises non-branched or linear polymers. The polymer can consist of several parts of different length, each part consisting of the same monomers with the monomers in different parts being different. To a person skilled in the art, it should seem obvious that for a macromolecular linker, it is often possible to determine only an average mass, so that the data regarding the mole masses represent an average ("Makromoleküle, Chemische Struktur and Synthesen", Volume 1, 4, H. Elias, 1999, ISBN 3-527-29872-X). For this reason, often there is no exact mass information for nuc-macromolecules.

In one preferred embodiment, the linker component comprises a linear, non-branched polymer that is not modified with further sterically demanding chemical structures such as dyes, fluorescent dyes, or ligands. Such linker components lead to a low sterical hindrance, e.g. in an enzymatic recognition of the nuc-components.

In another preferred embodiment, the polymer of the linker component is linear but the linker component is modified with one or several sterically demanding chemical groups, for example dyes. The presence of the sterically demanding group allows for a control of the enzymatic reaction in some analytic processes (Tcherkassov WO 02088382).

Further examples of sterically demanding groups are shown in the chapter 1.3.19.

Sterically demanding ligands or structures can be coupled to different linker parts. The average number of the sterically demanding ligands coupled to the linker can vary and amounts, for instance, between 1 and 3, 3 and 5, 5 and 20, 20 and 50. In the coupling of sterically demanding groups, it is necessary to take into consideration that a space-demanding structure coupled in the direct proximity of nucleotide-component can lead to the loss of the substrate properties. Sterically demanding ligands can be coupled uniformly or randomly over the entire length of the linker, or they can be coupled to the linker at a certain distance from the nuc-component. The distance between the nuc-component and the steric hindrance amounts, for instance, to 10 to 15, to 15 to 20, 20 to 25, 25 to 30, 30 to 35, 35 to 40, 40 to 45, 45 to 50, 50 to 55, 55 to 60, 60 to 70, 70 to 80, 80 to 90, 90 to 100, 100 to 200, 200 to 1000, 1000 to 5000 chain atoms. The sterically demanding group can be considered as a part of the linker or as a part of the marker. Which way to consider it can depend, for instance, on whether or not the sterically demanding group possesses certain signal properties.

1.3.3.2.3 Linker Coupling in a Nuc-Macromolecule

The linker is connected to the nuc-component on one side and to the marker component on the other side. The linker can have coupling units at his ends which fulfill this connecting function. The connection to the nuc-component was discussed above. The connection between the linker and the marker components is provided by coupling unit T. Short, non-branched connections no more than 20 atoms in the length are preferred. The respective structure of the coupling unit T depends upon the coupling position on the marker component and upon the respective polymer of the linker.

The coupling unit T is covalently connected to the polymer. The kind of the coupling depends on the kind of the polymer. In a preferred embodiment, the polymer has reactive groups at its ends such as NH2 (amino), OH (hydroxy), SH (mercapto), COOH (carboxy), CHO (aldehyde), acrylic, maleimide, or halogen groups, or alkyn-, Isothiocyanat- or Azid-Groups. Such groups can be provided as a reactive form, e.g. NHS-ester for carboxy-group. Such polymers are commercially available (e.g. Fluka, Iris-Biotech, Nanocs inc, Pierce Biotech). Some examples of the coupling units L are shown in Cherkasov et al WO 2005044836, Cherkasov et al WO2006097320, Cherkasov et al WO 2008043426, Cherkasov et al DE 10356837, Cherkasov et al DE 102004009704. For further examples of the chemical and affine connections please refer to the literature: "Nucleoside triphosphates and their analogs", Morteza Vaghefi, 2005 ISBN 1-57444-498-0; "Chemistry of protein conjugation and crosslinking" Shan S. Wong in 1993, "Bioconjugation: protein coupling techniques for the biomedical sciences", M. Aslam, in 1996.

The linker can also comprise other functional groups or parts, for example one or several groups that are cleavable under mild conditions, see also Cherkasov et al WO 2005044836, Cherkasov et al WO2006097320, Cherkasov et al WO 2008043426, Cherkasov et al DE 10356837, Cherkasov et al DE 102004009704.

A cleavable group within the linker allows the removal of a part of the linker and the marker component. After a cleavage reaction, a linker residue remains coupled to the nuc-component. Examples of cleavable groups are shown in Section 1.3.3.1.4.

1.3.3.3 Marker Component

The structure of the marker component is particularly adapted to its functions.

In the present application, the marker component particularly has one or more of the following functions: a) recognition of one or more target sequences, b) binding to a solid phase, c) generation of a specific signal. These functions are performed by different parts of the marker component.

In this application, the term "domain" is used. This term is used to describe a part or group of parts of the nuc macromolecule with a common function. Individual parts of the domain can be referred to as marker units. In this case, a domain consists of one or more marker units with the same function. The term "domain" should provide a person skilled in this area with a better overview of the possible combinations of individual structures and their functions. This term is not intended to be restricted to certain structures.

The term "marker unit" is used to describe structures fulfilling a certain function, and is an appropriate term to designate certain structures that will be well known to a person skilled in this area, e.g. biotin; dyes, including fluorescent dyes; oligonucleotides; quantum dots; nanoparticles; and reactive groups. For example, a dye or a microparticle or an amino group will be a known element to the expert. As in the field of polymer chemistry, individual marker units represent building blocks of a macromolecular structure. For the purpose of creating a clear and simple description, marker units with similar functions can be combined into domains. In the simplest case, a domain consists of only one marker unit, such as an anchor domain consisting of a biotin. However, several biotin molecules can be combined to form an anchor domain.

According to the invention, a marker component of the nuc macromolecules can comprise the following domains: one or more target domains, one or more anchor domains, and one or more signal domains. In a further embodiment, nuc macromolecules include suitable antagonists.

Target domain: the recognition of a target sequence or a plurality of target sequences is provided by a part of the marker component called a "target domain". Examples of target domains are nucleic acid chains or their analogs which can bind to the target sequence. Different target sequences can be recognized by different specific target domains or by a target domain with a broad sequence recognition pattern.

Anchor domain: binding to a solid phase is enabled by a further part of the marker component, a so-called "anchor domain". This anchor domain is capable of binding to a solid phase via an affine or covalent binding. Other examples of anchor domains are nucleic acid chains, such as oligonucleotides, which can bind to the complementary partner immobilized on a solid phase (complementary binding of nucleic acid chains or aptamer-protein binding). Further examples of anchor domain include biotin or haptens (e.g. dyes, digoxigenin, and DNP) or proteins with the ability to bind other molecules (such as streptavidin (SA), antibodies, and lectins). Many examples of affine binding are known to an expert. Generally, one partner of a binding pair is a constituent of a marker component (anchor domain), while another partner is an element of the solid phase (binding partner).

The signal domain of a marker component mediates the specific recognition or detection of nuc macromolecules. Several examples are given below, and are known to a person skilled in the area.

Antagonists

In one embodiment, the marker component comprises structures which inactivate the function of a particular domain reversibly. Such structures are designated as an antagonist to the respective domain. The effect of the antagonist is reversible, so that the properties of the domains can be restored.

Antagonist of the Anchor Domain:

The purpose of the anchor domain is to convey binding to the solid phase. In some embodiments, the anchor domain comprises oligonucleotides which bind via hybridization to a complementary immobilized binding partner. An antagonist of such an anchor domain, for example, represents a complementary oligonucleotide in the nuc macromolecule, which can reversibly bind the anchor domain and thereby prevents interaction with the binding partner on the solid phase (FIG. 3i). The effect of the antagonist is reversed, for example, due to binding of a nuc macromolecule to the target sequence and the incorporation of the nuc component (FIG. 7). Thus, the anchor domain with regained/restored binding capability can bind to the solid phase. In a further embodiment of the invention, an antagonist of the anchor domain of a nuc macromolecule can be cleaved off by chemical or enzymatic reaction.

Antagonist of the Signal Domain:

Quencher molecules represent examples of antagonists for signal domains with fluorescence properties. These antagonists can be brought into the proximity of the marker units having fluorescent properties via a cleavable chemical bond or via a hairpin-like structure of the nucleic acid chains ("molecular beacons", FRET pairs). By these means the signal is reduced or completely suppressed. After cleaving off of the quencher or through destruction of the hairpin structure of the nucleic acids, the distance between a quencher and the fluorescent dye increases. This leads to increase of the signal.

In the description of the invention, the antagonists will be discussed together with the respective domains that they reversibly block.

The individual domains and their antagonists are integrated into a marker component. The integration can be accomplished by coupling individual domains to each other or they can be connected using linkers or individual domains are linked to another structure, such as a core component of the marker.

Individual domains can comprise one or more marker units. In one embodiment a domain comprises only one marker unit. For example, a target domain comprises only one oligonucleotide that can bind to a target sequence. An example of an anchor domain having only one structural unit is biotin or an oligonucleotide. An example of a signal domain having only one structural unit is one fluorescent dye or one quantum dot.

In a further embodiment, a domain comprises several marker units. For example, several identical or different oligonucleotide sequences can be coupled in a nuc macromolecule and bind to the same position in the target sequence. In this case, the individual oligonucleotides represent marker units and their entirety represents a target domain. Similarly, several oligonucleotides or several biotin molecules can be combined to an anchor domain.

A nuc macromolecule can also comprise several target domains or multiple anchor domains or multiple signal domains. This is the case if the domains of a group differ in their function. For example, different target domains of a nuc macromolecule bind to different sites of a target sequence or to different target sequences. The function of binding to the solid phase can also be achieved by only one or a plurality of different anchor domains.

A nuc macromolecule can comprise a marker component which has only a single function or a combination of two or more functions. The composition of individual nuc macromolecule types depends on these particular functions.

The manner of presentation of the composition of the marker can, for example, be as follows: one target and one signal domain=[T1, S1], two different anchor domains and one signal domain=[A1, A2, S1], four different target domains and one anchor domain=[T1, T2, T3, T4, A1], three identical target domains and one anchor and one signal domain=[3×T1, A1, S1] etc.

The antagonists of individual domains can be pointed out, for example, by an additional letter, e.g. an antagonist to an anchor domain is indicated by [aA] and an antagonist to a signal domain by [aS]. The description of the composition of the marker can be indicated as follows: [aA1, T1, A1]. The antagonist [aA1] is reversibly blocking the binding properties of the anchor domain [A1].

Within a general structure for nuc macromolecules, such as (nuc-linker)n markers, the detailed composition of different types of nuc macromolecules can be represented, for example, as follows:

(nuc-linker)n-marker is a general description of nuc macromolecules.

(nuc-linker)n-[T1,S1] is a general description of nuc macromolecules with one target domain and one signal domain.

dUTP-linker-[T1,S1] represents a general description of nuc macromolecules with dUTP as nuc component and one target domain and one signal domain.

(dCTP-linker)5-[T1,S1] is a general description of nuc macromolecules with five dCTP-linker units and one target domain and one signal domain. If required, the description of individual components can be presented in more or less detail.

Since all nuc macromolecules comprise a linker between the nuc component and a marker component, an indication for a linker may be omitted from the list of the components of a particular type pf nuc macromolecules, e.g. (nuc1)-[T1,A1], (nuc2)-[T2, A2], etc.

Figure 3:
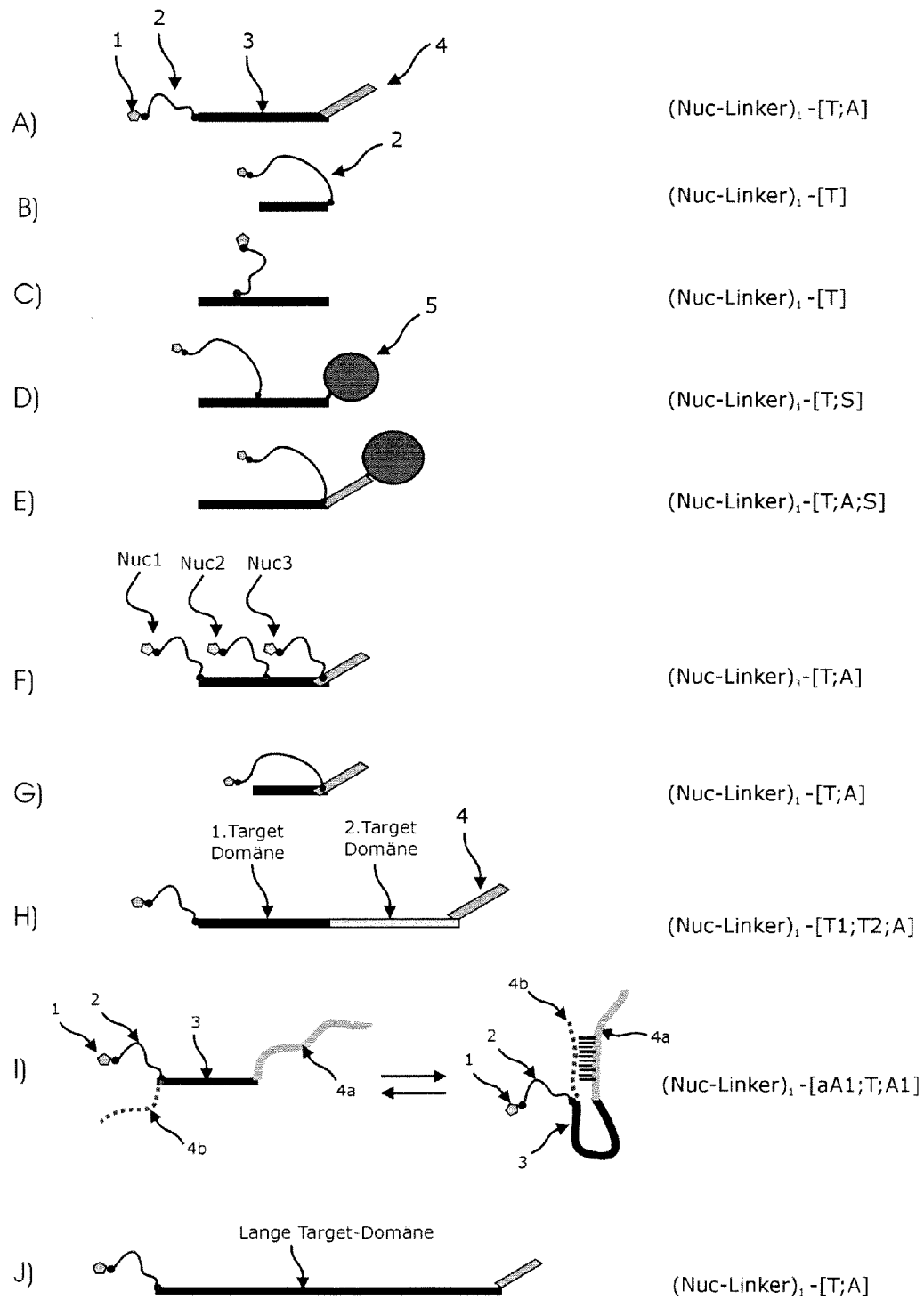
FIG. 3 shows various examples (A - j) of compositions of nuc-macromolecules with the general formula (nuc-linker)n-markers.
Figure 4:
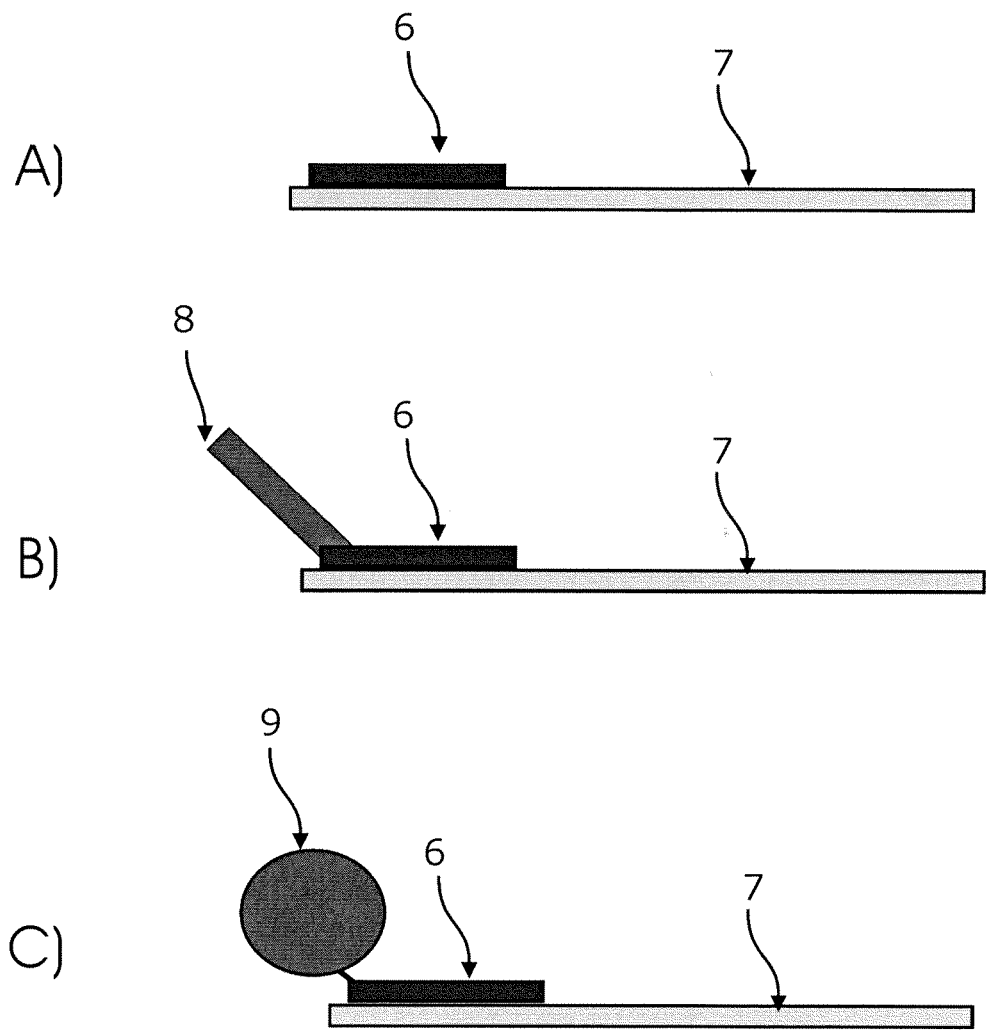
FIG. 4A, FIG. 4B and FIG. 4C depict three versions of the primer structure, showing a primer (6), template nucleic acid (7), anchor domain of the primer (8) and signal domain of the primer (9).

In the following, some examples of compositions of nuc macromolecules with general formula (nuc-linker)n-markers are presented (FIG. 3).

(Nuc-Linker)$_n$-[T]
(Nuc-Linker)$_n$-[A]
(Nuc-Linker)$_n$-[T,S]
(Nuc-Linker)$_n$-[T,A]
(Nuc-Linker)$_n$-[S,A]
(Nuc-Linker)$_n$-[T,A,S]
(Nuc-Linker)$_n$-[T$_Q$]
(Nuc-Linker)$_n$-[A$_R$]
(Nuc-Linker)$_n$-[T$_Q$,S$_P$]
(Nuc-Linker)$_n$-[T$_Q$,A$_R$]
(Nuc-Linker)$_n$-[S$_P$,A$_R$]
(Nuc-Linker)$_n$-[T$_Q$,A$_R$,S$_P$]

Individual constituents which belong to the marker are enclosed in [ ]: T=target domain, A=anchor domain, S=signal domain.

wherein the number of nuc components (coupled via a linker), (n), in one embodiment of the invention comprise ranges from 1 to 100, in another embodiment ranges from 100 to 10000. Often, this number can represent an average number in a population of nuc macromolecules of a certain type.

In one embodiment, the number of individual domains (P), (Q), and (R) independently of each other comprise ranges from 1 to 100; in another embodiment, this number comprises ranges between 100 and 10000. The properties of a single domain within a group (such as 100 anchor domains) can be identical or different. The effective concentration of individual domains or their variety or both may thereby be increased. Often, the number represents an average within the population of nuc macromolecules of a certain type.

A marker can comprise the following domains: In one embodiment, at least one target domain, or at least one anchor domain, or at least one signal domain. In a further embodiment, the marker comprises either a combination of at least one target domain and at least one signal domain or a combination of at least one target domain and at least one anchor domain or a combination of at least one anchor domain and at least one signal domain. In another embodiment, the marker comprises a combination of all three functions, wherein at least one target domain, at least one anchor domain, and at least one signal domain are combined. In another embodiment, the marker comprises either a combination of at least one target domain and at least one signal domain and at least one domain to antagonize the signal domain (such as a quencher) or a combination of at least one target domain and at least one anchor domain and an antagonist to the anchor domain.

Combinations between a target domain specific to the target sequence and an anchor domain within a single type of nuc macromolecules can be customized in such a way that the properties of a specific anchor domain are unique and characteristic with respect to the specific characteristics of the target domain. Through such a unique and characteristic combination, the anchor domain is assigned to the target sequence, such as nuc1-[T1, A1].

Each domain can be connected with another directly or with the aid of the core component.

Below, some examples of structures and functions of individual domains of the marker component will be discussed in more detail.

1.3.3.3.1 Target Domain.

Figure 5A:
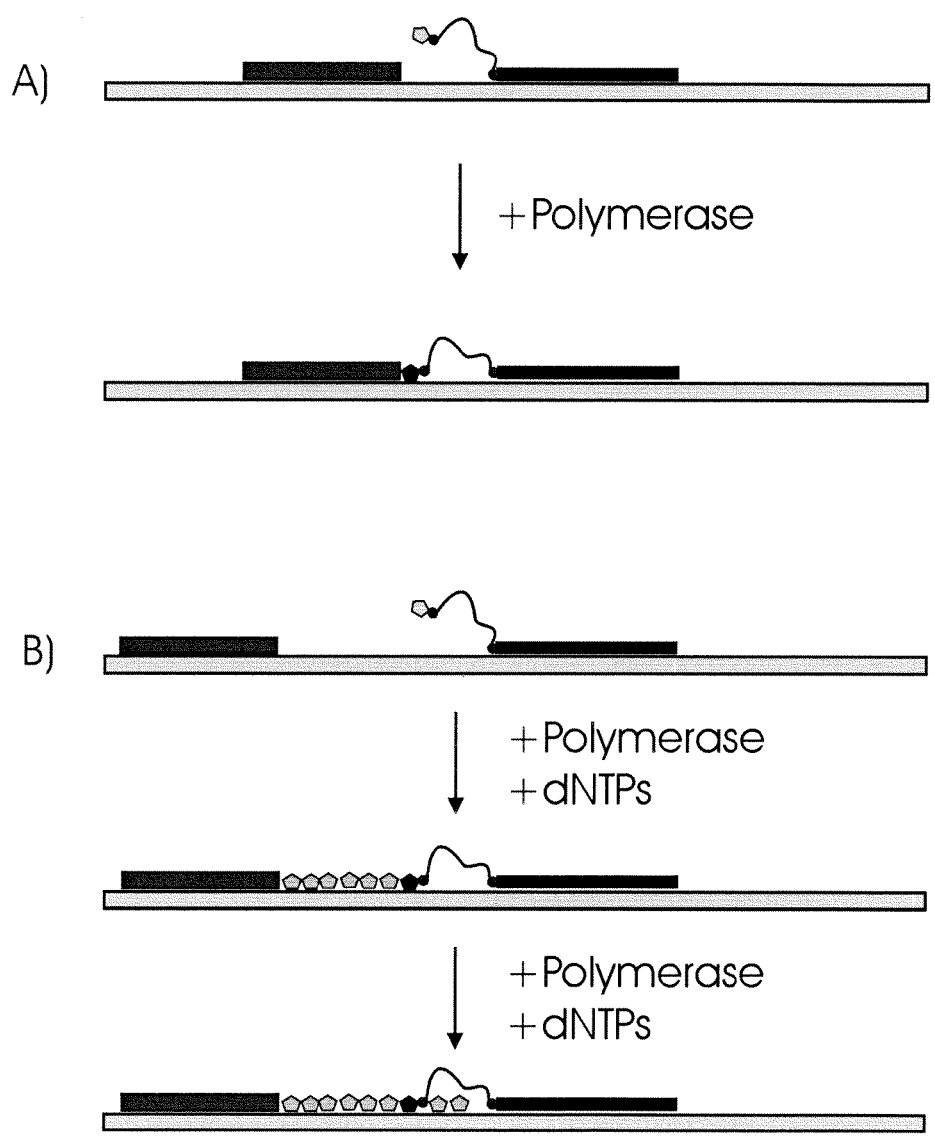
FIG. 5A and FIG. 5B each depict an incorporation reaction using a polymerase and nuc-macromolecule where the target domain of the nucleotide conjugate binds to the template via hybridization.

The target domain is responsible for the binding of the entire nuc macromolecule to the target sequence in a sequence-specific manner. Nuc macromolecules can bind to the target sequence sequence-specifically by means of a target domain prior to or during an enzymatic reaction like a primer or a probe bind to nucleic acid chains in a real-time PCR within a particular cycle. The nuc component of the attached nuc macromolecules can be incorporated into the growing strand by a polymerase (FIG. 5A).

Nucleobases like adenine, cytosine, guanine, thymine, and uracil (abbreviated as A, C, G, T, U) or analogs thereof linked to a sugar-phosphate backbone in the form of DNA or RNA or analogs thereof, such as PNA and LNA, can bind sequence-specifically to the nucleic acid strands. Various nucleic acid chains, such as DNA, RNA, protein nucleic acids (PNA), morpholino, and their analogs can represent the nucleic acid portion of the target domain. Generally speaking, substances capable of entering into a sequence-specific binding to a single- or a double-stranded nucleic acid chain are suitable for the target domain. Usually, such substances have nucleobases (A, C, T, G, U) or their derivatives which allow sequence-specific binding. The backbone can have a natural composition (sugar-phosphate backbone) or a variation thereof, such as PNA. Single target domains within a single species of nuc macromolecules can consist of one type of building blocks, for example DNA only or PNA only, or be a polymer with mixed composition, wherein at certain positions of sequence DNA, RNA, PNA, morpholino, LNA, or other modifications are introduced into the same chain.

In a case in which multiple target domains are combined within a single type of nuc macromolecules, individual domains can consist of different types of monomers; for example, one target domain can be composed of DNA, another of PNA, and still another of RNA.

To simplify the description, nucleic acid chains are discussed in detail in the form of DNA. Other types of nucleic acid chains can be constructed and used according to rules known by an expert in accordance with the examples with DNA oligonucleotides.

In a further embodiment, the linking of the target domain within a nuc macromolecule is achieved at one of its two ends such as via the 5' end or via the 3' end. Examples of the linking of an oligonucleotide via one of the ends will be known to a person possessing skills in the area. In another embodiment of the invention, the linking of the target domain is achieved through the internal position/region of the target domain, for example via a linker coupled to a base.

The target domain can be directly coupled via a linker to the nuc component, or it can be coupled to the core component of the nuc macromolecule.

In one embodiment of the application, the target domain is completely or partially degradable by the 5' to 3' exonuclease activity of a polymerase. The structure of the nuc macromolecules can be designed in such a way that the incorporated nuc component with the remainder of the nuc macromolecule remains in the extended complementary strand. This can be achieved, for example, through a coupling of the target domain to the rest of the nuc macromolecule at the 3' end of the target domain or in its vicinity.

In a further embodiment of the application, the target domain is resistant to a 5' to 3' exonuclease activity. This can be achieved, for example, through the use of PNA or other modifications.

A target sequence can be in the form of single- or double-stranded DNA or RNA. In one embodiment, the binding of the target domain to the target sequence can be carried out with the formation of double strands (according to the rules of Watson-Crick base pairing); in another embodiment, triple strands are formed (according to Hoogsteen rules). Examples of sequence-specific binding of nucleic acid chains will be known to a person possessing skills in the area. The length and the composition of the target domain are adjusted to such a degree that the target domain can bind to the target sequence under the respective reaction conditions.

Hereinafter, binding to a single strand is considered as an example. The composition of a target domain can be designed to be completely complementary to the target sequence ("perfect match") or differ in some positions ("Miss Match").

For a given target sequence, there are several methods that will be known to a person skilled in the composing of an appropriate sequence for the target domain. Because the target domain has to bind within the target sequence, rules may be applied, for example, which are used for the construction of a real-time PCR probe (see literature section amplification). On the other hand, rules for the design of microarray-oligonucleotides that will also be known to an expert can be applied. For example, for a known target sequence an appropriate complementary sequence with a length of about 10 to 50 nucleobases or about 15 to 30 nucleobases can be selected to bind to a single-stranded stretch of the respective target sequence.

Preferentially, a target domain of nuc macromolecules comprises nucleic acid chains with lengths in the following ranges: from 3 to 6, 6 to 9, 9 to 12, 12 to 14, 14 to 16, 16 to 18, 18 to 20, 20 to 25, 25 to 30, 30 to 40, 40 to 50, 50 to 60, 60 to 70, 70 to 100, 100 to 200, and 200-500 nucleobases. If a plurality of target domains is integrated within a nuc macromolecule, these may have different lengths. Individual target domains can be integrated within one continuous nucleic acid chain or represent stand-alone marker units within a nuc macromolecule.

In one embodiment of the application, the sequences of a target domain are complementary only to a target sequence and can only bind the target sequence.

In a further embodiment of the application, the sequence of a target domain is able to bind a plurality of different target sequences.

In a further embodiment of the application, a nuc macromolecule comprises several target domains consisting of different sequences, wherein said target domains are able to bind to different target sequences.

In a preferred embodiment of the application, sequences of the target domain are selected not to bind to anchor domains under applied reaction conditions and not to bind the respective partners provided with the solid phase.

In a further embodiment of the application, the sequence of the target domain of one type of nucleic macromolecules is selected in such a way that it is not able to bind to further target domains or anchor domains or other constituents of the same type of nuc macromolecules under conditions used in the reaction.

In a further embodiment of the application, the sequence of the target domain of one type of nucleic macromolecules is selected in such a way that it is not able to bind to further target domains or anchor domains or other constituents of the other nuc macromolecules used in the same reaction.

In a further embodiment of the application, the length and sequence of the target domain of one type of nuc macromolecules are designed so that it can discern changes in the target sequence under stringent reaction conditions (such as reaction temperature). These changes could be, for example, nucleotide exchange (e.g. adenosine instead of guanosine or instead of cytosine), nucleotide deletions, or nucleotide additions. For example, the target domain can, under given reaction conditions, discern changes in the target sequence in the following ranges: 1 to 2 nucleotides or 2 to 5 nucleotides or 5 to 10 nucleotides or 10 to 20 nucleotides or 20 to 50 nucleotides. The changed nucleobases may be localized at a single location in the target sequence or may be distributed over several locations in the target sequence.

In a further embodiment of the application, the length and sequence of the target domain of one type of nuc macromolecules is designed so that it can tolerate changes in the target sequence under less stringent reaction conditions (such as reaction temperature). These changes could be, for example, nucleotide exchange (e.g. adenosine instead of guanosine or instead of cytosine), nucleotide deletions, or nucleotide additions. For example, the target domain can, under given reaction conditions, tolerate changes in the target sequence in the following ranges: 1 to 2 nucleotides or 2 to 5 nucleotides or 5 to 10 nucleotides or 10 to 20 nucleotides or 20 to 50 nucleotides. These changes may be localized at a single position in the target sequence or may be distributed over several positions in the target sequence. In this embodiment, therefore, not only target sequences are labeled, but also other nucleic acid chains which are similar to a target sequence.

A target domain may be composed of a plurality of individual oligonucleotides which are integrated into one nuc macromolecule. A nuc macromolecule may also comprise several target domains; for example, oligonucleotides having different sequences can be arranged within a nuc macromolecule. Several target domains may be integrated within a single oligonucleotide chain. They can be linked in "end-to-end" manner or sequences of each target domain may even overlap each other or additional sequences may be located between individual domains to separate them.

The individual target domains can be within one type of nuc macromolecules of the same kind or different kinds of nucleic acid structure. For example, DNA-based target domains can be combined with PNA-based target domains within one type of nuc macromolecules. The synthesis of mixed nucleic acid chains consisting of, for example, DNA and PNA is known.

A target domain may comprise additional modifications, such as signal-emitting or signal-conveying molecules, such as dyes, including fluorescent dyes, or biotin or macromolecular substances such as enzymes or nanocrystals. Modified oligonucleotides can be purchased commercially, for example from MWG Biotech. Preferentially, the 3' end of such a target domain (e.g. DNA oligonucleotide) is not enzymatically active, i.e., a polymerase is not able to incorporate a further nucleotide into the 3' end of such an oligonucleotide. This can be achieved, for example, by the coupling of a group, such as a phosphate or amino group.

A target domain can perform the function of a core component providing a linkage between individual parts of the marker of a nuc macromolecule. The linker component may be coupled directly to the target domain.

In the following, an expert can find literature resources for the chemical synthesis of oligonucleotides and their modifications which can form target domains:

Singh et al Chem Soc Rev, 2010, v. 39, 2054-, "Oligonucleotide synthesis, methods and applications" Piet Herdewijn, 2004, ISBN 1-58829-233-9, "Protocols for oligonucleotide conjugates, synthesis and analytical techniques" Sudhir Agrawal, 1993, ISBN 0-89603-252-3, "Protocols for oligonucleotide conjugates, synthesis and properties" Sudhir Agrawal, 1993, ISBN 0-89603-247-7, "The aptamer handbook" Sven Klussmann, 2006, ISBN 10: 3-527-31059-2, "Pharmaceutical aspects of oligonucleotides" Patrick Couvreur, 2000, ISBN 0-748-40841-X, "Triple Helix forming Oligonucleotides" Claude Malvy, 1999, ISBN 0-7923-8418-0, "Artificial DNA, methods and applications" Yury E. Khudyakov, ISBN 0-8493-1426-7

In a further embodiment of the application, the sequences of the target domain are selected in such a way that they are capable of the formation of double-stranded stretches or hairpin structures within a target domain.

In a further embodiment of the application, the sequences of the target domain are selected in such a way that they are not capable of the formation of double-stranded stretches or hairpin structures within a target domain under particular reaction conditions.

In a further advantageous embodiment of the application, the target domain and other domains (e.g. anchor domain and/or signal domain) are positioned inside of a single nucleic acid chain. The target domain is positioned, for example, at the 5'-end part and the anchor domain or signal domain are at or near the 3'-end part of the nucleic acid chain. Such an arrangement of domains allows for a simultaneous synthesis of two domains during the synthesis of the oligonucleotide portion of the nuc macromolecule.

In other embodiments, one or more target domains may be surrounded by a plurality of anchor domains or signal domains within a single nucleic acid chain. One or more signal domains can also be surrounded by target domains.

In an advantageous embodiment of the invention, the sequences constituting the target domain and the anchor domain or the signal domain are overlapping. In this embodiment, some of the nucleobases belongs to at least two domains. The length of the sequence that encodes the common fragment of the target and anchor domains or target and signal domains can, for example, comprise 5% to 80% of the sequence of one of the domains.

In a further advantageous embodiment of the invention, sequences of the target domain and the anchor domain or the signal domain are separated by one or more spacer sequences. In one embodiment of the invention, such a spacer sequence has signal-conveying properties. In a further embodiment of the invention, a spacer sequence comprises a sequence complementary to a target domain or to an anchor domain or signal domain. These parts within the spacer sequence can be completely or only partially complementary to one of the domains. In such embodiments, such a spacer sequence has the function of an antagonist.

Preferentially, the 3' end of a target domain (e.g. DNA oligonucleotide) is not enzymatically active and is blocked, i.e., a polymerase is not able to incorporate a nucleotide into the 3' end of such an oligonucleotide. This can be achieved, for example, by the coupling of a group, for example a phosphate group or an amino group.

The target domain can fulfill the function of a core component and represent a linking element between individual parts of the marker of a nuc macromolecule. For example, the linker component may be coupled directly to the target domain.

Figure 5B:
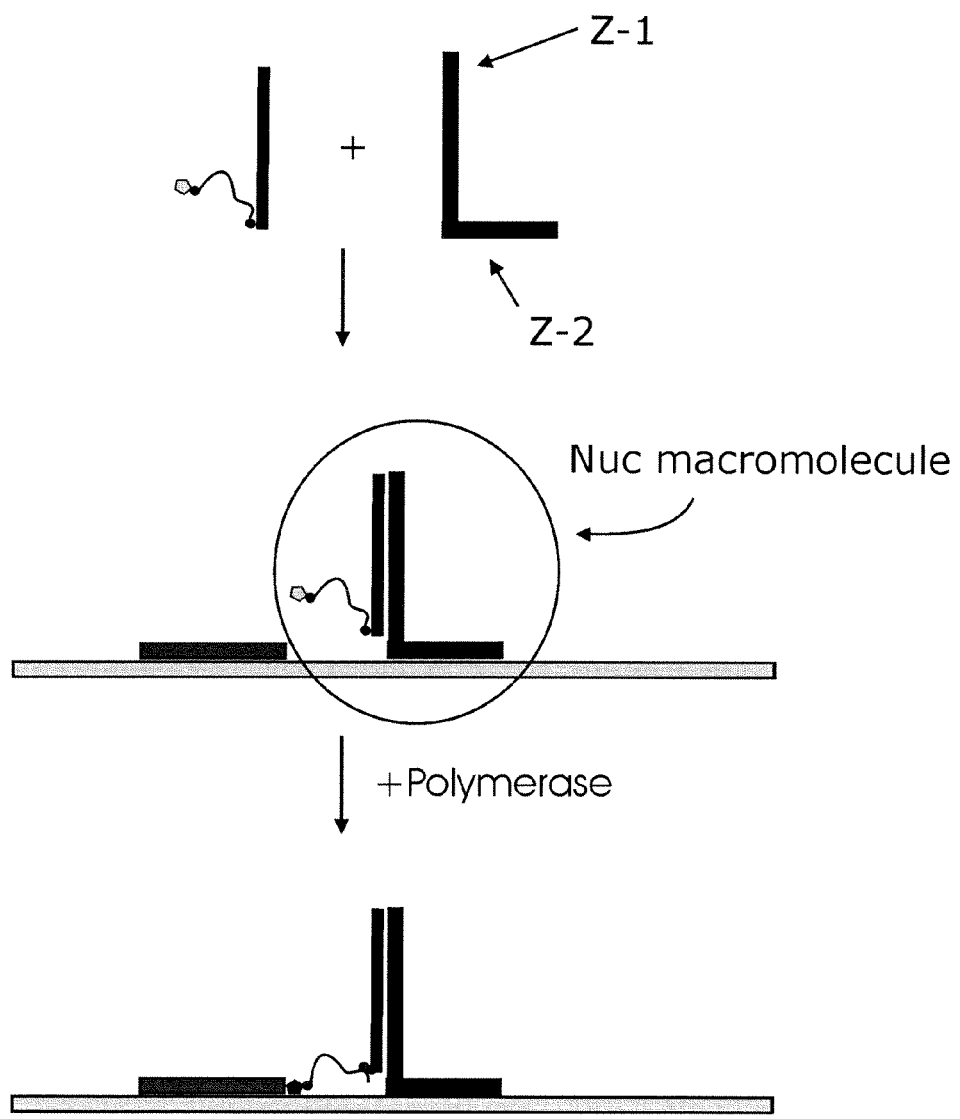

In another embodiment, the target domain of a nuc macromolecule binds to a hybridization probe (Z) prior to or during the reaction instead of binding to a target sequence (FIG. 5B). Such a probe preferentially comprises an oligonucleotide. This oligonucleotide can bind both the target domain of the nuc macromolecule (via sequence part Z-1) and the target sequence (via sequence part Z-2). Sequence part Z-2 is thus specific to the target sequence. In another embodiment, one type of nuc macromolecules having a target domain specific to the hybridization probe is brought into contact with a plurality of hybridization probes, each of them having identical binding sites (Z-1) for the target domain of a nuc macromolecule, but different binding sites for the target sequence (Z2). With this method it is possible to label different target sequences with a single type of nucleic macromolecules. Preferentially, the binding between the nuc macromolecule and the hybridization probe is stable under the conditions of a labeling reaction. This can be achieved, for example, by the sequence choice for the sequence segment (Z-1) and the target domain of the nuc macromolecules having a higher Tm, as compared to the Tm of the Z-2 segment of the hybridization probe.

The entire construct in FIG. 5B, consisting of nuc components covalently bound to each other, the linker, the oligonucleotide and oligonucleotides attached via affinity binding (hybridization probe binding caused by base pairing between two nucleic acid strands) is referred to as a nuc macromolecule. According to this embodiment of the application, the synthesis/formation of a nuc macromolecule suitable for reaction is occurring just before or during the labeling reaction. The oligonucleotide, which is covalently bound to the nuc component, may be referred to as a core component (see below), because of its function as a binding partner between different functionalities, i.e. a nuc component and a target domain.

Antagonists of the Target Domain

An antagonist of the target domain reversibly inhibits the function of binding to the target sequence. The inhibition can be complete or incomplete but still significantly reducing the ability of the target domain to bind to the target sequence. In one embodiment, a nuc macromolecule comprises nucleic acid chains which are fully or partially complementary to the target domain. These nucleic acid chains can be, for example, DNA, RNA, or PNA and bind between 5% and 90% of the sequence of a target domain. In a preferred embodiment, the target domain is present in open form under the reaction conditions of a labeling reaction. The antagonists are discussed in more detail in the section on the anchor domain.

1.3.3.3.2 The Anchor Domain of a Nuc Macromolecule and the Combination With the Solid Phase The purpose of the anchor domain is to provide a specific binding to a solid phase for a particular type of nuc macromolecule or a nucleic acid strand which is labeled with such a molecule. Nuc macromolecules or nucleic acid strands labeled with nue macromolecules (e.g. target sequences or their equivalents) can bind to a solid phase by means of an anchor domain, before or during or after an enzymatic reaction.

In some embodiments of the invention, a solid phase is provided for the analysis which is capable of the specific binding of at least one anchor domain. The bond between an anchor domain and a solid phase can be affine or covalent. There are many binding pairs, such as biotin-streptavidin or biotin-avidin, or antigen-antibody, or two complementary nucleic acid strands, or aptamer-target protein. Substances which can bind specifically to the anchor domain are designated as "binding partner."

The attachment of a binding partner of an anchor domain to the solid phase will be known to a person skilled in the area. The binding partners can be attached to the solid phase in a particular arrangement so that a unique spatial relationship of the binding events can detected. Examples of the spatially ordered attachment of binding partners for anchor domains to a solid phase are solid, two-dimensional microarrays (provided e.g. by Affymetrix, Eppendorf) or solid, one-dimensional test strips (for example Western blots provided by the company Dako or DNA strips provided by the company Innogenetics). The binding partner can be attached to a solid phase, while allocation of a particular binding partner and thus to a particular corresponding anchor domain on a solid phase can take place via specific coding, e.g. so-called liquid bead arrays (available from Luminex or Illumina). Other examples will be known to a specialist (see references below).

The solid phase can be provided in various forms. For example, reaction vessels, flat surface, beads, or gels can be used as the solid phase. The solid phase with attached binding partners can be provided as a part of an apparatus for fluid exchange. Such solid phases will be known to a person skilled in the area. Examples are lateral flow devices, microfluidic devices, and Mirotiter plates (see the relevant literature below).

In accordance with the invention, one or more such solid phases are provided which have the smallest possible non-specific binding of nucleic acid chains.

In one embodiment, the anchor domain comprises at least one biotin residue. The solid phase correspondingly comprises streptavidin or avidin.

In a further embodiment, the anchor domain comprises at least one streptavidin or avidin. The solid phase comprises corresponding biotin.

In a further embodiment, the anchor domain comprises at least one small antigen, one hapten (e.g. a dye such as fluorescein, digoxigenin, or DNP), or a larger antigen (e.g. protein). The solid phase comprises a corresponding suitable antibody.

If different nuc macromolecules are used in a reaction, their anchor domains comprise respectively different and distinct structures for each type of nuc macromolecules (such as antigens, haptens, or oligonucleotides). If a solid phase is used with a plurality of spatially arranged, separately attached binding partners directed against said structures (e.g. antibodies or complementary oligonucleotides), said different nuc macromolecules or the nucleic acid chains labeled with them can bind to different locations on a solid phase. Examples are immunoassays working on the principles of "lateral flow devices."

In a further embodiment, the anchor domain comprises at least one oligonucleotide. The solid phase comprises a correspondingly complementary oligonucleotide.

If different nuc macromolecules are used in a reaction, their anchor domains comprise respectively different and distinct oligonucleotides for each type of nuc macromolecules. By using a solid phase with a plurality of spatially arranged, separately attached nucleic acid chains directed against said anchor domains, said different nuc macromolecules or the nucleic acid chains labeled with them can bind to different locations on a solid phase.

In a further embodiment, an anchor domain comprises at least one oligonucleotide having an aptamer function. The solid phase comprises a specific protein corresponding to this aptamer. If different nuc macromolecules are used in a reaction, their anchor domains comprise respectively different and distinct aptamers (oligonucleotides) for each type of nuc macromolecules. If a solid phase is used with a plurality of spatially arranged, separately attached proteins directed against said anchor domains, said different nuc macromolecules or the nucleic acid chains labeled with them can bind to different locations on a solid phase. The anchor domain may also comprise proteins which can be bound by aptamers attached to a solid phase.

In a further embodiment of the application, the composition of the anchor domain (length and sequence of the oligonucleotides) of the used nuc macromolecules and the composition of the corresponding binding partners and the reaction conditions (e.g. reaction temperature, "stringent conditions") are designed in such a way that each of said anchor domains can be specifically recognized and bound by its respective binding partners.

In a further embodiment of the application, the composition of the anchor domain (length and sequence of the oligonucleotides) of the used nuc macromolecules, and the composition of the corresponding binding partners, and the reaction conditions (e.g. reaction temperature, "less stringent conditions") are designed in such a way that several different anchor domains can be bound by one binding partner. The composition of the anchor domains (e.g. by variation of the sequence of oligonucleotides) and the composition of the binding partners is designed in such a way that at least 2 or at least 3 to 5 or 5 to 10 anchor domains can be bound to a binding partner.

Examples of anchor domains with oligonucleotides will be discussed in more detail below. Such an anchor domain comprises, for example, the following variants of binding partners: an oligonucleotide of the anchor domain binds to a complementary oligonucleotide on the solid phase or an oligonucleotide of the anchor domain binds to a specific protein on the solid phase as an aptamer.

First, the structure of the oligonucleotides as anchor domains will be discussed.

Generally, substances capable of sequence-specific binding to the nucleic acid chains attached to the solid phase can be used for the composing of anchor domains. Usually, such substances comprise nucleobases (A, C, T, G, U) or their derivatives which allow specific binding. The backbone can have a natural composition (sugar-phosphate backbone) or a variation thereof, such as protein backbone in PNA. Nucleic acid chains within a single type of nuc macromolecules can consist of a single type of monomers, for example only DNA or PNA, or they can consist of a mixed composite polymer, where DNA, RNA, PNA, morpholino, LNA, or other modifications are combined into a single chain. Since different types of nucleic acid chains differ in their binding behavior, it may be reasonable to use a combination of different monomers. This can enable a better design of binding properties.

To simplify the presentation, nucleic acid chains in the form of DNA are discussed in detail. Other types of nucleic acid chains can be designed using known rules in accordance with the example with DNA that has been provided.

The length of the nucleic acid chains in an anchor domain preferentially comprises the following ranges: from 8 to 10, 10 to 12, 12 to 14, 14 to 16, 16 to 18, 18 to 20, 20 to 25, 25 to 30, 30 to 40, 40 to 50, 50 to 60, 60 to 70, 70 to 100, and 100 to 200 nucleotides.

In one embodiment, the coupling of the anchor domain in the nuc macromolecule is carried out via one of the two ends of the anchor domain, such as at the 5' end or 3' end. Examples of the coupling of an oligonucleotide via one of the ends will be known to a person possessing ordinary skills in the area. In another embodiment of the invention, the coupling is achieved via an internal region of the anchor domain, for example via a linker attached to a base. In an advantageous embodiment, the anchor domain is coupled to the nuc component via a linker. In a further advantageous embodiment of the application, the anchor domain and the target domain are positioned inside of a single nucleic acid chain. The target domain, for example, may occupy one part of the nucleic acid chain at or near the 5' end, while the anchor domain constitutes another part of the nucleic acid chain at or near the 3' end. Such an arrangement of anchor domain and target domain allows for a simultaneous synthesis of both domains during a solid phase synthesis of the oligonucleotide constituent of the nuc macromolecule. In other embodiments, one or several target domains may be surrounded by a plurality of anchor domains within a nucleic acid chain. On the other hand, one or several anchor domains can also be surrounded by target domains.

In an advantageous embodiment of the invention, sequences constituting the target domain and the sequences of the anchor domain are overlapping. In this embodiment, some of the nucleobases are constituents of both domains. For example, the length of the sequence which forms the common fragment of the target and anchor domains can amount to 5% to 80% of the sequence content of one of the domains.

In a further advantageous embodiment of the invention, sequences of the target domain and the anchor domain are separated by a spacer sequence. In one embodiment of the invention, such a spacer sequence has signal-transmitting properties. In a further embodiment of the invention, the spacer sequence comprises a sequence complementary to a target domain or to an anchor domain. These parts within the spacer sequence may be completely or only partially complementary. In such embodiments, a spacer sequence has the role of an antagonist and inhibits the binding properties of the other domains.

In an advantageous embodiment of the application, the anchor domain is resistant to 5'-3' exonuclease activity. This can be achieved, for example, by the use of PNA or other modifications.

A binding partner on the solid phase can be present in the form of a single-stranded or a double-stranded nucleic acid chain, such as DNA or RNA or PNA. In one embodiment, the binding of the anchor domain to the binding partner can take place in connection with the formation of double strands (according to the rules of Watson Crick base pairing); in a further embodiment, triple strands can be formed (according to Hoogsteen rules). In another embodiment, the anchor domain binds to a protein as an aptamer.

Examples of sequence-specific binding of nucleic acid chains will be known to a person skilled in the area (see "microarray" and "PCR" in the literature).

Binding to a single strand is considered as an example below. The composition of an anchor domain can have a full complementarity to the binding partner ("perfect match") or differ in some positions ("Miss Match").

The length of a nucleic acid strand of a binding partner attached to a solid phase preferentially comprises the following ranges: 8 to 10, 10 to 12, 12 to 14, 14 to 16, 16 to 18, 18 to 20, 20 to 25, 25 to 30, 30 to 40, 40 to 50, 50 to 60, 60 to 70, 70 to 100, and 100 to 200 nucleotides.

In one embodiment of the application, the sequence of an anchor domain is complementary to only one sequence of the binding partner and can only bind this one binding partner.

In a further embodiment of the application, a nuc macromolecule comprises several anchor domains consisting of different sequences, wherein each respective anchor domain is capable of annealing to a specific binding partner which is attached to a solid phase.

In another embodiment of the application, the sequences of an anchor domain are designed in such a way that they are not able to bind to the target sequence under the reaction conditions used.

In another embodiment of the application, the sequences of an anchor domain are designed in such a way that they are capable of forming a double-stranded stretch or hairpin structures within an anchor domain under the reaction conditions provided.

In another embodiment of the application, the sequences of an anchor domain are designed in such a way that they are not capable of forming a double-stranded stretch or hairpin structures within an anchor domain under the reaction conditions provided.

In another embodiment of the application, the sequences of an anchor domain are designed in such a way that they are not able to bind to the target domains or anchor domains or further constituents of the same type of nuc macromolecules under the reaction conditions provided.

In another embodiment of the application, the sequences of an anchor domain are designed in such a way that they are not able to bind to the target domains or anchor domains or further constituents of the other type of nuc macromolecules which are used in the particular reaction under the reaction conditions provided.

The anchor domain can be composed of a plurality of individual oligonucleotides which are integrated in a nuc macromolecule. Several anchor domains can be integrated in a nuc macromolecule; for example, several oligonucleotides having different sequences can be integrated within one nuc macromolecule. Several anchor domains can also be incorporated within one nucleic acid chain. They can be arranged directly one after another or their sequences can be overlapping or said domains can be separated by a further sequence.

Within one type of nuc macromolecules, individual anchor domains can consist of the same kind of nucleic acid or have different nucleic acid types. For example, DNA-based anchor domains can be combined with PNA-based anchor domains within a single type of nuc macromolecules.

Preferentially, the 3' end of such an anchor domain (e.g. a DNA oligonucleotide) is not enzymatically active and, for example, is blocked, i.e. a polymerase is not able to couple a nucleotide to the 3' end of such an oligonucleotide. This can be achieved for example by the coupling of a group, such as a phosphate group or an amino group.

The anchor domain can carry additional modifications, such as free amino groups, as well as other signaling or signal-transmitting molecules, such as dyes, including fluorescent dyes, or biotin or macromolecular substances such as enzymes or nanocrystals. Modified oligonucleotides can be purchased commercially, for example from MWG Biotech or TriLink BioTechnologies.

Other marker moieties, such as sugars and lectins, growth factors, hormones, sequence-recognizing proteins such as transcription factors, or corresponding receptor molecules can also be used as specific binding partners for an anchor domain of a nuc macromolecule.

In an advantageous embodiment, the binding partner for an anchor domain is attached to a solid phase. If more than one binding partner to one or more anchor domains is attached to a solid phase, their arrangement is preferentially designed in such a way that a unique spatial assignment of the binding events of the anchor domain to the binding partner is possible. This can be achieved, for example, by providing an array of immobilized binding partners.

The anchor domain can fulfill a function of a core component and provide a linkage between individual parts of the marker within one nuc macromolecule. Thus, the linker moiety can be coupled directly to the anchor domain.

Antagonists of the Anchor Domain

An antagonist of the anchor domain reversibly inhibits its binding to the solid phase. The inhibition can be complete or incomplete but still significant in terms of its reduction of the ability of the anchor domain to bind to the solid phase.

For example, nuc macromolecules comprise single-stranded oligonucleotides which constitute the anchor domains. Their binding partners are attached to a solid phase, for example complementary single-stranded oligonucleotides or proteins (if aptamer-protein interaction has been selected). Specific binding of the anchor domain to its binding partner can take place when the oligonucleotides of the anchor domain are present in single-stranded form.

A complementary oligonucleotide (antagonist 4b in FIG. 3i) coupled for example near the anchor domain (4a in FIG. 3i) within the marker of a nuc macromolecule can bind to the anchor domain via hybridisation and form a duplex. The anchor domain is hindered by this binding in its ability to bind to a binding partner. For example, such a structure of nuc macromolecules can be arranged as follows: the anchor domain and its antagonist may be placed on both sides of a target domain, so that the intramolecular formation of a partial duplex structure takes place (FIG. 3i). Thus, the anchor domain is blocked as long as nuc macromolecules are in a free state in solution and reaction conditions (temperature, ionic strength) favor the formation of the duplex between the anchor domain and its antagonists. A termination of the binding of the antagonist to the anchor domain can be achieved, for example through the use of higher temperatures and/or via the binding of the target domain to the target sequence and/or by enzymatic degradation by an endonuclease or exonuclease (such as the 5'-3' exonuclease of a polymerase). Thus, the anchor domain transferred can be put into a single-stranded state and can fullfill its function of binding to a binding partner.

The strength of the binding of the antagonist to the anchor domain can be modulated by the base composition of the antagonist oligonucleotide. Preferentially, oligonucleotides comprising the length-ranges between 6 and 10, 10 and 15, 15 and 20, 20 and 25, 25 and 30, 30 and 40, and 40 and 50 nucleotides are used.

The anchor domain may be blocked in its entire length or only partially. For example, blockade by the antagonist comprises 5% to 90% of the anchor sequence. The nature of an antagonist includes, for example, DNA, RNA, PNA, or a mixed sequence. The coupling of the antagonist within the nuc macromolecule can be realized in a fashion similar to that of the coupling of an anchor domain itself. For example, various domains and antagonists can be located on the same strand of a nucleic acid: the anchor domain, the target domain, and the antagonist to the anchor domain. The target domain forms the spacer between the anchor domain and the antagonist (FIGS. 3 and 7).

Such types of nuc macromolecules comprising anchor domains and their antagonists can therefore be present in at least two states: the first state with an open anchor domain which is capable of binding to their binding partner immobilized on the solid phase, the second state with a blocked anchor domain, where binding to the solid phase is prevented by the antagonist.

These two states can be modulated by changing the reaction conditions (e.g. reversibility of antagonization by changes of temperature, salt, pH, organic solvents, or irreversible elimination of the antagonization by enzymatic degradation of the antagonist or its cleaving off). Irreversible elimination of antagonization can be achieved for example as follows: the anchor domain is composed of DNA and the antagonist is composed of RNA. The RNA part can be degraded through the use of an appropriate RNase so that the anchor domain DNA is no longer inhibited.

The use of nuc macromolecules with antagonists may result in some benefits. For example, in one embodiment of the application, an undesired binding of excess nuc macromolecules to the solid phase can be reduced (FIG. 7). The binding of the labeled nucleic acids to the solid phase is carried out under conditions in which the anchor domains of non-incorporated nuc macromolecules are blocked by antagonists. Such conditions include, for example, temperatures well below the Tm of binding pairs consisting of antagonist and anchor domain. The nucleic acid chains which are labeled with such nuc macromolecules contain open, i.e. unblocked anchor domains (FIG. 7) and may bind to the solid phase. Thus, binding of the labeled target sequences to the solid phase is possible in the presence of an excess of unincorporated nuc macromolecules and no additional purification steps of labeled target sequences are required.

Such antagonists may also be used for the target domain and for the signal domain within a nuc macromolecule (see the relevant section).

In the following sources, an expert can find information with respect to the synthesis of oligonucleotides and their modifications, which can be anchor domains or their binding partners attached to the solid phase or antagonists of anchor domains:

"Oligonucleotide Synthesis, Methods and Applications" Piet Herdewijn, 2004, ISBN 1-58829-233-9

"Protocols for Oligonucleotide Conjugates, Synthesis and Analytical Techniques" Sudhir Agrawal, 1993, ISBN 0-89603-252-3

"Protocols for Oligonucleotide Conjugates, Synthesis and Properties" Sudhir Agrawal, 1993, ISBN 0-89603-247-7

"The Aptamer Handbook" Sven Klussmann, 2006, ISBN 10: 3-527-31059-2

"Pharmaceutical Aspects of Oligonucleotides" Patrick Couvreur, 2000, ISBN 0-748-40841-X "Triple Helix Forming Oligonucleotides" Claude Malvy, 1999, ISBN 0-7923-8418-0

"Artificial DNA, Methods and Applications" Yury E. Khudyakov, ISBN 0-8493-1426-7

In the following sources, an expert can find information with respect to the distribution of binding partners on the solid phase, the construction of spatially arranged arrays of binding partners, the attachment of biologically active molecules to the solid phase and equipment for the fluid exchange:

"Microfluidic Lab-on-a-chip for Chemical and Biological Analysis and Discovery" Paul C. H. Li, 2006, ISBN 1-57444-572-3

"Microfluidic for Biological Applications" Wei-Cheng Tian, 2008, ISBN 978-0-387-09479-3

"Preparation, Microfluidics, Detection Methods and Biological Applications" Kilian Dill, 2009, ISBN 978-0-387-72716-5

"DNA Microarray, a Practical Approach" M. Shena, 2002, ISBN 0-19-963777 6

"DNA Microarrays" David Bowtell, 2003, ISBN 0-87969-624-9

"Lateral Flow Immunoassays" Raphael Wong, 2009, ISBN 978-1-58829-908-6

"Nucleic Acid Hybridization" M. L. M. Anderson, 1999, ISBN 1-85996-007-3

1.3.3.3.3 Signal Domain (Functions and Composition)

Function of a Signal Domain

In one embodiment, the signal domain can have a signaling function. In another embodiment, it has a signal-transmitting function. In another embodiment, it has a catalytic function. In a further embodiment, the signal domain has more than one function and combines for example both signaling and signal-transmitting functions. Other combinations are obvious. Further examples of methods of detection are given in section 1.3.25.

The signal domain having signaling function comprises constituents which have been assembled within a nuc macromolecule during the chemical synthesis of a nuc macromolecule: for examples see the applications Cherkasov et al WO 2005044836, Cherkasov et al WO2006097320, Cherkasov et al WO 2008043426, Cherkasov et al DE 10356837, Cherkasov et al DE 102004009704.

A signal domain having signal transmitting function develops its signaling properties only after having reacted with signaling molecules. For example, a marker consists of several molecules of biotin, e.g. 100 biotin molecules. After the incorporation of the nuc macromolecules, a detection reaction is carried out with modified streptavidin molecules. In another example, the nucleic acid chains comprise the signal-transmitting function: after the incorporation of nuc macromolecules, a hybridization of uniform oligonucleotides with detectable moieties such as fluorescent dyes (MWG Biotech) to the marker is conducted. In another example, amino or mercapto groups, for example 50 amino groups per marker, have the signal-transmitting function. After the incorporation of the nuc macromolecules into the nucleic acid chain, a chemical modification with reactive components is conducted, for example modification of incorporated allyl-amino-dUTP by dyes described in Diehl et al. Nucleic Acid Research, 2002, V. 30, Nr. 16 e79.

In another embodiment, the signal domain has a catalytic function (in the form of an enzyme or ribozyme). Here, different enzymes can be used, such as peroxidase or alkaline phosphatase. Due to the linkage to the nuc component, the respective enzyme becomes covalently bound to the nucleic acid strand after a nuc macromolecule has been incorporated.

In one embodiment, a signal domain comprises one low molecular weight marker unit. In a further embodiment, the signal domain comprises one macromolecular marker unit. In a further embodiment, the signal domain comprises several low molecular weight marker units. In a further embodiment, the signal domain comprises multiple macromolecular marker units. In a further embodiment, the signal domain comprises a combination of low molecular and macromolecular units. The signal domain can have a signaling or signal-transmitting function.

These units can be molecules with low molecular mass, e.g. less than 2000 Da, or they can be also macromolecules. The number of the signal-giving or signal-transmitting units, which are combined into one signal domain, comprises the following ranges: 1 and 2, 2 to 5, 5 to 20, 20 to 50, 50 to 100, 100 to 500, 500 to 1000, 1000 to 10000, 10000 to 100000.

Figure 23:
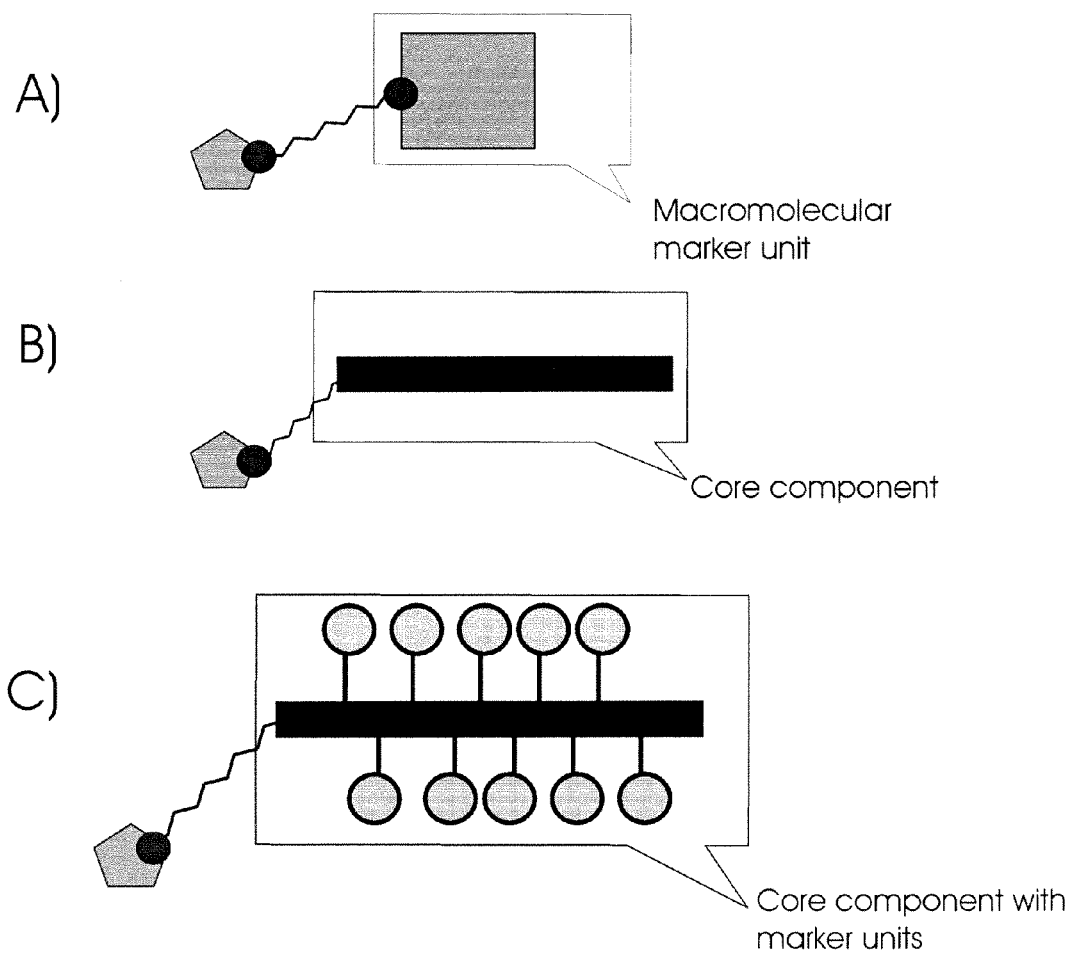
FIG. 23 depicts several marker units (A) combined into one signal domain (B), then in one embodiment these units are bound to a framework, the core component of the marker (C).

If several marker units are combined into one signal domain, then in one embodiment these units are bound to a framework, the core component of the marker (FIG. 23). This core component connects the units together. The core component can provide the connection to one or several nuc-linker components (FIG. 24). The core component can comprise low-molecular or macromolecular compounds.

1.3.3.3.3.1 Structure of the Signal-Giving or the Signal-Transmitting Units of the Signal Domain.

The structural marker units comprise the following groups:

1.3.3.3.3.1.1 Structures with Low Molar Mass:

Biotin molecules, hapten molecules (e.g. digoxigenin or dinitrophenol (DNP), radioactive isotopes (e.g., $P^{32}$, $J^{131}$), or their derivatives, rare earth elements, dyes, fluorescent dyes, quencher of the fluorescence (e.g. dabsyl) (many of these molecules are commercially available, e.g., from Molecular Probes, Inc or from Sigma-Aldrich) with the same or different spectral properties, groups of dyes undergoing FRET. Thermochromatic, photochromatic or chemoluminescent substances are available for example from Sigma-Aldrich, chromogenic substances are described for example as substrates for peptidases in "Proteolytic enzymes Tools and Targets", E. Sterchi, 1999, ISBN 3-540-61233-5).

Also chemically reactive groups, as for example amino-, carboxy-, merkapto-, aldehyde, iodine acetate, acrylic, dithio-, thioester-groups, can serve as signal-transmitting structural units. These reactive groups can be modified with signal-giving elements, such as dyes with suitable reactive groups (for instance, NHS esters, mercapto-, amino groups), e.g. after incorporation of nuc-macromolecules. General rules for the choice of a suitable pair of reactive groups are shown in "Chemistry of protein conjugation and crosslinking" Shan S. Wong 1993.

In a special embodiment, a combination comprising one nuc-component, one macromolecular linker component and one signal domain with a low molecular weight already fulfils the requirements of the present invention. Such compounds are also subject matter of this invention. They can be used both as intermediate compounds for the chemical synthesis of nuc-macromolecules with one macromolecular marker, e.g., dUTP-PEG-biotin, and as independent compounds for enzymatic reactions, as, for example, nucleotides labeled with only one dye.

Different fluorescent dyes can be used, and their choice is not limited as long as their influence of the enzymatic reaction is not substantial. Examples of such dyes are Rhodamine (Rhodamine 110, Tetramethylrhodamine, available from Fluka-Sigma), cyanine dyes (Cy2, Cy3, Cy3.5, Cy5, Cy5.5, Cy7 available from Amersham Bioscience), coumarine, Bodipy, fluorescein, Alexa Dyes: e.g., Alexa 532, Alexa 548, Alexa 555 (Molecular Probes). Many dyes are commercially available, for instance, from Molecular Probes Europe, Leiden, the Netherlands (hereinafter called Molecular Probes) or from Sigma-Aldrich-Fluka (Taufkirchen, Germany).

In one embodiment, the signal domain comprises several marker units. These marker units can have the same or different properties. For instance, fluorescent dyes with different spectral qualities can be used. In one embodiment, the fluorescent dyes that can form FRET pairs are selected.

1.3.3.3.3.1.2 Structures with High Mass (Macromolecules)

Nanocrystals

Nanocrystals, e.g. quantum dots, can serve as signal domain. Quantum dots with the same or different spectral qualities can be used within the same marker component. Examples of quantum dots are presented in U.S. Pat. No. 6,322,901, U.S. Pat. No. 6,423,551, U.S. Pat. No. 6,251,303, U.S. Pat. No. 5,990,479.

Nano- or Micro-Particles

Nano- or micro-particles can serve as signal domains. The diameters of these particles can range from 1 nm to 2 nm, from 2 nm to 5 nm, from 5 nm to 10 nm, from 10 nm to 20 nm, from 20 nm to 50 nm, from 50 nm to 100 nm, from 100 nm to 200 nm, from 200 nm to 500 nm, from 500 nm to 1000 nm, from 1000 nm to 5000 nm. The material of these particles can, for instance, be pure metals such as gold, silver, aluminum (as instances of particles capable of surface plasmon resonance), Protein-gold_conjugates: 3. Anal. Chem. 1998; v. 70, p. 5177-, Nucleic acid-gold_conjugates: J. Am. Chem. Soc. 2001; v. 123, p. 5164-, J. Am. Chem. Soc. 2000; v. 122, p. 9071-, Biochem. Biophys. Res. Commun 2000; v. 274, p. 817-, Anal. Chem. 2001; v. 73, p. 4450-, latex (e.g., Latex-Nano-particles), Anal. Chem. 2000; v. 72, p. 1979-, plastic (Polystyrene), paramagnetic compounds: Zhi Z L et al. Anal. Biochem, 2003; v. 318 (2): p. 236-43, Dressman D et al. Proc Natl Acad Sci U.S.A. 2003, v. 100 (15): p. 8817-22, metal particles, magnetic compounds: Jain KK. Expert Rev Mol. Diagn. 2003; v. 3 (2): p. 153-61, Patolsky F et al. Angew Chem Int Ed Engl 2003; v. 42 (21), p. 2372-2376, Zhao X et al. Anal Chem. 2003; v. 75 (14): p. 3144-51, Xu H et al. J Biomed Mater Res. 2003 Sep. 15; v. 66A(4): p. 870-9, Josephson U.S. Patent No. 2003092029, Kliche WO0119405.

Protein Molecules

Protein molecules can serve as signal domain. The proteins comprise the following groups: enzymes (e.g. peroxidase, alkaline phosphotase, urease, beta-galactosidase, peptidases), fluorescing proteins (e.g. from GFP-family or phycobiliproteins (e.g. Phycoerythrin, Phycocyanin) availbale e.g. from Molecular Probes Inc.), antigen-binding proteins (e.g. antibodies, tetramers, affibodies (Nord et. al Nature Biotechnology, 1997, v. 15, p. 772-) or their components (e.g. Fab fragments), nucleic acid-binding proteins (e.g. transcription factors).

Nucleic Acid Chains

Figure 25:
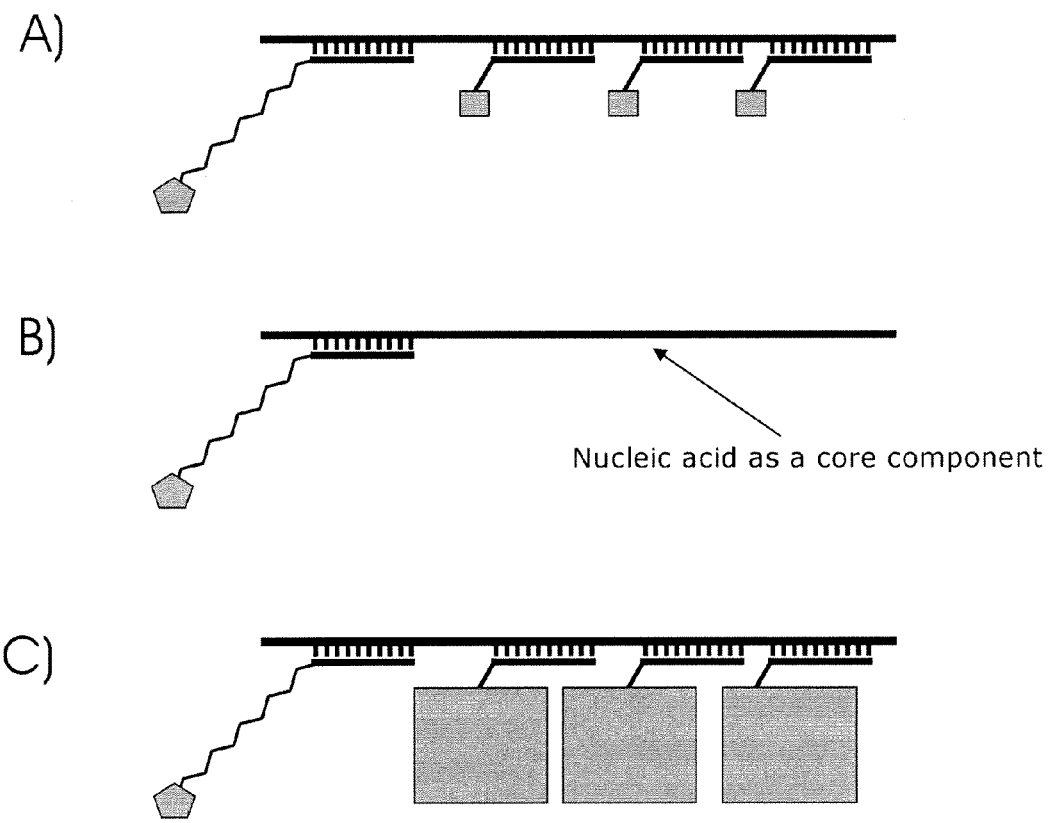
FIG. 25A, FIG. 25B and FIG. 25C show that labeled oligonucleotides can be used as marker units. (A) illustrates oligonucleotides labeled with detectable moiety with low molecular weight and (C) with large molecular weight.

Nucleic acid chains, including oligonucleotides (modified and non-modified), can act as signal domains. The length of these nucleic acid chains should fall preferentially within the following ranges (number of nucleotide monomers in a chain): 10 to 20, 20 to 50, 50 to 100, 100 to 200, 200 to 500, 500 to 1000, 1000 to 5000, 5000 to 10000, 10000 to 100000. DNA, RNA, PNA molecules can be used. Nucleic acid chains can carry additional modifications, such as, for example, free amino groups, dyes and other signal-giving molecules, e.g. macromolecular substances, enzymes or nanocrystals (FIG. 25). Modified nucleic acid chains are also commercially available, e.g. from MWG-Biotech, Trilink Biotechnologies. Further examples of macromolecules or macromolecular complexes which can be used, according to the scope of the present invention, as a marker or marker units in the marker component are described in the U.S. Pat. No. 4,882,269, the U.S. Pat. No. 4,687,732, WO 8903849, the U.S. Pat. No. 6,017,707, the U.S. Pat. No. 6,627,469.

Preferentially, the 3' end of the signal domain is blocked so that the target domain can not act as a primer.

Preferentially, the signal domain does not comprise sequences complementary to the target sequence or to the target domain or to the anchor domain or to the used primers.

1.3.3.3.4 Core Component of the Marker

The core component has the function of connecting several structural elements of the nuc-macromolecules. For instance, the core component connects several marker units together or individual domains can be coupled throught the core component. In a further embodiment, linker components can be bound to the core component (FIG. 5). The term "core-component" is functional and serves for illustration of possible structures of nuc-macromolecules. Different chemical structures that connect linker and marker-units can be called core-component. Examples for constituents of the core component will now be presented.

Constituents of the Core Component

In one embodiment, the core component consists of one or several low molecular compounds. They have the function of connecting the marker units together. A connection between the core component and the marker units can be covalent or affine. With covalent bonding, for instance, compounds with the general structural formula $(F)_m$—R—$(H)_n$ can act as a precursor, where (F) and (H) are reactive groups and (R) a connecting component. The number of such groups and their assembly can vary considerably. Many examples are known to the expert in the field, e.g. connections from the group of crosslinkers ("Chemistry of protein conjugation and crosslinking" Shan S. Wong in 1993 CRC Press Inc). The structure is not limited. It is preferentially water-soluble. For instance, parts (F) and (H) comprise independently the following groups: NH2 (amino), OH (hydroxy), SH (mercapto), COON (carboxy), CHO (aldehyde), acrylic or maleimide. Water-soluble polymeres like PEG or polypetide chains or short aliphatic chains represent examples for (R).

In a further embodiment, the core component consists of a hydrophilic, water-soluble polymer, whereby the said polymer can consist of the same or different monomers.

The following polymers and their derivates are examples of parts of the core component: polyamides (e.g. polypeptide like polyglutamin or polyglutamic acid) and their derivates, polyacrylic acid and its derivates, natural or synthetic polysaccharides (e.g. starch, hydroxy-ethyl-starch), dextran and its derivates (e.g. aminodextran, carboxydextran), dextrin, polyacrylamides and their derivates (e.g. N-(2-hydroxypropyl)-methacdylamide), polyvinyl alcohols and their derivates, nucleic acid chains, proteins. These polymers can be linear, globular, e.g. streptavidin or avidin, or can be branched, e.g. dendrimers. Also, cross-connected, soluble polymers, for instance, crosslinked polyacrylamides (crosslinker bisacrylamide in combination with polyacrylamide), are suitable.

Since the linker component as well as the marker component can contain water-soluble polymers, in one embodiment such a polymer can serve as a linker as well as as a core component. In this case, one part of such a polymer can be considered as a linker, another part as core component.

In a preferred embodiment of the invention, linear polymers or polymers containing few branches are used as core components, for instance, polyamides (e.g., polypeptides), poly-acrylic acid, polysaccharides, dextran, poly(acrylamides), polyvinyl alcohols. The polymer can consist of identical or different monomers. Especialy in this embodiment, the linker component can have less than 50 chain atoms. Thus, linker lengths of approx. 5 to 10, 10 to 20 or 20 to 50 chain atoms can be sufficient to preserve the substrate properties of the nuc-macromolecules for enzymes. Such a core component of the marker fulfils the function of the linker component: it creates spatial distance between sterically demanding marker units and active centers of the respective enzymes.

The water-soluble polymers preferentially have an average chain length of 20 to 1000000 chain atoms. For instance, an average chain length will be between 20 and 100, 100 and 500, 500 and 5000, 5000 and 10000 chain atoms.

In one embodiment, the polymer generally has a neutral form when dissolved in watery phase with a pH between 4 and 10 (e.g., dextran or polyacrylamide). In another embodiment, the polymer is charged if dissolved in a watery phase with a pH between 4 and 10. It can carry positive (e.g., polylysine) or negative charges (e.g., polyacrylic acid).

The coupling of marker units to a water-soluble polymer depends on the kind of the polymer. The reactive groups necessary for the coupling can already be present in the polymer (e.g., polylysine or polyacrylic acid) or can be introduced into the polymer in a separate step. For instance, many different variants for introducing reactive groups and chemical couplings are known for dextran. (Molteni L. Methods in Enzymology 1985, v. 112, 285, Rogovin A. Z. et al. J. Macromol Sci. 1972, A6, 569, Axen R. et al. Nature 1967, v. 214, 1302, Bethell G. S. et al. J. Biol. Chem. 1979, v. 254, 2572, Lahm O. et al. Carbohydrate Res. 1977, v. 58, 249, WO 93/01498, WO 98/22620, WO 00/07019).

In a further embodiment, a core component consists of a nanoparticle. For example, polystyrene or latex or dextran particles, which comprise reactive groups, such as amino, carboxyl group or streptavidin, can be used as core components. Such particles are commercially available. Nanoparticles or micro-particles of the core component can have different sizes. The dimensions of these particles can be in the following ranges: from 1 nm to 2 nm, from 2 nm to 5 nm, from 5 nm to 10 nm, from 10 nm to 20 nm, from 20 nm to 50 nm, from 50 nm to 100 nm, from 100 nm to 200 nm, from 200 nm to 500 nm, from 500 nm to 1000 nm, and from 1000 nm to 5000 nm.

The material of the particles can comprise, for example, pure metals such as gold, silver, and aluminum (for example, particles with surface plasmon resonance). Protein-Au-Conjugate: J. Anal. Chem. 1998, V. 70, S. 5177, —Nucleic acid-Au-Conjugates: J. Am. Chem. Soc. 2001, V. 123, S. 5164, J. Am. Chem. Soc. 2000, V. 122, S. 9071, Biochem. Biophys. Res. Commun 2000, V. 274, S. 817, Anal. Chem. 2001, V. 73, S. 4450), —Latex (e.g. Latex-nanoparticles, Anal. Chem. 2000, V. 72, S. 1979)—plastic (Polystyrene), —paramagnetic compounds/mixtures Zhi Z L et al. Anal Biochem. 2003 Jul. 15; 318(2):236-43, Dressman D et al. Proc Natl Acad Sci U S A. 2003 Jul. 22; 100(15):8817-22, —metal-particles/magnetic compounds/mixtures Jain K K. Expert Rev Mol. Diagn. 2003 March; 3(2):153-61, Patolsky F et al. Angew Chem Int Ed Engl. 2003 May 30; 42(21):2372-2376, Zhao X et al. Anal Chem. 2003 Jul. 15; 75(14):3144-51, Xu H et al. J Biomed Mater Res. 2003 Sep. 15; 66A(4):870-9, JOSEPHSON Lee et al. U.S. Pat. No. 2003092029, KLICHE KAY-OLIVER et al. WO0119405.

The core component has in a favored application several coupling positions to which further elements can be bound, e.g. structural marker units or nuc-linker-components.

For instance, polylysine molecules have multiple free amino groups to which several dye molecules, biotin molecules, hapten molecules or nucleic acid chains can be coupled. Polylysines of different molecular mass are commercially available (e.g. 1000-2000 Da, 2000-10000 Da, 10000-50000 Da).

Nucleic acid strands constitute a further example of the core component and these chains have the following length ranges (number of nucleotide monomeres in a chain): 10 to 20, 20 to 50, 50 to 100, 100 to 200, 200 to 500, 500 to 1000, 1000 to 5000, 5000 to 10000. These nucleic acids act as a binding partner for sequence complementary marker-units In one embodiment, the core component does not bind to the target sequence to be labeled. The marker units bound to the core component can comprise the target domain or an achor domain. In such embodiments, marker units are bound via affine linkage of the base paaring (called hybridization). Preferentially, the linkage between the core component and the marker units is stable under the reaction conditions.

In a further embodiment, the core component consists of a dendrimer, e.g. polypropylenimine or polyaminoamine. Examples of other dendrimers are known: Cientifica "Dendrimers", in 2003, Technology white papers No. 6, Klajnert et al. Acta Biochimica Polonica, 2001, v. 48; p 199-, Manduchi et al. Physiol. Genomics 2002, v. 10; p 169-, Sharma et al. Electrophoresis. 2003, v. 24; p 2733-, Morgan et al. Curr Opin drug Discov Devel. 2002; v. 5 (6); p 966-73, Benters et al. Nucleic Acids Res. 2002, v. 30 (2): pE10, Nils et al. J Theor Biol. 1997; v. 187 (2): p 273-84. Many dendrimers are commercially available (Genisphere, www.genisphere.com, Chimera Biotech GmbH).

Further combinations for the core component from the constituents described above are obvious to the specialist.

1.3.3.3.5 Coupling of the Marker Units or Domains

Marker units or domains can be bound to the core component or to the linker component by a covalent bond, for example, via a crosslinker (Chemistry of protein conjugation and cross linking, S. Wang, 1993, ISBN 0-8493-5886-8, "Bioconjugation protein coupling techniques for the biomedical sciences", M. Aslam, 1996, ISBN 0-333-58375-2), or via an affine bond, for example, biotin-streptavidin connection or hybridizing of nucleic acid chains or antigen-antibody interaction ("Bioconjugation: protein coupling techniques for the biomedical sciences", M. Aslam, in 1996, ISBN 0-333-58375-2).

In one embodiment, the coupling of the marker units to the core component is conducted already during the synthesis of the nuc-macromolecules.

In another embodiment, the chemically synthesized nuc-macromolecules comprise a marker component consisting only of a core component without marker units. The coupling of marker units to the core component is conducted after the nuc-macromolecules have been incorporated in the nucleic acid chain. Due to the large number of potential binding positions within the core component, the probability of the coupling of the marker units to the core component of incorporated nucleotides is therefore substantially larger in comparison to conventional nucleotide structures. The coupling chemistry depends in detail on the structure of the marker units and the structure of the core component.

Covalent Coupling: In one embodiment, the connection between the marker units and the core component can be resistant, e.g. to temperatures up to 100° C., to pH ranges between 3 and 12, and/or resistant to hydrolytical enzymes (e.g., esterases). In another embodiment of the invention, the connection is cleavable under mild conditions.

Examples of the coupling of nucleic acids to dendrimers (this corresponds to a coupling of marker units to the core component) are described, e.g., in Shchepinov et al. Nucleic Acids Res. 1999; v. 27 (15):p 3035-41, Goh et al. Chem Commun (Camb). 2002; (24): p 2954.

1.3.3.3.6 Coupling Between Linker and Marker

The connection between the linker component and the marker depends on the respective structures of the marker units or the structure of the core component. In one embodiment, the linker component is bound directly to the signal-giving or signal-transmitting marker unit. The marker can consist of only one or several marker units. In a further embodiment, one or several linker components are bound to the core component of the marker.

The connection between the linker component and the marker can be covalent as well as affine. Many examples are known to the specialist, e.g. "Bioconjugation: protein coupling techniques for the biomedical sciences", M. Aslam, in 1996, ISBN 0-333-58375-2. "Chemistry of protein conjugation and crosslinking" Shan S. Wong in 1993 CRC Press Inc).

Covalent Coupling: In one embodiment, the connection between the linker component and the marker can be resistant to, e.g., temperatures up to 130° C., pH ranges between 1 and 14, and/or resistant to hydrolytic enzymes (e.g. proteases, estarases). In another embodiment, the connection is cleavable under mild conditions.

According to some embodiments of this invention, macromolecular compounds used for the labeling of nucleotides comprise water-soluble polymers (see above). The linker of the nuc-macromolecules comprises water-soluble polymers too. A person skilled in the art should recognize that assignment of individual polymers to the linker or to the marker has a descriptive character.

1.3.3.3.7 Ratio of Nuc-Components in a Nuc-Macromolecule

One nuc-macromolecule can comprise on average 1 to 2, 2 to 5, 5 to 10, 10 to 30, 30 to 100, 100 to 1000, or more than 1000 nuc-components.

In one embodiment, all nuc-macromolecules have the same number of nuc-components per one nuc-macromolecule. For instance, a maximum of 4 biotin molecules can be bound per one strepavidin molecule; at a saturating concentration of nuc-linker components, a uniform population of nuc-macromolecules can be obtained.

In another embodiment, a nuc-macromolecule population has a defined average number of nuc-components per one nuc-macromolecule, however, in the population itself there is dispersion in the actual occupation of the nuc-macromolecules by nuc-components. In this case, the number of nuc-components per one nuc-macromolecule displays an average.

1.3.3.3.8 Ratio of Marker Units in a Nuc-Macromolecule

The number of marker units in one nuc-macromolecule falls within the following ranges: 1 and 2, 2 and 5, 5 and 20, 20 and 50, 50 and 100, 100 and 500, 500 and 1000, 1000 and 10000, 10000 and 100000, or more than 100000. In one embodiment, nuc-macromolecules have a definite number of signal-giving units per one marker. In another embodiment, a population of nuc-macromolecules has a varying number of marker units per one nuc-macromolecule and it does not need to have a definite value for every single nuc-macromolecule in a population.

In one embodiment, all the nuc-macromolecules have the same number of marker units per one nuc-macromolecule. For instance, a maximum of 4 biotin molecules can be bound per one strepavidin molecule, see "Avidin-Biotin-Technology", Methods in Enzymology v. 184, 1990.

In another embodiment, a nuc-macromolecule population has a defined average number of marker units per one nuc-macromolecule, however, in the population itself, there is dispersion in the actual occupation of the nuc-macromolecules by marker units. An increasingly more uniform occupation of the nuc-macromolecules by marker units can be achieved by the use of saturating concentration during the synthesis of the marker component.

For instance, in cases where only qualitative detection is important, the exact number of marker units per one nuc-macromolecule has a subordinate role. In such cases the availability of a stable signal is important in itself.

To an expert in the field it should be evident that the said marker components have substantially greater molecule size and molecule measures, than the respective nuc-components themselves. Other examples of macromolecular marker components should readily suggest themselves to an expert in the field.

1.3.3.4 Substrate Properties of the Nuc-Macromolecules 1.3.3.4.1 Substrate Properties of the Nuc-Component The nuc-component integrated in a nuc-macromolecule can serve as a substrate for different enzymes. For instance, a nucleoside triphosphate as the nuc-component serves as a substrate for a polymerase, so that the nuc-component can be incorporated in a growing strand by a polymerase and therefore the whole nuc-macromolecule can be coupled covalently to the strand.

On one hand, the substrate properties of the nuc component determine the substrate properties of the nuc macromolecules. For example, a nuc component can be a 2'-deoxy-nucleoside-triphosphate and thus represent a potential substrate for DNA polymerases or a ribonucleoside-triphosphate and therefore be a potential substrate for RNA polymerases. Further, the nuc-component can serve as a terminator, so that only a single nuc-macromolecule can be incorporated. In another embodiment, the nuc-component serves as a reversible terminator, which allows for an extension reaction controlled step-by-step, as described, for example, in Ju et al. the U.S. Pat. No. 6,664,079, Tcherkassov WO 02088382.

On the other hand, the marker (e.g. the target domain) can have a significant influence on the properties of nuc components: due to the binding of the target domain to the target sequence, the local concentration of nuc components can increase significantly. This increase in the local concentration can have an effect on the acceptance of the nuc component of the nuc macromolecule that is bound to the target sequence by a polymerase. For example, the discriminating capability of the polymerase regarding the nucleobase or other modifications of the nuc component can be changed. In addition, the competition between natural nucleotides available in the solution in a free state (such as dNTPs) and the nuc component of the nuc macromolecule that is bound to the target sequence can be shifted in favor of the incorporation of the nuc component.

These changes in the local concentration of the nuc component—a strong increase in the vicinity of the bound target domain—make it possible to use a much broader range of nucleotide analogues as nuc components, for example those which have very little incorporation efficiency under usual reaction conditions.

Further, the target domain provides the possibility of selective labeling in favor of target sequences. This is particularly advantageous in the presence of strong contamination with unwanted nucleic acid chains, i.e., interfering DNA: the specific yield of a reaction can be increased as compared with known, conventionally labeled nucleotides.

Coupling of antiviral nucleotide analogues as nuc components within the nuc macromolecule permits the selective suppression of viral polymerases.

The substrate properties of nuc macromolecules can be strongly affected by the presence of natural nucleotides. If no binding of the target domain to the target sequence has occurred, the presence of competing nucleotides in the reaction can prevent or greatly reduce the incorporation of nuc macromolecules into the growing strand. Conversely, if the target domain is bound to the target sequence, nuc components of the nuc macromolecules are incorporated into the growing strand despite the presence of highly concentrated competing nucleotides.

1.3.3.4.2 Substrate Properties of the Target, Anchor, and Signal Domains or Their Antagonists The nucleic acid constituents of a nuc macromolecule (e.g. the target domain, the anchor domain, the signal domain, or antagonists thereof), can also serve as a substrate for enzymes. For example, antagonists can be degraded by nucleases during the reaction (e.g. sequence-specific endonucleases or exonucleases such as 5'-3' exonuclease activities of polymerases).

1.3.4 Low Molecular Marker of a conventially modified nucleotides is a state-of-the-art labeling for nucleotides, for instance, with one or two biotin molecules, one or two dye molecules, one or two hapten molecules (e.g., digoxigenin).

1.3.5 Conventionally Modified Nucleotide—a nucleotide with a linker (average length between 5 and 30 atoms) and a marker. A conventionally modified nucleotide usually carries a marker with low molecular weight, e.g. one dye molecule or one biotin molecule or one hapten molecule (e.g. DNP or Digoxigenin).

These modifications can be used as the signal or anchor domain. Nucleic acid chains can be attached to a solid phase via biotin (function of an anchor domain), or a streptavidin labeled with a dye or an enzyme can be coupled via biotin (function of a signal domain).

1.3.6. Enzymes 1.3.6.1 Polymerases

In one embodiment, the nuc-macromolecules can be used as substrates for enzymes. Polymerases represent frequently used enzymes, which utilize nucleotides as substrates. They will be dealt with further as representative examples of other nucleotide-utilizing enzymes. One of the central abilities of polymerases consists in covalent coupling of nucleotide monomers to a polymer. Furthermore, the synthesis can be template-dependent (as for example DNA or RNA synthesis with DNA- or RNA-dependent polymerases) as well as independent of templates, e.g. terminal transferases (J Sambrook "Molecular Cloning" 3. Ed. CSHL Press in 2001).

If RNA is used as a substrate (e.g., mRNA) in the sequencing reaction, commercially available RNA-dependent DNA polymerases can be used, e.g. AMV reverse transcriptase (Sigma), M-MLV reverse transcriptase (Sigma), HIV reverse transcriptase without RNAse activity. For Klenow Fragment DNA polymerase a function as reverse transcriptase is also described. For certain applications, reverse transcriptases can be essentially free of RNAse activity ("Molecular cloning" in 1989, Ed. Maniatis, Cold Spring Harbor Laboratory), e.g. for use in mRNA labeling for hybridisation applications.

If DNA is used as a substrate (e.g. cDNA), all the following polymerases are suitable in principle: DNA-dependent DNA polymerases with or without 3'-5' exonuclease activity ("DNA-Replication" in 1992 Ed. A. Kornberg, Freeman and company NY), e.g. modified T7-Polymerase for example of the type "Sequenase version 2" (Amersham Pharmacia Biotech), Klenow fragment of the DNA-Polymerase I with or without 3'-5' exonuclease activity (New England Biolabs), T4 DNA Polymerase, phi29 DNA Polymerase, polymerase Beta of different origin ("Animal Cell DNA polymerases" in 1983, Fry M., CRC Press Inc, commercially available from Chimerx), thermostable polymerases such as, for example, Taq-Polymerase (New England Biolabs), Vent Polymerase, Vent exo minus Polymerase, Deep Vent Polymerase, Deep Vent exo minus Polymerase, Pfu Polymerase, Tli Polymerase, Tfl Polymerase, Tth Polymerase, Thermosequenase, Pwo-Polymerase, Terminator, Terminator I, Terminator II, Terminator III, Bst DNA Polymerase, Bst DNA Polymerase, Large Fragment, Phusion® High-Fidelity DNA Polymerase, Phusion® High-Fidelity Hot Start DNA Polymerase, Phire® Hot Start DNA Polymerase, Phire® Hot Start II DNA Polymerase, Phusion® Flash High-Fidelity DNA Polymerase, Crimson Taq DNA Polymerase, DyNAzyme™ EXT DNA Polymerase, DyNAzyme™ II Hot Start DNA Polymerase, 9° $N_m$ DNA Polymerase etc. (for example from New England Biolabs, or from Promega, or from Roche, or from Qiagen).

Using modern genetic engineering methods, it is possible to construct polymerases which differ in their capabilities from naturally occurring enzymes, for example by the absence of certain activities or improved enzymatic parameters such as precision or processivity. An increasing number of companies manufacture such thermolabile and thermostable polymerases, which are used as optimized enzymes for PCR or other amplification or labeling methods. The basic functions of polymerases are retained, however: they are able to incorporate nucleotides into complementary strands during the synthesis. Such polymerases can also be used for the methods described. An expert is aware of how to bring about an optimization of the reaction conditions.

In one embodiment of the application, polymerases without 5'-3' exonuclease activity such as Vent exo minus, Klenow exo minus are preferentially used.

In one embodiment of the application, polymerases with 5'-3' exonuclease activity such as Taq polymerase are preferentially used.

In one embodiment of the application, polymerases without strand displacement activity such as Vent exo minus are used.

In one embodiment of the application, polymerases with strand displacement activity such as Klenow exo minus are used.

DNA-dependent RNA polymerases can also be used, for example Ecoli RNA polymerase, T7 RNA polymerase, or SP6 RNA polymerase.

RNA-dependent RNA polymerases (RNA replicase) can be used for the amplification and labeling RNA, e.g. phi6 RNA polymerase (e.g. Q-beta replicase, polio replicase, 3Dpol, or replicase of hepatitis C virus, NS5b).

In the application, DNA-dependent DNA polymerases are considered as examples of polymerases.

Further literature sources and examples for selecting a proper polymerase, reaction conditions, etc. are presented in the chapter "Amplification Methods".

1.3.7 Cleavable Compound

A compound which is cleavable under mild conditions. This compound can represent a part in the linker and can be cleavable in one or several positions. It can be a chemically cleavable bond, such as, for example, disulfide, acetal, oxidative cleavable bonds (e.g. Linker comprising tartrate bond), thioester bonds (Short WO 9949082, Tcherkassov WO 02088382). It can also be a photo-chemically cleavable compound (Rothschild WO 9531429). It can also be an enzymatically cleavable compound (for instance, a peptide or polypeptide bond, Odedra WO 0192284), cleavable by peptidases, a poly- or oligo-saccharide bond, cleavable by disaccharidases, whereas the cleavage can be achieved by a specific enzyme between certain monomers of the cleavable bonds.

Several examples of cleavable compounds are known. The synthesis of such a compound is described, for instance, in (Tcherkassov WO 02088382, Metzker et al. Nucleic Acid Research 1994, v. 22, p. 4259-, Canard et al. Genes, 1994, v. 148, p. 1, Kwiatkowski U.S. Pat. No. 6,255,475, Kwiatkowski WO 0125247, Parce WO 0050642). A cleavable compound can be a part of the linker or can form the connecting part of the linker to the nucleotide, or the connecting part of the linker component to the marker component, or the connection between marker units and the core component.

1.3.8 DNA

Deoxyribonucleic acid of different origin and different length (e.g. oligonucleotides, polynucleotides, plasmides, genomic DNA, cDNA, ssDNA, dsDNA)

1.3.9 RNA—Ribonukleinsäure 1.3.10 PNA—Peptide Nucleic Acid 1.3.11 SNA—locked nucleic adds 1.3.12 Nucleotides dNTP—2'-deoxynucleoside triphosphate or their analoga, as a substrate for DNA polymerases and reverse-transcriptases, e.g. dATP, dGTP, dUTP, dTTP, dCTP.

NTP—Ribonucleoside triphosphate or their analoga, as a substrate for RNA polymerases, UTP, CTP, ATP, GTP.

Abbreviation "NT" is used for the description of the length of a particular nucleic acid sequence, e.g. 1000 NT. In this case "NT" means nucleoside monophosphates.

The plural is formed by the addition of the suffix "-s"; "NT" means, for example, "one nucleotide", "NTs" means "several nucleotides".

1.3.13 NAC

Nucleic acid chain (NSK abbreviation stands for German "Nukleinsäurekette"), DNA or RNA.

1.3.14 Term "the Whole Sequence"

The whole sequence is the sum of all the sequences to be analyzed in one experiment; it can comprise originally one or several NACs. Also, the whole sequence can display parts or equivalents of another sequence or sequence populations (e.g., mRNA, cDNA, Plasmid DNA with insert, BAC, YAC) and can originate from one species or various species. The "whole sequence" can comprise one or several target sequences.

1.3.15 NACF

The nucleic acid chains fragment (NSKF abbreviation stands for German "Nukleinsäurekettenfragment") (DNA or RNA) which corresponds to a part of the whole sequence, NACFs—the plural form—nucleic acid chain fragments. The sum of the NACFs forms an equivalent to the whole sequence. The NACFs can be, for instance, fragments of the whole sequence (DNA or RNA), which result after a fragmentation step.

1.3.16 Primer Binding Site (PBS)

A PBS is the part of the target sequence to which the primer binds.

1.3.17 Reference Sequence

A reference sequence is an already known sequence, divergences from which in the analysed sequence or sequences (e.g. whole sequence) have to be determined.

Reference sequences can be found in databases, such as, for example, the NCBI database.

1.3.1.8 Tm

Melting temperature 1.3.19 Steric Hindrance, Sterically Demanding Group or Ligand A sterically demanding group or ligand which (by its chemical structure) changes the properties of the nucleotides coupled with this group in such a way that these nucleotides cannot be inserted successively by a polymerase in an extension reaction. One or several sterically demanding groups coupled to the nucleotide base can lead to the stop or to the impedance of further synthesis. Many of the markers, currently used in research, represents a sterical hindrance for the enzymes. Biotin, digoxigenin and fluorescent dyes like fluorescein, tetramethylrhodamine, Cy3-dye, are examples of such sterically demanding groups (Zhu et al. Cytometry in 1997, v. 28, p. 206, Zhu et al. NAR 1994, v. 22, p. 3418, Gebeyehu et al., NAR 1987, v. 15, p. 4513, Wiemann et al. Analytical Biochemistry in 1996, v. 234, p. 166, Heer et al. BioTechniques 1994 v. 16 p. 54). Further examples for sterically demanding groups can be linear or branched polymers with a compact three-dimensional structure, as for example proteins or dendrimers. Another example for steric hindrance and its application is given in Cherkasov et al WO 2008043426.

1.3.20 Solid Phase Analysis

Solid phase is provided for the binding of labeled target sequences. A distinction is made between a direct and an indirect, i.e., transmitted binding of target sequences to the solid phase.

In this application, a direct binding of the target sequences or equivalents thereof is referred to in those cases wherein the target sequences or their equivalents participate in a binding event by themselves by forming complementary strands. In one embodiment, a solid phase which is capable of the sequence-specific binding of at least one target sequence or its equivalents is provided. Such a solid phase can, for example, comprise a nucleic acid chain which can specifically bind the target sequence by forming a complementary double strand. Examples of such solid phases will be known to a person skilled in the area (see the literature on microarrays). In one embodiment, the solid phase can sequence-specifically bind one or more target sequences. Examples of solid phases with spatially arranged attached oligonucleotides (addressable arrays) will be known to a person skilled in the area. Such solid phases are able to bind target sequences or their equivalents that result in spatial separation of the target sequences. The use of such methods allows an expert to differentiate between target sequences. Another example is a solid phase consisting of beads or particles. Such solid phases comprise specific oligonucleotides per each type of solid phase (bead array).

The term "indirect binding" comprises any other type of specific binding of the target sequences to a solid phase, for example transmitted by the anchor domain of a nuc macromolecule or the anchor domain of a primer or the anchor domain of a hybridization probe or by conventional modified nucleotides. Accordingly, in a further embodiment, a solid phase which is capable of specifically binding to least one anchor domain is provided. The nature of the bond between an anchor domain and a solid phase can be affine or covalent. A variety of affinity bonds between two specific partners are known. There are more or less specific binding pairs, such as biotin-streptavidin or biotin-avidin or antigen-antibody (for example hapten-antibody) or two complementary nucleic acid strands or aptamer-target protein. The anchor domain can be integrated as part of a nuc macromolecule or a primer or a hybridization probe. Examples of primer with anchor domains will be known to an expert. Examples of nuc macromolecules were discussed above.

The attachment to the solid phase or immobilizing on the solid phase of the binding partner for an anchor domain will be well known to an expert. The binding partners can be bound in a particular arrangement to the solid phase, so that a unique spatial assignment of the binding events can be undertaken. Examples of the spatially ordered binding of binding partners to a solid phase will be known to a person skilled in the area.

The solid phase can be provided in various forms. For example, reaction vessels, flat surfaces, beads, particles, or gels can be used as the solid phase. The solid phase with attached binding partners can, for example, be provided as a part of a device with fluid exchange or light-conducting properties. Such solid phases will be known to a person skilled in the area. Examples are lateral flow devices, microfluidic devices, and microtiter plates. Different arrays can be used as the solid phase, wherein arrays can comprise addressable positions for individual components of the reaction, such as binding partners for anchor domains, which are attached in a certain pattern on the solid phase to form an array. Beads can also be encoded in a characteristic way, for example via dyes or by diameter, so that an allocation of binding events is possible based on characteristic features of beads.

In one embodiment of the invention, the solid phase is provided, for example as a reaction vessel which comprises a section in which the labeling reaction is carried out and a further separate section in which the binding of the reaction products to the solid phase is taking place. The transfer of the liquid from the first section into the second is preferentially carried out without opening the vessel. The binding partners for anchor domains are preferentially attached on the solid phase in a spatial arrangement as an array.

According to the invention, one or several of such solid phases having the smallest possible non-specific binding of nucleic acid chains are provided.

The following literature sources should help an expert to implement combinations of known devices with a solid phase with the embodiments described in this invention. Further, the literature sources provide information to an expert with respect to the synthesis of oligonucleotides which act as anchor domains or their binding partners on the solid phase or as their antagonists and their modifications:

"Oligonucleotide Synthesis, Methods and Applications" Piet Herdewijn, 2004, ISBN 1-58829-233-9

"Protocols for Oligonucleotide Conjugates, Synthesis and Analytical Techniques" Sudhir Agrawal, 1993, ISBN 0-89603-252-3

"Protocols for Oligonucleotide Conjugates, Synthesis and Properties" Sudhir Agrawal, 1993, ISBN 0-89603-247-7

"The Aptamer Handbook" Sven Klussmann, 2006, ISBN 10: 3-527-31059-2

"Pharmaceutical Aspects of Oligonucleotides" Patrick Couvreur, 2000, ISBN 0-748-40841-X "Triple Helix Forming Oligonucleotides" Claude Malvy, 1999, ISBN 0-7923-8418-0

"Artificial DNA, Methods and Applications" Yury E. Khudyakov, ISBN 0-8493-1426-7

Concerning the arrangement of binding partners on a solid phase, the forming of spatially arranged arrays of binding partners, the binding of biologically active molecules to the solid phase, and technical means for the exchange of fluids, an expert can be referred to the following sources:

"Microfluidic Lab-on-a-chip for Chemical and Biological Analysis and Discovery" Paul C. H. Li, 2006, ISBN 1-57444-572-3

"Microfluidic for Biological Applications" Wei-Cheng Tian, 2008, ISBN 978-0-387-09479-3

"Preparation, Microfluidics, Detection Methods and Biological Applications" Kilian Dill, 2009, ISBN 978-0-387-72716-5

"DNA Microarray, a Practical Approach" M. Shena, 2002, ISBN 0-19-963777 6

"DNA Microarrays" David Bowtell, 2003, ISBN 0-87969-624-9

"Lateral Flow Immunoassays" Raphael Wong, 2009, ISBN 978-1-58829-908-6

"Nucleic Acid Hybridization" M. L. M. Anderson, 1999, ISBN 1-85996-007-3

1.3.21 Target Sequence

A target sequence is a sequence of a nucleic acid chain which is to be analyzed. In modern biotechnology and medicine, many examples of the analysis of selected sequences are known. In one embodiment, the analysis consists of the detection of the presence of a particular target sequence or several target sequences. In another embodiment, the analysis consists of the detection of the sequential arrangement of bases in the target sequence, wherein said sequence is of interest. In another embodiment, the analysis consists in measurement of the amount of the target sequence.

The target sequence of organisms may be present as DNA or RNA. In modern research and industry, modified nucleic acid chains can be used, so that a target sequence may also be an artificial sequence, with or without modifications.

In an analytical test, multiple target sequences can be present. Examples of complex mixtures of target sequences are mRNA or cDNA mixtures or target sequences which have been generated in a multiplex PCR or mixtures of fragments of genomic DNA. Viral nucleic acid chains such as mixtures of viral variants, e.g. HIV sequences, may also represent mixtures of target sequences. Isolates from the patient also provide a mixture of nucleic acid chains, which may contain multiple target sequences, such as viral and bacterial target sequences.

An amplification reaction is often used for the detection or analysis of a target sequence or multiple target sequences (e.g. conducted by means of a polymerase chain reaction, PCR; a ligase chain reaction, LCR; or an isothermal amplification). By these methods, equivalents of a target sequence can be generated, for example, as PCR fragments or LCR fragments. These amplification methods are conducted in such a way that the equivalents comprise the same information as the original target sequences. This allows an expert to draw conclusions regarding the target sequences in later steps of the analysis. For this reason, the amplified nucleic acid chains derived from a target sequence can also be considered and referred to as target sequences or equivalents of target sequences.

Owing to its great length, a target sequence can be represented by a plurality of amplified fragments. In one embodiment, the sum of the amplified fragments can be referred to as a target sequence. In a further embodiment, individual fragments are considered as independent target sequences.

An expert will recognize a similar situation with transformation of a target sequence from one format into another format, e.g. from DNA to RNA (transcription) or vice versa, generation of cDNA from mRNA by a reverse transcriptase. Those sequences which have been generated as a result of transformation are also referred to as target sequences or their equivalents.

In summary, target sequences or their equivalents can be considered as all kinds of sequences which have been derived from the original target sequence or have maintained original information from the starting target sequence and therefore allow conclusions regarding this initial target sequence to be drawn.

The target sequences can be derived from different species or belong to different genetic elements. Many organisms have been studied extensively in recent years. Thus, target sequences may represent, for example, PCR products or mRNA mixtures or small-RNA or plasmids. Many amplification and isolation methods have been established in order to enrich specific genetic elements.

The length of the target sequences can vary. For example, whole genomes can be considered as target sequences (e.g. the HIV genome), or several mRNA in a transcription profile.

On the other hand, individual base variations at a single position in the genome can be of interest (SNP analysis). In the later case, a fragment of the sequence around the position of interest (SNP) is selected and amplified. This fragment can then be referred to as the target sequence.

Often, there is a need for the analysis of multiple target sequences, e.g. while searching for a pathogen. In such a case, an occurrence of specific target sequences in a material is of interest.

The choice of the target sequence is dependent upon the task. As mentioned above, sequences of different origins can represent target sequences. In the following, some examples of organisms which provide a source for selection of target sequences are listed.

The origin of the target sequence can be any organism; examples are viruses, prokaryota, archea, and eukaryota. Within eukaryota, protozoa or multicellular organisms, such as animals, including fishes, and plants can serve as sources of target sequences.

In an advantageous embodiment of the application, target sequences are selected from the following organisms: human organisms comprising, for example, protein coding sequences, for example, receptors, oncogenes, MHC, blood groups, and/or regulatory regions of the genome. Furthermore, target sequences can originate from farm animals, research animals and pets, for example cattle, pigs, horses, dogs, cats, mice, rats, rabbits, and monkeys. Fishes can serve as a source of target sequences. Sequences originating from trees and plants, either in their natural form or in genetically modified versions, can represent target sequences of interest, e.g. rice, maize, wheat, colza.

Fungi and bacteria of importance for human medicine or for veterinary, agricultural, industry or military applications can represent the origin of target sequences. Examples of such bacteria are *Staphylococcus aureus, Streptococcus pyogenes, Streptococcus pneumoniae, Pseudomonas* sp., *Salmonella, Shigella, Yersinia, Campylobacter, Helicobacer, Legionella, Mycobacteria, Chlamydia, N. gonorrhea, Yersinia, Francisella tularensis, B. antracis, Aspergillus fumigatus*. Examples of viruses are human pathogens: HIV, HSV, HPV, CMV, HBV, HCV, influenza, SARS, FSME. Examples of parasites are causative agents of malaria (Plasmodiidae), *Leishmania*, Toxoplasma.

The target sequences can be derived from a genomic fragment or from plasmids or mobile genetic elements.

In one embodiment, sequences are selected from genes which are responsible for resistance to antibiotics. Examples include organisms such as MRSA or VRE or carriers of ESBL resistances or quinolone resistance. In another embodiment, target sequences are selected from genes which are responsible for pathogenetic elements such as toxin-coding or invasins or adhesins, for example diphterotoxin, shiga toxin, or TSST.

In another embodiment, target sequences are selected from organisms which are of significance in the food industry, such as brewer's yeast or dairy products such as cheese or yogurt cultures.

In many analytical approaches control sequences are included in a particular test. This helps to control the quality of a reaction. Such control sequences can also represent target sequences.

For examples of applications for the design of diagnostic assays, wherein the invented nucleotides and methods can be of advantage, an expert is referred to the following literature:
"PCR Protocols for Emerging Infectious Diseases", 1996, ISBN 1-55581-108-6

"Molecular Diagnostic PCR Handbook" Gerrit J. Viljoen, 2005 ISBN 1-4020-3403-2

"PCR Detection of Microbial Pathogens" Konrad Sachse, 2003, ISBN 1-58829-049-2

"Clinical Applications of PCR" Y. M. Dennis Lo, 2006, ISBN 1-58829-348-3

"Microarrays in Clinical Diagnostics" Thomas O. Joos, 2005, ISBN 1-58829-394-7

"Molecular Diagnostics" William B. Coleman, 2006, ISBN 1-58829-356-4

"Single Nucleotide Polymorphisms, Methods and Protocols" Pui-Yan Kwok, 2003, ISBN 0-89603-968-4

"Molecular Microbiology, Diagnostic Principles and Practice" Fred C. Tenover, 2004, ISBN 1-55581-221-X "Rapid Detection of Infectious Agents", Steven Specter, 1998, ISBN 0-306-45848-9

"Nucleic Acid Amplification Technologies, Applications to Disease Diagnosis" H. Lee, 1997, ISBN 1-881299-04-X "PCR Primers, a Laboratory Manual" Carl W. Dieffenbach, 2003, ISBN 0-87969-653-2

"Real-Time PCR, Current Technology and Applications" Julie Logan, 2009, ISBN 978-1-904455-39-4

"Rapid Cycle Real-Time PCR, Methods and Applications" S. Meuer, 2001, ISBN 3-540-66736-9

"PCR Primer Design" Anton Yuryev, 2004, ISBN 978-1-58829-725-9

"PCR Troubleshooting, the Essential Guide" Michael L. Altshuler, 2006, ISBN 1-904455-07-7

"PCR in Bioanalysis" Stephen J. Meltzer, 1998, ISBN 0-89603-497-6

"PCR Protocols" John M. S. Bartlett, ISBN 0-89603-642-1

"PCR Technology Current Innovations" Thomas Weissensteiner, 2004, ISBN 0-8493-1184-5

1.3.22 Primer

A primer is usually an oligonucleotide which is capable of binding to a complementary position in the target sequence and can be recognized by a polymerase. Nucleotides are incorporated into the 3' end of such primers.

A specialist knows many examples of primers. They are used for amplification of nucleic acid chains as well as for labeling reactions. They can sequence-specifically bind to the nucleic acid chains. Through the introduction of uniform primer binding sites and the use of appropriate uniform primers, many different nucleic acid chains can be amplified or labeled in one reaction. Hexamer primers are examples of nonspecific labeling. Other examples will be known to a person skilled in the area (see the literature references for PCR and microarrays). Primers can bind to the target sequences more or less specifically. In one embodiment, a primer is completely complementary to the target sequence and binds only to such a target sequence. In another embodiment, a primer comprises sequences which allow for binding to a plurality of target sequences.

In this application, primers can be used for a labeling reaction as well for an amplification. Depending on the application, primers can be used only for one task (either labeling or amplification) or they can be used for both. A specialist should recognize in which situations which primer should be used.

A primer can be modified through the coupling of further structures. These structures can be used, for example, for signaling or for binding to the solid phase. Such a modified primer comprises, for example, at least one signal domain or at least one anchor domain.

The structures of the anchor domain or the signal domain of a modified primer can be composed in accordance with the same principles as described for domains of a nuc macromolecule (see section on anchor domain and signal domain).

In one embodiment, for example, an anchor domain consisting of nucleic acid chain (such as DNA, PNA, LNA) is attached to the 5' end of the primer. In another embodiment, a biotin residue or a dye molecule, for example, can be coupled to the primer (as a signal or an anchor domain).

The use of modified primers allows the binding of nucleic acid chains to the solid phase. Primers labeled with a signal domain can be used for detection. Some examples are given below.

An expert can find examples of primer design in the following literature sources:
"Nucleic Acid Amplification Technologies, Applications to Disease Diagnosis" H. Lee, 1997, ISBN 1-881299-04-X
"PCR Primers, a Laboratory Manual" Carl W. Dieffenbach, 2003, ISBN 0-87969-653-2
"Real-Time PCR, Current Technology and Applications" Julie Logan, 2009, ISBN 978-1-904455-39-4
"Rapid Cycle Real-Time PCR, Methods and Applications" S. Meuer, 2001, ISBN 3-540-66736-9
"PCR Primer Design" Anton Yuryev, 2004, ISBN 978-1-58829-725-9
"PCR Troubleshooting, the Essential Guide" Michael L. Altshuler, 2006, ISBN 1-904455-07-7
"PCR in Bioanalysis" Stephen J. Meltzer, 1998, ISBN 0-89603-497-6
"PCR Protocols" John M. S. Bartlett, ISBN 0-89603-642-1
"PCR Technology Current Innovations" Thomas Weissensteiner, 2004, ISBN 0-8493-1184-5
"PCR Protocols for Emerging Enfectious Diseases", 1996, ISBN 1-55581-108-6
"Molecular Diagnostic PCR Handbook" Gerrit J. Viljoen, 2005 ISBN 1-4020-3403-2
"PCR Detection of Microbial Pathogens" Konrad Sachse, 2003, ISBN 1-58829-049-2
"Clinical Applications of PCR" Y. M. Dennis Lo, 2006, ISBN 1-58829-348-3
"Microarrays in Clinical Diagnostics" Thomas O. Joos, 2005, ISBN 1-58829-394-7
"Molecular Diagnostics" William B. Coleman, 2006, ISBN 1-58829-356-4
"Single Nucleotide Polymorphisms, Methods and Protocols" Pui-Yan Kwok, 2003, ISBN 0-89603-968-4
"Molecular Microbiology, Diagnostic Principles and Practice" Fred C. Tenover, 2004, ISBN 1-55581-221-X
"Rapid Detection of Infectious Agents", Steven Specter, 1998, ISBN 0-306-45848-9

The following sources show examples of modified oligonucleotides which can be used as a primer or can be bound to primers:
"Oligonucleotide Synthesis, Methods and Applications" Piet Herdewijn, 2004, ISBN 1-58829-233-9
"Protocols for Oligonucleotide Conjugates, Synthesis and Analytical Techniques" Sudhir Agrawal, 1993, ISBN 0-89603-252-3
"Protocols for Oligonucleotide Conjugates, Synthesis and Properties" Sudhir Agrawal, 1993, ISBN 0-89603-247-7
"The Aptamer Handbook" Sven Klussmann, 2006, ISBN 10: 3-527-31059-2
"Pharmaceutical Aspects of Oligonucleotides" Patrick Couvreur, 2000, ISBN 0-748-40841-X
"Triple Helix Forming Oligonucleotides" Claude Malvy, 1999, ISBN 0-7923-8418-0
"Artificial DNA, Methods and Applications" Yury E. Khudyakov, ISBN 0-8493-1426-7

1.3.23 Hybridization Probe

A hybridization probe is an oligonucleotide which is capable of binding to a target sequence in a sequence-specific manner. A hybridization probe can be used as an additional means for a detection reaction or for a coupling to the solid phase. A hybridization probe can be designed to be similar to a nuc macromolecule but without a nuc component.

A hybridization probe comprises at least one target domain and optionally at least one signal domain and/or at least one anchor domain. The structures of the target domain, the anchor domain, and the signal domain of a hybridization probe can be assembled according to the same principles as described for the domains of a nuc macromolecule (see signal domain section).

In one embodiment, for example, an anchor domain is designed as a nucleic acid chain (such as a DNA, PNA, LNA), which is bound to the 5' end or 3' end of the hybridization probe. In another embodiment, a biotin residue or a dye molecule, for example, can be coupled (as a signal domain) to the hybridization probe.

In one embodiment, a hybridization probe (consisting of a target domain and an anchor domain) can bind a nucleic acid strand which has been labeled with a nuc macromolecule (consisting of a target domain and a signal domain) and transmit its binding to a solid phase. In a further embodiment, a hybridization probe (consisting of a target domain and a signal domain) can bind a nucleic acid strand which has been labeled with a nuc macromolecule (consisting of a target domain and an anchor domain), and provide it with a specific signal.

In another embodiment of the invention, the hybridization probe has sequences which can undergo complementary binding with the core component of the nuc macromolecule.

1.3.24 Methods for Amplification of Nucleic Acid Chains.

There are a variety of known methods which are used for the amplification of nucleic acid chains. Examples are isothermal amplification and PCR and their various modifications, such as hot start PCR and multiplex PCR.

In an analytical approach, target sequences can be used as such or equivalents of target sequences (see above) or products of an amplification, the amplificats (equivalents of target sequences).

In this application, some methods are described. They are intended to illustrate the invention, not provide a limitation.

Examples of amplification of target sequences, or their equivalents, will be known to a person skilled in the area. Many scientific papers describe the amplification of target sequences using a PCR or an isothermal amplification and can be found in databases, for example in the NCBI database, PubMed. In such literature resources, the primer sequences as well as amplification conditions are indicated. Many target sequences are amplified using commercially available kits. Using examples of real-time PCR, sequences for probes can also be selected. These techniques will be known to a person skilled in the area.

Many examples of amplification methods which can potentially be used for replication of target sequences or can be combined with a labeling reaction are shown in the following sources.
"Nucleic Acid Amplification Technologies, Applications to Disease Diagnosis" H. Lee, 1997, ISBN 1-881299-04-X
"PCR Primers, a Laboratory Manual" Carl W. Dieffenbach, 2003, ISBN 0-87969-653-2
"Real-Time PCR, Current Technology and Applications" Julie Logan, 2009, ISBN 978-1-904455-39-4
"Rapid Cycle Real-Time PCR, Methods and Applications" S. Meuer, 2001, ISBN 3-540-66736-9

"PCR Primer Design" Anton Yuryev, 2004, ISBN 978-1-58829-725-9

"PCR Troubleshooting, the Essential Guide" Michael L. Altshuler, 2006, ISBN 1-904455-07-7

"PCR in Bioanalysis" Stephen J. Meltzer, 1998, ISBN 0-89603-497-6

"PCR Protocols" John M. S. Bartlett, ISBN 0-89603-642-1

"PCR Technology Current Innovations" Thomas Weissensteiner, 2004, ISBN 0-8493-1184-5

"PCR Protocols for Emerging Infectious Diseases", 1996, ISBN 1-55581-108-6

"Molecular Diagnostic PCR Handbook" Gerrit J. Viljoen, 2005 ISBN 1-4020-3403-2

"PCR Detection of Microbial Pathogens" Konrad Sachse, 2003, ISBN 1-58829-049-2

"Clinical Applications of PCR" Y. M. Dennis Lo, 2006, ISBN 1-58829-348-3

"Microarrays in Clinical Diagnostics" Thomas O. Joos, 2005, ISBN 1-58829-394-7

"Molecular Diagnostics" William B. Coleman, 2006, ISBN 1-58829-356-4

"Single Nucleotide Polymorphisms, Methods and Protocols" Pui-Yan Kwok, 2003, ISBN 0-89603-968-4

"Molecular Microbiology, Diagnostic Principles and Practice" Fred C. Tenover, 2004, ISBN 1-55581-221-X "Rapid Detection of Infectious Agents", Steven Specter, 1998, ISBN 0-306-45848-9

1.3.25 Methods of Detection

An expert knows many detection methods which are currently used in analysis.

Thus, direct detection methods (signal imaging methods) and indirect methods (signal transmitting methods), single-step methods, or multi-step methods, as well as physical, enzymatic, chemical, or electrochemical methods can be used for detection. Many signal-amplification methods are also known. It is up to an expert to choose which method of detection is better suited for a particular application. In this application, some examples are given. These examples are intended to demonstrate and not to restrict a potential diversity of detection methods which are compatible with the described structures of nuc macromolecules and methods of their use.

For example, fluorescence-based methods, methods based on color generation by an enzymatic reaction, like ELISA, or methods based on particles (such as colloidal gold or agglutination) can be used. Other examples are given in the chapter describing the signal domain of markers of nuc macromolecules.

Many detection methods are described in literature sources for solid phase and amplification (see the corresponding chapters). Some further sources are given below, where modern detection methods are described in detail.

"Fluorescent Energy Transfer Nucleic Acid Probes" Vladimir V. Didenko, 2006, ISBN 1-58829-380-7

"Protocols for Nucleic Acid Analysis by Nonradioactive Probes" Elena Hilario, 2006, ISBN 1-58829-430-7

"Nonisotopic DNA Probe Techniques" Larry J. Kricka, 1992, ISBN 0-12-426295-3

"Handbuch Immunchemische Färbemethoden", 2003, Dako-Cytomation, ISBN 3-00-011868-3

1.3.26 Further Enzymes

Different enzymes are used in modern diagnosis and research for labeling and amplification methods. These enzymes and their effect on the reactions will be known to a person skilled in the area. Their use can also be advantageous in combination with methods described in this application. Here are some examples:

Uracil-N-glycosidase is often used to avoid cross-contamination. The enzyme is thermolabile and is inactivated by PCR conditions.

Ligases are used for linking nucleic acid strands. Ligases can be added as thermolabile or thermostable variants into a reaction.

Pyrophosphatases can be supportive of a reaction due to the hydrolysis of pyrophosphate, the by-product of a reaction to the incorporation of nucleotides. Thermolabile or thermophilic forms can be purchased.

Helicase unfold the double strand. Their use is preferred for amplification under isothermal conditions.

Single-strand binding protein binds to single-stranded DNA and prevents the formation of secondary structures.

Some of these proteins or enzymes require cofactors or an energy carrier such as ATP. It will be obvious to an expert that these substances should be added to the appropriate reaction.

Within the optimization procedure of a reaction, the above-mentioned proteins or enzymes as well as their substrates/cofactors can be used.

In one embodiment, kits for labeling reactions comprise these enzymes and their substrates/cofactors.

1.4 IN THE FOLLOWING, SOME IMPORTANT ASPECTS OF THE INVENTION ARE SUMMARIZED

The invention describes new methods for labeling and detection of nucleic acid chains and neue group of macromolecular nucleotide conjugates.

1. A method for enzymatic synthesis of nucleic acid chains, wherein nucleotides are enzymatically incorporated into the complementary strand of at least one target sequence or equivalents thereof, wherein at least one of the nucleotides used has the following structure:

(Nuc-linker)n-marker wherein:

Nuc is a nucleotide (nuc-component)

Linker is a linker component, wherein the linker links the nuc-component to the macromolecular marker component Marker is a marker component, which comprises at least one nucleic acid sequence, called the target domain, complementary to the target sequence n is a positive integer from 1 to 1000

2. A method for enzymatic synthesis of nucleic acid chains, wherein nucleotides are enzymatically incorporated into the complementary strand of at least one target sequence or equivalents thereof, wherein at least one of the nucleotides used has the following structure:

(Nuc-linker)n-marker wherein:

Nuc is a nucleotide (nuc-component)

Linker is a linker component wherein the linker links the nuc-component to the macromolecular marker component Marker is a marker component which comprises at least one target domain and at least one anchor domain n is a positive integer from 1 to 1000

3. A method for enzymatic synthesis of nucleic acid chains, wherein nucleotides are enzymatically incorporated into the complementary strand of at least one target sequence or equivalents thereof, wherein at least one of the used nucleotides has the following structure:

(Nuc-linker)n-marker wherein:

Nuc is a nucleotide (nuc-component)

Linker is a linker component wherein the linker links the nuc-component to the macromolecular marker component Marker is a marker component which comprises at least one target domain and at least one signal domain
n is a positive integer from 1 to 1000

4. A method for enzymatic synthesis of nucleic acid chains, wherein nucleotides are enzymatically incorporated into the complementary strand of at least one target sequence or equivalents thereof, wherein at least one of the used nucleotides has the following structure:

(Nuc-linker)n-marker
wherein:
Nuc is a nucleotide (nuc-component)
Linker is a linker component wherein the linker links the nuc-component to the macromolecular marker component
Marker is a marker component which comprises at least one target domain and at least one anchor domain and at least one signal domain
n is a positive integer from 1 to 1000

5. A method for enzymatic synthesis of nucleic acid chains, wherein nucleotides are enzymatically incorporated into the complementary strand of at least one target sequence or equivalents thereof, wherein at least one of the used nucleotides has the following structure:

(Nuc-linker)$_n$-marker
wherein:
Nuc is a nucleotide (nuc-component)
Linker is a linker component wherein the linker links the nuc-component to the macromolecular marker component
Marker is a marker component which comprises at least one anchor domain
n is a positive integer from 1 to 1000

6. A method for the synthesis of nucleic acid chains in accordance with any one of claims 1 to 5, comprising at least one polymerase 7. A method for the synthesis of nucleic acid chains in accordance with any one of claims 1 to 6, comprising at least one primer 8. A method for the synthesis of nucleic acid chains in accordance with any one of claims 1 to 7, comprising at least one further kind of nucleotides 9. A method for the synthesis of nucleic acid chains comprising the following steps:
a) synthesis of a complementary strand to at least one target sequence or its equivalents, in accordance with the methods of any of claims 1 to 8
b) detachment of the extended complementary strand from the target sequence or its equivalents
c) where appropriate, repeating the steps a) to b)

10. A method for the synthesis of nucleic acid chains comprising the following steps:
a) synthesis of at least one complementary strand to at least one target sequence or its equivalents, in accordance with the methods of any of claims 1 to 8 using at least one kind of polymerase and a nucleotide composition comprising at least one kind of nuc-macromolecules and at least one kind of further nucleotides (having nucleobases A, C, T, and G or their equivalents)
b) detachment of the extended complementary strand from the target sequence, or its equivalents
c) where appropriate repeating the steps a) to b)

11. A method for the analysis of nucleic acid chains comprising the following steps:
a) synthesis of at least one complementary strand to at least one target sequence or its equivalents, in accordance with the methods of any of claims 1 to 10, wherein one kind of nuc-macromolecule specific to the respective target sequence is used and comprises a characteristic anchor domain
b) providing a solid phase which can specifically bind the respective anchor domain of the type of nuc macromolecules used in step (a)
c) incubating the nucleic acid strands synthesized in step (a) with the solid phase provided in step (b) under conditions which permit specific binding of the respective anchor domain to the solid phase.
d) detection of the binding event in the nucleic acid strands in step (c)

12. A method for the analysis of nucleic acid chains comprising the following steps:
a) synthesis of at least one complementary strand to at least one target sequence or its equivalents in accordance with the methods of any of claims 1 to 10, wherein a plurality of nuc-macromolecules specific to a respective target sequence is used and each of the respective kind of nuc-macromolecules comprises a characteristic anchor domain
b) providing a solid phase which can bind the respective anchor domain of the type of nuc-macromolecules used in step (a), wherein the binding of each anchor domain is specific and adressable and takes place in spatially separate, optically distinguishable areas of the solid phase
c) incubating the nucleic acid strands synthesized in step (a) with the solid phase provided in step (b) under conditions which permit specific binding of the respective anchor domain to the solid phase.
d) detection of the binding event in the nucleic acid strands in step (c)

13. A method for the analysis of nucleic acid chains comprising the following steps:
a) synthesis of at least one complementary strand to at least one target sequence or its equivalents, in accordance with the methods of any of claims 1 to 10, wherein one kind of nuc-macromolecule specific to the respective target sequence is used and each nuc-macromolecule comprises at least one signal domain
b) providing a solid phase capable of the specific and addressable binding of the synthesized nucleic acids labeled with nuc-macromolecules from step (a), wherein the binding takes place in spatially separate, optically distinguishable areas of the solid phase. The binding can be accomplished by one of the methods selected from the group consisting of: binding via hybridization to the newly synthesized, labeled strand of the respective nucleic acid or binding via the anchor domain of a nuc-macromolecule or binding via labeled primer or binding via labeled probe or binding via labeled nucleotides.
c) incubating the nucleic acid strands synthesized in step (a) with the solid phase provided in step (b) under conditions which permit specific binding of the respective anchor domain to the solid phase.
d) detection of the binding event in the nucleic acid strands in step (c)

14. A method for the analysis of nucleic acid chains comprising the following steps:
a) synthesis of at least one complementary strand to at least one target sequence or its equivalents, in accordance with the methods of any of claims 1 to 10, wherein several kinds of distinct nuc-macromolecules specific to the respective target sequence are used and each nuc-macromolecule comprises at least one signal domain
b) providing a solid phase, which is capable of the specific and adressable binding of the nucleic acids labeled with nuc-macromolecules synthesized in step (a), wherein the binding takes place in spatially separate, optically distinguishable areas of the solid phase. The binding can be accomplished by one of the methods selected from the group consisting of:

binding via hybridization to the newly synthesized, labeled strand of the respective nucleic acid or binding via the anchor domain of a nuc-macromolecule or binding via labeled primer or binding via labeled probe c) incubating the nucleic acid strands synthesized in step (a) with the solid phase provided in step (b) under conditions which permit specific binding of the respective anchor domain to the solid phase.

d) detection of the binding event in the nucleic acid strands in step (c)

15. A further aspect of the invention relates to macromolecular nucleotide compounds according to one of the aspects 1 to 11, wherein the nuc-component comprises the following structures (FIG. 22A), wherein:

Base is selected independently from the group of adenine, or 7-deazaadenine, or guanine, or 7-deazaguanine, or thymine, or cytosine, or uracil, or their modifications, wherein (L) is the linkage between the nuc-component and the linker component (coupling unit L) and X is the coupling position of the coupling unit (L) to the base.

$R_1$— is H $R_2$— is selected independently from the group of H, OH, halogen, $NH_2$, SH or protected OH group $R_3$—is selected independently from the group of H, OH, halogen, $PO_3$, SH, $N_3$, $NH_2$, O—$R_{3-1}$, $P(O)_m$—$R_{3-1}$ ((m) is 1 or 2), NH—$R_{3-1}$, S—$R_{3-1}$, Si—$R_{3-1}$ wherein $R_{3-1}$ is a chemically, photochemically or enzymatically cleavable group or comprises one of the following modifications: —CO—Y, —$CH_2$—O—Y, —$CH_2$—S—Y, —$CH_2$—$N_3$, —CO—O—Y, —CO—S—Y, —CO—NH—Y, —$CH_2$—CH=$CH_2$, wherein Y is an alkyl, for instance $(CH_2)_n$—$CH_3$ wherein n is a number between 0 and 4, or a substituted alkyl, for instance with halogen, hydroxy group, amino group, carboxy group.

$R_4$— is H or OH $R_5$— is selected independently from the group of OH, or a protected OH group, or a monophosphate group, or a diphosphate group, or a triphosphate group, or is an alpha thiotriphosphate group.

16. A further aspect of the invention relates to macromolecular nucleotide compounds according to one of the aspects 1 to 11, wherein the nuc-component comprises the following structures (FIG. 22B), wherein:

Base is selected independently from the group of adenine, or 7-deazaadenine, or guanine, or 7-deazaguanine, or thymine, or cytosine, or uracil, or their modifications capable of enzymatic reactions.

$R_1$— is H $R_2$— is selected independently from the group of H, OH, halogen, $NH_2$, SH or protected OH group $R_3$— is selected independently from the group of O—$R_{3-2}$-L, $P(O)_m$—$R_{3-2}$-L and (m) is 1 or 2, NH—$R_{3-2}$-L, S—$R_{3-2}$-L, Si—$R_{3-2}$-L, wherein $R_{3-2}$ is the coupling position of the linker to the nucleotide and L is the coupling unit (L) of the linker.

$R_4$— is H or OH $R_5$— is selected independently from the group of OH, or a protected OH group, or a monophosphate group, or a diphosphate group, or a triphosphate group, or is an alpha-thiotriphosphate group.

17. A further aspect of the invention relates to macromolecular nucleotide compounds according to one of the aspects 1 to 11, wherein the nuc-component comprises the following structures (FIG. 22B), wherein:

Base is selected independently from the group of adenine, or 7-deazaadenine, or guanine, or 7-deazaguanine, or thymine, or cytosine, or uracil, or their modifications capable of enzymatic reactions.

$R_1$— is H $R_2$— is selected independently from the group of H, OH, halogen, $NH_2$, SH or protected OH group $R_3$— is selected independently from the group of H, OH, halogen, $PO_3$, SH, $NH_2$, O—$R_{3-1}$, $P(O)_m$—$R_{3-1}$ ((m) is 1 or 2), NH—$R_{3-1}$, Si—$R_{3-1}$ wherein $R_{3-1}$ is a chemically, photochemically or enzymatically cleavable group.

$R_4$— is H or OH $R_5$— is selected independently from the group of O—$R_{5-1}$-L, or P—$(O)_3$—$R_{5-1}$-L (modified monophosphate group), or P—$(O)_3$—P—$(O)_3$—$R_{5-1}$-L (modified diphosphate group) or P—$(O)_3$—P—$(O)_3$—P—$(O)_3$—$R_{5-1}$-L (modified triphosphate group), wherein $R_{5-1}$ is the coupling position of the coupling unit (L) to the nucleotide and coupling unit (L) is a linkage between nuc-component and the linker component.

18. A further aspect of the invention relates to macromolecular nucleotide compounds according to aspects 15 to 17, wherein the coupling unit (L) comprises the following structural elements:

$R_6$—NH—$R_7$, $R_6$—O—$R_7$, $R_6$—S—$R_7$, $R_6$—SS—$R_7$, $R_6$—CO—NH—$R_7$, $R_6$—NH—CO—$R_7$, $R_6$—CO—O—$R_7$, $R_6$—O—CO—$R_7$, $R_6$—CO—S—$R_7$, $R_6$—S—CO—$R_7$, $R_6$—$P(O)_2$—$R_7$, $R_6$—$(CH_2)_n$—$R_7$, $R_6$—$(CH_2)_n$—$R_7$, $R_6$-A-$(CH_2)_n$—$R_7$, $R_6$—$(CH_2)_n$—B—$R_7$, $R_6$-(CH=CH—$)_n$—$R_7$, $R_6$-(A-CH=CH—$)_n$—$R_7$, $R_6$—(CH=CH—B—$)_n$—$R_7$, $R_6$—(CH=CH—$CH_2$—B—$)_n$—$R_7$, $R_6$-A-CH=CH—$(CH_2$—$)_n$—$R_7$, $R_6$—(—CH=CH—$CH_2)_n$—B—$R_7$, $R_6$—(C≡C—$)_n$—$R_7$, $R_6$-(A-C≡C—$)_n$—$R_7$, $R_6$—(C≡C—B—$)_n$—$R_7$, $R_6$—(C≡C—B—$)_n$—$R_7$, $R_6$—(—C≡C—$CH_2$—B—$)_n$—$R_7$, $R_6$-A-C≡C—$(CH_2$—$)_n$—$R_7$, $R_6$—(—C≡C—$CH_2)_n$—B—$R_7$, $R_6$—(—C≡C—$CH_2$—$CH_2)_n$—B—$R_7$ wherein $R_6$ is the nuc-component, $R_7$ is the rest of the linker, and A and B comprise independently the following structural elements: —NH—, —O—, —S—, —SS—, —CO—NH—, —NH—CO—, —CO—O—, —O—CO—, —CO—S—, —S—CO—, —$P(O)_2$—, —Si—, —$(CH_2)_n$—, wherein (n) ranges from 1 to 5, a photolabile group 19. A further aspect of the invention relates to macromolecular nucleotide compounds according to aspects 15 to 17, wherein the linker-component comprises a hydrophilic, water-soluble polymer.

20. A further aspect of the invention relates to a method according to one of the aspects 1 to 17, wherein the solid phase is selected independently from the group of: paper, metal, silicone, glass, ceramic, plastic, gel or their modification.

21. A kit for the labeling of nucleic acid chains in accordance with the method of any of claims 1 to 20 which comprises the following components:

one or several types of polymerases at least one kind of nucleotide analoga (nuc macromolecule) in accordance with claims 1 to 19 solid phase for binding of labeled nucleic acid chains

22. A kit for the labeling of nucleic acid chains in accordance with the method of any of claims 1 to 21, which comprises one or several of the following components from the following list, provided as a solution in concentrated or deluted form or also as a mixture of dry substances:

one or several types of polymerases at least one kind of nucleotide analoga (nuc macromolecule) in accordance with claims 1 to 19 solutions for carrying out enzymatic reactions composition for incorporation reaction, including at least one of further nucleoside triphosphates composition for the binding of labeled nucleic acid chains to the solid phase composition for washing the solid phase after the incorporation reaction composition for optical detection of the signals on the solid phase 23. A kit for the amplification and labeling of nucleic acid chains in accordance with the method of any of claims 1 to 22, which comprises one or several components from the following list:

one or several types of polymerases one or several primers for amplification of nucleic acid chains at least one kind of nucleotide analoga (nuc macromolecule) in accordance with claims 1 to 19 solutions for carrying out enzymatic reactions composition containing four dNTPs or NTPs composition for the binding of labeled nucleic acid chains to the solid phase composition for washing the solid phase after the incorporation reaction composition for optical detection of the signals on the solid phase 24. A kit for the amplification and labeling of nucleic acid chains according to the method of any of claims 1 to 23, which comprises at least one of the polymerases from the following list:

Reverse Transcriptases: M-MLV, RSV, AMV, RAV, MAV, HIV

DNA Polymerasen: Klenow Fragment DNA Polymerase, Klenow Fragment exo minus DNA Polymerase, T7 DNA Polymerase, Sequenase 2, Vent DNA Polymerase, Vent exo minus DNA Polymerase, Deep Vent DNA Polymerase, Deep Vent exo minus DNA Polymerase, Taq DNA Polymerase, Tli DNA Polymerase, Pwo DNA Polymerase, Thermosequenase DNA Polymerase, Pfu DNA Polymerase 25 A kit for the labeling of nucleic acid chains according to the method of any of claims 1 to 24, wherein components of the composition are provided in a premixed form.

26 A kit for the labeling of nucleic acid chains according to the method of any of claims 1 to 25, which comprises one or several solid phases for the binding of the labeled nucleic acid chains selected from the following list:

Plan, transparent solid phase

Plan, transparent solid phase which is provided as a component of a flow cell or a chip Solid phase in form of nanoparticles or microparticles Solid phase in form of nanoparticles or microparticles, which have paramagnetic properties Microtiter plate Striptest or Lateral-Flow-Device 27 A method for enzymatic synthesis of nucleic acid chains, wherein nucleotides are enzymatically incorporated into the complementary strand of at least one target sequence or equivalents thereof, wherein at least one of the nucleotides used has the following structure:

(Nuc-linker)n-marker wherein:

Nuc is a nucleotide (nuc-component)

Linker is a linker component, wherein the linker links the nuc-component to the macromolecular marker component Marker is a marker component which comprises at least one oligonucleotide complementary to the target sequence, called the target domain, n is a positive integer from 1 to 1000

28. A method for enzymatic synthesis of nucleic acid chains, wherein nucleotides are enzymatically incorporated into the complementary strand of at least one target sequence or equivalents thereof, wherein at least one of the nucleotides used has the following structure:

(Nuc-linker)n-marker wherein:

Nuc is a nucleotide (nuc-component)

Linker is a linker component wherein the linker links the nuc-component to the macromolecular marker component Marker is a marker component which comprises at least one oligonucleotide complementary to the target sequence and at least one further oligonucleotide for the binding to the solid phase or for the signal generation n is a positive integer from 1 to 1000

29. A method for enzymatic synthesis of nucleic acid chains, wherein nucleotides are enzymatically incorporated into the complementary strand of at least one target sequence or equivalents thereof, wherein at least one of the nucleotides used has the following structure:

(Nuc-linker)n-marker wherein:

Nuc is a nucleotide (nuc-component)

Linker is a linker component wherein the linker links the nuc-component to the macromolecular marker component Marker is a marker component which comprises at least one oligonucleotide complementary to the target sequence and at least one biotin moiety for the binding to the solid phase or for the signal generation n is a positive integer from 1 to 1000

30. A method for enzymatic synthesis of nucleic acid chains, wherein nucleotides are enzymatically incorporated into the complementary strand of at least one target sequence or equivalents thereof, wherein at least one of the nucleotides used has the following structure:

(Nuc-linker)n-marker wherein:

Nuc is a nucleotide (nuc-component)

Linker is a linker component wherein the linker links the nuc-component to the macromolecular marker component Marker is a marker component which comprises at least one oligonucleotide complementary to the target sequence and at least one characteristic dye moiety for the signal generation n is a positive integer from 1 to 1000

31. A method for enzymatic synthesis of nucleic acid chains, wherein nucleotides are enzymatically incorporated into the complementary strand of at least one target sequence or equivalents thereof, wherein at least one of the nucleotides used has the following structure:

(Nuc-linker)n-marker wherein:

Nuc is a nucleotide (nuc-component)

Linker is a linker component, wherein the linker links the nuc-component to the macromolecular marker component Marker is a marker component comprising at least one oligonucleotide which is capable of the binding to a solid phase, called the anchor domain, n is a positive integer from 1 to 1000

32. A method for the enzymatic synthesis of nucleic acid chains comprising the following steps:

Performing an enzymatic synthesis of at least one nucleic acid chain (the target sequence) with at least one polymerase, with at least one primer that is capable of binding to the specific target sequence, and with at least one conjugate type (one type of nuc-macromolecule), said conjugate (nuc macromolecule) comprises at least one nucleoside triphosphate or its analog, which can be recognized by a polymerase as a substrate, and at least one oligonucleotide, wherein the oligonucleotide is capable of specifically hybridizing to the target sequence, said polymerase incorporates the said nucleoside triphosphate or its analog during the enzymatic synthesis into the growing strand complementary to the target sequence, Detection of the incorporation event of the conjugate (nuc macromolecule)

33. A method for the enzymatic synthesis of nucleic acid chains comprising the following steps:

Performing an enzymatic synthesis of at least one nucleic acid chain (the target sequence) with at least one polymerase, with at least one primer that is capable of binding to the specific target sequence, with at least one conjugate type (one type of nuc-macromolecule), said conjugate type (nuc macromolecule) comprises at least one nucleoside triphosphate or its analog, which can be recognized by a polymerase as a substrate, and at least one oligonucleotide, wherein the oligonucleotide is capable of specifically hybridizing to the target sequence downstream from the 3' position of the primer, said polymerase incorporates said nucleoside triphosphate or its analog into the growing strand complementary to the target sequence during the enzymatic synthesis, Detection of the incorporation event of the conjugate (nuc macromolecule)

34. A method for the enzymatic synthesis of nucleic acid chains comprising the following steps:

Performing an enzymatic synthesis of at least one nucleic acid chain (the target sequence) with at least one polymerase, with at least one primer that is capable of binding to the specific target sequence, with at least one conjugate type (one type of nuc-macromolecule) and at least one hybridizing probe said conjugate type (nuc macromolecule) comprises at least one nucleoside triphosphate or its analog, which can be recognized by a polymerase as a substrate, and at least one oligonucleotide, wherein the oligonucleotide is capable of specifically hybridizing to the target sequence downstream from the 3' position of the primer, said hybridizing probe comprises at least one oligonucleotide, wherein the oligonucleotide is capable of specifically hybridizing to the target sequence downstream from the 3' position of said oligonucleotide of the conjugates (nuc macromolecule)

said polymerase incorporates said nucleoside triphosphate or its analog into the growing strand complementary to the target sequence during the enzymatic synthesis, Detection of the incorporation event of the conjugate (nuc macromolecule)

35. A method for the enzymatic synthesis of nucleic acid chains comprising the following steps:

Incubating of at least one nucleic acid chain (the target sequence) with at least one polymerase, with at least one primer that is capable of binding to the specific target sequence, with at least one conjugate type (one type of nuc-macromolecule)

said conjugate type (nuc macromolecule) comprises at least one nucleoside triphosphate or its analog, which can be recognized by a polymerase as a substrate, and at least one oligonucleotide, wherein the oligonucleotide is capable of specifically hybridizing to the target sequence Incubation under conditions which allow for specific hybridization of primers and/or conjugate (and/or optionally a hybridization probe) to the nucleic acid chain (the target sequence)

Incubation under conditions which allow an enzymatic coupling of the conjugate by the polymerase. Said polymerase incorporates the nucleoside triphosphate or its analog into the growing strand complementary to the target sequence during the enzymatic synthesis, Detection of the incorporation event of the conjugate (nuc macromolecule)

36. A method in accordance with any one of claims 32 to 35, wherein said nucleic acid chain (target sequence) is present in a sample 37. A method in accordance with claim 36, wherein said sample is a biological or diagnostical material, or a food sample, or an envirenmental sample or an analytical sample 38. A method in accordance with any one of claims 32 to 37, wherein said nucleic acid chain (target sequence) is provided in single-stranded form, 39. A method in accordance with any one of claims 32 to 37, wherein said nucleic acid chain (target sequence) is provided in double-stranded form, 40. A method in accordance with any one of claims 32 to 37, wherein said nucleic acid chain (target sequence) is provided in double-stranded form, and the method comprises components or steps to transform the double stranded form of the nucleic acid chain into a single stranded form.

41. A method in accordance with any one of claims 1 to 40, wherein said oligonucleotide (target domain of the nuc macromolecule) is not extendable by a polymerase 42. A method in accordance with any one of claims 32 to 41, wherein the method is employed under conditions, which allow for selective binding of said oligonucleotide (target domain) to the target sequence 43. A method in accordance with any one of claims 32 to 41, wherein the method is conducted under conditions which allow for predominantly selective binding of said oligonucleotide (target domain) to the target sequence 44. A method in accordance with any one of claims 32 to 43, wherein at least one of the components of the method (Primer and/or conjugate (nuc macromolecule) and/or the target sequence and/or hybridization probe and/or polymerase) is attached to a solid phase 45. A method in accordance with any one of claims 32 to 45, wherein the enzymatic synthesis is conducted in several steps 46. A method in accordance with any one of claims 32 to 45, wherein the enzymatic synthesis is conducted in several steps and these steps are conducted at different temperature 47. A method in accordance with any one of claims 32 to 45, wherein the enzymatic synthesis is conducted in several steps and at least one of these steps comprises a denaturation of the double stranded nucleic acid chains 48. A method in accordance with any one of claims 32 to 47, wherein the enzymatic synthesis is conducted in several steps and these steps are cyclicaly repeated 49. A method in accordance with any one of claims 1 to 48, wherein the method is used to amplify at least one nucleic acid chain 50. A method in accordance with any one of claims 1 to 48, wherein the method is used to label at least one nucleic acid chain
51. A method in accordance with any one of claims 1 to 48, wherein the method is used to detect at least one nucleic acid chain in an assay
52. A method in accordance with any one of claims 1 to 48, wherein the method is used for amplification and parallel labeling of at least one nucleic acid chain
53. A method in accordance with any one of claims 32 to 48, wherein the method is used to detect the presence of at least one nucleic acid chain in an assay though the amplification and labeling.
54. A method in accordance with any one of claims 32 to 48, wherein the method is used to detect at least two different nucleic acid chains in an assay
55. A method in accordance with any one of claims 32 to 54, wherein the method is used to detect and/or to label and/or to amplify at least two nucleic acid chains in an assay, wherein at least two specific components corresponding to a particular nucleic acid chain, e.g at least one specific primer and/or at least one specific conjugate (nuc macromolecule) and/or at least one specifc hybridization probe, are used.
56. A method in accordance with any one of claims 32 to 54, wherein the method is used to detect and/or to label and/or to amplify at least two nucleic acid chains in an assay, wherein at least one common component corresponding for at least two particular nucleic acid chain is used, e.g at least one common primer and or at least one common conjugate (nuc macromolecule) and/or at least one common hybridization probe.
57. A method in accordance with any one of claims 32 to 56, wherein the method is used to detect and/or to label and/or to amplify nucleic acid chains, wherein at least two types of conjugates (nuc macromolecules) are used and these conjugates have oligonucleotides (target domains), which can bind to different positions on the target sequence.
58. A method in accordance with any one of claims 1 to 57, wherein the method for amplification comprises a Polymerase Chain Reaction (PCR)
59. A method for amplification (PCR) comprising the following steps:
Providing a PCR with at least one nucleic acid chain (the target sequence) from a sample, with at least one polymerase, with at least two PCR primers that are capable of binding to the specific target sequence, with at least one conjugate type (one type of nuc-macromolecule)
said conjugate type (nuc macromolecule) comprises at least one nucleoside triphosphate or its analog, which can be recognized by said polymerase as a substrate, and at least one oligonucleotide, wherein the oligonucleotide is capable of specifically hybridizing to the target sequence between the two PCR primers
Providing of oligonucleotide primers, wherein the one primer has a complementary sequence to one strand of the target sequence and can start an extension reaction and the other primer has a complementary sequence to the other strand of the target sequence and can start an extension reaction, whereby both primers are selected so that their binding sites within the target sequence are located on either side of the binding site of said conjugate (nuc-macromolecule)
Amplification of the target sequence, if present in the sample, using a polymerase and conditions of a PCR: (a) hybridization of the primers and of the conjugate to the target sequence, (b) extension of the primers and incorporation of conjugates (c) where appropriate, separation of the synthesized double strands of the target sequence, (d) where appropriate, repeating steps (a) to (c) several times
Detection of the incorporation event of the conjugate (nuc macromolecule)
60. A method in accordance with any one of claims 1 to 57, wherein the method for amplification is a transcription
61. A method in accordance with any one of claims 1 to 57, wherein the method for amplification is an isothermal amplification
62. A method in accordance with any one of claims 1 to 57, wherein the method for amplification is a ligase chain reaction (LCR)
63. A method in accordance with any one of claims 1 to 59, wherein the method is used to label at least one amplified nucleic acid chain
64. A method in accordance with any one of claims 1 to 59, wherein the method is used to detect at least one amplified nucleic acid chain in a sample
65. A method in accordance with any one of claims 1 to 64, wherein the method is used to quantify at least one amplified nucleic acid chain in a sample
66. A method in accordance with any one of claims 1 to 64 for quantification of an unknown amount of one target sequence in the sample, wherein a control experiment is carried out with a known amount of an identical or a different target sequence, and the results of measurement of the signal intensity from both experiments are compared to each other.
67. A method in accordance with any one of claims 1 to 66, wherein the method is used to detect and/or to label and/or to amplify and/or quantify nucleic acid chains, wherein the labeled nucleic acid chains (target sequenses or their equivalents) are isolated from other components of the reaction prior the signal measurement.
68. A method in accordance with any one of claims 32 to 67, wherein said conjugate comprises at least one of the structures in accordance with any one of claims 1 to 31.
69. A method in accordance with any one of claims 32 to 67, wherein the primer and/or the conjugate and/or the hybridization probe comprises a reporter (a signal domain).
70. A method in accordance with any one of claims 32 to 69, wherein the signal intensity of the reporter is measured after the incorporation of the conjugate into the growing strand, wherein the reporter (a signal domain) is bound to the primer and/or the conjugate and/or the hybridization probe
71. A method in accordance with any one of claims 32 to 70, wherein the method is used to quantify the target sequence in a sample through the measurement of the signal from the said reporter
72. A method in accordance with any one of claims 32 to 71, wherein the primer and/or the conjugate and/or the hybridization probe comprises an anchor domain which is a modification capable of affine binding to a binding partner.
73. A method in accordance with any one of claims 1 to 72, wherein a solid phase capable of affine binding of at least one anchor domain of said primer and/or said conjugate (nuc macromolecule) and/or said hybridization probe is provided
74. A method in accordance with any one of claims 1 to 72, wherein a solid phase capable of specific affine binding of at least one target sequence or their equivalents is provided
75. A method in accordance with claim 74, wherein a solid phase capable of specific binding via hybridization of at least one target sequence or its equivalents is provided.
76. A method in accordance with any of claims 73 to 75 comprising at least the following steps:

contacting of the reaction solution after the enzymatic reaction with said solid phase, and incubation under conditions that allow the target sequences or their potentially labeled equivalents to bind to this solid phase, and where appropriate washing the solid phase 77. A method in accordance with any one of claims 32 to 72, wherein the primer and/or the conjugate comprises a further modification (the core component), which is a modification capable of affine or covalent binding with further parts of conjugate (linker, nuc component, signal domain, anchor domain, target domain)

78. A method in accordance with any one of claims 1-77, wherein said conjugate comprises at least one nucleoside triphosphate which is coupled via a linker to the 5' end of said oligonucleotide.

79. A method in accordance with any one of claims 1-78, wherein the oligonucleotide of said conjugate comprises at least one additional sequence part which is not complement to the target sequence.

79. A method in accordance with any one of claims 1-79, wherein the oligonucleotide does not hybridize with itself 80. A method in accordance with any one of claims 32-79, wherein at least one other kind of nucleotide (not nuc macromolecules) is used in the reaction.

81. A method in accordance with claim 80, wherein the "other type" of nucleotides is selected from the group of naturally occurring nucleotides (e.g. dATP, dGTP, dCTP, dTTP, dUTP, ATP, GTP, CTP, and UTP) and/or modified nucleotides (e.g. nucleotides labeled with biotin, for example dUTP-biotin or dCTP-biotin, or terminators like ddTTP, ddCTP, ddATP, and ddGTP or fluorescently labeled nucleotides like dUTP-Cy3 or dUTP-TAMRA).

82. A method in accordance with any one of claims 1-81, wherein said polymerase is a thermolabile polymerase 83. A method in accordance with any one of claims 1-81, wherein said polymerase is a thermostable polymerase 84. A method in accordance with any one of claims 1-81, wherein said polymerase is a reversible inactivated thermostable polymerase (a hot-start-polymerase)

85. A method in accordance with any one of claims 1-81, wherein said polymerase has a strand displacement activity 86. A conjugate (a nuc-macromolecule) which comprises at least the following components:
At least one nucleotide
At least one oligonucleotide
At least one linker
wherein the nucleotide is a nucleoside triphosphate or its analog which is able to be incorporated into a primer by a polymerase,
the oligonucleotide is capable of binding to a target sequence,
the linker is placed between the nucleoside triphosphate and the oligonucleotide 87. A conjugate (a nuc-macromolecule) according to aspect 86, wherein the said conjugate is used in one of the methods according to any one of the aspects 32 to 85.

88. A conjugate (a nuc-macromolecule) according to aspect 86, wherein the said conjugate comprises at least one reporter (a signal domain)

89. A conjugate (a nuc-macromolecule) according to one of the aspects 86-88, wherein the said conjugate comprises a modification (an anchor domain), which is capable of affinity binding to the binding partner.

90. A conjugate (a nuc-macromolecule) according to one of the aspects 86-89, wherein the said conjugate comprises a further modification (the core component), which is a modification capable of affine or covalent binding with further parts of conjugate (linker, nuc component, signal domain, anchor domain, target domain)

91. Conjugate (a nuc-macromolecule) in accordance with any claims 86-90, wherein the said oligonucleotide (target domain of the nuc macromolecule) is not suitable for extention by a polymerase.

92. Conjugate (a nuc-macromolecule) in accordance with any claims 86-91, wherein at least one oligonucleotide is composed of one or several types of nucleic acids, selected from the group consisting of: DNA, RNA, PNA, LNA 93. Conjugate (called a nuc-macromolecule) in accordance with any claim 86-92, wherein the length of at least one oligonucleotide is at least 6 nucleotides.

93. Conjugate (called a nuc-macromolecule) in accordance with any claim 86-92, wherein the length of at least one oligonucleotide is at least 15 nucleotides.

95. Conjugate (called a nuc-macromolecule) in accordance with any claim 86-94, wherein at least one oligonucleotide does not hybridize to itself.

96. Conjugate (called a nuc-macromolecule) in accordance with any claim 86-95, wherein at least one oligonucleotide of the conjugates comprises at least one sequence portion which is not complement to the target sequence 97. Conjugate (called a nuc-macromolecule) in accordance with any claim 86-96, wherein the said conjugate comprises at least one nucleoside-triphosphate or an analogon of it, which is linked to the 5 end of the said oligonucleotide via a linker 98. Conjugate (called a nuc-macromolecule) in accordance with any claim 86-96, wherein the said conjugate comprises at least one nucleoside-triphosphate or an analogon of it, which is linked to the 3' end of the said oligonucleotide via a linker 99. Conjugate (called a nuc-macromolecule) in accordance with any claim 86-96, wherein the said conjugate comprises at least one nucleoside-triphosphate or an analogon of it, which is linked to an internal position of the said oligonucleotide via a linker 100. Conjugate (called a nuc-macromolecule) in accordance with any of the claims 86-99, wherein at least one linker between said nucleotide and said oligonucleotide in said conjugate has a length of at least 5 chain atoms 101. Conjugate (called a nuc-macromolecule) in accordance with any of the claims 86-100, wherein at least one linker between said nucleotide and said oligonucleotide in said conjugate has a length of at least 20 chain atoms 102. Conjugate (called a nuc-macromolecule) in accordance with any claim 86-101, wherein the oligonucleotide of the conjugates comprises at least one further sequence portion which is not complement to the target sequence 103. Conjugate (called a nuc-macromolecule) according to any one of claims 86-102, wherein at least one nucleotide comprises a kind of nucleobases capable of base pairing with one of the nucleobases in the target sequence (adenine, guanine, cytosine, thymine, uracil).

104. Another subject of the invention are methods according to any of the previously aspects, wherein the labeling of complementary strands of the target sequences with nuc-macromolecules is conducted in parallel to the amplification.

105. Another subject of the invention are methods according to any of the previously aspects, wherein the labeling of complementary strands of the target sequences with nuc-macromolecules is conducted in parallel to the amplification and further nucleic acid chains not belonging to the target sequecen are present in the sample 106. Another subject of the invention are methods according to any of the previously aspects, wherein the labeling of complementary strands of the target sequences with nuc-macromolecules is conducted in parallel to the amplification and more than one target sequence is present in a sample and correspondignly more than two specific macromolecules are used.
107. Another subject of the invention are methods according to any of the previously aspects, wherein the labeling of complementary strands of the target sequences with nuc-macromolecules is conducted in parallel to the amplification and more than one target sequence is present in a sample and the labeling is done by one uniform but specific nuc macromolecule
108. Another subject of the invention are methods according to any of the preceding aspects, wherein amplification and labeling of the nucleic acid chains occurs by cyclic steps, for example PCR. Such methods comprise some of the following steps:
Denaturation of target sequences
Binding of the primer and the nuc-macromolecules to target sequences
Incubation of the mixture under conditions that allow for an extension of the bound primer and incorporation of nuc macromolecules
Denaturation of the newly synthesized strands
Iteration of the process several times
These processes are, for example, associated with the change in the temperature of the reaction, as is known for PCR.
109. Another subject of the invention are methods according to any of the preceding aspects, wherein amplification and labeling of the nucleic acid chains are achieved during cyclic steps, wherein a plurality of enzymes with a distinct substrate properties are combined in an assay for example, reverse transcriptases and DNA polymerases.
110. Another subject of the invention are methods according to any of the preceding aspects, wherein amplification and labeling of the nucleic acid chains are achieved during cyclic steps, wherein the used polymerases are provided in reversibly inactivated form and are activated during the reaction, e.g. hotstart polymerases.
111. Another subject of, the invention are methods according to any of the preceding aspects, wherein amplification and labeling of the nucleic acid chains are achieved during cyclic steps, wherein the used primer are provided in reversibly inactivated form and are activated during the reaction, e.g. hotstart primer.
112. Another subject of the invention are methods according to any of the preceding aspects, wherein amplification and/or labeling of the nucleic acid chains is achieved using a polymerase capable of strand displacement.
113. Another subject of the invention are methods of any of the previously cited aspects in which amplification and/or labeling of the nucleic acid chains is conducted in a reaction mixture comprising one or more proteins and according substrates, which are capable of separation of double stranded form of nucleic acid into single stranded form. For example, ATP dependent helicases can be such proteins.
115. Further object of this application are methods and components for carrying out these methods according to any one of the preceding aspects. where labeled nucleic acid chains are specifically bound to a solid phase.
116. Further object of this application are methods and components for carrying out these methods according to any one of the preceding aspects. where labeled nucleic acid chains are specifically bound to a solid phaseand can be specifically detected.
117. Further object of this application are methods and components for carrying out these methods according to any one of the preceding aspects. where labeled nucleic acid chains are specifically bound to a solid phaseand can be specifically detected through spacial arrangment of the signals
118. Further object of this application are methods and components for carrying out these methods according to any one of the preceding aspects. where labeled nucleic acid chains are specifically bound to a solid phaseand can be specifically detected and further nucleic acid chains not belonging to the target sequences are present in assay.
119 Another subject of the invention are methods of any of the previously cited aspects in which the labeling of the complementary strands of the target sequences with a nuc-macromolecules takes place parallel to the amplification of target sequences, wherein the target sequences belong to different biological organisms selected independently from the group consisting of: viruses, bacteria fungi, unicellular parasites, multicellular parasites, mammals, plants, fish.
120. Another subject of the invention are methods of any of the previously cited aspects where the nucleic acid chain (the target sequence) is a viral nucleic acid sequence or a fragment thereof.
121. Another subject of the invention are methods of any of the previously cited aspects where the nucleic acid chain (the target sequence) is a bacterial nucleic acid sequence or a fragment thereof.
122. Another subject of the invention are methods of any of the previously cited aspects where the nucleic acid chain (the target sequence) is a fungal nucleic acid sequence or a fragment thereof.
123. Another subject of the invention are methods of any of the previously cited aspects where the nucleic acid chain (the target sequence) is a mammal nucleic acid sequence or a fragment thereof.
124. Another subject of the invention are methods of any of the previously cited aspects where the nucleic acid chain (the target sequence) is a plant nucleic acid sequence or a fragment thereof.
125. Another subject of the invention are methods of any of the previously cited aspects where the nucleic acid chain (the target sequence) is a unicellular parasite nucleic acid sequence or a fragment thereof.
126. Another subject of the invention are methods of any of the previously cited aspects where the nucleic acid chain (the target sequence) is a multicellular parasite nucleic acid sequence or a fragment thereof.
127. Another subject of the invention are methods of any of the previously cited aspects to identify or detect the pathogen in the biological materials of human origin.
128. Another subject of the invention are methods of any of the previously cited aspects to identify or detect the pathogen in the biological materials of animal origin.
129. Another subject of the invention are methods of any of the previously cited aspects to identify or detect the pathogen in the biological material of animal origin, wherein animals are selected from the following group: animals (mammals of different species such as cattle, pig, horse, dog, cat, sheep, camels, birds of different kinds, chicken, Trutan, fish of different species).
130. Another subject of the invention are methods of any of the previously cited aspects to identify or detect the pathogen in the biological material of plant origin, wherein the plants are selected from the group consisting of: such wheat, rice, potato, corn, canola, hops, grapes).
131. Another subject of the invention are methods of any of the previously cited aspects to identify or detect malign or abnormal cells in biological material of human or aminal origin.
132. Another subject of the invention are methods of any of the previously cited aspects to identify or detect variation in the nucleic acid sequences in biological material of human origin.
133. Another subject of the invention are methods of any of the previously cited aspects to identify or detect variation in the nucleic acid sequences in biological material of human origin, wherein the target sequences are located within the sequences of receptors, membrane proteins, transcription factors or in their vicinity.
134. Another subject of the invention are methods of any of the previously cited aspects to identify or detect variation in the nucleic acid sequences in biological material of human origin, wherein the methylation pattern are detected.
135. Another subject of the invention are methods of any of the previously cited aspects to identify or detect variation in the nucleic acid sequences in biological material of human origin, wherein the SNPs are detected.
136. Another subject of the invention are methods of any of the previously cited aspects to identify or detect variation in the nucleic acid sequences in biological material of human origin, wherein the mutations (e.g. translocations, delitions, insertions) of the DNA are detected.
137. Another subject of the invention are methods of any of the previously cited aspects to identify or detect of nucleic acid sequences in biological material, wherein genetic segments of organisms accociated with toxin production, or antibiotic resistance are analyzed. Examples of such toxins represent Shiga toxin, Toxic Shok syndrome toxin (TSST), C. dificile toxin. Examples of resistance-associated genes are MecA gene in S. aureus, or beta lactamases.
138. Another subject of the invention are methods of any of the previously cited aspects for quantitative analysis of nucleic acid chain in the biological material, wherein the signal intensity of at least one with the conjugate labeled nucleic acid chain is measured.
139. Another subject of the invention are methods of any of the previously cited aspects for quantitative analysis of nucleic acid chain in the biological material, wherein the signal intensity of at least two with the conjugate labeled nucleic acid chains is measured and these signal intensities are compared with each other.
140. Another subject of the invention are methods of any of the preceding aspects for analysis or detection of nucleic acid sequences in foods.
141. Another subject of the invention are methods of any of the preceding aspects for analysis or detection of nucleic acid sequences in water.
142. Another subject of the invention are nucleotide analogs having a structure: nucleotide linker (X)
wherein (X) is an amino-reactive group
143 Another subject of the invention are nucleotide analogs comprising on the base a linker and a reactive N-Hydroxisuccinimidyl group (NHS-ester) or their derivatives, for (e.g. sulfo-NHS).
144. Another subject of the invention are nucleotide analogs comprising on the base a linker and a reactive Isothiocyanate group or their derivatives.
145. Another subject of the invention are methods for the modification of macromolecules or particles by nucleotides, wherein macromolecules or particles comprise at least one amino group and the modification is carried out with a modified nucleotide having the formula Nucleotide-Linker-(X).
146. Another subject of the invention are methods for the modification of macromolecules or particles by nucleotides, wherein macromolecules are selected from the following group: proteins or derivatives thereof, dendrimers, nucleic acid chains, or derivatives thereof (for example PNA or LNA), oligo-polysaccharides or their derivatives, lipids.
147 Another subject of the application are kits comprising the components to allow to perform inventive method according to previously cited aspects. Such kits comprise conjugates (nuc-macromolecules) according to any of the preceding aspects, and at least one of the following components: buffers, polymerases, dNTPs, primers, control sequences and solid phase.
148 Another subject of the application are kits with components for the manufacturing of novel nuc macromolecules. These components include:
At least a reactive nuc component or nuc-linker component, which can be coupled to the oligonucleotides. For example, components of such a kit are nuc components or Nuc-Linker component (with an amino-reactive group such as an NHS ester, or an isothiocyanate), or a thiol-reactive group (e.g. nuc-components with a maleimide group).
At least one oligonucleotide having a sequence capable of binding specifically to the target sequence
Buffer solutions for the coupling of nuc components to the oligonucleotides

1.5 EXAMPLES OF EMBODIMENTS 1.5.1 General procedure for the labeling reaction
1.5.2 Examples of nucleic acid chain/sample material I target sequences
1.5.3 Examples of solutions
1.5.4 Polymerases for labeling reaction
1.5.5 Primer for the labeling reaction
1.5.6 Target sequence-specific hybridization probes
1.5.7 Nucleotides
1.5.8 Nucleotide compositions
1.5.9 Binding of labeled nucleic acids to the solid phase and detection
1.5.9.1 Use of nuc macromolecules with a uniform anchor domain.
1.5.9.2 Use of nuc macromolecules with different anchor domains.
1.5.9.2.1 Several nuc macromolecules with different specific combinations of target-anchor domains
1.5.9.2.2 Several nuc macromolecules with different specific combinations of nuc component—anchor domain
1.5.9.3 Binding to the solid phase by a sequence specific modified primer
1.5.9.4 Binding to the solid phase by means of a modified hybridization probe
1.5.9.5 Binding to the solid phase by a modified nucleotide
1.5.9.6 Direct binding of the labeled target sequence, or equivalents thereof to the solid phase with attached, addressable, complementary nucleic acid chains
1.5.10 Detection of the bound labeled nucleic acid chains
1.5.10.1 Nuc macromolecules with T-A-S-domains 1.5.10.2 Nuc macromolecules with T-S domains or S domains
1.5.10.3 Sequence specific signaling by a modified primer
1.5.10.4 Signal via a modified hybridization probe
1.5.10.5 Signal via a modified nucleotide
1.5.11 Process variants: use of nuc macromolecules in the labeling reaction
1.5.11.1 Labeling by primer extension
1.5.11.2 Several nuc macromolecules and one target sequence
1.5.11.3 Multiple nucleic acid chains
1.5.10.4 Labeling in several cycles at isothermal vs. cyclic variation of temperature conditions
1.5.10.5 Amplification with labeling
1.5.10.6 Detection of a specific target sequence in a material
1.5.10.7 Examples of the detection of sequence variants in a specific target sequence (distinction of related target sequences, such as SNP detection)
1.5.11 Examples of kits
1.5.12 Other enzymes for the use of nuc macromolecules
1.5.13 Notes for chemical coupling
1.5.14 Examples of synthesis of nuc macromolecules
1.5.15 Examples of enzymatic labeling reactions of target sequences with nuc macromolecules 1.5.1 General Procedure of the Labeling Reaction:

As an example, the labeling of a single stranded DNA with nuc macromolecules can be considered. For a labeling reaction, nucleic acid chains are provided and contacted with a primer, and a polymerase, and at least one kind of nuc macromolecules and incubated under conditions which allow the primer to be extended by the polymerase. Through the incorporation of nuc macromolecules into the growing strand, domains of nuc macromolecules are coupled to those growing strands of nucleic acid chains.

In an advantageous embodiment of the application, the nucleic acid chains are labeled with nuc macromolecules, which comprise at least one target domain specific for the target sequence. This domain binds to the target nucleic acid chain to be labeled at the 3'-side of the primer allowing the nuc macromolecules to bind in a sequence-specific way to the nucleic acid chain to be labeled.

The nuc component of the nuc macromolecule is preferentially chosen so that it is capable of forming a complementary base pair with at least one nucleotide in the target sequence. Such nucleotide is located preferentially in the 3' direction of the hybridized primer, so that a polymerase is capable of incorporation of the nuc component into the growing strand during the extension of the 3' end of the primer.

Due to the high local concentration of the nuc component in the vicinity of the target domain, it is also possible to use a nuc component which does not makes a base-pair with a nucleotide in the target sequence but is incorporated anyway by a polymerase disregarding the proper base pairing.

In a further advantageous embodiment of the application, nucleic acid chains are labeled with nuc macromolecules which comprise at least one target domain, and at least one anchor domain. The anchor domain is able to bind to a binding partner on a solid phase. After a labeling reaction, a solid is provided which comprises such a binding partner. Labeled nucleic acid chains can be specifically bound to this solid phase by incubation with such a solid phase.

In a further advantageous embodiment of the application, nucleic acid chains are labeled with nuc macromolecules which comprise at least one target domain and at least one signal domain. After a labeling reaction, the labeled nucleic acid sequence can be detected based on the specific signal to the signal domain. In the following, individual components of the labeling reaction and examples of their combinations are discussed individually.

1.5.2 Examples of Nucleic Acid Chain/Starting Material/Target Sequences:

Different nucleic acids can be used as a template for the synthesis of complementary strands. Many methods are known to one skilled in the art, how to isolate nucleic acids from the material and to provide a target sequence therefrom. Either DNA or RNA can serve as a template. Using appropriate amplification techniques, target sequences can be provided in sufficiently high concentrations (see the "amplification").

The length of the target sequences, for example, ranges between 20 and 50, 50 and 200, 200 and 500, 500 and 2000, 2000 and 10000, 10000 and 1000000 nucleotides or is over one million nucleotides. Individual segments of a gene or a complete genome can be defined as the target sequence.

Double stranded nucleic acid chains and single stranded nucleic acid chains or mixtures of double and single stranded nucleic acid chains can be provided. In a preferred embodiment of the invention, only one target sequence is provided.

In a further preferred embodiment of the invention, multiple target sequences can be provided. The number of different target sequences ranges preferentially from 2 to 5, 5 to 10, 10 to 20, 20 to 50, 50 to 100, 100 to 500, 500 to 1000, 1000 to 10000, more than 10000.

In a further preferred embodiment of the invention. further control sequences are added to the target sequences in order to control the quality of the analysis. The use of such control sequences is known to an expert.

In a further preferred embodiment of the invention, multiple target sequences are provided, whose number is greater than 1000. For example, such mixture can be a mRNA mixture or a cDNA mixture.

The target sequences can be amplified with different techniques (e.g. PCR, LCR, isothermal amplification, or by TMA (transcription mediated amplification).

The amplification of target sequences can be carried out in solution or on a solid phase.

In one embodiment of the invention, target sequences for a labeling reaction are already provided in an amplified form, for example, as products of a PCR reaction, or an LCR reaction, or an isothermal amplification or plasmids. The nucleic acid chains to be labeled can be provided in single-stranded or double stranded form. Further examples of the amplification of nucleic acids are known to a person skilled in the art.

In one embodiment, the amplification and the labeling of target sequences with nuc macromolecules is conducted in separate reactions.

In a further preferred embodiment, the amplification and the labeling of target sequences with nuc macromolecules in done a single reaction.

Before analysis, target sequences can be preselected using other techniques such as hybridization to microarrays.

The target sequences can be provided in a solution or attached to a solid phase.

The attachment to a solid phase can be covalent or affine. The solid phase can be in the form of, for example, flat surfaces, or beads, or nanoparticles, or gels. The attached target sequences can be used with a solid phase in certain combinations, for example, they can form an array on the solid phase, or the solid phase can comprise coding elements which allow a subsequent assignment of the solid phase and the target sequence. The coding can be done via in color.

In one embodiment of the invention, target sequences are provided in purified form. Several methods and techniques known to a person skilled in the art of how to purify nucleic acid chains (see the "amplification"). In another embodiment, the target sequences can be provided as a part of a sample material, such as blood, secretions, reaction mixture etc. Such materials are often referred to as a biological matrix in which the target sequences to be examined are contained.

Such biological matrix can also comprise other sequences except the target nucleic acid chains. Isolation of target sequences leads often to co-isolation of these non-target sequences. Such nucleic acid chains (non-target sequences) can also be considered as an accompanying nucleic acid chains or contamination. Also by-products of an amplification reaction may represent such contamination.

In one embodiment of the invention, a labeling reaction of target nucleic acid sequences comprises other nucleic acid chains (accompanying nucleic acid chain) which should not be labeled or should not be detected. DNA or RNA from a biological material can be such nucleic acids.

The various combinations of components are shown below.

1.5.3 Examples of Solutions

Usable solutions should allow for an enzymatic incorporation of nucleotides into the growing strand of nucleic acid chains. Aqueous buffer solutions are preferred as solutions for the labeling reaction. Many buffers are commercially available as concentrated form, such 10× concentration, (e.g. from New England Biolabs, Roche Molecular Diagnostics, Abbott, Qiagen, etc.). Suitable buffer substances, for example, Tris, HEPES and phosphate are used. The pH value is typically between 7 and 9, though, many polymerases can also work between pH 5 and 10. Other monovalent cations such as Li (+), Na (+), K(+), NH4 (+) are used in combination with anions such as Cl (−), S04 (2-) often added. Divalent cations such as Mg (2+) or Mn (2+) are added together with anions. Organic additives such as DMSO, glycerol, detergents (e.g. Tween), Betaine, PEG, antioxidants (such as DTT) are also often added to reactions. EDTA is often used in low concentrations to complex heavy metals.

The compositions of the solutions can vary and an optimal concentration of individual components can be adjusted by titration.

The corresponding buffers are preferentially part of a kit for the labeling of target sequences with nuc macromolecules. They are preferentially provided in concentrated or dry form.

1.5.4 Polymerases for Labeling Reaction:

DNA-dependent DNA polymerases, RNA-dependent DNA polymerases (reverse transcriptases), DNA-dependent RNA polymerases and RNA-dependent RNA polymerases can be used for the labeling reaction. Examples of polymerases are shown in the "Terms and Definitions" section.

In a preferred embodiment, polymerases without 3'-5'-exonuclease activity are used. In another preferred embodiment, polymerases with 3'-5'-exonuclease activity are used.

In a preferred embodiment, polymerases without 5'-3'-exonuclease activity are used. In another preferred embodiment, polymerases with 5'-3'-exonuclease activity are used.

In one embodiment, thermally labile polymerase, such as Klenow fragment, are used. In a further embodiment, thermostable polymerases, such as Taq polymerase or Vent polymerase exo minus are used.

So-called hot start polymerases can be used. These are polymerases whose activity is reversibly inactivated by an antibody or by a chemical modification. Such polymerases are activated, for example, by heating.

Mixtures of several polymerases can be used. Such a mixture comprises, for example, polymerases with different substrate properties such as reverse transcriptase and DNA-dependent polymerase, or thermilabile and thermostable enzymes can be combined.

The polymerases can be provided in dissolved form or in dry form. They can be provided with other substances in compositions, for example, for storage, combined with stabilizing substances such as glycerol or PEG. Compositions with polymerases can be provided, which are intended for storage at 4° C. or room temperature, such preparations are commercially available, for example, from GE Healthcare.

In a preferred embodiment of the application, polymerases are provided as constituents of a composition, wherein the said composition is provided in a dry state. The activation of the polymerase can be achieved by the addition of a liquid.

In a preferred embodiment of the application, one or several polymerases or compositions thereof are constituents of a kit and are preferentially provided in concentrated form.

In one embodiment, the same polymerase can be used for the amplification and for the labeling reaction of target sequences.

Appropriate polymerases are preferentially part of a kit for the labeling of target sequences with a nuc macromolecules.

1.5.5 Primer for the Labeling Reaction

In an advantageous embodiment of the invention, at least one oligonucleotide is used as a primer for enzymatic labeling of the target sequences in a reaction. The primer must be accepted by the polymerase used. Examples of oligonucleotides having a primer function are known to those skilled in art.

A primer for the labeling reaction is provided preferentially in the form of DNA. In another embodiment, primer is provided in form of RNA.

The length of the primer is preferentially between 6 and 10, 10 and 15, 15 and 20, 20 and 25, 25 and 30, 30 and 40, 40 and 50, 50 and 100, or even longer than 100 nucleotides. At least a part of the primer sequence can bind to the target sequence to form a double strand, according to Watson-Crick base pairing.

Preferentially this portion of the primer is located at the 3'-end of the primer so that an enzymatic incorporation reaction can take place after the binding of the primer to the target sequence.

In one embodiment, a primer is fully complementary to the target sequence.

Since sequence variants often occur in nature, it can be useful in some applications, if the primer can differ such sequence variants. In a further embodiment, the composition of the primer deviates from the ideal complementary composition with regard to the target sequence so that a mismatch can occur in the vicinity of the 3' end of the primer (such as one or more bases within the primer are not complementary to a target sequence variant). Such mismatch can be used to differentiate between sequence variants.

There are different designs for position of the primer within the target. In one embodiment, the primer is located at one end of the target sequence. In another embodiment, the primer is located within the target sequence. In a further embodiment, at least one target sequence-specific primer pair is used for the amplification and the labeling. In a further embodiment, at least one primer in such a primer pair is labeled with a signal domain. In a further embodiment, at least one primer in such a primer pair is labeled with an anchor domain.

A common primer or a plurality of different primers can be used in an analysis of multiple target sequences.

In a further embodiment, several primers per one target sequence can be used for the labeling reaction, wherein a plurality of primers can be capable of binding to one strand, or both strands of the target sequence. In one embodiment, such a primer mix comprises primer sequences which have similar binding site in the target sequence and can bind different variants of the target sequence through the base variations in the primer compositions. Such primers can be used, for example, for SNP analysis. In another embodiment, such primer mix comprises primer sequences which have different binding sites along the target sequence. Such primers can be used, for example, for multiple labeling of target sequences.

In a further embodiment, a plurality of target sequences is labeled in a labeling reaction with nuc macromolecules, wherein each target sequence is combined with at least one specific primer.

In a further embodiment, a plurality of target sequences is labeled in a labeling reaction with nuc macromolecules, wherein at least one primer can bind to one or several target sequences.

In a further embodiment, uniform primers are used for different target sequences. Examples of such primer sequences are oligo-dT for cDNA synthesis. In another example, a uniform primer binding site can be introduced into all of the target sequences, for example by means of a ligation, for subsequent labeling reaction with a uniform primer.

In one embodiment, the Tm of the primer and the Tm of the target domain of the used nuc macromolecules can be adapted to each other, wherein differences in Tm do not exceed +/−5° C.

In another embodiment, the sequence of the primer (or a pair of primers or a set of primers) is designed in such a way that the Tm of the primer is above the Tm of the target domain of the used nuc macromolecule, wherein the difference exceeds for example 5° C. or even 50° C.

In another embodiment, the sequence of the primer (or a pair of primers or a set of primers) is designed in such a way that the Tm of the primer is below the Tm of the target domain of the used nuc macromolecule, wherein the difference exceeds for example 5° C. or even 50° C.

Individual binding events (primer binding and nuc macromolecule binding) can be controlled by temperature changes in combination with according adjustments in Tm of primers and of target domains of the nuc macromolecules. Since DNA polymerases extend only bound primers, the process of primer extension can also be controlled. The binding of the target domain of the nuc macromolecule to the target sequence favors its incorporation into the primer. Thus, by adjusting the Tm of the target domain to the reaction conditions, the incorporation of nuc macromolecules can also be controlled.

Modifications

In a further embodiment, oligonucleotides with a primer function comprise one or several modifications. Examples of modifications are dyes, haptens (antigens), biotin, are additional oligonucleotide sequences, protein sequences, PNA sequences.

In a further embodiment, a primer comprises at least one anchor domain. In a further embodiment, a primer comprises at least one signal domain. The structures of the anchor domain or signal domain of the primers can be identical with those of the nuc macromolecules or different as well. Examples of modified primers are known to one skilled in the art.

In one embodiment, the primers for the labeling reaction are provided in a solution form.

In a further embodiment, the primers immobilized on a solid phase are provided. The attached primers can be provided in combination with the solid phase, in which a unique association of the primer sequences to determined feature of the solid phase is possible, for example, to a position on the solid phase, for example, if a planar solid phase is used, or a color or a diameter, for example, if beads are used.

In one embodiment, primers for the labeling reaction differ from those used for the amplification of target sequences.

In a further embodiment, the same primers are used for the amplification and the labeling of target sequences.

The corresponding primers are preferentially part of a kit for the labeling of target sequences with nuc macromolecules.

1.5.6 Target Sequence-Specific Hybridization Probes

A hybridization probe is an oligonucleotide which is capable of sequence specific binding to the target sequence.

In one embodiment of the invention, a hybridization probe can comprise a signal domain. Through the specific hybridization of labeled oligonucleotides to the respective target sequence labeled with nuc macromolecules, a signal-giving or signal transmitting molecule can be introduced.

In a further embodiment of the invention, hybridization probes comprising an anchor domain are used. The hybridization probes can be bound to the solid phase via such anchor domain such as hapten, biotin, oligonucleotide. Target sequences labeled with nuc macromolecules can be specifically bound to the solid phase through such oligonucleotides.

1.5.7 Nucleotides

In a preferred embodiment of the application, nuc macromolecules comprising the following components (domains) are used in an enzymatic labeling reaction:

Nuc-linker-(target domain-1)-(anchor domain-1)

Wherein:

Nuc is a nuc component

Linker is a linker component

Target-domain-1 can specifically bind/hybridize to a sequence segment in the target sequence in accordance with Watson-Crick base pairing. Oligonucleotides represent examples of target-domain-1. The structure of the oligonucleotides can be DNA, RNA, PNA, LNA, or morpholino.

Anchor-domain-1 can specifically bind to a binding partner. This binding partner is preferentially attached to a solid phase. Oligonucleotides (such as DNA, RNA, PNA, LNA or morpholino) or haptens (such as dyes) or biotin provide examples of anchor-domain-1. The respective binding partner attached to the solid phase can be, for example, oligonucleotides, antibodies, or streptavidin.

In a preferred embodiment of the application, several different kinds of nucmacromolecules comprising the following components (domains) are used in an enzymatic labeling reaction:

Nuc-linker-(target domain-n)-(anchor domain-n)

Wherein:

Nuc is a nuc component

Linker is a linker component

Target-domains-n can specifically bind/hybridize to a sequence segment in the target sequence in accordance with Watson-Crick base pairing. The number of target domains (n) corresponds to the number of target sequences to be labeled.

Anchor-domains-n can specifically bind to the respective binding partner. These binding partners are preferentially attached to a solid phase. The number of anchor-domains (n) corresponds to the number of target sequences to be labeled.

The respective anchor domains are distinctly specific for the respective target domains.

In a preferred embodiment of the application, several different kinds of nuc macromolecules comprising the following components (domains) are used in an enzymatic labeling reaction:

Nuc-linker-(target domain-1)-(anchor domain-n)

Wherein:

Nuc is a nuc component

Linker is a linker component

Target-domain-1 can specifically bind/hybridize to a sequence segment in the target sequence in accordance with Watson-Crick base pairing.

Anchor-domains-n can specifically bind to the respective binding partner. These binding partners are preferentially bound to a solid phase. The number of anchor-domains (n) is in the range between 2 and 100 and corresponds to the number of target sequences to be labeled.

The target domain is uniform and is combined with the respective distinctly specific anchor domain.

In a preferred embodiment of the application, several different kinds of nuc macromolecules comprising the following components (domains) are used in an enzymatic labeling reaction:

Nuc-linker-(target domain-n)-(anchor domain-1)

Wherein:

Nuc is a nuc component

Linker is a linker component

Target-domains-n can specifically bind/hybridize to a sequence segment in the target sequence in accordance with Watson-Crick base pairing. The number of target-domains (n) corresponds to the number of target sequences to be labeled.

Anchor-domain-1 can specifically bind to the respective binding partner. These binding partners are preferentially bound to a solid phase, The anchor domain is uniform and is combined with the respective distinctly specific target domain.

In a preferred embodiment of the application, several different kinds of nuc-macromolecules are used in an enzymatic labeling reaction, wherein at least two kinds of nuc macromolecules are selected from the following group:

Nuc-linker-(target domain-1)-(anchor domain-1)

Nuc-linker-(target domain-n)-(anchor domain-n).

Nuc-linker-(target domain-1)-(anchor domain-n)

Nuc-linker-(target domain-n)-(anchor domain-1)

In a further preferred embodiment of the application, nuc macromolecules comprising the following components are used:

Nuc-linker-(target domain-1)-(signal-domain-1)

Wherein:

Wherein:

Nuc is a nuc component

Linker is a linker component

Target-domain-1 can specifically bind/hybridize to a sequence segment in the target sequence in accordance with Watson-Crick base pairing. Oligonucleotides represent examples of target-domain-1. The structure of the oligonucleotides can be DNA, RNA, PNA, LNA, or morpholino.

Signal-domain-1 can be identified through a distinctly specific signal, for example, a fluorescent signal, or it enables the binding of a further signal-generating partner (e.g. oligonucleotide or hapten or biotin). The respective signal-generating binding partner can be, for example, labeled oligonucleotides, labeled antibodies, or labeled streptavidin.

In a preferred embodiment of the application, several different kinds of nuc macromolecules comprising the following components (domains) are used in an enzymatic labeling reaction:

Nuc-linker-(target domain-n)-(signal-domain-n)

Wherein:

Nuc is a nuc component

Linker is a linker component

Target-domains-n can specifically bind/hybridize to a sequence segment in the target sequence in accordance with Watson-Crick base pairing. The number of target-domains (n) corresponds to the number of target sequences to be labeled.

Signal-domain-n can be differentiated through a distinctly specific signal. The number of signal-domains (n) corresponds to the number of target sequences to be labeled.

The respective signal domains are distinctly specific for the respective target domains.

In a preferred embodiment of the application, several different kinds of nuc-macromolecules comprising the following components (domains) are used in an enzymatic labeling reaction:

Nuc-linker-(target domain-1)-(signal domain-n)

Wherein:

Nuc is a nuc component

Linker is a linker component

Target-domain-1 can specifically bind/hybridize to a sequence segment in the target sequence in accordance with Watson-Crick base pairing.

Signal-domain-n can be differentiated through a distinctly specific signal. The number of signal-domains (n) can be in the range between 2 and 100.

The target domain is uniform and is combined with the respective specific signal domains.

In a preferred embodiment of the application, several different kinds of nuc-macromolecules comprising the following components (domains) are used in an enzymatic labeling reaction:

Nuc-linker-(target domain-n)-(signal-domain-1)

Wherein:

Nuc is a nuc component

Linker is a linker component

Target-domain-1 can specifically bind/hybridize to a sequence segment in the target sequence in accordance with Watson-Crick base pairing. The number of target-domains (n) corresponds to the number of target sequences to be labeled.

Signal-domain-1 can be identified through a distinctly specific signal (e.g. a fluorescent signal) or it enables the binding of a further signal-generating partner.

The signal domain is uniform and is combined with the respective specific target domains.

In a preferred embodiment of the application, several different kinds of nuc-macromolecules are used together in an enzymatic labeling reaction, wherein at least two kinds of nuc macromolecules are selected from the following group:

Nuc-linker-(target domain-1)-(signal domain-1)

Nuc-linker-(target domain-n)-(signal domain-n).

Nuc-linker-(target domain-1)-(signal domain-n)

Nuc-linker-(target domain-n)-(signal domain-1)

In a further preferred embodiment of the application, nuc macromolecules are used, which comprise the following components (domains):

Nuc-linker-(target domain-1)-(anchor-domain-1)-(signal-domain-1)

Wherein:

Nuc is a nuc component

Linker is a linker component

Target-domain-1 can specifically bind hybridize to a sequence segment in the target sequence in accordance with Watson-Crick base pairing. Oligonucleotides represent examples of target-domain-1. The structure of the oligonucleotides can be DNA, RNA, PNA, LNA, or morpholino.

Signal-domain-1 can be identified through a distinctly specific signal, for example a fluorescent signal, or it enables the binding of a further signal-generating partner (e.g. oligonucleotide or hapten or biotin). The respective signal-generating binding partners can be, for example, labeled oligonucleotides, labeled antibodies, or labeled streptavidin.

Anchor-domain-1 can specifically bind to the respective binding partner. This binding partner is preferentially bound to a solid phase. Oligonucleotides (such as DNA, RNA, PNA, LNA or morpholino) or haptens (such as dyes) or biotin provide examples of anchor-domain-1. The respective binding partner attached to the solid phase can be, for example, oligonucleotides, antibodies, or streptavidin.

In a further preferred embodiment of the application, several different kinds of nuc macromolecules are used in enzymatic labeling reactions, which comprise the following components (domains):

Nuc-linker-(target domain-n)-(anchor-domain-n)-(signal-domain-n)

Wherein:

Nuc is a nuc component

Linker is a linker component

Target-domains-n can specifically bind/hybridize to a sequence segment in the target sequence in accordance with Watson-Crick base pairing. The number of the target-domains-n corresponds to the number of the target sequences which are supposed to be labeled.

Anchor-domains-n can specifically bind to the respective binding partner. These binding partners are preferentially bound to a solid phase. The number of the anchor-domains-n corresponds to the number of the target sequences which are supposed to be labeled.

Each of the signal-domain-n can have a distinctly specific signal property. The number of the signal-domains-n corresponds to the number of the target sequences which are supposed to be labeled.

The respective signal-domains and anchor-domains are specific for the respective target domains.

In one embodiment, non-labeled nucleotides, for example, dNTPs (dATP, dCTP, dTTP, dGTP, or analogs thereof, such as 7-deaza-dATP), NTPs (ATP, GTP, CTP, UTP, or analogues thereof) are used in addition to nuc macromolecules in a labeling reaction for extension of the growing nucleic acid strand.

In another embodiment, conventionally labeled nucleotides, such as dUTP-biotin, fluorescein-dUTP, dCTP-Cy3, are used for labeling of the growing nucleic acid strand in addition to nuc macromolecules.

The nuc-macromolecules, dNTPs and conventionally modified nucleotides can be used in different combinations and compositions. Such compositions are preferentially components of kits. Below, some of advantageous compositions are presented.

1.5.8 Compositions of Nucleotides

Compositions including one or several different types of nuc macromolecules without further nucleotides, e.g. without dNTP or NTP).

The labeling of nucleic acid chains occurs through the incorporation of nuc components of nuc macromolecules at the 3' end of the primer opposite the complementary bases in the target sequence.

Compositions, including one or more different types of nuc macromolecules and a set of nucleotides, which allow a complete synthesis of nucleic acid chains, such as 4×dNTP or 4×NTP. Natural substrates for polymerases such as dNTP (dATP, dCTP, dGTP and dTTP) and their analogues can be used. These analogues may include modifications at the base such as dITP and dUTP or sugar modifications such as ddNTP or 3'-amino-3'-deoxy-NTP or phosphate modifications such as alpha-thio-dNTPs or tetraphosphates. Due to the use of dNTP, a primer extension can occur so that a complementary strand to the target sequence can be synthesized.

Simultaneously, an incorporation of nuc components of nuc macromolecules occurs at the 3' end of the growing strand opposite complementary bases in the target sequence, which results in a labeling of the nucleic acid chains. The extent and the specificity of the labeling of the nucleic acid chains can be influenced by the varying of the concentrations and ratios between nuc macromolecules and dNTPs; see below.

Compositions, including one or more different types of nuc macromolecules and a set of nucleotides, which allows for only incomplete, limited primer extension such as only one or two or three dNTP or NTP. Natural substrates for polymerases such as dNTP (dATP, dCTP, dGTP and dTTP) and their analogues can be used. These analogues may include modifications at the base such as dITP and dUTP or sugar modifications such as ddNTP or 3'-amino-3'-deoxy-NTP or phosphate modifications such as alpha-thio-dNTPs or tetraphosphates. Due to the use of dNTP, a primer extension can occur so that a complementary strand to the target sequence can be synthesized.

Simultaneously, an incorporation of nuc components of nuc macromolecules occurs at the 3' end of the growing strand opposite complementary bases in the target sequence, which results in a labeling of the nucleic acid chains. The extent and the specificity of the labeling of the nucleci acid chains can be influenced by the varying of the concentrations and ratios between nuc macromolecules and dNTPs; see below. The length of the synthesized complementary strand can be controlled by limiting the composition of the dNTP set.

Compositions, including one or more different types of nuc macromolecules and a set of nucleotides, which allow a complete synthesis of nucleic acid chains, such as 4×dNTP or 4×NTP, and one or several conventially labeled nucleotides. Natural substrates for polymerases such as dNTP (dATP, dCTP, dGTP and dTTP) and their analogues can be used. These analogues include modifications at the base such as dITP and dUTP or sugar modifications such as ddNTP or 3'-amino-3'-deoxy-NTP or phosphate modifications, such as alpha-thio-dNTPs or tetraphosphates. Conventionally labeled nucleotides can be used as modified nucleotides, which include, for example a dye or a fluorescent dye or an affinity moiety, such as Cy3, Rhodamine, Alexa dyes, or Atto-dyes, or biotin, or digoxigenin. Due to the use of dNTP, a primer extension can occur so that a complementary strand to the target sequence can be synthesized.

Simultaneously, an incorporation of nuc components of nuc-macromolecules occurs at the 3' end of the growing strand opposite complementary bases in the target sequence, which results in a labeling of the nucleic acid chains. The extent and the specificity of the labeling of the nucleic acid chains can be influenced by the varying of the concentrations and ratios between nuc macromolecules and dNTPs; see below A non-specific labeling of nucleic acid chains with dyes, fluorescent dyes or affinity moieties can take place due to the use of modified nucleotides.

In a preferred embodiment, nuc macromolecules are used alone or together with other nucleotides (see above) in an aqueous buffer solution. Nuc macromolecules can be used as components of kits in dissolved form (for example provided as a concentrated solution) or in dry form. The dried substances can be dissolved in a reaction mixture immediately before the test with an aqueous solution or an organic solution, for example DMSO.

In a further preferred embodiment, nuc macromolecules are attached to a solid phase. The attachment is carried out in a way, which allows the target domain of the nuc macromolecules not to lose its ability for specifically hybridization to the target sequences, and to retain the substrate property for polymerases. In one embodiment, the attachment is done in a way, which allows a specific identification of the individual types of nuc macromolecules on a solid phase. For example, such identification can be achieved by a spatial arrangement of the solid phase, similar to a DNA microarray.

Hereinafter, embodiments are described which provide nuc macromolecules in an aqueous buffer solution. Ratios of concentrations of nuc macromolecules and unlabeled nucleotides (such as dNTP) can be adapted so that nuc macromolecules can be incorporated by polymerases. Advantageous embodiments of the method include the following conditions and ranges between them:

Ratios of concentration of nuc macromolecule and not labeled nucleotides (e.g. dNTP) compriese for example the following ranges: 1:100000000 to 1:10000000; 1:10000000 to 1:1000000; 1:1000000 to 1:100000; 1:100000 to 1:10000; 1:10000 to 1:1000; 1:1000 to 1:100; 1:100 to 1:10; 1:10 to 1:1; 1:1 to 10:1; 10:1 to 100:1; 100:1 to 1000:1; 1000:1 to 10000:1.

By changing the ratios of concentrations, it is possible to influence the portion of the nucleic acid chain which is labeled in an approach and which remains unlabeled due to incorporation of non labeled nucleotides (e.g. dNTP) instead of a nuc macromolecule.

Nuc macromolecules can be incorporated by a polymerase in the absence of non-labeled nucleotides (e.g. dNTP) of the same kind both sequence-specifically and sequence-unspecifically. The target sequence-specificity is favored by the target domain of a nuc macromolecule. The presence of the dNTP of the same base type as the base type of the nuc component causes natural nucleotides and nuc components of the nuc macromolecule to compete for the incorporation. The target-sequence-non-specific incorporation of nuc macromolecules can be competetively suppressed by dNTP at increasing concentrations of dNTP. This can be achieved for example by the use of concentrations of natural nucleotides in the range from 1 to 100 μmol/l. At still higher concentrations of natural nucleotides, the sequence-specific incorporation of nuc macromolecules can also be suppressed; this can be achieved for example by the use of concentrations in the range from 100 μmol/l to 100 mmol/l.

The concentrations of nuc macromolecules and unlabeled nucleotides can range between 10 pmol/l and 100 mmol/l. Particularly preferred ranges are between 100 nmol/l and 1 mmol/l. Even more preferred, concentration ranges are between 100 nmol/l and 100 μmol/l.

Preferentially, the absolute concentrations of nuc macromolecules in a reaction are in the following ranges (concentrations for nuc macromolecules): 10 pmol/l to 10 nmol/l, 10 nmol/l to 100 nmol/l, 100 nmol/l to 1 μmol/l, 1 μmol/l to 10 μmol/l, 10 μmol/l to 100 μmol/l, 100 μmol/l to 1 mmol/l. Concentrations of non-labeled nucleotides: 10 nmol/l to 100 nmol/l, 100 nmol/l to 1 μmol/l, 1 μmol/l to 10 μmol/l, 10 μmol/l to 100 μmol/l, 100 μmol/l to 1 mmol/l, higher than 1 mmol/l.

Since more natural or modified nucleotides (for example lebelled with a dye or biotin) can be used, their concentration is preferentially in the following ranges: 10 nmol/l to 100 nmol/l, 100 nmol/l to 1 μmol/l, 1 μmol/l to 10 μmol/l, 10 μmol/l to 100 μmol/l, 100 μmol/l to 1 mmol/l, 1 mmol/l to 100 mmol/l. In detail, a titration should be carried out to achieve an optimal labeling.

Concentrations of individual nucleotide species (nuc-macromolecules, dNTP, conventionally labeled nucleotides and other nuc macromolecules) can be individually adjusted in a reaction mixture. When using multiple nuc macromolecules, their concentrations and concentration ratios can be adjusted according to requirements of the analysis.

In one embodiment, a composition of nuc macromolecules and other components of the test (for example such as primers and dNTPs) is assembled in such way, that in case of an occurring labeling reaction the nuc macromolecules are consumed as completely as possible. The concentration of nuc macromolecules in the reaction solution ranges for example between 10 pmol/l to 1 nmol/l, 1 nmol/l to 10 nmol/l, 10 nmol/l to 100 nmol/l, 100 nmol/l to 300 nmol/l, 300 nmol/l to 1 μmol/l, 1 μmol/l to 10 μmol/l.

Addition of individual reagents (primers, nucleotides, polymerase, and optionally also other reagents) can be done in one step or can be distributed over a number of individual steps. For example, nuc macromolecules can be provided already at the begin of the labeling reaction in a particular test. The individual reagents can be provided in dried or concentrated form as a pre-mixed composition, for example, dNTP and nuc macromolecules are premixed at a fixed ratio. By adding a solution with target sequences to such provided mixture, the components are dissolved in the reaction solution to allow a labeling reaction.

The nucleotide compositions comprising nuc macromolecules are preferentially components of a kit.

1.5.9 Binding of Labeled Nucleic Acids to the Solid Phase and Detection

In a preferred embodiment of the invention, the binding of labeled target sequences to a solid phase follows a labeling reaction of target sequences with nuc macromolecules. Subsequently, a detection of the binding of the target sequences to the solid phase is conducted.

Detection and differentiation of labeled target sequences can be achieved through the use of nuc macromolecules with target-sequence-specific combinations of nuc components, target domains, anchor domains, and signal domains. This detection and differentiation can be achieved through the binding to the solid phase or through binding to different positions on the solid phase or further characterized by different signal characteristics, such as light properties of the signal domain.

Specific features of nuc macromolecules such as specific signal, specific binding behavior on the solid phase, and specific binding to the target sequence can be combined with specific features (signaling, binding to the solid phase, binding to the target sequence) of the other reaction partner. For example, signal domains or anchor domains can be coupled to primers (modified primers), hybridization probes, or modified nucleotides.

In a preferred embodiment, signal properties and binding properties with regard to the solid phase are distributed among several different assay participants in a particular assay, for example to nuc macromolecules, primers, further nucleotides, and hybridization probes.

In one embodiment, nuc macromolecules with at least one anchoring domain in combination with a target domain are preferentially used in combination with at least one labeled primer, which has signal-emitting or signal-transmitting properties (e.g. the primer is coupled to a signal domain). In another embodiment, nuc macromolecules with one or more anchor domains in combination with a target domain are preferentially used in combination with labeled nucleotides which have signaling or signal-transmitting properties. In another embodiment, nuc macromolecules with one or more anchor domains in combination with a target domain are preferentially used in combination with at least one labeled hybridization probe which has signaling or signal-transmitting properties (e.g. the hybridization probe is coupled with a signal domain).

In one embodiment, nuc macromolecules with one or more signal domains in combination with a target domain are preferentially used in combination with at least one modified primer which can bind to the solid phase in a specific way (for example, an anchor domain is coupled to the primer). In a further embodiment, nuc macromolecules with one or more signal domains in combination with a target domain are preferentially used in combination with labeled nucleotides which can specifically bind to the solid phase, for example other nuc macromolecules or biotin-carrying conventional nucleotides. In a further embodiment, nuc macromolecules with one or more signal domains in combination with a target domain are preferentially used in combination with at least one labeled hybridization probe which can specifically bind to the solid phase (e.g. an anchor domain is coupled to the hybridization probe).

In one embodiment, nuc macromolecules with one or more anchor domains (such as anchor domain 1) in combination with a target domain are preferentially used in combination with at least one modified primer which can bind to the solid phase in a specific way (for example an anchor domain 2 is coupled to the primer), wherein the anchor domain 1 of the nuc macromolecule differs from anchor domain 2 of the primer with regard to binding properties). In a further embodiment, nuc macromolecules with one or more anchor domains (such as anchor domain 1) in combination with a target domain are preferentially used in combination with labeled nucleotides which can specifically bind to the solid phase such as other macromolecules with a nuc anchor domain 2. In a further embodiment, nuc macromolecules with one or more anchor domains (such as anchor domain 1) in combination with a target domain are preferentially used in combination with at least one labeled hybridization probe which can specifically bind to the solid phase (e.g. anchor domain 2 is coupled to the hybridization probe). Anchor domains 1 and 2 differ with regard to their binding properties.

In one embodiment, nuc macromolecules with at least one anchor domain but without a target domain are preferentially used in combination with at least one labeled primer which has signal-emitting or signal-transmitting properties (such primer is coupled to a signal domain). In another embodiment, nuc macromolecules with one or more anchor domains but without a target domain are preferentially used in combination with labeled nucleotides having the signaling or signaling-transmitting properties. In another embodiment, nuc macromolecules with one or more anchor domains but without a target domain are preferentially used in combination with at least one labeled hybridization probe having signaling or signal-transmitting properties (e.g. hybridization probe is coupled to a signal domain).

In one embodiment, nuc macromolecules with one or more signal domains, but without a target domain are preferentially used in combination with at least one labeled primer capable of binding to the solid phase in a specific way (for example an anchor domain is coupled to the primer). In a further embodiment, nuc macromolecules with one or more signal domains, but without a target domain are preferentially used in combination with labeled nucleotides which can specifically bind to the solid phase, for example other nuc macromolecules. In a further embodiment nuc macromolecules with one or more signal domains but without a target domain are preferentially used in combination with at least one labeled hybridization probe which can specifically bind to the solid phase (e.g. an anchor domain is coupled to the hybridization probe).

In one embodiment, nuc macromolecules with one or more anchor domains (such as anchor domain 1) but without a target domain are preferentially used in combination with at least one labeled primer which can bind to the solid phase in a specific way (e.g. an anchor domain-2 is coupled to the primer). In a further embodiment, nuc macromolecules with one or more anchor domains (such as anchor domain 1) but without a target domain are preferentially used in combination with labeled nucleotides which can specifically bind to the solid phase, for example other macromolecules with a nuc-anchor domain-2. In a further embodiment, nuc macromolecules with one or more anchor domains (such as anchor domain 1) but without a target domain are preferentially used in combination with at least one labeled hybridization probe which can specifically bind to the solid phase (e.g. an anchor domain-2 is coupled to the hybridization probe).

In one embodiment, the provided solid phase and the anchor domain represent together a specific combination, in which the solid phase and anchor domain both comprise components which are capable of a specific affinity binding. Examples for such specific combinations are known. Linkages between antigen and antibody, biotin-streptavidin (or Biotin-Avidin), oligonucleotide-oligonucleotide (as a DNA, RNA, PNA, LNA, etc.) aptamer-transmitted binding, sugar molecules and lectins are preferentially used. Particularly preferred are the biotin-streptavidin, antigen-antibody, oligonucleotide-oligonucleotide binding and binding via aptamers because a variety of binding combinations can be achieved due to variations in binding partners such as for example sequences of oligonucleotides. Other examples of an anchor domain for nuc macromolecules, modified primers, hybridization probes are described in section "Definitions and Terminology". I The binding partners of the anchor domains are preferentially bound to a solid phase. Examples of such solid phases include beads or wells (for example, a microtiter plate), or reagent vessels, or a microfluidic chamber, or strips or LFD ("lateral flow device") with a reaction field. Further examples of solid phases are known to one skilled in the art.

Some examples of methods for labeling of target sequences and its subsequent binding to the solid phase are presented in FIGS. 6 to 15.

An example of a labeling method for a target sequence or its equivalents with a subsequent binding to the solid phase is shown in FIG. 6. The following components are provided (FIG. 6A): one type of nuc macromolecules (1-4 in FIG. 6) with a target domain and an anchor domain, a single-stranded target sequence (7 in FIG. 6), one primer labeled with a signal domain (6 and 9 in FIG. 6), a DNA polymerase, and further nucleotides such as dNTPs. These components are incubated under conditions that allow the polymerase to incorporate dNTPs and nuc macromolecules into the growing strand (FIG. 6B). A solid phase (12 in FIG. 6) which provides a binding partner (11 in FIG. 6) for the anchor domain is provided.

The labeling reaction is preferentially designed in such a way that nuc macromolecules are incorporated as completely as possible. If an excess of nuc macromolecules should be used, labeled nucleic acid chains can be purified of excess free nuc macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc macromolecule (13 in FIG. 6). The detection is done via the signal domain of the primer.

A further example of a labeling method for a target sequence or its equivalents with a subsequent binding to the solid phase is shown in FIG. 7. The following components are provided: one type of nuc macromolecules (1-4 in FIGS. 7A and 7B) with a target domain, an anchor domain (4a in FIG. 7A), and an antagonist of the anchor domain (4b in FIG. 7A). Further components such as single-stranded target sequence, one primer labeled with a signal domain, a DNA polymerase, and further nucleotides such as dNTPs (FIG. 7B) are provided.

The anchor domain and its antagonist are separated by the binding of the target domain to the target sequence. After the incorporation of the nuc component into the growing strand, this state is fixed. In this embodiment of the method, polymerases that show little or no exonuclease activity and no or very little "strand-displacement" activity are preferentially used. In another embodiment, a nuc component which leads to a termination in the synthesis is used; for example, a nuc component comprises ddNTP (such as ddUTP or ddCTP). These components are incubated under conditions that allow the polymerase to incorporate the dNTPs and nuc macromolecules into the growing strand (FIG. 7C).

A solid phase which comprises a binding partner for the anchor domain is provided.

After the incorporation reaction, an incubation of the labeled target sequences or their equivalents with the solid phase is conducted under conditions which permit the specific binding of the anchor domain of incorporated nuc macromolecules to the immobilized binding partner. Preferentially, the anchor domains of the un-incorporated nuc macromolecules are blocked by their antagonists under these conditions. The labeled target sequence binds to the solid phase via the anchor domain of the incorporated nuc macromolecule. The detection reaction is achieved by means of the signal domain of the primer. The non-incorporated, free nuc macromolecules do not interfere with the binding of labeled target sequences because their anchor domains are blocked by the antagonists.

Figure 8:
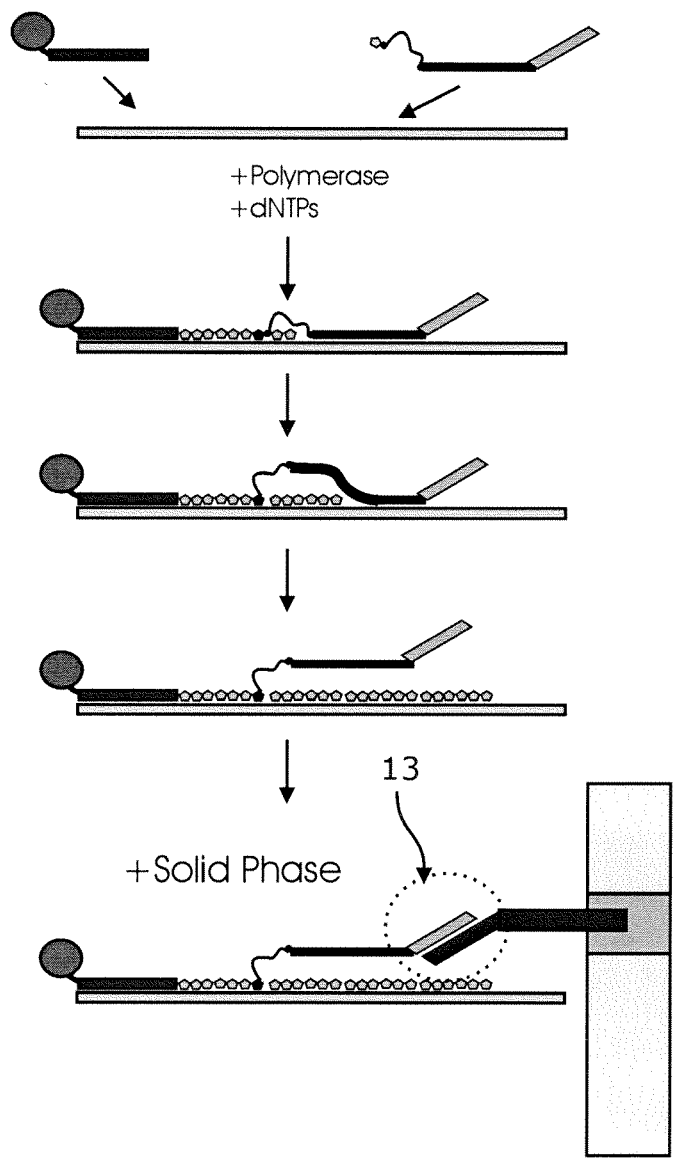
FIG. 8 shows a further example of a labeling method for a target sequence or its equivalents with a subsequent specific binding (13) to the solid phase. The incorporated nucleotide conjugate is displaced from the template during the synthesis reaction by the strand displacing activity of the polymerase. The incorporated nucleotide conjugate comprises an anchor domain and extended primer comprises a detectable signal domain.

A further example of a labeling method for a target sequence or its equivalents with a subsequent binding to the solid phase is shown in FIG. 8. The following components are provided: one type of nuc macromolecules with a target domain and an anchor domain, a single-stranded target sequence, one primer coupled with a signal domain, a DNA polymerase, and further nucleotides such as dNTPs. These components are incubated under conditions that allow the polymerase to incorporate dNTPs and nuc-macromolecules into the growing strand. A polymerase which has a "strand displacement" activity is used. A solid phase which comprises a binding partner for the anchor domain is provided. The labeling reaction is preferentially conducted in such a way that nuc-macromolecules are incorporated as completely as possible. If an excess of nuc-macromolecules should be used, labeled nucleic acid chains can be purified from nuc-macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc-macromolecule. Since the polymerase is able to displace the target domain of the nuc-macromolecules, several nuc macromolecules can be incorporated into the same growing strand. The detection is done via the signal domain of the primer.

A further example of a labeling method for a target sequence or its equivalents with a subsequent binding to the solid phase is shown in FIG. 9. The following components are provided: one type of nuc macromolecules with a target domain and an anchor domain, a single-stranded target sequence, a primer, a DNA polymerase, and further nucleotides such as dNTPs and one kind of labeled nucleotides such as nuc-macromolecules having a signal domain or conventionally labeled nucleotides such as dUTP-16-biotin or Cy3-dCTP. These components are incubated under conditions that allow the polymerase to incorporate dNTPs and nuc-macromolecules into the growing strand. A polymerase which has a "strand-displacement" activity is used. A solid phase which comprises a binding partner for the anchor domain is provided. The labeling reaction is preferentially conucted in such a way that nuc-macromolecules are incorporated as completely as possible. If an excess of nuc macromolecules should be used, labeled nucleic acid chains can be purified from nuc macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc macromolecule. Since the polymerase is able to displace the target domain of the nuc macromolecules, several nuc macromolecules and several nucleotides labeled with the signal domain can be incorporated into the same growing strand.

Figure 10:
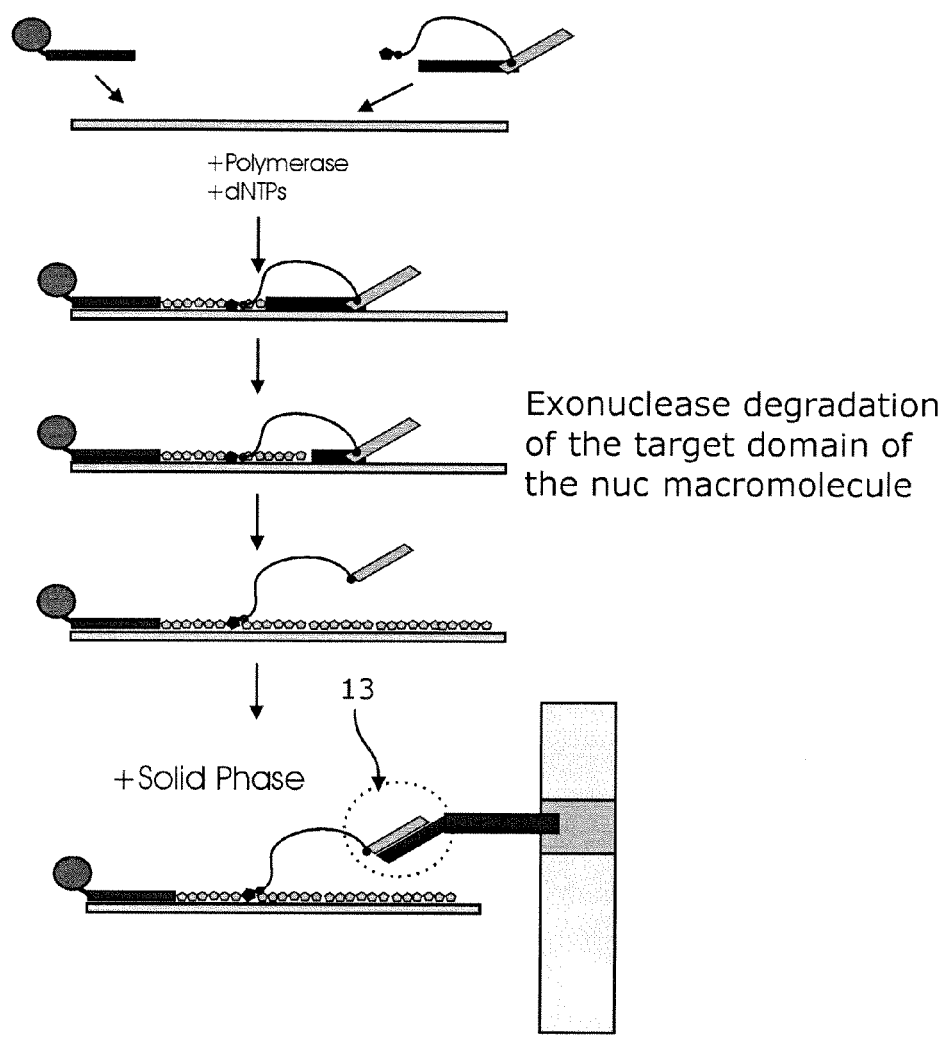
FIG. 10 depicts a further example of a labeling method for a target sequence or its equivalents with a subsequent specific binding (13) to the solid phase. Parts of the incorporated nucleotide conjugate are digested by nuclease activity of the polymerase.

A further example of a labeling method for a target sequence or its equivalents with a subsequent binding to the solid phase is shown in FIG. 10. The following components are provided: one type of nuc macromolecules with a target domain and an anchor domain, a single-stranded target sequence, one primer labeled with a signal domain, a DNA polymerase having a 5-3 exonuclease activity, and further nucleotides such as dNTPs. The linker component is linked not to the target domain, but instead to an other part of the marker, e.g. to the anchor domain of the marker. These components are incubated under conditions that allow the polymerase to incorporate dNTPs and nuc macromolecules into the growing strand. During the reaction, the target domain of the nuc macromolecule bound to the target sequence is degradated while the reaction proceeds (FIG. 10). A solid phase which comprises a binding partner for the anchor domain is provided. The labeling reaction is preferentially conducted in such a way that nuc-macromolecules are incorporated as completely as possible. If an excess of nuc-macromolecules should be used, labeled nucleic acid chains can be purified from nuc-macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc macromolecule. Since the polymerase is able to degrade the target domain of the nuc macromolecule, multiple nuc macromolecules can be incorporated into the same growing strand. The detection reaction is done via the signal domain of the primer.

An example is shown in FIGS. 11 and 12 demonstrating a possible design for a reaction to test a particular solution for presence of a target sequence. In the process shown in FIG. 11, the target sequence with the newly synthesized complementary strand is attached directly to the solid phase. In the method illustrated in FIG. 12, a separation of the double strand is included. A strand separation can result in a further increase of the specificity of the analysis.

A further example of a labeling method for a target sequence or its equivalents with a subsequent binding to the solid phase is shown in FIG. 13. The following components are provided: one type of nuc macromolecules with a target domain, an anchor domain and a signal domain, a single-stranded target sequence, a primer, a DNA polymerase, and further nucleotides such as dNTPs. These components are incubated under conditions that allow the polymerase to incorporate dNTPs and nuc-macromolecules into the growing strand (FIG. 13B). A solid phase which comprises a binding partner for the anchor domain is provided. The labeling reaction is preferentially conducted in such a way that nuc-macromolecules are incorporated as completely as possible. If an excess of nuc-macromolecules should be used, labeled nucleic acid chains can be purified from nuc-macromolecules by a known method. The labeled target sequences or their equivalents are incubated with the solid phase under conditions which permit the specific binding of the anchor domain to the immobilized binding partner. The labeled target sequence binds to the solid phase via the anchor domain of the incorporated nuc macromolecule. The detection reaction is done by the signal domain of the nuc macromolecule.

A further example of a labeling method for a target sequence or its equivalents with a subsequent binding to the solid phase is shown in FIG. 14. The following components are provided: one type of nuc macromolecule with a target domain and a signal domain, a single-stranded target sequence, a primer with an anchor domain, a DNA polymerase, and further nucleotides such as dNTPs. These components are incubated under conditions that allow the polymerase to incorporate dNTPs and nuc-macromolecules into the growing strand (FIG. 14B). A solid phase which comprises a binding partner for the anchor domain is provided. The labeling reaction is preferentially conducted in such a way that nuc-macromolecules are incorporated as completely as possible. If an excess of nuc-macromolecules should be used, labeled nucleic acid chains can be purified from nuc-macromolecules and labeled primers by a known method. The labeled target sequences or their equivalents are incubated with the solid phase under conditions which permit the specific binding of the anchor domain to the immobilized binding partner. The labeled target sequence binds to the solid phase via the anchor domain of the primer. The detection is done via the signal domain of the nuc macromolecule.

A further example of a labeling method for a target sequence or its equivalents with a subsequent binding to the solid phase is shown in FIG. 15. The following components are provided: one type of nuc macromolecule with a target domain and the anchor domain-1, a single-stranded target sequence, a primer with the anchor domain-2, a DNA polymerase, and further nucleotides such as dNTPs. These components are incubated under conditions that allow the polymerase to incorporate dNTPs and nuc-macromolecules into the growing strand (FIG. 15B). The first solid phase (solid phase-1) which comprises a binding partner for the anchor domain-1 of the nuc-macromolecule is provided, as well as the second solid phase (solid phase-2) which comprises a binding partner for the anchor domain-2 of the primer is provided. Both solid phases are provided, for example, as particles in an aqueous suspension. The labeling reaction is preferentially conducted in such a way that nuc-macromolecules are incorporated as completely as possible. If an excess of nuc-macromolecules should be used, labeled nucleic acid chains can be purified from nuc macromolecules and labeled primers by a known method. The labeled target sequences or their equivalents are incubated with both solid phases under conditions that allow the specific binding of the both anchor domains to the respective immobilized binding partner.

The labeled target sequence binds to both phase via the anchor domains. The detection reaction is done through the visual perception of the binding of the two solid phases to each other such as an agglutination.

In a further embodiment of the invention, a plurality of binding partners are attached to a solid phase in a spatial arrangement so that a correlation of particular binding partner to a specific position on the solid phase can be achieved. Individual components of a solid phase are combined to form an array. Microtiter plates or their analogs, BeadArrays, are examples of such arrays. Further examples of such solid phases are microarrays, bead arrays, western blot strips, "Lateral Flow Devices," and membrane arrays set with multiple reaction fields. Some examples of solid phases with one or more binding partners are described in the section "Terms and Definitions," and will be known to an expert.

Figure 16:
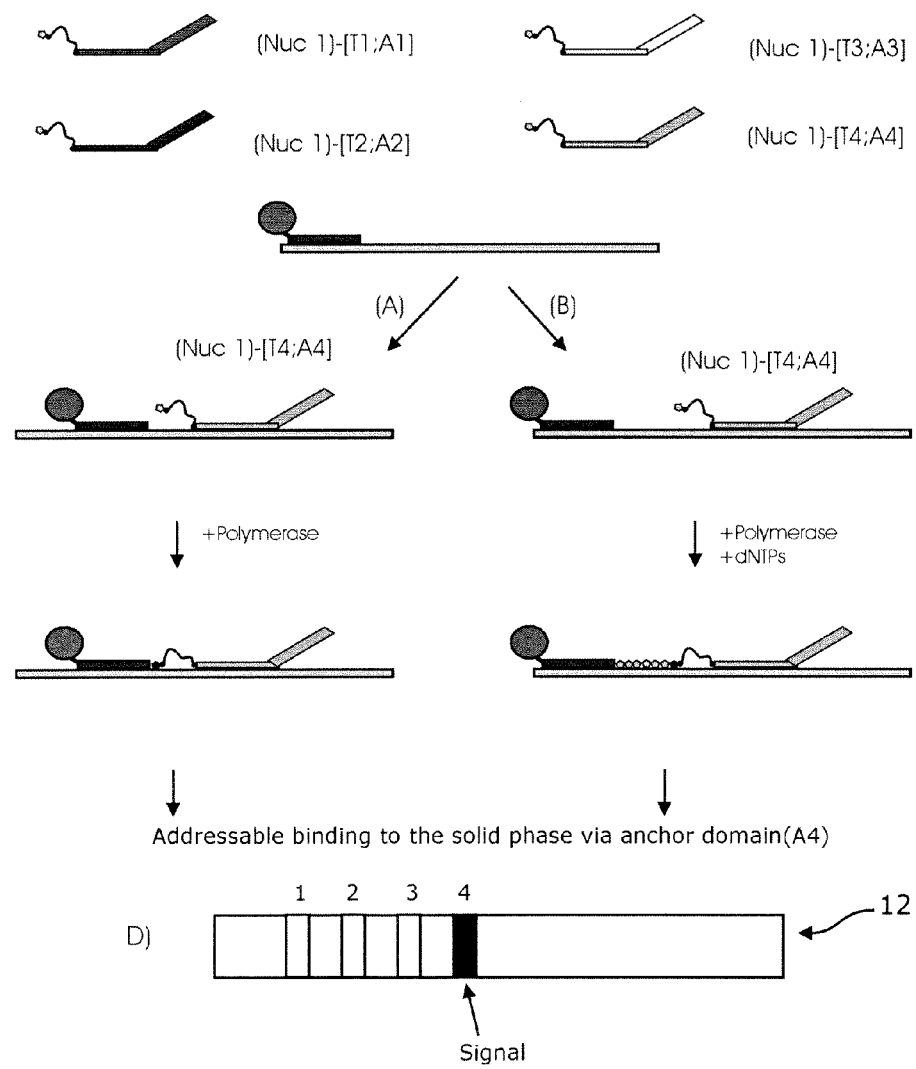
FIG. 16, FIG. 17 and FIG. 19 show a spacial attribution of the labeled nucleic acid chain achieved by the binding of target sequences each labeled with a target-sequence specific anchor domain to a solid phase with spatially arranged binding partners for the respective anchor domains.
Figure 17:
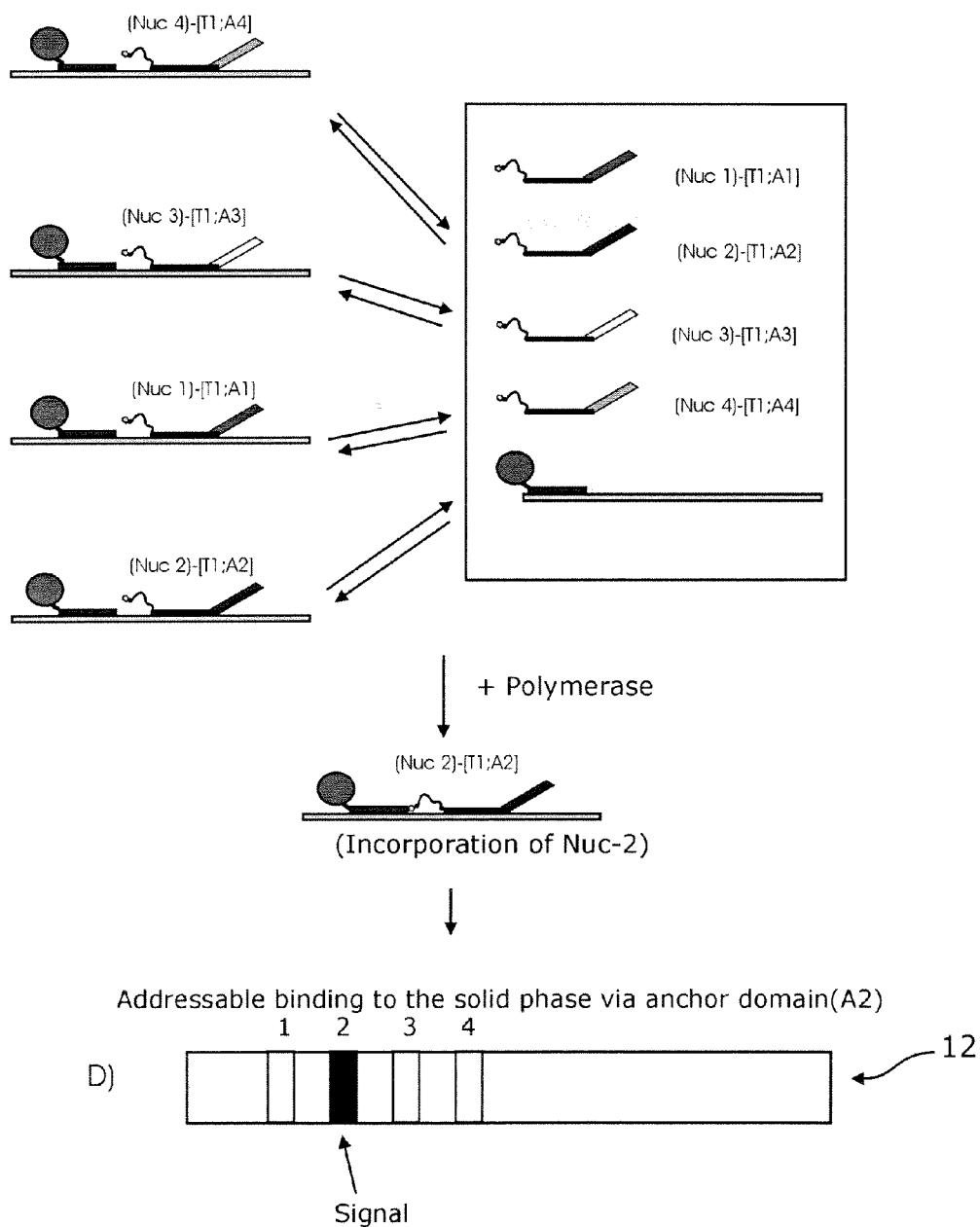
Figure 19:
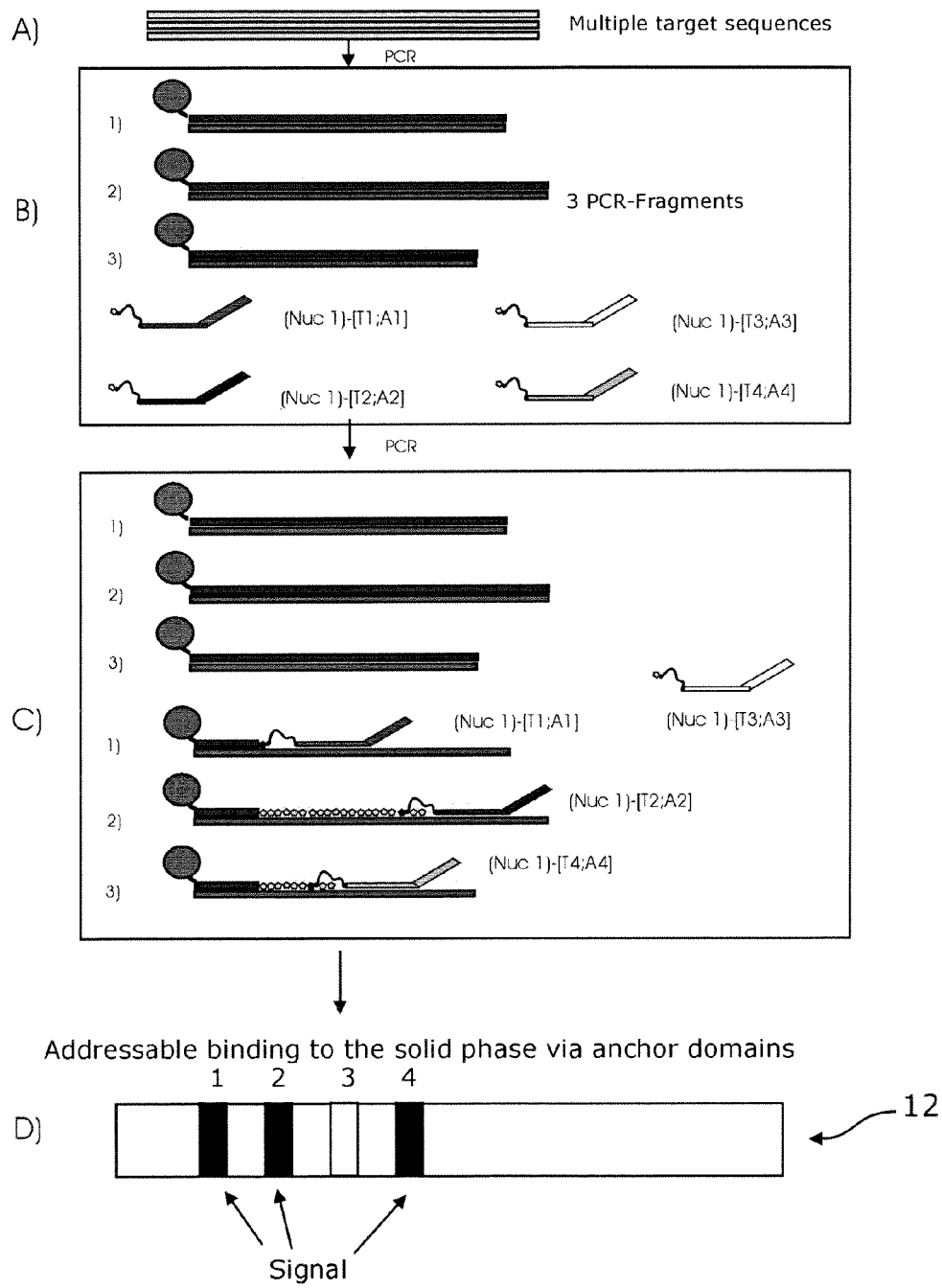

A spacial attribution of the labeled nucleic acid chain is achieved by the binding of target sequences each labeled with a target-sequence-specific anchor domain to a solid phase with spatially arranged binding partners for the respective anchor domains (FIGS. 16, 17, and 19).

Target sequences which are labeled with nuc macromolecules and bound to the solid phase can be detected with one of the known method of detection.

A further example is presented for a labeling method for a target sequence or its equivalents with a subsequent binding to the solid phase. The following components are provided: one type of nuc-macromolecules with a target domain and a signal domain, a single-stranded target sequence, a primer, a DNA polymerase, and further nucleotides such as dNTPs. These components are incubated under conditions that allow the polymerase to incorporate dNTPs and nuc-macromolecules into the growing strand.

A solid phase which comprises at least one nucleic acid chain (e.g. oligonucleotide) complementary to the target sequence or to their equivalents is provided. Such nucleic acid chains are preferentially immobilized on the solid phase. If the provided solid phase comprises a plurality of complementary nucleic acid chains, they are attached in a spatial arrangement, i.e. in form of an addressable array. An expert knows such solid phases, e.g. DNA microarray. The labeling reaction is preferentially conducted in such a way that nuc-macromolecules are incorporated as completely as possible. If an excess of nuc-macromolecules should be used, labeled nucleic acid chains can be purified of nuc-macromolecules and primers, if necessary, by a known method. The labeled target sequences or their equivalents are incubated with the solid phase under conditions which permit the specific binding of the labeled target sequence, or their equivalents, to the immobilized nucleic acid chains. The labeled target sequence binds to the solid phase directly via the formation of double strands with the complementary immobilized nucleic acid chains. The detection reaction is done by means of signal domain of the incorporated nuc macromolecule.

In the following, examples of combinations of the solid phase and the anchor domains are presented. The anchor domain can be constituents of the nuc macromolecules, or those of the modified primers, or those of the hybridization probes.

1.5.9.1 Use of Nuc Macromolecules with a Uniform Anchor Domain.

Nuc macromolecules comprising at least one uniform anchor domain are provided for a labeling reaction. A solid phase with a binding partner which is able to bind specifically to that uniform anchor domain is provided.

Using nuc macromolecules with only one type of anchor domains, the binding of labeled target sequences to the solid phase is conducted via one binding partner attached to the solid phase. The nuc component and target sequences can be uniform or different.

For example, only one type of nuc macromolecules is used in the reaction. A binding to the solid phase is achieved after incorporation of this nuc macromolecule into the target sequence or its equivalent and a subsequent incubation with the solid phase.

For example, multiple nuc macromolecules with different target domains and uniform anchor domains can be used for a test directed to a group of target sequences. If one of the target sequences of interest is presented in a sample, an incorporation of the nuc macromolecule into the growing strand occurs. Subsequently, the labeled target sequence or its equivalent is bound to the solid phase.

The detection of the binding of the target sequence to the solid phase can be achieved, for example, via the signal domain of an incorporated nuc macromolecule or a primer or a hybridization probe.

1.5.9.2 The Use of Nuc Macromolecules with Different Anchor Domains.

Nuc macromolecules having different anchor domains can be used in the labeling reaction. A solid phase with several binding partners which are capable of specifically binding to each of these different anchor domains is provided. Preferentially, binding partners are attached in a particular spatial arrangement. The binding of labeled target sequences to such a solid phase results in the distribution of labeled nucleic acids with incorporated anchor domains on the solid phase with a specific binding partner.

After a subsequent detection based on the resulting signal pattern, a target sequence presented in a sample can be identified. Thus, multiple parameters (such as the presence of different target sequences) can be analyzed.

The detection of the binding of the target sequence to the solid phase can be conducted, for example, via the signal domain of the incorporated nuc macromolecule or of the primer or of a hybridization probe.

1.5.9.2.1 In One Embodiment, Several Different Nuc Macromolecules with Different Specific Combinations of Target Domain with Anchor Domains can be Used for Labeling.

The nuc components and signal domain of nuc macromolecules can be uniform or different. In one embodiment, nuc macromolecules are used which comprise the target domain, the anchor domain, and the signal domain. In a further embodiment, nuc macromolecules are used which comprise the target domain and the anchor domain.

Through the specific combination of target domains and anchor domains within one type of nuc macromolecule, an assignment of anchor domains to certain target sequences can be achieved. After the incorporation of the nuc component into the growing strand by the polymerase, the anchor domain is also coupled in a target-sequence-specific way.

For example, a plurality of target sequences has to be analyzed. The target domains [T] of individual types of nuc macromolecules are complementary to these target sequences. The respective anchor domain of nuc macromolecules is selected specifically for each target sequence (i.e. the anchor domain [A] is assigned to the respective target sequence, for example nuc1-[T1, A1], nuc1-[T2, A2], nuc1-[Tn, An], etc.). During labeling, each target sequence obtains a respectively specific anchor domain. After the labeling reaction, labeled target sequences can bind to the solid phase specifically via the anchor domains. After the detection step, it can be determined which of the target sequences was bound to which position on the solid phase.

1.5.9.2.2 In Another Embodiment, a Plurality of Nuc Macromolecules with Different Specific Combinations of Nuc Component—Anchor Domain can be Used for the Labeling.

The target domains or signal domans can be uniform or different or they can be even absent.

Preferentially in such an embodiment, at least four different specific anchor domains are used, each for a specific base of the nuc component, for example dATP is combined with the anchor domain 1, dCTP is combined with the anchor domain 2, dGTP is combined with the anchor domain 3 and dUTP is combined with the anchor domain 4.

1.5.9.3 Binding to the Solid Phase by a Modified, Sequence Specific Primer.

In one embodiment, the following components are used in the labeling reaction: a target sequence, at least one polymerase, at least one primer which comprises an anchor domain, at least one type of nuc macromolecules which comprise at least one target domain and at least one signal domain, optionally further nucleotides. Upon binding of the labeled target sequence to the solid phase via the anchor domain of the primer, this target sequence can be identified through the signal of the incorporated nuc macromolecules.

In another embodiment, the following components are used in a labeling reaction: primers which comprise an anchor domain 1, at least one kind of nuc macromolecules which comprise at least one target domain and at least one anchor domain 2. The anchor domain of primer is different from the anchor domain of nuc macromolecules.

Upon binding of the labeled target sequence to the solid phase via the anchor domain of the primer, the second solid phase can bind to the anchor domain of the nuc macromolecule. Using microparticles, the binding of both solid phases can be detected as agglutination. Agglutination is taking place only, if the labeling reaction of the target sequences or their equivalents has been successful. Using a lateral flow device (FIG. 19), the binding of both solid phases can be detected through formation of a visible line (for example, when using colored microparticles or colloidal gold).

If a plurality of target sequences has to be detected, a plurality of different primers, each with a specific anchor domain, can be used in combination with several types of nuc macromolecules, each with a specific target domain, and at least one signal domain or at least one anchor domain. The signal-domains and the anchor domains of the used nuc macromolecules can be uniform or different.

1.5.9.4 Binding to the Solid Phase by Means of a Modified Hybridization Probe

Hybridization probes comprising a target domain and an anchor domain can be used for the labeling reaction together with at least one kind of nuc macromolecules comprising at least one target domain and at least one signal domain. Each target domain is specific for a particular target sequence. Upon binding of the labeled target sequence to the solid phase via the anchor domain 1 of the hybridization probe, this target sequence can be detected through the signal of the incorporated nuc macromolecules.

If a plurality of target sequences has to be detected, a plurality of different hybridization probes, each having a specific anchor domain, can be used in combination with several types of nuc macromolecules, each having a specific target domain, and for example at least one signal domain. The signal domains of the used nuc macromolecules can be uniform or different.

1.5.9.5 Binding to the Solid Phase by a Modified Nucleotide

Modified nucleotides having a low molecular weight (e.g. dUTP-16-Biotin, or dUTP-digoxigenin, or dUTP-fluorescein) and comprising an anchor domain can be used in the labeling reaction together with at least one kind of nuc macromolecules which comprise at least one target domain and at least one signal domain. A solid phase is provided which is able to bind the low molecular weight markers of conventional nucleotides, such as streptavidin or antibodies against digoxigenin or against fluorescein. Upon binding of the labeled target sequence to the solid phase via the said modified nucleotide with low molecular weight, this target sequence can be detected through the signal of the incorporated nuc macromolecules.

1.5.9.6 Direct Binding of the Labeled Target Sequence, or the Equivalents Thereof to the Solid Phase with Attached, Addressable and Complementary to the Target Sequence Nucleic Acid Chains In one embodiment, a labeling reaction comprises the following components: a target sequence, at least one polymerase, at least one primer used in combination with at least one kind of nuc macromolecules which comprise at least one target domain and at least one signal domain, and optionally other nucleotides. After labeling of the target sequences with the nuc macromolecules, the strands are separated, for example by temperature or alkali, e.g. NaOH solution. A solid phase is provided which comprises addressable, to a respective target sequence complementary oligonucleotides. The mixture is brought in contact with the provided solid phase, wherein the labeled nucleic acid chains can bind to the complementary nucleic acid chains attached to the solid phase. The detection reaction is done via the signal domain of the incorporated nuc macromolecules.

In one embodiment, the labeling reaction comprises a target sequence, at least one polymerase, at least one primer used in combination with at least one kind of nuc macromolecules which comprise at least one target domain and at least one anchor domain, and optionally further nucleotides. After the labeling of the target sequences with the nuc macromolecules, strands are separated, for example by temperature or alkali, e.g. NaOH solution. The mixture is brought in contact with the provided solid phase (1) so that the labeled nucleic acid chains can bind to the complementary nucleic acid chains attached to the solid phase.

After the binding of the labeled target sequence to the solid phase (1) through the formation of double strands with the attached nucleic acid strands of the solid phase, a second solid phase (2) can bind to the anchor domain of nuc macromolecules. When microparticles are used, the detection can be achieved for example through the agglutination. Agglutination is only positive, if the target sequences or their equivalents have been successfully labeled. By the use of a lateral flow devices, the binding of the two solid-phase can be detected through the formation of a visible line (e.g. using colored micro-particles or colloidal gold).

Such a type of binding of labeled nucleic acid chains to the solid phase is known to one skilled in the art, e.g DNA microarray technology (for examples see references in section 1.3.20).

If multiple target sequences have to be analyzed, a solid phase with addressable attached nucleic acid chains can be used. Nuc macromolecules are accordingly adapted to the target sequences to be examined.

1.5.10 Detection of Bound Labeled Nucleic Acid Chains

Many existing methods can be used for detection of nucleic acids labeled with nuc macromolecules. On the one hand, incorporated nuc macromolecules can comprise one or more signal domains with signaling or signal transmitting entities, on the other hand, other components of the system can comprise signaling or signal transmitting elements. Such elements are, for example, labeled primers, labeled nucleotides, hybridization probe and intercalating dyes.

Characteristic signals from dyes, chromogenic substances, fluorescent dyes, electrochemical markers or particles (e.g. nano or micro beads) can be used for detection. Examples of individual components are shown in the chapter "signal domain" and "detection methods" in more detail. Depending on signalling, different systems for detection of the signal can be used. Examples are known to one skilled in the art.

In one embodiment, for example, signaling is used to detect the binding of the labeled nucleic acid chains to the solid phase. In another embodiment, the signalling is used, for example, to detect different sequence variants within the target sequence.

Different methods of signal enhancement or signal amplification can be used for the signalling which are known to a person skilled in the art.

In an advantageous embodiment of the invention, the intensities of the received signals are measured. Signal intensities from the target sequences can be compared to signal intensities of the control sequences or to those of each other.

In an advantageous embodiment, these intensities can be recorded in digital form, stored and imaged.

In the following, some examples for detection reactions of nucleic acid chains on a solid phase are presented. Different detection methods can be combined with various structures of the nuc macromolecules.

1.5.10.1 Nuc-Macromolecules with T-A-S-Domains

Using at least one kind of nuc macromolecules with T-A-S-domains, the detection of bound labeled nucleic acid sequences can be done through the signal domain (S-domain of the nuc macromolecules).

1.5.10.2 Nuc Macromolecules with T-S-Domains or S-Domains

Using at least one kind of nuc macromolecules with a target domain or a signal domain, the detection of the bound target sequences or their equivalents can be preferentially achieved through the signal domain of the incorporated nuc macromolecules. The binding of the labeled nucleic acid chains to the solid phase can be done by means of other reactants.

For example, modified primers, hybridization probes or modified nucleotides can be used with an anchor domain (see above).

1.5.10.3 Signaling by a Sequence Specific, Modified Primer

Sequence-specific primers with signal domains can be used in the labeling reaction.

In this embodiment, the detection of the bound target sequences or equivalents thereof is done through the signal domain of these labeled primers. In a preferred embodiment, the binding of the labeled nucleic acid chains is to the solid phase is achieved via the incorporated nuc macromolecules which comprise at least an anchor domain.

In a further embodiment, the binding of the labeled nucleic acid chains to the solid phase is achieved via the incorporated nuc macromolecules comprising at least an anchor domain and a target domain.

1.5.10.4 Signaling Through a Modified Hybridization Probe

Sequence-specific probe with signal domains can be used in a labeling reaction.

In this embodiment, the detection of the bound target sequences or equivalents thereof is achieved via the signal domain of this labeled probe. In a preferred embodiment, the binding of the labeled nucleic acid chains is to the solid phase is achieved via the incorporated nuc macromolecules which comprise at least an anchor domain.

In a further embodiment, the binding of labeled nucleic acid chains to the solid phase is achieved via the incorporated nuc macromolecules comprising at least an anchor domain and a target domain.

1.5.10.5 Signaling by a Modified Nucleotide

Modified nucleotides having a signal domain (e.g. nucleotides labeled with fluorescent dyes or biotin, e.g. dUTP-16-Biotin) can be used in a labeling reaction. In this embodiment, the detection of the bound target sequences or equivalents thereof is achieved via the signal domain of these modified nucleotides. In a preferred embodiment, the binding of labeled nucleic acid chains is to the solid phase is achieved via the incorporated nuc macromolecules which comprise at least an anchor domain.

In a further embodiment, the binding of labeled nucleic acid chains to the solid phase is achieved via the incorporated nuc macromolecules comprising at least an anchor domain and a target domain.

Below, further examples of advantageous combinations are presented.

1.5.11 Process Variants: The Use of Nuc Macromolecules for the Labeling 1.5.11.1 Labeling Reaction Through a Primer Extension In one embodiment of the application, target sequences are provided in a single stranded form. In a further embodiment, double-stranded target sequences can be provided at the start. In this case, a denaturation step of the double strand, for example, by means of elevated temperature is included before or during the labeling step or a separation of double strands is achieved by an enzyme, for example, by means of a helicase. Typically, the target sequence is provided in a buffered aqueous solution.

An oligonucleotide having a primer function is added to the provided single stranded target sequence (hereinafter referred to as primer). The mixture is incubated under conditions which allow for the sequence-specific hybridization of the primer to the binding site within the target sequence. Such conditions are well known for an expert and are described in the literature. Under such conditions, an extendable primer-target sequence complex is established. At least one type of polymerases, at least one kind of nuc macromolecules, and optionally further components (such as natural nucleotides, modified nucleotides, or hybridization probes) are added to these complexes. The solution is incubated under conditions which allow the polymerase to perform a primer extension. During this step, the nuc component of nuc macromolecules are incorporated into the growing nucleic acid strand by the added polymerase. Thus, the target sequence or a complementary strand to the target sequence (an equivalent to the target sequence) is labeled with a nuc-macromolecule.

In one embodiment, nuc macromolecules comprising at least one target domain are used (for example, combinations of at least one target domain and one anchor domain, or at least one target domain and one signal domain, or at least one target domain and one anchor domain, and one signal domain). The target sequence-specific target domain of the nuc macromolecules can bind to the provided target sequence downstream from the 3' position of the primer. The reaction conditions are adjusted in such a way that the target domain of the nuc macromolecules can bind to its respective binding site within the target sequence.

Notably, the melting temperatures of the primer and the target domain should be concidered for the choice of the reaction conditions. The temperature of the reaction is preferentially chosen so that both the primer and the target domain of the nuc macromolecules can bind to the target sequence. The extent of the binding can be influenced. In one embodiment, the reaction temperature below the Tm of the primer and the Tm of the target domain is applied. In a further embodiment of the application, the temperature higher than the Tm of the primer and the Tm of the target domain is chosen, for example in the range of Tm+5° C. or in the range Tm+10° C.

Thus, only a small part of the target domains bind to the target sequences. In another embodiment, the reaction temperature is below the Tm of the primer but over the Tm of the target domain of the nuc macromolecule. In a further embodiment, the reaction temperature is above the Tm of the primer but below the Tm of the target domain of the nuc macromolecule. In another embodiment, a temperature gradient is used during the reaction, wherein the temperature is gradually adapted so that the hybridization of the primer and the target domain can occur successively, not simultaneously.

In one embodiment of the invention, the Tm of the target-sequence-specific target domains of a nuc macromolecule is higher than the Tm of the corresponding specific primer. Thereby, the nuc-macromolecules can bind to the target sequences at higher temperatures than the primers. This can ensure that the primer being extended meets nuc macromolecules already bound to the target sequence.

In another embodiment of the invention, the Tm of the target domain of the nuc macromolecules is lower than that of the used primers. Thus, a primer-extension can take place at higher temperatures without interfering of the nuc macromolecules with the incorporation reaction.

In another embodiment of the invention, the Tm of the target domain of the nuc-macromolecules and the Tm of the primers is approximately the same. Thus, the binding properties of the nuc macromolecules and those of the primer are about the same.

The order of addition of the components may vary. For example, individual components of the labeling reaction can be added one by one or in combinations (compositions). For example, the required nucleotides are premixed in certain proportions. Buffers and salts can also be added in certain pre-mixed proportions. Other combinations are obvious to an expert. Such compositions can be provided as components of kits.

After this labeling step, the labeled nucleic acid chain (target sequence or its equivalents) can be isolated from excess of unincorporated nucleotides. Isolation and purification of nucleic acid chains is well known to a person skilled in the art.

Subsequently, nucleic acid chains are brought in contact with a solid phase and detected, as described in the chapter "amplification". Labeled nucleic acid chains can also be brought into contact with the solid phase and detected directly after the labeling reaction, without isolation and purification.

The binding of the nucleic acid chains to the solid phase can be achieved directly via complementary immobilized nucleic acid chains or indirectly, i.e. enabled via an anchor domain.

Other components can also be used in such reaction, e.g. labeled primers, hybridization probes, and labeled nucleotides, as described in other chapters.

One or more types of nuc macromolecules can participate in such a reaction, as described in other chapters.

One or more target sequences can be amplified and labeled. The detection of the target sequence can be achieved via the binding to the solid phase with a subsequent detection reaction as described in other chapters.

1.5.11.2 Labeling of One Target Sequence with Multiple Nuc Macromolecules

One target sequence is provided for the analysis.

A solid phase comprising a plurality of the specific binding partners for the anchor domains of nuc macromolecules is provided. The binding partners are preferentially attached in a defined spatial arrangement which allows for a visual distinction between individual positions of the attached binding partners. The anchor domains can be constituents of the nuc macromolecules, or modified primers, or hybridization probes, or modified nucleotides with low molecular markers.

In a reaction, a plurality of nuc macromolecules comprising target domains complementary to the target sequence can be used. In one embodiment, the individual target domains of the nuc-macromolecules bind at different sequence positions within the said target sequence. In a further embodiment, the target domains of the nuc macromolecules bind to the target sequence at the same position. In a further embodiment, the target domains of the nuc macromolecules bind to the target sequence at the adjacent positions which may also overlap each other. For example, the target domain within one type of nuc macromolecules are used in combination with at least one anchor domain, or at least with one signal domain, or at least with one anchor domain and one signal domain.

Specific positions of the target sequence can be selected for the binding of the target domains by variable adjustments in the target domain. Thereby, the target sequence can be tested for the presence of specific sequence regions.

Nuc-macromolecules can be used alone or in combination with a set of natural nucleotides such as dNTPs.

Nuc macromolecules that have bound with their target domains to the target sequence are clearly favored in the enzymatic reaction. This results in the labeling of the target sequences or equivalents thereof with the corresponding specific nuc macromolecules.

In one advatageous embodiment, the nuc macromolecules comprise at least one target domain and at least one anchor domain. The detection is performed by the use of nuc macromolecules with signal domains, or primers modified with signal domains, or hybridization probes with signal domains or conventionally labeled nucleotides.

In a further advatageous embodiment, the nuc-macromolecules comprise at least one target domain and at least one signal domain. The binding to the solid phase is achieved through the use of nuc macromolecules with anchor domains, or primers modified with anchor domains, or hybridization probes with anchor domains, or by direct hybridization of labeled target sequences to complementary nucleic acid strands immobilized on the solid phase.

Incubation of the labeled nucleic acid chains with the solid phase leads to the binding of the anchor domains to the binding partners immobilized on the solid phase. Thereby, the labeled target sequences or their equivalents can be bound to the solid phase. After a detection reaction, an optical mapping of the bound nucleic acid chains to the respective positions of the binding partners can be made. Thus, a conclusion about the presence of specific target sequences in the reaction mixture is possible.

The binding of the nucleic acid chains to the solid phase can be achieved directly via complementary immobilized nucleic acid chains or indirectly, i.e. enabled via an anchor domain.

Other components can also be used in such reaction, e.g. labeled primers, hybridization probes, and labeled nucleotides, as described in other chapters.

One or more types of nuc macromolecules can participate in such a reaction, as described in other chapters.

One or more target sequences can be amplified and labeled. Detection of the target sequence can be achieved via the binding to the solid phase with a subsequent detection reaction as described in other chapters.

1.5.11.3 Multiple Nucleic Acid Chains

A plurality of target sequences can be tested in a single reaction.

A solid phase comprising a plurality of specific binding partners for the anchor domains is provided. The binding partners are preferentially attached to the solid phase in a characteristic way, for example, they are attached in a distinct spatial arrangement which allows for a visual distinction between individual positions of the immobilized binding partners. The anchor domains can be constituents of the nuc macromolecules, or modified primers, or hybridization probes, or modified nucleotides with low molecular markers.

To detect each target sequence, in one embodiment, at least one kind of nuc macromolecules with a corresponding target domain specific to a particular target sequence is used. Thus, a plurality of different nuc macromolecules comprising different target domains corresponding to their target sequences is used in a reaction. Preferentially, the target sequences of nuc macromolecules are not complementary to each other. The target domains preferentially form specific combinations with at least one anchor domain, or at least one signal domain, or at least with one anchor domain and one signal domain within a single type of nuc macromolecules. This results in compositions of nuc macromolecules such as Nuk1-[T1; A1] to Nuk1-[Tn, An].

In another embodiment, nuc macromolecules comprise the target domain which can bind to more than one target sequence. These target sequences belong, for example, to a target sequence group. Within this group sequences have homologies, i.e. target sequences differ from one another more or less.

Using nuc macromolecules which are potentially capable of labeling of different target sequences of a defined target-sequence-group, it is possible to tolerate sequence variations. The labeling is therefore not strictly specific for a particular target sequence but rather specific for a particular group. Such group specificity is useful, for example, in detection of viruses with a strong ability to sequence variation. Nuc macromolecules comprise, for example, several target domains.

In another example, nuc macromolecules comprise a target domain, consisting of nucleic acid chain that is long enough so that single-base variations in the target sequence have hardly any effect on the binding behavior of the target domain to the target sequence at given reaction conditions, or reaction conditions (e.g. temperature) are used which allow for the binding of the target domain to the target sequence without a "perfect match".

Nuc-macromolecules can be used alone or in combination with a set of natural nucleotides such as dNTPs. The incorporation of nuc macromolecules bound with their target domains to the target sequence is clearly favored in the enzymatic reaction. This results in a labeling of the target sequences or equivalents thereof, each with specific nuc-macromolecules.

In one advatageous embodiment, nuc macromolecules comprise at least one target domain and at least one anchor domain. The detection is performed by the use of the nuc macromolecules with the signal domains or modified primers with the signal domains, or hybridization probes with the signal domains or conventionally labeled nucleotides.

In a further advatageous embodiment, nuc macromolecules comprise at least one target domain and at least one signal domain. The binding to the solid phase is achieved by the use of further nuc macromolecules with the anchor domains or modified primers with the anchor domains, or hybridization probes with the anchor domains, or by direct hybridization of the labeled target sequences to complementary nucleic acid strands immobilized on the solid phase.

Incubation of labeled nucleic acid chains with the solid phase leads to the binding of the anchor domains to the binding partner immobilized on the solid phase. Thereby, the labeled target sequences or their equivalents can be bound to the solid phase, too. After a detection reaction, an optical attribution of the bound nucleic acid chains to the respective positions of the binding partners can be made. Thus, a conclusion about the presence of specific target sequences in the reaction mixture is possible.

The binding of the nucleic acid chains to the solid phase can be achieved directly via complementary immobilized nucleic acid chains or indirectly, i.e. enabled via an anchor domain.

Other components can also be used in such reaction, e.g. labeled primers, hybridization probes, and labeled nucleotides, as described in other chapters.

One or more types of nuc macromolecules can participate in such a reaction, as described in other chapters.

One or more target sequences can be amplified and labeled. Detection of the target sequence can be achieved via the binding to the solid phase with a subsequent detection reaction as described in other chapters.

1.5.10.4 Labeling of a Target Sequence at Isothermal Conditions or Cyclic Variation of Temperature One or more target sequences can be provided. One or more primers are hybridized to the provided target sequences. The extension of the primer with nuc-macromolecules or still further nucleotides is done using a polymerase.

Nuc macromolecules comprising one target domain complementary to the target sequence are used.

The labeling is conducted by a cyclic reaction: each cycle includes the hybridization of the primers to the primer binding site in the target sequence and the binding of the nuc macromolecules by their target domain to the target sequence so that an extendable primer-template complex is formed. This complex is extended by the polymerase and the nuc macromolecules are incorporated into the primer under extension. After the labeling step, the extended primers are separated from the target sequence. This can, be achieved, for example, by the rising of the temperature or by means of an enzyme such as a helicase or a polymerase with strand-displacement activity.

An excess of labeling primers and an excess of nuc macromolecules is provided. In the next step, not yet extended primers can bind to the target sequence and form new extandable complexes, which are then labeled with nuc macromolecules. If a temperature denaturation of primer-target sequence complexes is selected, the cyclical temperature changes can be designed similar to PCR. The number of cycles can be, for example, between 2 and 500. Thereby, an accumulation of extended, labeled primers is achieved. The denaturation of the primer-template-complexes can be carried out enzymatically, isotherminal conditions can be used in this case.

In the embodiment with the thermal denaturation of extended primers, an appropriate thermostable polymerase is used preferentially. The temperature is increased so that the elongated strand can dissociate of the template. Though the lowering of the temperature, a hybridization of primers and nuc macromolecules to the template is achieved. Then, the newly hybridized primer can be extended by the polymerase and nuc macromolecules can be incorporated.

The change in temperature can be carried out, for example, in a PCR equipment, e.g. in a thermal cycler.

The labeled nucleic acid chains are analyzed as described in other chapters.

1.5.10.5 Amplification and Labeling

In a particularly advantageous embodiment of the application, the labeling reaction takes place in the same batch as the amplification, wherein amplification and labeling steps are conducted one after another. In another embodiment, the labeling is carried out parallel to the amplification of the target sequences. In this embodiment, amplification primers can be used as labeling primer.

Various examples of amplification of nucleic acid chains are known. As described in these methods, a segment of the target sequence or the complete target sequence is amplified using primers, often provided as a primer pairs. The amplification can be exponential such as PCR or linear.

The reaction can be characterized by the cyclic change of the temperature or can be carried out at a constant temperature (isothermal).

By the choice of temperature, buffer and concentration, a process comprising the conversion of the target sequences into single-stranded form, hybridization of the primer and its extension is conducted. This process can be repeated several times.

An expert should know hot to carry out a PCR.

In one embodiment, same primers are used for the amplification reaction and for the labeling reaction. In a further embodiment, an additional primer is used for the labeling reaction.

For carrying out a PCR, the following components are typically provided in a reaction mixture: at least one target sequence, at least one primer pair suitable for this target sequence, at least one appropriate polymerase such as a thermostable polymerase, at least one kind nuc macromolecules having a target domain matching the target sequence, further natural nucleotides (such as dATP, dGTP, dCTP, dTTP), and an appropriate buffer solution.

The amplification reaction is carried out by cyclic changes of the temperature, wherein the following cyclic steps are repeated: annealing, primer extension and denaturation of newly formed strands.

By the addition of nuc macromolecules comprising at least a target domain which can be hybridized to the target sequence (the target domain binds to the target sequence downstream from the 3' side of a corresponding primer), nuc macromolecules can bind to the single-stranded target sequences (FIG. 18-21).

This occurs similar to the probe in a real-time PCR method. After the binding of the primers and the nuc macromolecules to the target sequence (hybridiation step/annealing in PCR), a primer extension reaction proceeds including the incorporation of nuc macromolecules. After completion of the primer extension, the resulting duplexes are denatured, for example, by an increase of the temperatur. Then, a new cycle with hybridization of the primer and of the nuc macromolecule, and a corresponding primer extension is conducted. These cycles can be repeated several times, so that an accumulation of extended primers is achieved. The newly synthesized strands contain nuc macromolecules. Specifically labeled nucleic acid chains have been generated by the incorporation of nuc macromolecules into the growing strand, The reaction conditions (e.g. buffer and temperature), the Tm of the primer and the Tm of the target domain of the nuc macromolecules are selected so that both primer and nuc macromolecule can bind to the target sequences during the hybridization step. In this embodiment, the amplification can proceed parallel to the labeling.

Typically, a mixture of nuc macromolecules and natural nucleotides is provided for the reaction. The concentration ratios in such a mixture can vary. For example, the concentrations of natural nucleotides ranges between 50 and 500 µmol/l and the concentration of the nuc macromolecules between 0.1 and 2 µmol/l. Other examples of concentrations of nucleotides are described in section 1.5.8. The concentration of the primers ranges, for example, between 0.1 and 2 µmol/l.

The conditions of the reaction (temperature) and the structure and concentration of the individual components can be adjusted so that at the beginning of the process the amplification of the fragments of the target sequences, or their equivalents, predominates. With the increase of concentration of the amplified fragments (equivalent to the target sequence) in later stages of the amplification, the labeling of the amplified strands take place. At very low concentrations of target sequences at the beginning of the amplification process, the probability of the binding and of the incorporation of nuc macromolecules into the target sequence, or their equivalents is low. With increasing concentrations of target sequences during the amplification process, the frequency of binding events and incorporation of nuc macromolecules into the growing nucleic acid chains also increases, In the following, some examples of combinations of PCR and labeling reaction are presented. Labeled primers comprising a signal domain are used for signal generation in these examples. One of the primers of a target sequence-specific primer pair is selected for this purpose.

Figure 18:
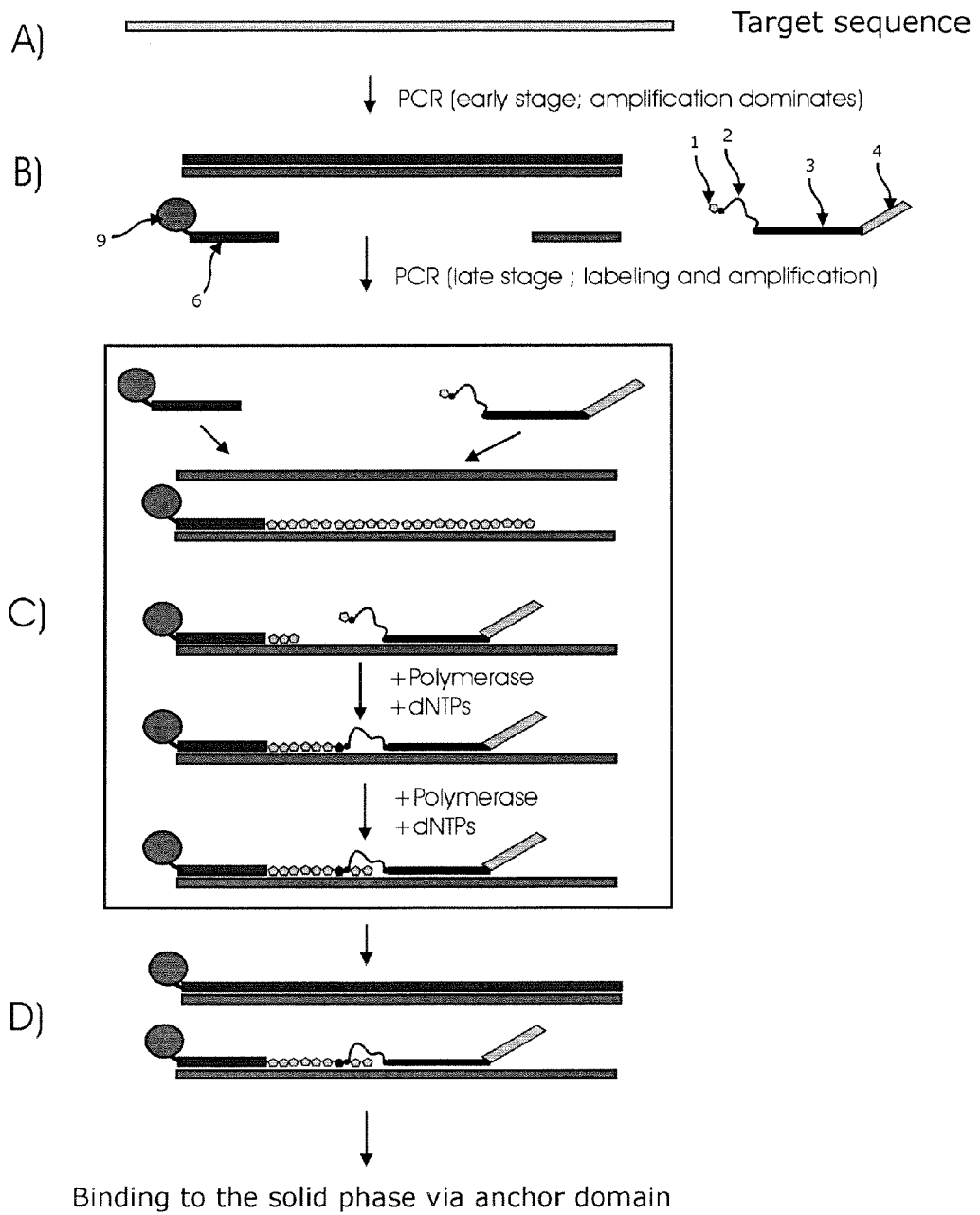

In one embodiment, PCR is used as amplification method (FIG. 18). Nuc macromolecules comprising a target domain complementary to the potential PCR fragment of the DNA and a target-sequence-assigned anchor domain can be used. The Tm of the target domain, for example, is in the same range, as the Tm of the used primers, +/−5° C. The PCR primers are used as a labeling primer and comprise, for example, either a signal domain or an anchor domain. The appropriate combinations of labeled primers and nuc macromolecules are described in previous chapters.

The concentration of primers range according to the known rules of a PCR, for example, between 10 nmol/l and 100 nmol/l, 100 nmol/l and 300 nmol/l, 300 nmol/l and 1 µmol/l, 1 µmol/l and 10 µmol/l The concentration of the nuc macromolecules in the reaction solution ranges, for example, from 10 pmol/l to 100 pmol/l, 100 pmol/l to 1 nmol/l, 1 nmol/l to 10 nmol/l, 10 nmol/l to 100 nmol/l, 100 nmol/l to 300 nmol/l, 300 nmol/l pmol to 1 µmol/l, 1 µmol/l and 10 µmol/l. The ratios of the concentrations of the PCR primers and nuc macromolecules are, for example, in the following areas (concentration of PCR primers to nuc macromolecules): 1:100 bis 1:10, 1:10 bis 1:1, 1:1 bis 10:1, 10:1 bis 100:1, 100:1 bis 1000:1. The concentration of dNTPs (dATP, dCTP, dGTP, dTTP), for example, is between 10 µmol/l and 1 mmol/l of each.

The times for each temperature-step are, for example, between 1 sec and 10 min.

In some embodiments, the differences between the Tm of the primers and the Tm of the target domain of the used nuc macromolecules can exceed 5° C., for example, differences can be up to 50° C. These differences can be used to control amplification reaction and labeling reaction. In one embodiment, the Tm of the primer is, for example, 15° to 20° higher than the Tm of the target domain of the nuc macromolecules. The nuc macromolecules can be used in concentrations that are significantly lower than the concentrations of dNTPs. During the initial cycles of the PCR, temperatures for the annealing step can be selected around the Tm of the primer (for example, calculated as Tm of the primer minus 5-10 degree), whereby an extension of the primer and the complementary strand with natural nucleotides can occur.

The target domains of the nuc macromolecules, however, can not bind to the target sequences, as their Tm is much lower than the used hybridization temperature. Since the target domain does not bind to the target sequence under these conditions and their concentration is significantly lower than that of the dNTP, the dNTPs are incorporated preferentially. Subsequently, further cycles are conducted with the temperature in the annealing step below the Tm of the target domain of the nuc macromolecule. Due to the change of the temperature (the temperature was reduced from that around the Tm of the primer to that around the Tm of the target domain), both primers and the target domains of the nuc macromolecules can bind to the target sequence.

Due to high local concentrations of nuc components of the bound nuc macromolecules to the target sequences, these nuc macromolecules can be incorporated into the growing strand, despite the presence of the dNTPs so that the target sequences are labeled. In this ebodiment, the target domain is located preferentially further apart in 3' direction from the primer. Preferentially, the distance between the 3' end of the primer and the 5' end of the target domain is at least 10 nucleotides, in a further embodiment, at least 50 nucleotides, in a further embodiment at least 100 nucleotides, in a further embodiment at least 200 nucleotides.

By controlling the reaction temperatures, the binding of the primers and the target domains can be made variable so that either the amplification reaction only or both amplification and labeling reaction can proceed.

In a further embodiment, a further primer (labeling primer) is used for the labeling the target sequence in addition to the amplification primers. This primer can specifically bind the same strand of the target sequence as the target domain of a nuc macromolecule. Preferentially, the labeling primer is located within the target sequence and upstream from the 5' side of the bound target domain of a nuc macromolecule. During the amplification, PCR fragments of the target sequence are generated using the amplification primer. The labeling primer binds preferentially between one amplification primer and the target domain of the bound nuc macromolecule.

The Tm of the labeling primer is preferentially in the same temperature range as the Tm of the target domain of the nuc macromolecule. For example, the Tm of the labeling primer can differ from the Tm of amplification primer (the Tm of labeling primer is lower than the Tm of amplification primers) so that during a PCR, initially the PCR fragments are generated and then a labeling reaction can proceed with a labeling primer. In a reaction, the concentration of a labeling primer can be higher than the concentration of PCR primers.

In a further embodiment, more than one labeling primers having different binding sites within a target sequence are used together with several corresponding specific nuc macromolecules. The labeling primers bind to the target sequence on the 5' side of the binding site of the target domain of a nuc macromolecule so that an incorporation reaction can take place. Preferentially, those labeling primers are provided with a signal-domain or an anchor domain.

In a further embodiment, additional oligonucleotides are used to compete with the target domain of a nuc macromolecule for the binding position in the target sequence.

In one embodiment, such oligonucleotides have the same sequence composition as the target domain of the nuc macromolecules. In another embodiment, their sequence composition differs from the target domain in at least one nucleotide.

In a further embodiment, a plurality of oligonucleotides differing in their sequence composition from the target domain in at least one nucleotide is provided. Due to the presence of such oligonucleotides in the mixture, the target domains compete for the binding site within the target sequence. Therefore, less specific binding of the target domain to the target sequence, can be suppressed, thus contributing to higher specificity of the analysis.

After the PCR, PCR fragments can be purified from the excess of primers or nuc macromolecules or be used direclty in the analysis. The analysis is performed for example by the binding to a solid phase having addressable binding partners.

In one embodiment, the concentrations of the nuc macromolecules are preferentially chosen in a way that after the labeling reaction most nuc macromolecules are incorporated into the target sequences and no additional purification of the labeled nucleic acid chains for the subsequent binding to the solid phase is required.

In a further embodiment, the concentration of one PCR primer may be higher than that of the other primer. This allows a certain degree of asymmetry in the generation of the PCR fragments to be achieved: thereby, the concentration of one strand can be increased.

In another embodiment, various primers for the labeling reaction and for the amplification reaction are combined in an assay. For example, primer pairs with higher Tm are used for the amplification and at least one primer with a lower Tm for the labeling reaction of newly generated PCR products. The Tm of the primer for the labeling reaction is, for example, in the same range as the Tm of the target domain of nuc macromolecules.

In a further embodiment, multiple target sequences are amplified by means of PCR (FIG. 19). Such multiplex PCR is well known to an expert. Several primer pairs are used for amplification, so that multiple PCR fragments arise. Nuc macromolecules can be used in such reaction, each of which comprises a specific target domain and a corresponding specific anchor domain. The target domains of the nuc macromolecules are chosen in such a way that they can specifically bind to the resulting PCR fragments.

The anchor domains of the nuc macromolecules are specifically combined together with the respective target domains so that respective anchor domain with the corresponding target domain of a nuc macromolecule forms a specific pair. For example, it is expected that four target sequences may be present in a mixture. A multiplex PCR with four specific primer pairs and four specific nuc macromolecules is conducted (FIG. 19). The nuc macromolecules can have the following composition: (Nuc1-Linker)-[T1;A1], (Nuc1-Linker)-[T2;A2], (Nuc1-Linker)-[T3;A3], (Nuc1-Linker)-[T4;A4] (in the figure, an indication to the linker is omitted).

The detection of the presence of three of the four expected target sequences is achieved by means of the binding to the solid phase and visualization. The binding is achieved via the binding partners having addressable positions on the solid phase.

Figure 20:
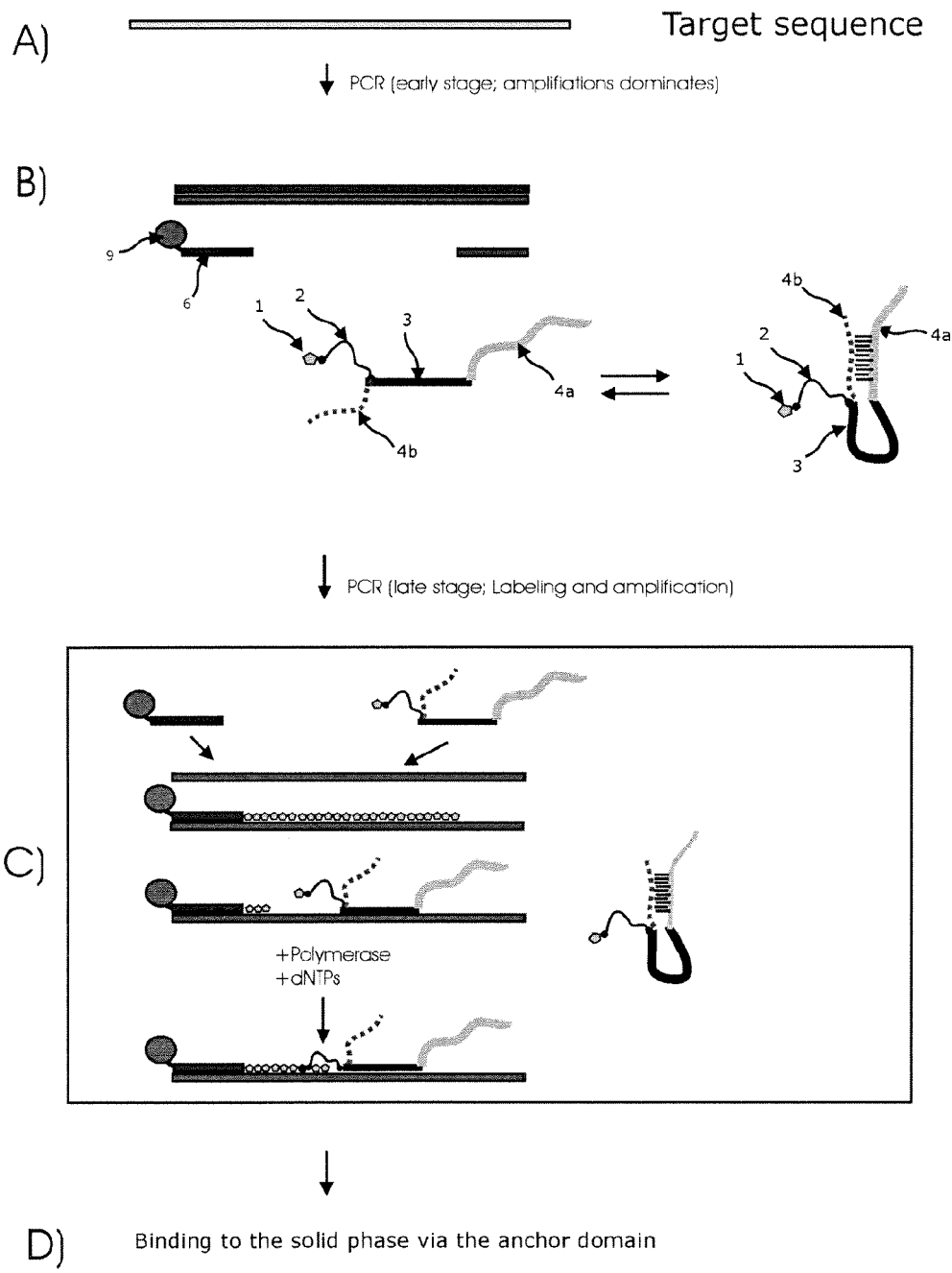

In another embodiment, nuc macromolecules comprising a target domain, an anchor domain and an antogonist to the anchor domain are used in a PCR (FIG. 20).

The structure of the nuc macromolecule and the cyclic reaction conditions are selected in such a way that during the reaction, the target domain of the nuc macromolecules can bind to the target sequence. Further, the conditions of the reaction are selected so that the anchor domain of the free, unincorporated nuc macromolecules can be present during the reaction in an open or a locked state, but preferentially in the open state.

After the incorporation of the nuc macromolecules, the anchor domain is presented in the open state. This is achieved, for example, through the spatial separation of the anchor domain and the antagonist after the hybridization of the target domain. After the labeling reaction, the temperature is decreased so that antagonist can bind the anchor domain within the unincorporated nuc-macromolecules and thus block it, The anchor domains of the incorporated nuc macromolecules remain open and capable of binding to the solid phase. This mixture is brought into contact with a solid phase and incubated under conditions that permit the binding of the anchor domains of the incorporated nuc-macromolecules to the immobilized binding partner. Since the anchor domains of the unincorporated nuc macromolecules are blocked, they do not interfere with the binding of the labeled target sequences.

Figure 21:
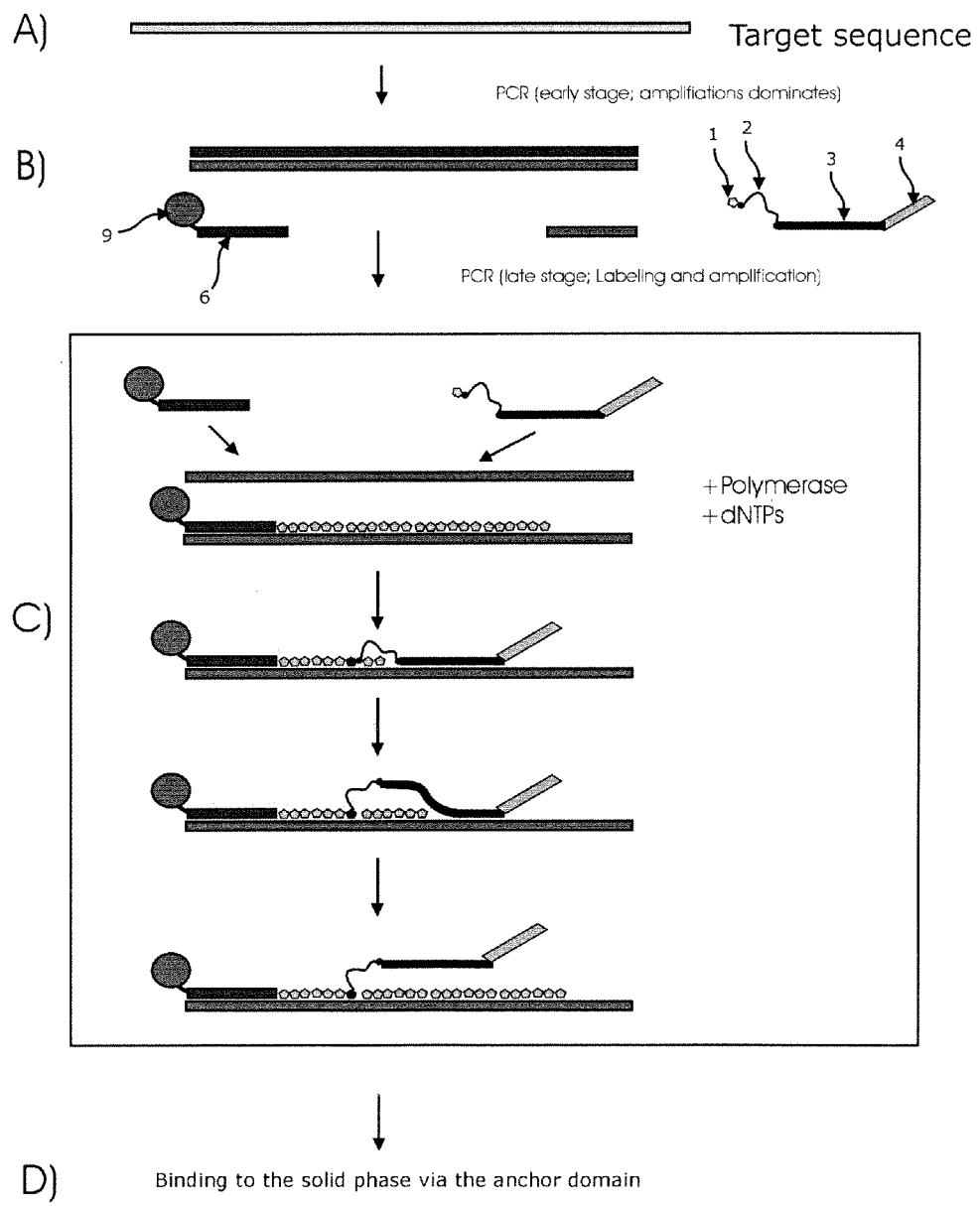

In another embodiment, a polymerase having a strand displacement activity is used in the PCR reaction (FIG. 21). Nuc macromolecules comprising a target domain and an anchor domain are used. During the PCR, the binding and the incorporation of nuc macromolecules occurs into the PCR fragments of the target sequence. As the polymerase is able to displace the target domain of the target sequence, additional natural dNTPs or nuc macromolecules are incorporated.

The labeled PCR fragments can be bound to a solid phase. In such a reaction, for example, one type of nuc macromolecules comprises a target domain [T1] and an anchor domain [A1], and a different type of nuc macromolecules comprises another target domain [T2] and a signal-domain [S1]. By the incorporation of both types of nuc macromolecules, PCR fragments are specifically labeled with the signal domain and the anchor domain.

Other components can also be used in such reaction, e.g. labeled primers, hybridization probes, and labeled nucleotides, as described in other chapters.

One or more types of nuc macromolecules can participate in such a reaction, as described in other chapters.

One or more target sequences can be amplified and labeled.

Detection of the target sequence can be achieved via the binding to the solid phase with a subsequent detection reaction as described in other chapters.

1.5.10.6 Detection of a Specific Target Sequence in a Material

Many examples of diagnostic tests will be known to a person skilled in the area. Usually, internal controls for amplification, binding, and detection are included in a test designed for the detection of one or more specific sequences from an organism in a test material.

With regard, for example, to the target sequences of the desired organisms and the structures of the nuc macromolecules, such control sequences are designed according to the rules described in other chapters. A labeling reaction is performed as described above.

Such a labeling reaction comprises, for example, several nuc macromolecules with target domains which are complementary to the target sequences of interest.

The target sequences can be amplified with different techniques, for example using a multiplex PCR. In a further embodiment, such a reaction comprises a plurality of primers specific to the target sequences or primer pairs which allow amplification of the desired target sequences.

Following the amplification and labeling reaction, detection of the labeled target sequences is conducted. In the case of the presence of a target in the material, it is detected by specific labeling with nuc macromolecules.

In one embodiment, the strength of the generated signal is measured. The amount of target sequences in the starting material can be estimated by correlating this signal strength to that from internal controls.

The individual reagents are preferentially provided in premixed form so that only the addition of the material is necessary to start the reaction. Provided reagents are preferentially provided as a kit.

1.5.10.7

Examples of the Detection of Sequence Variants in a Specific Target Sequence (Distinction of Related Target Sequences Such as SNP Detection)

In some cases, sequence variants of a target sequence which differ by one or few nucleotides have to be differentiated. An assay for such a task can be designed in different ways.

In one embodiment, the differentiation is accomplished by primers: only primers supporting an extension reaction of a specific sequence are used. For example, a primer has a discriminatory nucleotide in the 3' end position which can bind to only a particular type of the sequence. Another type of the sequence would form a mismatch, and thus it cannot be extended or the extension is insufficient. In such an embodiment, the nuc macromolecules can be used for binding to the solid phase (i.e. nuc macromolecules include at least one anchor domain) or they can be used for detection (i.e. nuc-macromolecules include at least one signal domain).

In another embodiment, sequence-specific or sequence-selective amplification is conducted with selective primers, for example by means of a PCR reaction. The nuc macromolecules can be used for binding to the solid phase (i.e. nuc macromolecules include at least one anchor domain) or they can be used for detection (i.e. nuc macromolecules include at least one signal domain).

In another embodiment, the differentiation can be carried out by the target domain of the nuc macromolecules. Multiple nuc macromolecules whose target domains are complementary to different variants of the target sequence (FIG. 16) can be used.

Nuc macromolecules having perfectly complementary target domains are preferentially incorporated into the growing strand. The target domains within a single type of nuc macromolecules are used, for example, in combinations such as at least a target domain and an anchor domain or at least a target domain and a signal domain or of a target domain, an anchor domain, and a signal domain.

An appropriate variation of the target sequence can be identified through the binding to the solid phase and a detection reaction.

In another embodiment, the differentiation can be achieved by the incorporation of a nuc component of a nuc macromolecule. The nuc component is combined with a specific anchor domain (FIG. 17) or signal domain, which allows for a specific attribution of the incorporated nuc component after the binding to a solid phase.

For example, dATP is combined with the anchor domain 1, dCTP with the anchor domain 2, dGTP with the anchor domain 3, and dUTP with the anchor domain 4.

In one embodiment, the nuc macromolecules comprise only an anchor domain.

In another embodiment, the nuc macromolecules comprise at least one target domain and an anchor domain. The signal domain can be bound to the corresponding primers.

After a labeling reaction, a binding reaction to the solid phase with addressable binding partners is conducted. By known encoding of nuc components by means of the anchor domain/binding partner on the solid phase, the type of nuc component can be determined.

Combinations of various methods are possible.

In one embodiment, nuc macromolecules comprise at least one target domain and at least one anchor domain. The detection is performed by the use of nuc macromolecules with signal domains or modified primers with signal domains or hybridization probes with signal domains or conventionally labeled nucleotides.

In a further embodiment, nuc macromolecules comprises at least one target domain and at least one signal domain. The binding to the solid phase is performed by the use of nuc macromolecules with anchor domains or modified primers with anchor domains or hybridization probes with anchor domains or by direct hybridization of labeled target sequences to the complementary nucleic acid strands which are immobilized on the solid phase.

Incubation of labeled nucleic acid chains with the solid phase allows the anchor domains to bind to the binding partners immobilized on the solid phase. Thereby, the labeled target sequences or their equivalents can also be bound to the solid phase.

After a detection reaction, an optical attribution of the bound nucleic acid chains to the respective positions of the binding partners can be made. Thus, a conclusion about the presence of specific target sequences in the reaction mixture is possible.

The binding of the nucleic acid chains to the solid phase can be conducted directly through a complementary immobilized nucleic acid chain or indirectly transmitted via an anchor domain.

In such a reaction, other components such as labeled primers, hybridization probes, labeled nucleotides can be used, as described in other sections.

One or several types of nuc macromolecules can participate in such a reaction as described in other sections.

One or several target sequences can be amplified and labeled. The detection of the target sequence can be achieved through the binding to the solid phase with a subsequent detection reaction, as described in other sections.

1.5.11 Composition Kit for Labeling and/or Amplification of Nucleic Acids.

Generally, one or more kits comprise components which are necessary for the performance of enzymatic incorporation reactions with inventive nuc macromolecules and an optional subsequent analysis (for example individual substances such as nuc macromolecules, polymerase, dNTPs and primers or their compositions, reaction mixtures, and solid phase).

The composition of the kit can vary depending on the application, wherein the type of application can range from a simple primer extension reaction to an amplification with labeling and a subsequent analysis by means of a solid phase.

The kits can optionally comprise either positive and/or negative controls and instructions for performance of the method.

Optionally, kits can comprise materials and reagents for the preparation of components of the kit for the biochemical reactions or the genetic material such as components for preparation of the target sequence. Means for purification of labeled nucleic acid chains from an excess of nuc macromolecules can be components of kits.

Usually, the kit components are provided in commercial reaction vessels, wherein the volume of the vessels can vary between 0.2 ml and 1 l. Vessel arrays such as microtiter plates can be preloaded with components which support the automatic delivery of reagents.

A kit for labeling nucleic acid chains (target sequences) can optionally include multiple components for practicing the invention disclosed in the specification.

Below, some examples are given:
Means and solutions for isolating target sequences from a biological material
One or more devices for handling of the solutions.
One or more primers for amplification and labeling of target sequences.
These primers can optionally comprise at least one anchor domain and/or a signal domain.
One or more DNA polymerases or RNA polymerases or reverse transcriptases.
  For example, Klenow Fragment Polymerase, Klenow exo minus Fragment, phi29 DNA Polymerase, T7 DNA Polymerase, Sequenase 2™, Taq Polymerase, Vent™ Polymerase, Deep Vent™ Polymerase, Vent™ exo minus DNA Polymerase, Deep Vent™ exo minus DNA Polymerase, Pwo DNA Polymerase, Tli DNA Polymerase, Tth DNA Polymerase, so called Hot-Start-Polymerases, T7 RNA Polymerase, T4 RNA Polymerase, reverse Transcriptasen, e.g. Moloney Murine Lekemia Virus (M-MLV), Rous Sarcoma Virus (RSV), Avian Myeloblastosis Virus (AMV), Rous Assocciated Virus (RAV), Myeloblastosis Assocciated Virus (MAV), Human Immunodeficiency Virus (HIV).

The polymerases are preferentially provided in a storage solution, this storage solution, for example, comprises the following substances:
Buffer Tris-HCl, HEPES, Borate, Phosphate, Acetate (concentrations range for example from 10 mM to 200 mM)
Salt, e.g. NaCl, KCl, NH4Cl, concentrations range for example from 10 mM to 500 mM.
PEG or other inert polymer, e.g. Mowiol (concentrations range for example from 1 to 50% (w/v)
Glycerol (concentrations range for example from 1% to 70%)
Reducing agents, e.g. DTT (concentrations range for example from 0.1 to 50 mM)
Further substances can be included in a storage solution which support the stability of an enzyme. Examples of such substances are known, see description of products from enzyme manufacturers such as Promega, Invitrogen, Roche, etc.
One or several kinds of nuc macromolecules (nucleotide analogs) that can be present as in form of acid or as salts (e,g, sodium, potassium, ammonium or lithium can be used as an ion). Nuc macromolecules can be provided in dry form or in form of a solution, e.g. solved in water or in a buffer, e.g. Tris-HCl, HEPES, borate, phosphate, acetate, or in a storage solution, which can comprise the following components individually or in combination:
buffer Tris-HCl, HEPES, borate, phosphate, acetate (concentrations range for example from 10 mM and 200 mM)
salts, e.g. NaCl, KCl, NH4Cl, MgCl2,
PEG or other inert polymer, such as Mowiol in concentration from 1 to 20% (w/v)
glycerol in concentration between 1% and 50%
marker or marker units of modified nuc macromolecules, in particular in the embodiments, in which affine bound is used between the linker and the marker or between marker and core component.
DMSO
One or more reaction buffers for performing the amplification and/or the labeling reaction and/or the binding to the solid phase and/or the detection of the binding events on the solid phase
One or more sets of natural nucleotides or analogs thereof (e.g. dATP, dGTP, dCTP, dTTP, dUTP, dITP or ATP, CTP, GTP, UTP)
One or more sets of terminators (e.g. ddATP, ddGTP, ddCTP, ddTTP, ddUTP)
One or more types of conventionally labeled nucleotides, such as fluoresently labelld or biotin-labeled dUTP or dCTP analogues
One or more target-sequence-specific hybridization probes with an anchor domain or a signal domain
Other enzymes which support amplification or labeling method, proteins and cofactors, such as helicase and ATP, single strand binding protein
One or more reaction vessels for carrying out individual reactions
Solid phase for the binding of labeled target sequences, such as a lateral flow device or an array. Such a solid phase can comprise, for example, a binding partner for anchor domains of nuc macromolecules, or those of primers, or those of hybridization probes.

Such a solid phase can also comprise oligonucleotides which can bind to the target sequence.
One or more reagents for the detection of binding events of the labeled target sequences to the solid phase (e.g. enzymes and chromogenic substrates, or nanoparticles)
Where appropriate, control sequences to verify the success of individual steps
A guide to conduct and analyse of the reactions
1.5.12 Other Enzymes for Use of Nuc Macromolecules Nucleotides as monomers play a central role in various metabolic processes, such as the storage and transmission of genetic information in the cell ("Genes V" B. Lewin, 1994). Nucleotides are also known as an energy source of the cell (ATP, UTP), signal transmitter (messengers, GTP) in intracellular signal transduction ("Biochemistry and Pathobiochemistry", G. Löffler, 2003). For this reason, nucleotides and their analogues are used as therapeutics and diagnostics.

Integrated into nucleic acid polymers (nucleic acid chains), nucleotide monomers compose the basis for the storage of information in living organisms.

Nuc macromolecules have the potential to find applications in different areas of biotechnology application.

The possibility of a coupling of nucleotides to a macromolecule, while maintaining the substrate properties of the nucleotides openes many ways for a specific targeting of the modified nucleotides within an organism or a cell, so that nuc macromolecules represent a new basic model for nucleotide prodrugs.

Different types of polymerases represent the main target group for the use of nuc macromolecules ("DNA replication," Kornberg, $2^{nd}$ Ed. 1992), in particular, DNA-dependent DNA polymerases, RNA-dependent DNA polymerases, DNA-dependent RNA polymerases and RNA-dependent RNA polymerases. Both, thermostable and thermolabile polymerases can be used such as Klenow polymerase or Taq polymerase. Other examples of possible polymerases can be found in the publications cited in this patent application.

Another example of enzymes provide transferases such as terminal deoxynucleotidyltransferase ("Molecular Cloning", Maniatis, third Ed. 2001). Other enzymes and proteins can be used (for example, kinases, receptors), which utilize nucleotides as substrates, energy source, as cofactors or messenger substances.

Enzymes differ in their ability to accept modified nucleotides as substrates. It should be obvious to an expert, that various functional tests must be used to study and apply certain properties of nucleotides. Examples of different test procedures for labeling nucleic acids are in H. Held et al. Nucleic Acid Research 2002, V. 30, S. 3857, M. Metzger et al. Nucleic Acid Research 1994, V. 22, 4259, M. Herrlein et al. Helvetica Chimica Acta 1994, V. 77, S. 586, B. Canard et al. PNAS 1995, V. 92, S. 10859, Canard U.S. Pat. No. 5,798,210, J. Hovinen et al. J. Chem. Soc. Perkin 1994, 1994, 211 and other patents and literature sources cited through this application.

1.5.13 General Suggestions for the Synthesis of Nuc-Macromolecules

The nuc-macromolecules according to the invention can be synthesized in different ways. The order of the chemical steps during the coupling steps can vary. For instance, the linker component can be coupled to the nuc-component first, and the marker component can be coupled afterwards. On the other hand, one or more linkers can be coupled to the marker component and then to the nuc-component(s).

The coupling between individual components of nuc-macromolecules can be covalent or affine by its nature. The linking of individual components of the nuc-macromolecules can thereby be accomplished both by chemical and by enzymatical coupling. Couplings to amino or thiol groups represent examples of covalent binding (D. Jameson et al. Methods in Enzymology 1997, v. 278, p. 363-, "The chemistry of the amino group" S. Patai, 1968, "The chemistry of the thiol group" S. Patai, 1974). Biotin-streptavidin bonding, hybridization between complementary strands of nucleic acids or antigen-antibody interactions represent examples of affinity binding.

The macromolecular markers often offer a variety of possibilities for coupling. One macromolecular marker can have a number of coupling positions for the linkers, e.g. several binding sites for biotin, as is true in the case for streptavidin. A macromolecular marker can comprise several amino or thiol groups. The core component of a marker can be modified by a different number of signal-giving or signal-transmitting units. The exact ratio between these marker units can vary. Examples for the modification of polymers with dyes are known (Huff et al. U.S. Pat. No. 5,661,040, D. Brigati U.S. Pat. No. 4,687,732). If nucleic acids are used as macromolecular markers, they can comprise different parts for the coupling of other macromolecules. Other macromolecules, e.g. enzymes, can be bound to one macromolecular marker.

A nuc-macromolecule can carry macromolecular markers with different detection properties, for instance, a nuc-macromolecule can carry several dye molecules as well as sites for the affinity binding (e.g., via hybridization) of further macromolecules.

The coupling between the nuc-components and the linker components is preferentially covalent. Many examples of a covalent coupling to nucleotides or their analogues are known (Jameson et al. Method in Enzymology, 1997, v. 278, p. 363-, Held et al. Nucleic acid research, 2002, v. 30 p. 3857-, Short U.S. Pat. No. 6,579,704, Odedra WO 0192284). The coupling can be accomplished, for instance, to phosphate, amino-, hydroxy- or mercapto groups.

Often, the linker component can be built up in several steps. In the first step, for instance, a short linker with a reactive group is coupled to the nucleotide or nucleoside, e.g., propargylamine-linker to pyrimidines Hobbs et al. U.S. Pat. No. 5,047,519 or other linkers, e.g. Kievan U.S. Pat. No. 4,828,979, Seela U.S. Pat. No. 6,211,158, U.S. Pat. No. 4,804,748, EP 0286028, Hanna M. Method in Enzymology 1996v. 274, p. 403, Zhu et al. NAR 1994 v. 22 p. 3418, Jameson et al, Method in Enzymology, 1997, v. 278, p. 363-, Held et al. Nucleic acid research, 2002, v. 30 p. 3857-, Held et al. Nucleosides, nucleotides & nnucleic acids, 2003, v. 22, p. 391, Short U.S. Pat. No. 6,579,704, Ward et al. U.S. Pat. No. 4,711,955, Engelhardt et al. U.S. Pat. No. 5,241,060 Taing et al. U.S. Pat. No. 6,811,979, Odedra WO 0192284, Herrlein et al. Helvetica Chimica Acta, 1994, V. 77, p. 586, Canard U.S. Pat. No. 5,798,210, Kwiatkowski U.S. Pat. No. 6,255,475, Kwiatkowski WO 01/25247, Parce WO 0050642, Faulstich et al. DE 4418691, Phosphoroamidite (Glen Research Laboratories, http://www.glenres.com/, Trilink Biotechnologies, S. Agrawal "Protocols for oligonucleotide conjugation", Humana Press 1994, M. Gait "Oligonucleotide synthesis: a practical approach" IRL Press, 1990), dissertation "Synthese basenmodifizierter Nukleosidtriphosphate und ihre enzymatische Polymerisation zu funktionalierter DNA", Oliver Thum, Bonn 2002. Some compounds are commercially available, e.g., from Trilink Biotechnologies, Eurogentec, Jena Bioscience.

These short linkers serve as coupling units L or their parts, and are constituents of the linker component in the completed nuc-macromolecule.

The coupling of the nucleotide or nucleoside with a short linker to a linker-polymer can be accomplished in the second step. Polymers with reactive functional groups are commercially available (Fluka).

After the coupling of the nucleotide to the polymer, the marker component now can be coupled as the last step.

It is often advantageous to couple a short linker to a nucleoside and then, if necessary, to convert this modified nucleoside into a nucleoside triphosphate (synthesis of triphosphates can be found, for instance, in the following citations: Held et al. Nucleosides, nucleotides & nnucleic acids, 2003, v. 22, p. 391, Faulstich et al. DE 4418691, T. Kovacs, L. Ötvös, *Tetrahedron Letters, Vol* 29, 4525-4588 (1988) or dissertation "Synthese basenmodifizierter Nukleosidtriphosphate und ihre enzymatische Polymerisation zu funktionalierter DNA", Oliver Thum, Bonn 2002). Further modifications can be carried out with nucleoside triphosphate analogs.

Precursors for modified nucleosides are available, for instance, from Trilink Biotechnologies (San Diego, APPROX., the USA) or from Chembiotech (Muenster, Germany).

The coupling between the linker component and the marker component can occur, for instance, between the marker component and the reactive groups on the linker component. Reagents for such couplings are described in detail in "Chemistry of protein conjugation and crosslinking", S. Wang, 1993, ISBN 0-8493-5886-8. The abovementioned patents also describe the methods for handling and coupling several macromolecules for different types of macromolecules. Further examples (for proteins) of couplings to and between the macromolecules are described in "Bioconjugation: protein coupling techniques for the biomedical sciences", M. Aslam, 1996, ISBN 0-333-58375-2; "Reactive dyes in protein an enzyme technology", D. Clonis, 1987, ISBN 0-333-34500-2; "Biophysical labeling methods in molecular biology" G. Likhtenshtein, 1993, 1993, ISBN 0-521-43132-8; "Techniques in protein modification" R. Lundblad, 1995, ISBN 0-8493-2606-0; "Chemical reagents for protein modification" R. Lundblad, 1991, ISBN 0-8493-5097-2; for nucleic acids in "Molecular-Cloning", J. Sambrook, Vol. 1-3, 2001, ISBN 0-87969-576-5, for other types of polymers in "Makromoleküle, Chemische Struktur and Synthesen", Vols. 1, 4, H. Elias, 1999, ISBN 3-527-29872-X.

Because the marker component usually comprises many coupling positions, it is possible to carry out further modifications with the assembled nuc-macromolecules. For instance, further modifications can block or change excess free amino groups.

Depending on the field of application and reaction conditions under which nuc-macromolecules are used, different types of chemical bonds between separate parts of the macromolecules can be advantageous. Thus, for instance, nuc-macromolecules that have covalent, thermostable bonds between different parts are suitable for processes that involve steps at higher temperatures, hybridization or PCR for example.

In the following, some possible methods for synthesis of nuc-macromolecules will be described for the sake of example. These are not intended to restrict the possible synthesis paths or to restrict the possible nuc-macromolecule structures.

The some embodiments, nuc-macromolecules with polyethylene glycol (PEG) as a linker component are used. Examples of the coupling of PEG to other molecules are shown in "Poly(ethylene glycol): chemistry and biological applications", 1997. In particular, very different reactive groups can be used for the coupling: N-succinimidyl carbonate (U.S. Pat. No. 5,281,698, U.S. Pat. No. 5,468,478), amines (Buckmann et al. Makromol. Chem. V. 182, p. 1379 (1981), Zalipsky et al. Eur. Polym. J. V. 19, p. 1177 (1983)), succinimidyl propionate and succinimidyl butanoate (Olson et al. in Poly(ethylene glycol) Chemistry & Biological Applications, 170-181, Harris & Zalipsky Eds., ACS, Washington, D.C., 1997; U.S. Pat. No. 5,672,662), succinimidyl succinate (Abuchowski et al. Cancer Biochem. Biophys. v. 7, p. 175 (1984), Joppich et al., Makromol. Chem. 1v. 80, p. 1381 (1979), benzotriazole carbonate (U.S. Pat. No. 5,650,234), glycidylether (Pitha et al. Eur. J. Biochem. v. 94, p. 11 (1979), Elling et al., Biotech. Appl. Biochem. v. 13, p. 354 (1991), oxycarbonylimidazole (Beauchamp, et al., Anal. Biochem. v. 131, p. 25 (1983), Tondelli et al. J. Controlled Release v. 1, p. 251 (1985)), p-nitrophenyl carbonate (Veronese, et al., Appl. Biochem. Biotech., v. 11, p. 141 (1985); and Sartore et al., Appl. Biochem. Biotech., v. 27, p. 45 (1991)), aldehyde (Harris et al. J. Polym. Sci. Chem. Ed. v. 22, p. 341 (1984), U.S. Pat. No. 5,824,784, U.S. Pat. No. 5,252,714), maleimide (Goodson et al. Bio/Technology v. 8, p. 343 (1990), Romani et al. in Chemistry of Peptides and Proteins v. 2, p. 29 (1984)), and Kogan, Synthetic Comm. v. 22, p. 2417 (1992)), orthopyridyl-disulfide (Woghiren, et al. Bioconj. Chem. v. 4, p. 314 (1993)), Acrylol (Sawhney et al., Macromolecules, v. 26, p. 581 (1993)), Vinylsulfone (U.S. Pat. No. 5,900,461). Additional examples for coupling PEG to other molecules are shown in Roberts et al. Adv. Drug Deliv. Reviews v. 54, p. 459 (2002), U.S. Patent No. 2003124086, U.S. Patent No. 2003143185, WO 03037385, U.S. Pat. No. 6,541,543, U.S. Patent No. 2003158333, WO 0126692

Other similar polymers can be coupled in a similar way. Examples of such polymers are poly(alkylene glycol), copolymers of ethylene glycol and propylene glycol, poly (olefinic alcohols), poly(vinylpyrrolidone), poly(hydroxy-alkylmethacrylamide), poly (hydroxyalkyl methacrylate), poly(saccharide), poly(x-hydroxy acids), poly(acrylic acid), poly(vinyl alcohol).

The purification of the nuc-components of the nuc-macromolecules is accomplished using conventional means of nucleotide chemistry: for instance, with silica gel chromatography in a water-ethanol mixture, HPLC methods (ion exchange chromatography in a salt gradient and reverse-phase chromatography in a water-methanol gradient). Sigma-Aldrich, for example, offers optimized chromatography columns for nucleotide purification. HPLC purification of nucleotides is preffered.

The purification of macromolecular linker components and marker components can be performed through ultrafiltration, gel electrophoresis, gel filtration and dialysis, see "Bioconjugation: protein coupling techniques for the biomedical sciences", M. Aslam, 1996, ISBN 0-333-58375-2.

The mass of the nuc-macromolecules differs substantially from the mass of the nucleotides. For this reason it is advantageous to use the ultrafiltration for the final purification steps. Since only an average mass is calculated for the nuc-macromolecules, ultrafiltration is also suitable as an analytic method for separation of synthesis products.

It is possible to apply different methods of the macromolecular chemistry for the characterization of the nuc-macromolecules, e.g., UV-vis spectroscopy, fluorescence measurement, mass spectroscopy, fractionation, size exclusion chromatography, ultracentrifugation and electrophoretic technologies, like IEF, denaturating and non-denaturating gel electrophoresis ("Makromoleküle, Chemische Struktur and Synthesen", Band 1, 4, H. Elias, 1999, ISBN 3-527-29872-X, "Bioconjugation: protein coupling techniques for the biomedical sciences", M. Aslam, 1996, ISBN 0-333-58375-2).

Examples for coupling reactions of individual components of nuc macromolecules are given in patent applications Cherkasov et al WO 2005044836, Cherkasov et al WO2006097320, Cherkasov et al WO 2008043426, Cherkasov et al DE 10356837, Cherkasov et al DE 102004009704. Nuc macromolecules can be purchased from Genovoxx GmbH (custom synthesis).

1.5.14 Examples of Synthesis of Nuc Macromolecules

In the following, synthesis of nuc macromolecules in which the target domain consists of DNA is described. There are many known methods for covalent labeling of the DNA. The labeling can be conducted at different positions of the nucleic acid chain (5' position, 3' position, internal portions). Multiple labels can be attached to one DNA.

The modification can be conducted via chemical or enzymatic reactions. On the one hand, the coupling of a substance can be carried out already during the chemical/enzymatic synthesis of nucleic acids (for example, by the use of phosphoramidites or by the use of modified nucleotides and a polymerase or by the use of a ligase reaction).

On the other hand, the coupling can proceed via one or more intermediate steps such as through the introduction of a reactive group and be accomplished after the synthesis.

Below, examples which describe some of these variants are presented for demonstration.

Synthesis of Nuc Linker Components with Reactive Groups.

The coupling of nuc components and marker components such as oligonucleotides can be achieved by many methods. For example, many methods are known which describe the linking of two structures each having a reactive amino group by a crosslinker. Oligonucleotides modified with one or more amino groups can be purchased commercially. Optionally, the amino group can be present at the 5' end or at the 3' end, or in the internal area of an oligonucleotide. In the following examples, amino-reactive nuc components which are provided as precursors are described. Such amino-reactive nucleotides can be linked to the oligonucleotides.

1.5.14.1 Synthesis of dUTP-PEG(8)-NH2

Aminoallyl-dUTP, 5 mg (AA-dUTP purchased from Jena Biosciences) was dissolved in phosphate buffer, pH 8.0 solution, to a concentration of 50 mmol/l.

Fmoc-PEG(8)-NHS (obtained from Iris Biotech GmbH) was dissolved in DMSO to a concentration of 100 mmol/l.

The solution of Fmoc-PEG(8)-NHS (approx. 8 equivalents) was added to the solution of dUTP-AA, until AA-dUTP was completely reacted (control via TLC).

Purification of dUTP-PEG(8)-Fmoc was carried out on DEAE-HPLC in a Tris-HCl buffer and NaCl gradient. The fractions containing product were collected and further purified by reversed-phase C-18 column with water-ethanol gradient. The eluate containing dUTP-PEG(8)-Fmoc was evaporated, dried, and dissolved in anhydrous DMF.

Pipiridin was added to the solution of dUTP-PEG (8)-Fmoc in DMF up to a concentration of 1%. The product, dUTP-PEG (8)-NH2, was precipitated and dried.

Further, dUTP-PEG3400-NH2 and dUTP-PEG5000-NH2 were obtained by a similar method, wherein Fmoc-PEG3400-NHS and Fmoc-PEG5000-NHS have been used (obtained from Iris Biotech GmbH). For materials and methods see Cherkasov et al. WO 2005 044836.

Thus, further reactive groups can be coupled to the amino group on the linker. At this stage, various cross-linkers can be used for the preparation of an amino-reactive derivative. An expert will be familiar with many examples of crosslinkers.

1.5.14.2 Synthesis of dUTP-PEG (8)-NHS

Glutarate-(NHS)2 was first dissolved in DMF and after that was added in excess to a solution of dUTP-PEG(8)-NHS in DMF (5 mmol/l). The product, dUTP-PEG(8)-NHS was precipitated, washed with DMF, and dried.

Similarly, dUTP-PEG(3400)-NHS and dUTP-PEG (5000)-NHS were obtained.

In another embodiment of this example, phenyldiisothiocyanate can be used instead of glutarate-(NHS)2, resulting in products dUTP-(PEG)8-ITC or dUTP-PEG(3400)-ITC accordingly.

An expert will recognize that other cross-linkers with other functionalities such as other linker lengths or other amino-reactive groups can be used. Further additional functionalities such as cleavability of the linker can be introduced by an appropriate choice of the cross-linker such as reductively or oxidatively cleavable linkers (e.g. dithiodipropionic acid-(NHS)2, tartrate-(NHS)2). Many cross-linkers are commercially available, for example from Thermo Scientific or Sigma-Aldrich or IRIS GmbH.

1.5.14.3 Synthesis of dUTP-Glutarate-NHS

DUTP-AA (aminoallyl-dUTP, by Trilink Biotechnologies, pH 7.0), was dried and suspended in dry DMSO up to a calculated concentration of 50 mmol/l. Glutarate-(NHS)2 (obtained from Thermo Scientific Germany) was dissolved in DMSO to concentrations of 300 mmol/l.

The suspension of dUTP-AA was added to solution of Glutarate-(NHS)2 and incubated for 2 h at 37° C. under vigorous stirring until the solution became transparent.

The conversion of dUTP-AA was monitored by TLC.

The purification of dUTP-glutarate-NHS was carried out by precipitation from diethyl ether/DMF mixture (v:v 90:10). The pellet contained the product. The product was dissolved in DMSO and frozen.

In a similar manner, further dUTP-R—X analogs can be synthesized, wherein (R) represents any linker and (X) can be any reactive group. The reactive group can, for example, react with amino groups or thio groups or carboxyl groups.

Examples of other commercially available short linkers (cross-linkers) are presented in the cross-linker Guide Thermo Scientific (www.piercenet.com). These linkers can comprise, for example, a PEG segment, for example PEG5 or PEG9 (Thermo Scientific: BS(PEG)5 or BS(PEG)9). These linkers can also comprise a cleavable linkage such as a reductively cleavable bond, for example dithiodispropionic acid-(NHS)2 or an oxidative cleavable bond such as tartrate-(NHS)2.

Other nucleotide analogs (e.g. N-(6-Aminohexyl)-dCTP (available from AmpliChem), N6 (6-Amino)hehyl-dATP, 5-Propargylamino-dCTP, 7-Propargylamino-7-deaza-dATP, 7-Propargylamino-7-deaza-dGTP are available from Jena Bioscience and can be modified in a similar manner.

The NHS group of the linker can react with an amino group of another molecule, for example with one of an oligonucleotide.

Coupling of Amino-Reactive Nuc Components to the Oligonucleotide.

Such coupling will be known to one skilled in the area: oligonucleotides with one or more amino groups are reacted with an excess of amino-reactive components in a solution, such as with NHS derivatives or with isothiocyanate derivatives. The purification of the modified oligonucleotide can be done for example by means of HPLC (DEAE and RP) and will also be known to a person skilled in the area.

Below, some examples of the preparation of nuc macromolecules which contain a nuc component, a linker, and an oligonucleotide are described. All oligonucleotides were synthesized by MWG Operon Germany.

1.5.14.4: dU-PEG(8)-[T1,A1]-TAMRA

This example illustrates the coupling of the nuc component at the 5' end of a sequence-specific oligonucleotide with a target domain and an anchor domain. The oligonucleotide, target domain-1, anchor domain 1-TAMRA, abbreviated as [T1, A1]-TAMRA were synthesized by MWG (see list of sequences):

Target domain-1, anchor domain 1-TAMRA, abbreviated as [T1, A1]-TAMRA (SEQ ID NO. 10

```
                                        (SEQ ID NO. 10)
NH2- cgtattaccgcggctgctggcacAAAAAAAAAAAAAAAAAAAA
AAAAA -TAMRA
```

This sequence contains a target sequence: indicated by small letters, and an anchor sequence indicated by capital letters. This oligonucleotide contains an amino group at the 5' end, which is coupled via a spacer-C6. The TAMRA reporter is coupled as a fluorescent marker at the 3' end.

The oligonucleotide was dissolved in a phosphate buffer, pH 8.0. An excess of dUTP-PEG(8)-NHS (5 mmol/l, in DMF) was added to this solution. The reaction proceeded at room temperature in good yields. The subsequent purification of the product was carried out by DEAE column and RP-C18 column. The product (dU-PEG(8)-[T1,A1]-TAMRA) was dried and then dissolved in water at 50 μmol/l concentration and frozen. Other nuc macromolecules were synthesized in a similar manner (Table 1).

1.5.14.5: dU-PEG(4)-[T1,A1]-TAMRA

Synthesis of nuc macromolecules with "click chemistry" (components obtained from Baseclick GmbH, Germany).

This example illustrates the coupling of the nuc component at the 5' end of a sequence-specific oligonucleotide having a anchor domain at the 3' end. The oligonucleotide [T1, A1]-TAMRA was used, sequence see Example 1.5.14.4 and in the list of sequences.

The oligonucleotide was dissolved in a phosphate buffer, pH 8.0. An excess of NHS-PEG4-N3 (10 mmol/l, in DMSO, obtained from Baseclick GmbH, Germany) was added to this solution. The reaction proceeded at room temperature in good yields.

The subsequent purification of the product was carried out by DEAE column and RP-C18 column. The product was dried and then dissolved in water resulting in 1 mmol/l concentration. The resulted N3-PEG4-oligonukleotide carries an azide group, which is coupled via a short PEG linker.

The coupling of the nuc component:

dU-Alkyne-C8, 5 µl, (10 mmol/l dissolved in water, obtained from Baseclick GmbH, Germany) was added to N3-PEG4-Oligonukleotide (5 µl, 1 mmol/l) and then 10 µl DMSO/t-Butanol was added. After that, a fresh Click-solution (1 V 0.1 M CuBr in DMSO/t-butanol and 2 V 0.1 M TBTA in DMSO/t-butanol) was added. The reaction proceeded at room temperature for 24 hours.

The subsequent purification of the product was carried out by DEAE and RP-C18.

The product was dried and then dissolved in water resulting in 100 µmol/l concentration. The product (dU-PEG(4)-[T1, A1]-TAMRA) contains a nuc component which is coupled via a short linker to the oligonucleotide.

An azide functionality or alkynes functionality can be introduced into various positions of a nucleotide (e.g. at the base or sugar) or an oligonucleotide (e.g. at the 3' end or 5' end or in the internal positions). Also several functionalities can be added. Nuc macromolecules with one or more nuc components can be obtained with by coupling of corresponding nuc components.

Examples of the coupling of nucleic acid molecules via click chemistry are given in the following references:

A. H. El-Sagheer, T. Brown, Chem. Soc. Rev. 2010, 39, 1388-1405. Click Chemistry with DNA.

J. Lahann, Wiley VCH 2009. Click Chemistry for Biotechnology and Materials Science.

F. Morvan, A. Meyer, G. Pourceau, S. Vidal, Y. Chevolot, E. Souteyrand, J.-J. Vasseur Nucleic Acids Symposium Series 2008, 52, 47-48. Click Chemistry and Oligonucleotides: How a simple reaction can do so much.

P. M. E. Gramlich, C. T. Wirges, A. Manetto, T. Carell, Angew. Chem. Int. Ed. 2008, 47, 8350-8358. Postsynthetic DNA Modification through the Copper-Catalyzed Azide-Alkyne Cycloaddition Reaction.

P. M. E. Gramlich, S. Warncke, J. Gierlich, T. Carell, Angew. Chem. Int. Ed. 2008 3442-3444. Click-Click-Click: Single to Triple Modification of DNA.

P. M. E. Gramlich, C. T. Wirges, J. Gierlich, T. Carell, Org. Lett. 2008, 10, 249-251. Synthesis of Modified DNA by PCR with Alkyne-Bearing Purines Followed by a Click Reaction.

F. Seela, V. R. Sirivolu, P. Chiteppu, Bioconjugate Chem. 2008, 19, 211-224. Modification of DNA with Octadiynyl Side Chains: Synthesis, Base Pairing, and Formation of Fluorescent Coumarin Dye Conjugates of Four Nucleobases by the Alkyne-Azide "Click" Reaction.

X. Ming, P. Leonard, D. Heindl, F. Seela, Nucleic Acids Symp. Ser., 2008, 52, 471. Azide-alkyne "click" reaction performed on oligonucleotides with the universal nucleoside 7-octadiynyl-7-deaza-2-deoxyinosine.

M. Meldal, C. W. Tornoe, Chem. Rev. 2008, 108, 2952-3015. Cu-Catalyzed Azide-Alkyne Cycloaddition.

T. Ami, K. Fujimoto, Chembiochem. 2008, 9, 2071-4. Click Chemistry as an Efficient Method for Preparing a Sensitive DNA Probe for Photochemical Ligation.

C. D. Hein, X. Liu, D. Wang, Pharm. Res. 2008, 25, 2216-2230. Click Chemistry, A Powerful Tool for Pharmaceutical Sciences.

B. Le Droumaguet, K. Velonia, Macromol. Rapid Commun. 2008, 29, 1073-1089. Click Chemistry: A Powerful Tool to Create Polymer-Based Macromolecular Chimeras.

C. T. Wirges, P. M. E. Gramlich, K. Gutsmiedl, J. Gierlich, G. A. Burley, T. Carell, QSAR Comb. Sci. 2007, 26, 1159-1164. Pronounced Effect of DNA Hybridization on Click Reaction Efficiency.

J. Gierlich, K. Gutsmiedl, P. M. E. Gramlich, A. Schmidt, G. Burley, T. Carell, Chem. Eur. J. 2007, 13, 9486-9494. Synthesis of Highly Modified DNA by a Combination of PCR with Alkyne-Bearing Triphosphates and Click Chemistry.

D. M. Hammond, A. Manetto, J. Gierlich, V. A. Azov, P. M. E. Gramlich, G. A. Burley, M. Maul, T. Carell, Angew. Chem. Int. Ed. 2007, 46, 4184-4187. DNA Photography: An Ultrasensitive DNA-Detection Method Based on Photographic Techniques.

F. Seela, V. R. Sirivolu, Nucleosides, Nucleotides and Nucleic Acids, 2007, 26, 597. Nucleosides and Oligonucleotides with Diynyl Side Chains: The Huisgen-Sharpless Cycloaddition "Click reaction" Performed on DNA and their Constituents.

M. Fischler, U. Simon, H. Nir, Y. Eichen, G. A. Burley, J. Gierlich, P. M. E. Gramlich, K. Gogoi, M. V. Mane, S. S. Kunte, V. A. Kumar, Nuclei Acids Res. 2007, 35, 139. A versatile method for the preparation of conjugates of peptides with DNA/PNA/analog by employing chemo-selective click reaction in water.

F. Seela, V. Ramana Sirivolu, Chemistry & Biodiversity, 2006, 3, 509. DNA Containing Side Chains with Terminal Triple Bonds: Base Pair Stability and Functionalization of Alkynylated Pyrimidines and 7-Deazapurines.

J. Gierlich, G. A. Burley, P. M. E. Gramlich, D. M. Hammond, T. Carell, Org. Lett. 2006, 8, 3639-3642. Click Chemistry as a Reliable Method for the High-Density Postsynthetic Functionalization of Alkyne-Modified DNA.

Overview of the Synthesized Nuc Macromolecules

TABLE 1

| name of the nuc macro-molecule (conjugate) | nuc component | Position of the nuc component | Linker component | Target Domain [Tn] | Anchor Domain [An] |
|---|---|---|---|---|---|
| dU-P4-[T1,A1] | dU | 5' end | PEG 4 | Target Domain 1 | Anchor Domain 1 |
| dU-P8-[T1,A1] | dU | 5' end | PEG 8 | Target Domain 1 | Anchor Domain 1 |
| dU-P3000-[T1,A1] | dU | 5' end | PEG 3000 | Target Domain 1 | Anchor Domain 1 |
| dU-P8-SS-P8-[T2] | dU | 5' end | PEG8-SS-PEG8 | Target Domain 2 | |
| dU-P3000-[T2] | dU | 5' end | PEG 3000 | Target Domain 2 | |
| dU-P3000-[T2] | dU | 5' end | PEG 5000 | Target Domain 2 | |
| dU-P3000-[T2]-3' | dU | 3' end | PEG 3000 | Target Domain 2 | |
| dU-P5000-[T2]-3' | dU | 3' end | PEG 5000 | Target Domain 2 | |

TABLE 1-continued

| name of the nuc macromolecule (conjugate) | nuc component | Position of the nuc component | Linker component | Target Domain [Tn] | Anchor Domain [An] |
|---|---|---|---|---|---|
| dU-Glut-[T3,A3] | dU | 5' end | Glutarate | Target-Domain 3 | Anchor-Domain 3 |
| dC-Glut-[T3,A3] | dC | 5' end | Glutarate | Target Domain 3 | Anchor Domain 3 |
| dU-Tart-[T1,A1] | dU | 5' end | Tartrate | Target Domain 1 | Anchor Domain 1 |
| dU-DTBP-[T1,A1] | dU | 5' end | Dithiobis-propionate | Target Domain 1 | Anchor Domain 1 |

The oligonucleotides with a target domain and optionally with an anchor domain used for the synthesis are shown in the list of sequences.

1.5.15 Examples of Enzymatic Labeling Reactions of Target Sequences with Nuc Macromolecules All polymerases were purchased from commercial suppliers (e.g. New England Biolabs or Promega).

Incorporation of Nuc Macromolecules in a Primer-Dependent Reaction:

The substrate properties of synthesized nuc macromolecules were tested for several polymerases in incorporation reactions.

An incorporation reaction was performed in an incorporation of buffer 1 (50 mmol/l Tris-HCl, 50 mmol/l NaCl, 5 mmol/l MgCl2, 10% glycerol), or an incorporation of buffer 2 (1× reaction buffer (1× ThermoPol thermophilic polymerases) from New England Biolabs).

Different polymerases were tested (e.g. Klenow exo minus, Taq polymerase, Vent exo minus polymerase, Terminator, Terminator II, Deep Vent exo minus, Sequenase, Tth polymerase, Tli polymerase).

Reactions were performed in a total volume of 10 to 20 µl. The following concentrations of components were typically used: primer (labeled with a fluorescent dye or unlabeled) 0.1 to 1.5 µmol/l, templates (M1-M10) from 1 nmol/l to 1.5 µmol/l, nuc macromolecules from 0.1 to 10 µmol/l, natural nucleotides (dATP, dCTP, dGTP, dTTP) were used in concentrations of 0.1 µmol/l to 10 mmol/l (the concentrations used are indicated in the respective experiment).

The concentrations of polymerases obtained from commercial suppliers were arbitrarily designated as 1× concentration. The dilutions of polymerases (for example 1:10 to 1:1000) relate to this initial concentration and are specified in the respective experiment.

The solid phase was represented by streptavidin-magnetic beads, which comprise a binding partner for the respective anchor domain, such as dT48 for a dA25-anchor domain.

The analysis of the extended fragments was carried out using gel electrophoresis in a 10% polyacrylamide gel under denaturing conditions (approximately 85-90° C.), The gel images were made using a gel documentation system.

In the summary, the following properties of nucleic macromolecules were determined:

The synthesized nuc macromolecules (comprising at least one nuc macromolecule, a linker, at least one target domain, at least one anchor domain, and at least one signal domain) are suitable as substrates for DNA polymerases and can be incorporated into the primer in a primer extension reaction in a template-dependent reaction at a corresponding complementary position for the respective nuc components.

Nuc macromolecules can be accepted as substrates by thermolabile and thermostable polymerases, The novel nuc macromolecules can be used in a primer-dependent labeling reaction such as a primer extension.

Nuc macromolecules compete with the corresponding natural nucleotides for incorporation into the growing strand opposite the respective complementary position in the template. The ability of the nuc macromolecules to compete for the incorporation depends on whether the target domain of the nuc macromolecule is hybridized to the respective template or not:

The incoporation of nuc macromolecules hybridized to the respective template is clearly preferred. It takes up to 10 mmol/l concentration of natural nucleotides to suppress the incorporation of a hybridized nuc macromolecule.

The incorporation of nuc macromolecules non-hybridized to the template is strongly suppressed by natural nucleotides of the same type as nuc components of the corresponding nuc macromolecule.

Nuc macromolecules with structures comprising a relatively short linker between the nuc component and the marker component (for example up to 200 chain atoms, more preferentially up to 100 chain atoms, more preferentially up to 50 chain atoms, more preferentially up to 20 chain atoms) are preferred in labeling reactions in the presence of natural nucleotides of the same type as the nuc component of the nuc macromolecules (e.g. dTTP presence in a reaction with nuc macromolecules comprising dUTP).

Nuc macromolecules having structures comprising a relatively short linker (see above) and at least one nuc component attached to the 5' end or in the vicinity of the 5' end of the target domain are preferred in labeling reactions in the presence of natural nucleotides of the same type as the nuc component of the nuc macromolecules (e.g. dTTP presence in a reaction with nuc macromolecules comprising dUTP).

The inventive nuc macromolecules can be used in a labeling reaction comprising cycles. The cyclic labeling reaction includes at least one cycle wherein a change of the reaction temperature is carried out. For example, one such cycle includes at least a denaturation step (for example at 95° C.) in which the target sequences can be converted from double-stranded form into a single-stranded form. Furthermore, such a cycle includes at least one hybridization step of a primer and of a target domain of a nuc macromolecule. Furthermore, such a cycle includes at least one step for the extension of the primer and incorporation of nuc macromolecules. The steps of the hybridization and extension can take place at the same or different temperatures. These steps can be repeated at least two times.

The labeling can be performed on nucleic acid chains which are immobilized on a solid phase.

Nuc macromolecules which are attached to a solid phase can be used for labeling of target sequences.

Under appropriate reaction conditions, for example at hybridization temperature, nuc macromolecules can distinguish target sequences by their target domains and label only specific target sequences.

Under appropriate reaction conditions, for example at hybridization temperature, nuc macromolecules can distinguish target sequences by their target domains, wherein a group of target sequences with similar binding sites for target domain of a nuc macromolecule can be labeled.

Several nuc macromolecules can be provided in a labeling reaction and label their specific target sequences under appropriate reaction conditions, for example at hybridization temperature.

Nuc macromolecules can selectively label their specific target sequences in the presence of another type of nucleic acid chains (for example genomic DNA) under appropriate reaction conditions.

Nuc macromolecules can label single-stranded forms of the target sequence.

Nuc macromolecules can label double-stranded forms of the target sequence (e.g. PCR fragments) when double strands were separated from each other and an appropriate hybridization step is included in a cyclic labeling reaction for a respective target domain of a nuc macromolecule.

Nuc macromolecules can label target sequences during a PCR.

Target sequences which were labeled with nuc macromolecules can be bound to a solid phase via the coupled/introduced anchor domain of nuc macromolecules.

The extent of labeling of target sequences and, hence, the signal intensity of the labeled target sequences can be influenced by the reaction conditions. For example, by changing the concentration of competing natural nucleotides of the same kind as the nuc component of the nuc macromolecules or by the number of cycles in a cyclic labeling reaction or by the initial amount of target sequences or by hybridization temperature for the target domain or primer.

Parts of nuc macromolecules (e.g. target domain of nuc macromolecules) can be degraded by the 5'-3' exonuclease activity of a polymerase (e.g. Taq polymerase).

The "strand displacement" activity of the polymerases can displace the target domain of a nuc macromolecule from the bound state to the target sequence, and continue the synthesis of the labeled strand.

Below, some examples are given to demonstrate the substrate properties of nuc macromolecules.

1.5.15.1 Enzymatic Incorporation of dU-PEG(8)-[T1,A1]-TAMRA (I)

In this experiment, incorporation of dU-PEG(8)-[T1,A1]-TAMRA (I) into the primer in the presence of different sets of further natural nucleotides was tested.

Components:
Incorporation buffer 1
Nuc macromolecule: dU-PEG(8)-[T1,A1]-TAMRA (5 µmol/l)
Natural nucleotides (dTTP, dATP, dCTP, dGTP) were added to the final concentrations, as described in the legend

```
Polymerase: Klenow exo minus,   1:10
Primer:     A50-T719            (1 µmol/l)
(this primer has an anchor domain A50)
Template:   M1                  (1 µmol/l)
```

(SEQ ID NO. 13)
5' GTT TTC CCA GTC ACG ACG GGAG gtg cc agc agc cgc ggt aat acg ACCA cctatagtgagtcgtatta 3'
Binding site for nuc macromolecule is underlined.

Primer, templates, natural nucleotides and nuc macromolecule (dU-PEG(8)-[T1,A1]-TAMRA) were combined to a reaction solution and were heated to 90° C. and then allowed to cool down to room temperature, so that the primers and the target domain of the nuc macromolecule could bind/hybridize to the template (target sequence). Polymerase was added to this solution and the reaction was allowed to proceed at room termperature for 10 min. Then the reaction was loaded directly onto a gel, and the reaction products were separated. The result is presented in FIG. 26. The composition of individual reactions is given in the legend.

It can be seen that dU-PEG(8)-[T1,A1]-TAMRA can be used as a substrate by Klenow exo minus (Lane 1). It can be incorporated into the primer in the presence of dTTP at increasing concentrations (up to 1 mmol/l) (Lanes 2 to 7), and in the presence of additional nucleotides (dATP, dGTP, dCTP, Lane 7).

The compound, dU-PEG(8)-[T1,A1]-TAMRA, can compete with free dTTP (1 mmol/l) for incorporation into the primer by polymerase due to its binding to the template.

In control experiments (not shown here), it was determined that dU-PEG(8)-[T1,A1]-TAMRA can be incorporated into the primer even when it is not hybridized to the template. However, the presence of dTTP resulted in suppression of this reaction.

Thus, dTTP presented at a concentration of only 5 µmol/l could significantly reduce the incorporation of the compound, dU-PEG(8)-[T1,A1]-TAMRA, if it was not bound to the template. The presences of competing nucleotides in a concentraion of 100 µmol/l resulted in a complete suppression of the incorporation of dU-PEG(8)-[T1,A1]-TAMRA if it was not hybridized to the template.

Taken together, the specific binding of dU-PEG(8)-[T1,A1]-TAMRA to the template resulted in a significant favoring of incorporation of this nuc macromolecule in the presence of competing nucleotides. This effect was interpreted as follows: the local concentration of the nuc component is increased greatly due to binding to the template, so that polymerase can preferentially incorporate this nucleotide.

1.5.15.2 Enzymatic Incorporation of dU-PEG(8)-[T1,A1]-TAMRA. (II)

In this experiment, incorporation of dU-PEG(8)-[T1,A1]-TAMRA. (II) into the primer by several polymerases was tested in the presence of other natural nucleotides.

Components:
Incorporation buffer 1
Nuc macromolecule: dU-PEG(8)-[T1,A1]-TAMRA (5 µmol/l)
Natural nucleotides (dTTP, dATP, dCTP, dGTP) were added to the final concentrations, as described in the legend

```
Polymerase:   Klenow exo mi-    1:10 bis 1:1000
              nus,
              Taq Polymerase    1:100
              Vent exo minus  - 1:100
              Polymerase
Primer:       A50-T719          (1 µmol/l)
(this primer has an anchor domain A50)
Template:     M2                (1 µmol/l)

Template 2:
```
(SEQ ID NO. 14)
5' GTT TTC CCA GTC ACG ACG GGAG gtg cc agc agc cgc ggt aat acg AGT CTT CTCA cctatagtgagtcgtatta
The binding site for the nuc macromolecule is underlined.

The reaction solution was prepared as in 1.5.15.1. Primer, templates and nuc macromolecules were hybridized by heating the reaction solution to 90° C. and subsequently allowing it to cool to RT.

Figure 27:
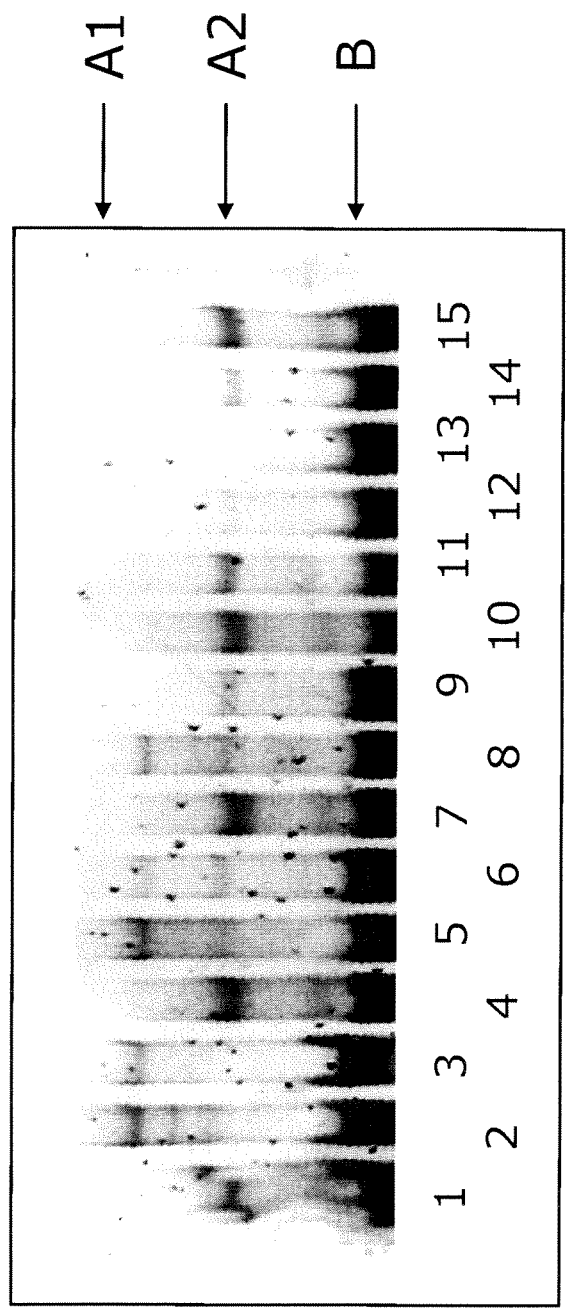
FIG. 27 shows analysis of reaction products by gel electrophoresis after incorporation reaction described in example 1.5.15.2.

DATP, dGTP, dCTP were added to this solution at a final concentration of 100 µmol/l and dTTP at 0 to 10 mmol/l (details in the legend to FIG. 27). The reaction was started by the addition of an appropriate polymerase (Klenow exo minus in dilution 1:10, 1:100, 1:1000, Taq 1:100 and Vent exo minus, 1:100). The labeling reaction was conducted for 12 hrs at 37° C. The reaction mixtures were analyzed by gel electrophoresis. The result is depicted in FIG. 27. The composition of individual reactions is given in the legend.

Results:

Acceptance of dU-PEG(8)-[T1,A1]-TAMRA.

All used polymerases accepted dU-PEG(8)-[T1,A1]-TAMRA as substrate in the primer extension reaction (FIG. 27, Lanes 1, 4, 7, 10, 15). The presence of dATP, dCTP, and dGTP did not disturb the incorporation. Only a partial extension of the primer was achieved (FIG. 27, arrow A2), since the absence of dTTP prevented full primer extension.

Competition with dTTP

Incorporation of dU-PEG(8)-[T1,A1]-TAMRA by all polymerases was observed in the presence of dTTP up to 100 µmol/l concentration (Lanes 2, 5, 8, 11, and 14). The incorporation of dU-PEG(8)-[T1,A1]-TAMRA by Vent minus and by Taq Polymerase was strongly or even completely suppressed under applied reaction conditions in the presence of dTTP, at 10 mmol/l, (Lane 12 for Taq, Lane 13 for Vent exo minus). In contrast, Klenow exo minus can incorporate dU-PEG(8)-[T1,A1]-TAMRA hybridized to the template even at this high concentration of competing nucleotides (Lanes 3, 6, and 9).

Strand-Displacement Activity of Polymerases

The ability of Klenow exo minus to effect strand displacement resulted in a complete synthesis of the complementary strand to M2 in the presence of dTTP (Lanes 2, 3, and 5)

Taq polymerase and Vent exo minus were unable to detach the target domain of nuc macromolecule hybridized to the matrix under the same conditions, for which reason these polymerases did not show strand displacement activity. The incorporation by Vent exo minus and Taq proceeded only up to the target domain; a complete synthesis of the complementary strand was not observed under the applied conditions. A complete synthesis of the complementary strand could be achieved, however, under cyclic labeling conditions (see below).

5'-3' Exonuclease Activity of Taq

Taq polymerase has a 5'-3' exonuclease activity. Despite this activity, the primer was labeled with the inventive nucleotides.

Effect of the Polymerase Concentration

Klenow fragment was used at different concentrations, from 1:10 to 1:1000. The best results for the strand displacement reaction were achieved at higher concentrations of Klenow exo minus.

1.5.15.3 Choice of Nuc Macromolecules and Polymerases for a Labeling Reaction.

For a specific labeling reaction of target sequences (nucleic acid chains), it is crucial that nuc macromolecules can be incorporated depending on their binding to these target sequences. Several reaction parameters have influence on the result. The choice of polymerases, the reaction conditions (such as concentration of competing natural nucleotides) as well as the structure of nuc macromolecules can have such an influence. For illustrative purposes, some of these parameters were varied (polymerases, concentration of competing nucleotides, structure of nuc macromolecules).

In the following, various polymerases were compared with regard to their ability to incorporate the nuc macromolecules, hybridized to a template, in the presence of competing nucleotides (in these examples, dTTP).

Very good incorporation: Klenow exo minus, Taq, Therminator polymerase, Therminator Polymerase II (all enzymes from New England Biolabs)

Good incorporation: Vent exo minus, Tth polymerase

Moderate incoporation: Sequenase 2, Deep Vent exo minus

The structure of the nuc macromolecules can have an effect on their ability to be incorporated by the polymerase in the presence of competing nucleotides. The best incorporation results (in the presence of competing nucleotides) were achieved with structures of nuc macromolecules having a nuc component which is coupled via a relatively short linker at the 5' end of the target domain.

The role of the binding and the role of the position of the target domain on a target sequence.

Comparison of the incorporation capability of the nuc macromolecules "with" and "without" binding to the template indicated that the presence of dTTP (100 µmol/l) can completely prevent incorporation of nuc macromolecules with dUTP (as nuc component) but without binding of the target domain to the template. The presence of dTTP at lower concentrations (1 to 10 µmol/l) can significantly reduce the incorporation of such nuc macromolecules.

This situation changes dramatically upon the binding of the target domains to the corresponding complementary position of the template downstream from the 3' direction of the primer (wherein there is at least one nucleotide position in the template between the 5' end of the target domain and the 3' end of the primer, which is able to form a base pair with the nuc component of the hybridized nuc macromolecule): the nuc macromolecules bound to the template are preferentially incorporated. Even concentrations of natural nucleotides in the solution up to 100 µmol/l or even 10 mmol/l cannot completely suppress the incorporation.

The position of the binding of a target domain to the target sequence can be varied depending on the experiment. Typically, the target domain is designed in such a way that its potential binding site is located in the 3' direction from the labeling primer. Preferentially, the position of the target domain in the target sequence is selected in such a way as to provide at least one nucleotide position in the template between the target domain and the primer which is able to form a complementary base pair with the nuc component of the hybridized nuc macromolecule.

The degree of labeling of a target sequence can be managed in accordance with a reaction procedure, the respective concentrations of the natural nucleotides, the polymerase and the reaction conditions: coupling of the nuc component at the 5' end of the target domain or to the parts close to the 5' end of the target domain (with short linkers having only 10 to 100 chain atoms, for example) allows an incorporation of the nuc macromolecules bound to the template in the presence of high concentrations of natural nucleotides.

1.5.15.4 Cyclic Primer Extension Reaction

The labeling of target sequences can be conducted in a single step of primer extension or during multiple cycles of primer extension. Here, an example for the labeling of target sequences in multiple cyclic steps is presented.

For better illustration of the importance of the hybridization of a target domain to the target sequence for labeling, a plurality of different target sequences were used with the same primer-binding site. The primer is labeled with a fluorescent dye (T7-19-Cy3) at the 5' position. The nuc macromolecule (dU-PEG(4)-[T1,A1]-TAMRA) used for the labeling has dUTP as its nuc component, which is coupled via a short linker at the 5' end of the target domain. Further, this nuc macromolecule has an anchor domain and a signal domain (TAMRA) at the 3' end.

Components:

ThermoPol Buffer 1x

Nuc macromolecule: dU-PEG(4)-[T1,A1]-TAMRA (0.5 µmol/l)

Natural nucleotides (dTTP 50 µmol/ll, dATP, dCTP, dGTP each 100 µmol/l)

```
Polymerase: Taq Polymerase   1:100
Primer:     T719-Cy3         (0.5 µmol/l)
(This primer has a signal domain, Cy3-dye)
Templates: M2, M4, M8, M9    (each 0.1 µmol/l)

Template 2:
                                        (SEQ ID NO. 14)
5' GTT TTC CCA GTC ACG ACG GGAG gtg cc agc agc
cgc ggt aat acg AGT CTT CTCA cctatagtgagtcgtatta
(already present)

Template 4:
                                        (SEQ ID NO. 16)
5' GTT TTC CCA GTC ACG ACG GGAG gtg cc agc
ggt aat acg AGT CTT CTGA cctatagtgagtcgtatta Template 8:
                                        (SEQ ID NO. 20)
5' GTT TTC CCA GTC ACG ACG GGAG gtg cc agc agc
cgc AGT TTT TTT AGT CTT CTGA cctatagtgagtcgtatta Template 9:
                                        (SEQ ID NO. 21)
5' GTT TTC CCA GTC ACG ACG GGAG cgc ggt aat acg
AGT CTT CTCA cctatagtgagtcgtatta
(The potential binding sites for the target
domain are underlined)
```

Template M2 and the target domain have a completely complementary sequence along the entire length of the target domain (complementary region is underlined).

Template M4 has complementary sequences for both ends of the target domain (complementary region is underlined).

Template 8 has complementary sequences only for the 3' end of the target domain. (complementary region is underlined). The 5' end of the target domain is not hybridized to the target sequence.

Template 9 has complementary sequences for the 5' end of the target domain (complementary region is underlined). The 3' end of the target domain is not hybridized to the target sequence.

Such sequences can be considered as examples of deviations from the target sequence (e.g. mutations in the target sequence). Likewise, such sequences can be considered as pairs of the target sequence/target domains, wherein the target domain is not completely complementary to the target sequence (template 4). This experiment serves as example of a reaction process wherein the Tm of the target domain is less than the Tm of primers. Further, this experiment represents the case when the 5 end of the target domain is not hybridized to the target sequence.

The reaction solution was prepared as in example 1.5.15.1.

Primer, templates, natural nucleotides (dNTPs) and nuc macromolecules were provided in a buffer solution. The solutions were initially incubated at 95° C. for 15 min.

During this time, the Taq polymerase was added to the reaction (Hot Start of the reaction to avoid side reactions). To stop the reaction, EDTA was added to the final concentration of 10 mmol/l. The reaction mixtures were subsequently separated on a gel.

The cyclic labeling reactions were carried out under different temperatures in several cyclic steps.

A cycle comprised a hybridization step, an extension step and a denaturation step.

The extension step (70° C. for 1 min) and the denaturation step (95° C. for 30 sec) were carried out equally for all templates.

Since the given target domain and target sequences comprised differences in complementary areas, it was interesting to test at which hybridization temperature the incorporation of nuc macromolecules occurs. Consequently, different hybridization temperatures were tested. Since in preliminary experiments the ability of the nuc macromolecule to be incorporated on the target sequence (M2, full complementary to the target domain) had already been tested, this reaction was used as a positive control (hybridization at 55° C.).

The following temperatures were chosen as hybridization temperatures: 35° C., 45° C., and 55° C.

Cyclic reactions (each 20 cycles) were conducted in a PCR device under the following conditions:

| Cycler Program : hybridization at 35° C. | | |
|---|---|---|
| Denaturation: | 95° C. | 30 sec |
| Hybridization: | 45° C. | 1 min |
| Extension: | 70° C. | 1 min |
| Cycler-Program : hybridization at 35° C. | | |
| Denaturation: | 95° C. | 30 sec |
| Hybridization: | 45° C. | 1 min |
| Extension: | 70° C. | 1 min |
| Cycler Program : hybridization at 55° C. | | |
| Denaturation: | 95° C. | 30 sec |
| Hybridization: | 55° C. | 1 min |
| Extension: | 70° C. | 1 min |

As a control of the signal intensity and the position of the extension product in the gel, primer extension (1× cycle) of the respective template without a nuc macromolecule was used (37° C., 12 hrs). The concentration of individual components (primer, template, polymerase, dNTPs were the same as in the cyclic labeling). In this reaction, primer was extended with natural nucleotides.

Figure 28:
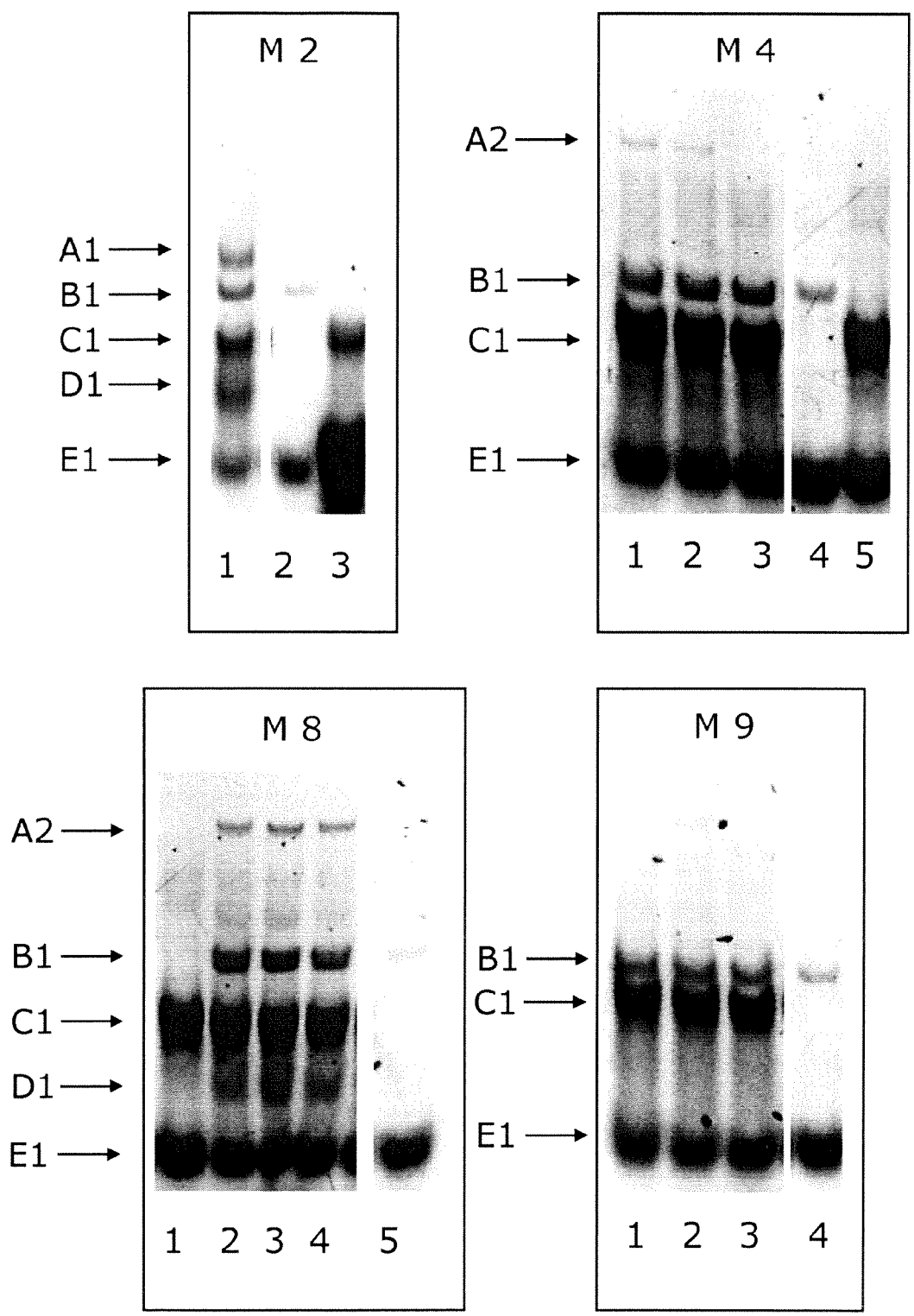
FIG. 28 shows analysis by gel electrophoresis of cyclic primer extension reactions using different templates (M2, M4, M8 and M9) described in example 1.5.15.4.

The results of the reaction are summarized in FIG. 28

It can be seen that the primer extension has taken place during the cyclic primer extension, the amount of extended primers has increased (compare the intensity of the bands in a simple cyclic reaction and primer extension).

The labeling of the newly synthesized strands depends significantly on whether the nuc macromolecule has bound to the template under particular reaction conditions via its target domain. The reaction at M2 template with Taq polymerase at 55° C. hybridization temperature resulted in a good yield: the labeled product is clearly visible (FIG. 28, M2, Lane 1, Arrow A1). The labeling with the template (M8) at all hybridization temperatures (35° C., 45° C., 55° C.) is clearly visible, too (see FIG. 28, M8, Lanes 2-4, Arrow A2). In the reaction with template (M4), only a very weak labeling is visible at a hybridization temperature of 35° C. and 45° C. (see FIG. 28, M4, Lanes 1, 2, Arrow A2). No labeling could be detected at 55° C. In the reaction with template 9, no labeling was detected at any hybridization temperature; the incorporation of dU-PEG(4)-[T1,A1]-TAMRA was completely suppressed by natural nucleotides.

This example illustrates that the binding of the target domain of a nuc macromolecule can be used for the specific recognition of a target sequence: under stringent hybridization conditions only nuc macromolecules which were bound to the target sequence could be incorporated into the growing strand. Changes in the binding site in the target sequence can lead to a loss of or reduction in the labeling. On the other hand, the target domain can still bind to the changed position in the target sequence if less stringent conditions (e.g. lower temperatures) are used.

The example with template 8 illustrates that polymerase accepts nuc macromolecules even if their 5' end is not hybridized to the template.

1.5.15.5 Labeling of Target Sequences During or Parallel to their Amplification in the PCR and Subsequent Binding and Isolation of Labeled Target Sequences with a Solid Phase Via the Anchor Domain of the Incorporated Nuc Macromolecules.

The labeling of target sequences can take place parallel to their amplification. PCR is one of the usual methods for amplification of nucleic acid chains. Here, an example is shown for the labeling of target sequences parallel to the amplification. After PCR, labeled DNA fragments were isolated by a specific binding to a solid phase. This isolation is enabled by a specific binding of the anchor domain of incorporated nuc macromolecules to the binding partner immobilized on a solid phase.

Components:

| | | |
|---|---|---|
| ThermoPol Buffer 1x | | |
| Nuc macromolecule: dU-PEG(4)- [T1,A1]-TAMRA | | (0.5 µmol/l) |
| Nuc macromolecule: dU-PEG(8)- [T1,A1]-TAMRA | | (0.5 µmol/l) |
| Natural nucleotides (dTTP 50 µmol/II, dATP, dCTP, and dGTP each 100 µmol/l) | | |
| Polymerase: | Taq-Polymerase | 1:100 |
| | Vent exo minus | 1:100 |
| Primer: | T719-Cy3 | (0.5 µmol/l) |
| | U19 | |
| (T7-19-Cy3 Primer has a signal domain: Cy3-dye) | | |
| Template: | M2 | (10 nmol/l) |
| dT48-Magnetic beads | | (1 vial) |

One PCR primer was labeled with a fluorescent dye (Cy3) at the 5 end. The other PCR primer was unlabeled. Nuc macromolecules used for the labeling (dU-PEG(4)-[T1,A1]-TAMRA and dU-PEG(8)-[T1,A1]-TAMRA) had dUTP as their nuc component, which was coupled via a short linker (PEG 4 or PEG 8) at the 5' end of the target domain.

Further, these nuc macromolecules had an anchor domain and a signal domain (TAMRA) at the 3' end. The binding site of the template 2 for the target domain is fully complementary.

Both PCR primers, template (M2), natural nucleotides (dNTPs), and nuc macromolecules were provided in a buffer solution. The solution was initially incubated at 95° C. for 15 min. During this time Taq Polymerase or Vent exo minus polymerase was added to the reaction (hot start of the reaction, to minimize side reactions). To stop the reaction, EDTA was added to the final concentration of 10 mmol/l. Subsequently, the reaction mixtures were separated on a gel.

The following PCR conditions were used:

| | | |
|---|---|---|
| Cycler Program: | | |
| Denaturation: | 95° C. | 30 sec |
| Hybridization: | 55° C. | 1 min |
| Extension: | 70° C. | 1 min |
| Cycling: 20 cycles | | |
| Hold: | 4° C. | |

Subsequently, a part of the reaction was brought in contact with a suspension of magnetic beads with dT48. After an incubation period of 5 min in Thermo-Pol1x, the beads were washed with incorporation buffer 1. The beads were loaded directly onto the gel. The detachment of the PCR fragments of beads was achieved by the use of elevated temperature of about 85° C.

The solid phase was prepared prior to the experiment as follows: Streptavidin Magnetic beads (Promega) were loaded with an oligonucleotide dT48 having a biotin moiety at the 3' end and washed. The dT48 oligonucleotide represents an example of a binding partner for an anchor domain. Such beads were able to bind nucleic acid chains labeled with nuc macromolecules.

Figure 29:
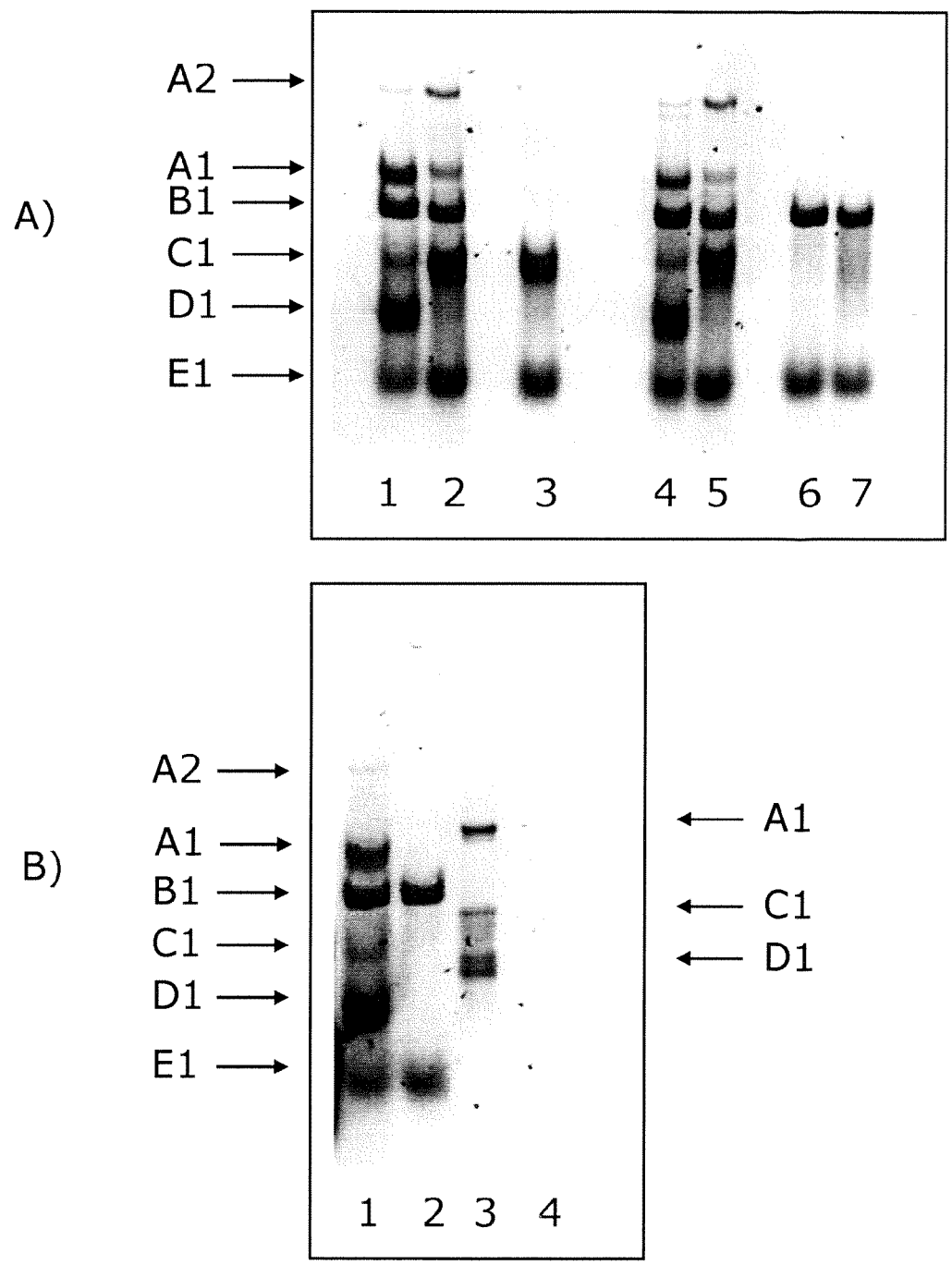
FIG. 29A and FIG. 29B shows the results of a PCR reaction (example 1.5.15.5) using the methods described herein. A significant formation of PCR fragments was observed: labeled nuc macromolecules PCR products (Arrow A1 and A2, FIG. 29A) and PCR products without nuc macromolecules (Arrow B1, FIG. 29). Specific isolation of PCR fragments modified with nuc macromolecules by solid phase is shown in FIG. 29B.

The result of the reaction is summarized in FIG. 29. A significant formation of PCR fragments was observed: labeled nuc macromolecules PCR products (Arrow A1 and A2, FIG. 29 A) and PCR products without nuc macromolecules (Arrow B1, FIG. 29 A). Interestingly, Taq polymerase was able to generate only low amounts of fully extended labeled PCR fragments (Arrow A1) vs. (Arrow A2). On the other hand, Vent exo minus polymerase could generate significantly a higher proportion of fully extended fragments through their strand-displacement activity under reaction conditions (Arrow A2).

Specific isolation of PCR fragments modified with nuc macromolecules by solid phase is shown in FIG. 29 (B). It can be recognized, that only PCR fragments with incorporated nuc macromolecules having an anchor domain could be isolated (Arrow A1, Lane 3). PCR products without incorporated nuc macromolecules did not bind to the solid phase and therefore could not be isolated (Lane 4 has no signals).

1.5.15.6 Detection of Bacterial DNA by PCR Amplification and Labeling with Nuc-Macromolecules An expert will know many methods based on the real-time PCR method. In such methods, for example, a labeled probe capable of binding to the complementary target sequence is added into the reaction and the amount of product is measured during the reaction.

The signal or measurable increment of the signal is detected if the probe has hybridized to the respective target sequence, and is partially degraded by the 5'-3' activity of a thermostable polymerase (e.g. U.S. Pat. Nos. 5,538,848, 5,723,591, 5,876,930, 6,030,787, 6,171,785, 5,487,972).

Such methods for the detection of specific DNA segments in biological material can be found in a very large number of publications. The authors describe the isolation conditions of the nucleic acid chains, the specific primers, the probe composition and the appropriate reaction conditions for the amplification and detection of target sequences. Numerous variants of this method, including multiplex PCR methods, real-time PCR diagnostic methods, and combinations with reverse transcriptases (RT-PCR) have been published since the introduction of real-time PCR in the 90s.

The present application makes use of this state of the art. In one advantageous embodiment of this application, the specific binding of a target domain of a nuc macromolecule to the target sequence takes place under conditions which allow an amplification of nucleic acid chains (such as PCR), similar to real-time PCR. An expert can therefore apply the existing knowledge of the real-time PCR. In particular, this relates to the composition of PCR primers, the target domain, and reaction conditions, as well as other combinations such as multiplexing and combinations with reverse transcriptases.

For demonstration purposes, primers and probe composition published in a publication (Nadkarni M. A. et al, Microbiology, 2002, v. 148 257-) were used for labeling with nuc-macromolecules during a PCR reaction.

The primers (forward and reverse primers, see the list of sequences) were adopted without changes. The sequence composition of the described double-labeled probe (FAM/

TAMRA) was adopted for the sequence composition of the target domain of the nuc macromolecule with the following changes. Instead of fluorescein, a nuc component was coupled via a short linker at the 5' end of the target domain and an anchor domain consisting of 25 dA residues was added to the 3' end of the target domain. The 3' end of the anchor domain carried a fluorescent dye (TAMRA).

The resulting oligonucleotide was [T1, A1]-TAMRA, which was used for the synthesis of nuc macromolecules as an example of the marker.

Some properties of the resulting nuc macromolecule with this oligonucleotide (e.g. dU-PEG(4)-[T1,A1]-TAMRA or dU-PEG(8)-[T1,A1]-TAMRA) have been already described in the preceding examples; see examples 1.5.15.1 to 1.5.15.5.

In this example, the application of this nuc macromolecule for detection of a presence of bacterial DNA is shown. A real-time PCR for detection of the 16 S ribosomal genomic portion of bacteria was selected. The primer and the probe were placed within conserved regions of the 16 S sequence.

Components:

| | | |
|---|---|---|
| ThermoPol Buffer 1x | | |
| Nuc macromolecule: dU-PEG(4)- [T1,A1]-TAMRA | | (0.5 µmol/l) |
| Natural nucleotides (dTTP, dATP, dCTP, and dGTP each | | 200 µmol/l) |
| Polymerase: | Taq Polymerase | 1:100 |
| Primer: | Forward Primer | (1 µmol/l) |
| | Reverse Primer | (1 µmol/l) |
| Probe (FAM/TAMRA) | | (1 µmol/l) |
| Template: | genomic DNA from *E. coli* | (0.5 ng/µl) |
| dT48-Magnetic beads | | (1 vial) |

The composition of the primer and the probe (FAM/TAMRA) corresponded to those described in the cited paper (see the list of sequences). Preparation of the dT48 beads was described in the previous example.

Reagents were pipetted at RT and heated up to 95° C., then Taq Polymerase was added. Following this, PCR cycles were carried out according to the following scheme:

| First 25 cycles: | | |
|---|---|---|
| Denaturation: | 95° C. | 30 sec |
| Hybridization: | 55° C. | 1 min |
| Extension: | 70° C. | 1 min |
| Next 25 cycles: | | |
| Denaturation: | 95° C. | 30 sec |
| Hybridization: | 55° C. | 1 min |
| Extension 1: | 60° C. | 1 min |
| Extension 2: | 70° C. | 1 min |
| Hold: | 4° C. | |

The PCR fragments were purified in part via ultrafiltration and/or via binding to the dT48 Magnetic Beads.

The analysis was performed by gel electrophoresis (10% acrylamide gel, acrylamide/bisacrylamide mixture Rotiphorese Roth) under denaturing conditions at 90° C., 150V.

The detection of the signals was performed using TAMRA dyes of the nuc macromolecule or by staining of the nucleic acid chains with ethidium bromide after electrophoresis.

Figure 31:
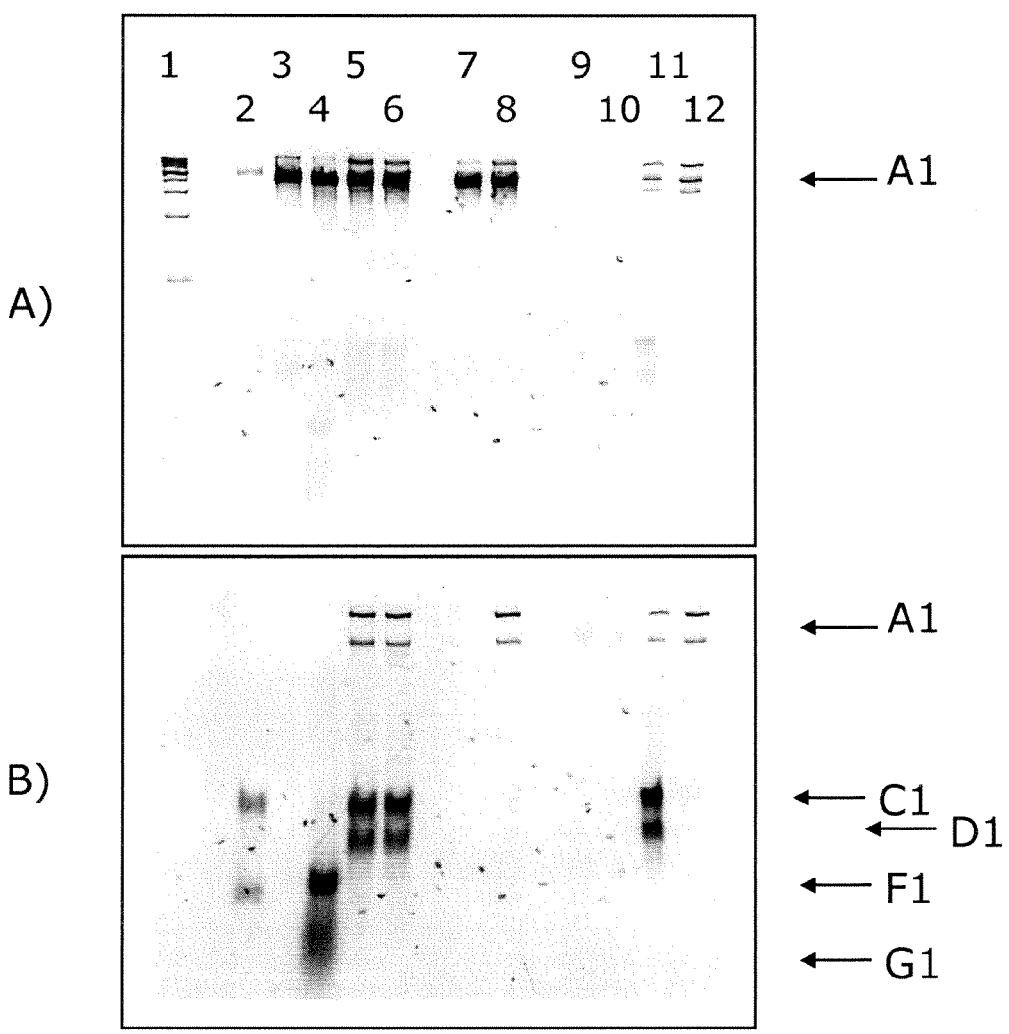
FIG. 31 shows gel electrophoresis of bacterial DNA reaction products following PCR and labelling (example 1.5.15.6).. In A and B imaging of fluorescence signals from nuc macromolecules was conducted (Part B), then the gel was stained with ethidium bromide and a further image was made (A).

The result of the labeling is shown in FIG. 31.

The PCR was successful under the applied conditions (bands of approximately 500 bp). The nuc macromolecules (dU-PEG(4)-[T1,A1]-TAMRA) were incorporated into the PCR products (Arrow A1, Lanes 5 and 6, FIG. 31 B). This was achieved despite a relatively high concentration of dTTP (200 µmol/l at the start of the reaction). The added DMSO (5%) in this reaction had no effect (the intensity of the bands in Lanes 5 and 6 is approximately equal). Two bands of high molecular mass correspond to a completely (upper band) and an incompletely labeled PCR product.

In a control reaction, the real-time PCR probe (FAM/TAMRA) was not incorporated (Lane 4), because it is not a nuc macromolecule. In this reaction, the PCR products did not carry a fluorescent label. The probe was partly degraded by the 5'-3' exonuclease activity of Taq polymerase, since it was hybridized to the target sequence during the reaction, as was expected for a real-time PCR test.

The labeled PCR products could be purified of primers and unincorporated nuc macromolecules via ultrafiltration MWCO 100 kDa (Lanes 7 and 8).

The labeled PCR fragments could be bound to the dT48 magnetic beads via introduced nuc macromolecules carring anchor domain directly after the PCR. The non-labeled PCR fragments did not bind to the dT48 beads, because they had no anchor domain.

Since the reaction also contained unincorporated nuc macromolecules, they also were bound to the beads (Lane 11). The labeled PCR fragments purified with ultrafiltration were free of nuc macromolecules and could be isolated in pure form by the beads (Lane 12).

This example shows how reagents and methods developed using real-time PCR can be used in combination with nuc macromolecules.

Below, literature sources are given which describe the amplification of nucleic acid chains and detection with specific probes. The composition of the primers and reaction conditions for the labeling with nuc macromolecules can be obtained from the following literature. The composition of the target domain of a particular type of nuc macromolecules that are specific to a respective target sequence can be derived from the composition of the probes described for real-time PCR.

Further, literature sources that describe microarray applications can also be used as a resource for the choice of appropriate target domains and anchor domains of nuc macromolecules. Some examples of such papers are also provided.

The literature sources are sorted by type of application to provide an easier overview of the potential application fields for nuc macromolecules. These sources should be understood to be examples of potential applications, and not limitations of the invention. The literature sources were found in the PubMed database.

Blood Group Determination:

Methods Mol Biol. 2009; 496:25-37. (Real-time PCR assays for high-throughput blood group genotyping.), Cancer Diagnostics:

Biomed Pharmacother. 2004 January; 58(1):1-9. (Prediction of hormone sensitivity by DNA microarray.), Breast Cancer. 2006; 13(2):123-8. (Basic research for hormone-sensitivity of breast cancer.) BMC Mol Biol. 2010 Feb. 1; 11:12. (Identification of endogenous control genes for normalisation of real-time quantitative PCR data in colorectal cancer.), Int 3 Oncol. 2006 February; 28(2):297-306. (Usefulness and clinical significance of quantitative real-time RT-PCR to detect isolated tumor cells in the peripheral blood and tumor drainage blood of patients with colorectal cancer.), Int J Cancer. 2004 Jan. 10; 108(2):219-27. (Quantitative real-time RT-PCR for detection of disseminated tumor cells in peripheral blood of patients with colorectal cancer using different mRNA markers.), J Biomed Sci. 2010 May 12; 17:37. (Rapid detection of epidermal growth factor receptor mutations with multiplex PCR and primer extension in lung cancer.) Endocr Relat Cancer. 2009 December; 16(4):1241-9. Epub 2009 Sep. 11. (Oestrogen receptor 1 mRNA is a prognostic factor in ovarian cancer patients treated with neo-adjuvant chemotherapy: determination by array and kinetic PCR in fresh tissue biopsies.) Prostate. 2009 Jun. 1; 69(8):810-9. (Quantitative RT-PCR analysis of estrogen receptor gene expression in laser microdissected prostate cancer tissue.) BMC Cancer. 2008 Nov. 21; 8:339. (Risk estimation of distant metastasis in node-negative, estrogen receptor-positive breast cancer patients using an RT-PCR based prognostic expression signature.) Lung Cancer. 2005 December; 50(3):375-84. Epub 2005 Sep. 30. (Epidermal growth factor receptor gene mutation in non-small cell lung cancer using highly sensitive and fast TaqMan PCR assay.) Am J Manag Care. 2005 May; 11(5):313-24. (Economic analysis of targeting chemotherapy using a 21-gene RT-PCR assay in lymph-node-negative, estrogen-receptor-positive, early-stage breast cancer). Int J Oncol. 2004 April; 24(4):861-7. (Minimal residual disease detection in breast cancer: improved sensitivity using cytokeratin 19 and epidermal growth factor receptor RT-PCR.) Clin Cancer Res. 2003 Nov. 1; 9(14):5346-57. (Identification of patients with transitional cell carcinoma of the bladder overexpressing ErbB2, ErbB3, or specific ErbB4 isoforms: real-time reverse transcription-PCR analysis in estimation of ErbB receptor status from cancer patients.) J Cell Mol Med. 2009 May 13. [Epub ahead of print] (High sensitivity of both sequencing and real-time PCR analysis of KRAS mutations in colorectal cancer tissue.) Clin Chem Lab Med. 2009; 47(5):530-6. (MYC quantitation in cell-free plasma DNA by real-time PCR for gastric cancer diagnosis.) Appl Immunohistochem Mol Morphol. 2009 May; 17(3):247-54. (An alternative and reliable real-time quantitative PCR method to determine HER2/neu amplification in breast cancer.) Clin Biochem. 2009 February; 42(3):194-200. Epub 2008 Nov. 6. (The detection of circulating tumor cells of breast cancer patients by using multimarker (Survivin, hTERT and hMAM) quantitative real-time PCR.). Cancer Sci. 2008 October; 99(10):1977-83. (Detection of colorectal cancer cells from feces using quantitative real-time RT-PCR for colorectal cancer diagnosis.) Eur J Cancer. 2009 January; 45(1):74-81. Epub 2008 Nov. 12. (Harmonisation of multi-centre real-time reverse-transcribed PCR results of a candidate prognostic marker in breast cancer: an E11-FP6 supported study of members of the EORTC—PathoBiology Group.) Med Oncol. 2009; 26(3):303-8. Epub 2008 Nov. 12. (Real-time quantitative RT-PCR assessment of PIM-1 and hK2 mRNA expression in benign prostate hyperplasia and prostate cancer.)

Br J Cancer. 2008 Nov. 18; 99(10):1644-50. Epub 2008 Oct. 28. (Protein kinase Cdelta expression in breast cancer as measured by real-time PCR, western blotting and ELISA.) Gynecol Oncol. 2009 January; 112(1):55-9. Epub 2008 Oct. 26. (The detection of differentially expressed microRNAs from the serum of ovarian cancer patients using a novel real-time PCR platform.) Jpn J Clin Oncol. 2008 November; 38(11):770-6. Epub 2008 Oct. 8. (Quantitative real-time RT-PCR detection for survivin, CK20 and CEA in peripheral blood of colorectal cancer patients.) Hepatogastroenterology. 2008 May-June; 55(84):1131-5. (Detection of circulating gastric cancer cells in peripheral blood using real time quantitative RT-PCR.) World J Surg Oncol. 2008 Jun. 11; 6:56. (Real time PCR analyses of expression of E-cadherin, alpha-, beta- and gamma-catenin in human breast cancer for predicting clinical outcome.) Int J Biol Markers. 2008 January-March; 23(1):$10^{-7}$. (Real-time reverse-transcription PCR to quantify a panel of 19 genes in breast cancer: relationships with sentinel lymph node invasion.) Urol Oncol. 2008 November-December; 26(6):634-40. Epub 2008 Jan. 14. (Real-time quantitative RT-PCR assay of prostate-specific antigen and prostate-specific membrane antigen in peripheral blood for detection of prostate cancer micrometastasis.) Lung Cancer. 2008 February; 59(2):147-54. Epub 2008 Jan. 4. (Quantitative reverse transcriptase real-time polymerase chain reaction (qRT-PCR) in translational oncology: lung cancer perspective.) BMC Mol Biol. 2007 Nov. 27; 8:107. (Evaluation and validation of candidate endogenous control genes for real-time quantitative PCR studies of breast cancer.) J Cancer Res Ther. 2005 October-December; 1(4):221-6. (Fluctuation of circulating tumor cells in patients with lung cancer by real-time fluorescent quantitative-PCR approach before and after radiotherapy.)

Clin Chim Acta. 2007 September; 384(1-2):52-6. Epub 2007 Jun. 6. (Development of real-time quantitative reverse transcription-PCR for Her2 detection in peripheral blood from patients with breast cancer.) J Immunol Methods. 2007 Jun. 30; 323(2):180-93. Epub 2007 May 15. (A multimarker real-time RT-PCR for MAGE-A gene expression allows sensitive detection and quantification of the minimal systemic tumor load in patients with localized cancer.) Neurol Res. 2007 July; 29(5):435-40. (p 53, BCL-2 and BAX in non-small cell lung cancer brain metastases: a comparison of real-time RT-PCR, ELISA and immunohistochemical techniques.) Clin Cancer Res. 2007 Feb. 15; 13(4):1192-7. (Quantitative detection of micrometastases in pelvic lymph nodes in patients with clinically localized prostate cancer by real-time reverse transcriptase-PCR.) Gastric Cancer. 2006; 9(4):308-14. Epub 2006 Nov. 24. (Detection of cancer cells disseminated in bone marrow using real-time quantitative RT-PCR of CEA, CK19, and CK20 mRNA in patients with gastric cancer.) Ann NY Acad Sci. 2006 September; 1075:230-4. (Quantification of total plasma cell-free DNA in ovarian cancer using real-time PCR.) Br J Cancer. 2006 Jul. 17; 95(2):218-25. Epub 2006 Jun. 6. (Biomarker selection for detection of occult tumour cells in lymph nodes of colorectal cancer patients using real-time quantitative RT-PCR.) Int J Biol Markers. 2006 January-March; 21(1):30-9. (Simultaneous quantitative detection of relevant biomarkers in breast cancer by quantitative real-time PCR.) Int J Cancer. 2006 Oct. 1; 119(7):1654-9. (A highly specific real-time RT-PCR method for the quantitative determination of CK-19 mRNA positive cells in peripheral blood of patients with operable breast cancer.) Breast Cancer Res Treat. 2009 December; 118(3):455-68. Epub 2008 Dec. 30. (Molecular characterization of circulating tumor cells in large quantities of contaminating leukocytes by a multiplex real-time PCR.) Clin Chem. 2007 July; 53(7):1206-15. Epub 2007 May 24. (Optimal markers for real-time quantitative reverse transcription PCR detection of circulating tumor cells from melanoma, breast, colon, esophageal, head and neck, and lung cancers.)

Mol Diagn Ther. 2006; 10(1):41-7. (Detection of circulating tumor cells in peripheral blood of breast cancer patients during or after therapy using a multigene real-time RT-PCR assay.) Anticancer Res. 2006 March-April; 26(2B):1567-75. (Multigene real-time PCR detection of circulating tumor cells in peripheral blood of lung cancer patients.) Eur J Med Res. 2009 Dec. 7; 14 Suppl 4:237-40. (Real-time PCR quantification of plasma DNA in non-small cell lung cancer patients and healthy controls.) Lung Cancer. 2009 April; 64(1):92-7. Epub 2008 Sep. 19. (Circulating plasma DNA as diagnostic biomarker in non-small cell lung cancer.) Lung Cancer. 2005 July; 49(1):1-12. (Circulating tumour-derived DNA and RNA markers in blood: a tool for early detection, diagnostics, and follow-up?) Pathobiology. 2010; 77(1):38-45. Epub 2010 Feb. 25. (Real-time RT-PCR analysis for evaluating the Her2/neu status in breast cancer.)

Cattle Testing

J Clin Microbiol. 2010 Sep. 15. (Specific Detection of Rinderpest Virus by Real-Time RT-PCR in Preclinical and Clinical Samples of Experimentally Infected Cattle.), Water Res. 2010 March; 44(5):1381-8. (Monitoring bacterial indicators and pathogens in cattle feedlot waste by real-time PCR)., J Virol Methods. 2009 October; 161(1):122-7. (A short target real-time RT-PCR assay for detection of pestiviruses infecting cattle.), Vet Microbiol. 2008 Nov. 25; 132(1-2):158-64. (Diagnostic specificity of a real-time RT-PCR in cattle for foot-and-mouth disease and swine for foot-and-mouth disease and classical swine fever based on non-invasive specimen collection.), Mol Cell Probes. 2008 April; 22(2):90-5. (Real-time multiplex PCR assay for rapid detection and toxintyping of *Clostridium perfringens* toxin producing strains in feces of dairy cattle.), Foodborne Pathog Dis. 2006 Winter; 3(4):337-46. (Development and evaluation of a real-time FRET probe based multiplex PCR assay for the detection of prohibited meat and bone meal in cattle feed and feed ingredients.), J Virol Methods. 2003 August; 111(2):95-100. (Detection of carrier cattle and sheep persistently infected with foot-and-mouth disease virus by a rapid real-time RT-PCR assay.)

Detection of Parasites (e.g. Malaria)

Clin Microbiol Infect. 2010 Mar. 13. (Multiplex real-time PCR for the diagnosis of malaria: correlation with microscopy.) Exp Parasitol. 2007 August; 116(4):427-32. (Real-time PCR versus conventional PCR for malaria parasite detection in low-grade parasitemia.) J Clin Microbiol. 2004 February; 42(2):636-8. (Evaluation of the RealArt Malaria LC real-time PCR assay for malaria diagnosis.) Mol Biochem Parasitol. 2003 October; 131(2):83-91. (Real-time quantitative PCR for analysis of genetically mixed infections of malaria parasites: technique validation and applications.) J Clin Microbiol. 2002 November; 40(11):4343-5. (Real-time fluorescence-based PCR for detection of malaria parasites.) Clin Microbiol Infect. 2010 Aug. 12. (Validation of a four-primer real-time PCR as a diagnostic tool for single and mixed *Plasmodium* infections.) Malar J. 2009 Dec. 9; 8:284. (Multiplex real-time quantitative PCR, microscopy and rapid diagnostic immuno-chromatographic tests for the detection of *Plasmodium* spp: performance, limit of detection analysis and quality assurance.) Clin Microbiol Infect. 2010 August; 16(8):1305-11. (Comparison of three real-time PCR methods with blood smears and rapid diagnostic test in *Plasmodium* sp. infection.) J Clin Microbiol. 2009 April; 47(4):975-80. (Multiplexed real-time PCR assay for discrimination of *Plasmodium* species with improved sensitivity for mixed infections.)

Other parasites: Freezing of stool samples improves real-time PCR detection of *Entamoeba dispar* and *Entamoeba histolytica*. J Microbiol Methods. 2010 March; 80(3):310-2., Detection of Clonorchis sinensis in stool samples using real-time PCR. Ann Trop Med Parasitol. 2009 September; 103(6): 513-8., Parasitological diagnosis combining an internally controlled real-time PCR assay for the detection of four protozoa in stool samples with a testing algorithm for microscopy. Clin Microbiol Infect. 2009 September; 15(9):869-74. Multiplex real-time PCR for the detection and quantification of *Schistosoma mansoni* and *S. haematobium* infection in stool samples collected in northern Senegal. Trans R Soc Trop Med Hyg. 2008 February; 102(2):179-85. Comparison of microscopy, real-time PCR and a rapid immunoassay for the detection of *Giardia lamblia* in human stool specimens., Clin Microbiol Infect. 2007 December; 13(12):1186-91. Novel real-time PCr for detection of *Schistosoma japonicum* in stool. Southeast Asian J Trop Med Public Health. 2006 March; 37(2):257-64. Real-time PCR in clinical practice: a powerful tool for evaluating *Leishmania chagasi* loads in naturally infected dogs. Ann Trop Med Parasitol. 2010 March; 104(2):137-43. The development of a real-time PCR assay for the quantification of *Leishmania infantum* DNA in canine blood. Vet J. 2009 November; 182(2):356-8. Comparison between quantitative nucleic acid sequence-based amplification, real-time reverse transcriptase PCR, and real-time PCR for quantification of *Leishmania* parasites.

J Clin Microbiol. 2008 January; 46(1):73-8. Rapid identification of *Leishmania* complexes by a real-time PCR assay. Am J Trop Med Hyg. 2005 December; 73(6):999-1004. Diagnosis of pulmonary infection with *Toxoplasma gondii* in immunocompromised HIV-positive patients by real-time PCR. Eur J Clin Microbiol Infect Dis. 2006 June; 25(6):401-4.

Real-time PCR for quantitative detection of *Toxoplasma gondii*. J Clin Microbiol. 2000 November; 38(11):4121-5. Development of a real-time PCR for the differentiation of the G1 and G2/G3 genotypes of *Echinococcus granulosus*. Parasitol Res. 2009 July; 105(1):255-9. Epub 2009 Mar. 14.

Detection of bacteria (e.g. meningitis) Real-time PCR detection of five prevalent bacteria causing acute meningitis. APMIS. 2009 November; 117(11):856-60. Rapid detection of eight causative pathogens for the diagnosis of bacterial meningitis by real-time PCR. J Infect Chemother. 2009 April; 15(2):92-8. Increased detection rate in diagnosis of herpes simplex virus type 2 meningitis by real-time PCR using cerebrospinal fluid samples. J Clin Microbiol. 2007 August; 45(8):2516-20. Broad-range real time PCR and DNA sequencing for the diagnosis of bacterial meningitis. Scand J Infect Dis. 2006; 38(1):27-35. Rapid diagnosis of bacterial meningitis by using multiplex PCR and real time PCR. Pediatr Int. 2004 October; 46(5):551-4. Rapid real-time PCR for determination of penicillin susceptibility in pneumococcal meningitis, including culture-negative cases. J Clin Microbiol. 2002 February; 40(2):682-4. Simultaneous detection of *Neisseria meningitidis, Haemophilus influenzae*, and *Streptococcus pneumoniae* in suspected cases of meningitis and septicemia using real-time PCR. J Clin Microbiol. 2001 April; 39(4):1553-8.

Detection of the diarrhea causing pathogens: Multiplex real-time RT-PCR for the simultaneous detection and quantification of transmissible gastroenteritis virus and porcine epidemic diarrhea virus. J Virol Methods. 2007 December; 146(1-2):172-7. A one-step multiplex real-time RT-PCR for detection and typing of bovine viral diarrhea viruses. Vet Microbiol. 2006 Aug. 25; 116(1-3):37-44. Prospective multicenter evaluation of a new immunoassay and real-time PCR for rapid diagnosis of *Clostridium difficile*-associated diarrhea in hospitalized patients. J Clin Microbiol. 2005 October; 43(10):5338-40. Increased detection of rotavirus using a real time reverse transcription-polymerase chain reaction (RT-PCR) assay in stool specimens from children with diarrhea. J Med Virol. 2004 March; 72(3):496-501. Real-time PCR for simultaneous detection and genotyping of bovine viral diarrhea virus. J Virol Methods. 2003 December; 114(1):21-7. Development of a serogroup-specific DNA microarray for identification of *Escherichia coli* strains associated with bovine septicemia and diarrhea. Vet Microbiol. 2010 May 19; 142(3-4):373-8. A novel DNA microarray for rapid diagnosis of enteropathogenic bacteria in stool specimens of patients with diarrhea. J Microbiol Methods. 2008 December; 75(3): 566-71. DNA microarray for direct identification of bacterial pathogens in human stool samples. Digestion. 2008; 78(2-3): 131-8 Development of a panel of multiplex real-time polymerase chain reaction assays for simultaneous detection of major agents causing calf diarrhea in feces. J Vet Diagn Invest. 2010 July; 22(4):509-17. A set of novel multiplex Taqman real-time PCRs for the detection of diarrhoeagenic *Escherichia coli* and its use in determining the prevalence of EPEC and EAEC in a university hospital. Ann Clin Microbiol Antimicrob. 2010 Jan. 22; 9:5 Comprehensive and rapid real-time PCR analysis of 21 foodborne outbreaks. Int J Microbiol. 2009; 2009:917623. Detection of noroviruses in fecal specimens by direct RT-PCR without RNA purification J Virol Methods. 2010 February; 163(2):282-6. Broadly reactive TaqMan assay for real-time RT-PCR detection of rotavirus in clinical and environmental samples. JIN2@cdc.gov. J Virol Methods. 2009 February; 155(2):126-31. A real-time PCR assay for the detection of *Salmonella* in a wide variety of food and food-animal matricest. J Food Prot. 2007 May; 70(5):1080-7. Real-time reverse transcription-PCR for detection of rotavirus and adenovirus as causative agents of acute viral gastroenteritis in children. J Clin Microbiol. 2006 September; 44(9):3189-95.

Detection of the sepsis causing agents: DNA microarray for the identification of pathogens causing bloodstream infections. Expert Rev Mol Diagn. 2010 April; 10(3):263-8. DNA microarray-based identification of bacterial and fungal pathogens in bloodstream infections. Mol Cell Probes. 2010 February; 24(1):44-52. Identification and characterization of bacterial pathogens causing bloodstream infections by DNA microarray. J Clin Microbiol. 2006 July; 44(7):2389-97. Detecting sepsis-associated bloodstream infection acquired in intensive care using multi-pathogen real-time PCR. J Infect. 2009 October; 59(4):296-8. Detection of bloodstream infection in neonatal foals with suspected sepsis using real-time PCR. Vet Rec. 2009 Jul. 25; 165(4):114-7. Multiplex real-time PCR and blood culture for identification of bloodstream pathogens in patients with suspected sepsis. Clin Microbiol Infect. 2009 June; 15(6):544-51. Diagnosis of bloodstream infections in immunocompromised patients by real-time PCR. J Infect. 2009 May; 58(5):346-51. Improved detection of blood stream pathogens by real-time PCR in severe sepsis. Intensive Care Med. 2010 January; 36(1):49-56. Detecting sepsis-associated bloodstream infection acquired in intensive care using multi-pathogen real-time PCR. J Infect. 2009 October; 59(4):296-8. Laboratory diagnosis of late-onset sepsis in newborns by multiplex real-time PCR. J Med Microbiol. 2009 April; 58(Pt 4):533-4. Molecular identification of bloodstream pathogens in patients presenting to the emergency department with suspected sepsis. Shock. 2010 July; 34(1):27-30. Multiplex PCR to diagnose bloodstream infections in patients admitted from the emergency department with sepsis. J Clin Microbiol. 2010 January; 48(1):26-33. Improved detection of blood stream pathogens by real-time PCR in severe sepsis. Intensive Care Med. 2010 January; 36(1):49-56. Preliminary clinical study using a multiplex real-time PCR test for the detection of bacterial and fungal DNA directly in blood. Clin Microbiol Infect. 2010 June; 16(6):774-9. Utility of a commercially available multiplex real-time PCR assay to detect bacterial and fungal pathogens in febrile neutropenia. J Clin Microbiol. 2009 August; 47(8):2405-10. Rapid diagnosis of sepsis and bacterial meningitis in children with real-time fluorescent quantitative polymerase chain reaction amplification in the bacterial 16S rRNA gene. Clin Pediatr (Phila). 2009 July; 48(6):641-7, Multiplex real-time PCR and blood culture for identification of bloodstream pathogens in patients with suspected sepsis. Clin Microbiol Infect. 2009 June; 15(6):544-51. Detection of cytomegalovirus in whole blood using three different real-time PCR chemistries. J Mol Diagn. 2009 January; 11(1):54-9. A multiplex real-time PCR assay for rapid detection and differentiation of 25 bacterial and fungal pathogens from whole blood samples. Med Microbiol Immunol. 2008 September; 197(3):313-24., Detection of various viruses, e.g. HIV or HPV: Comparison of real-time PCR methods for measurement of HIV-1 proviral DNA. J Virol Methods. 2010 March; 164(1-2):135-8. Real-time RT-PCR for automated detection of HIV-1 RNA during blood donor screening. Methods Mol Biol. 2010; 630: 319-35 Low-cost HIV-1 diagnosis and quantification in dried blood spots by real time PCR. PLoS One. 2009 Jun. 5; 4(6): e5819. Single-point mutations causing more than 100-fold underestimation of human immunodeficiency virus type 1 (HIV-1) load with the Cobas TaqMan HIV-1 real-time PCR assay. J Clin Microbiol. 2009 April; 47(4):1238-40. Detection and quantitation of HPV in genital and oral tissues and fluids by real time PCR. Virol J. 2010 Aug. 19; 7:194. Evaluation of a prototype real-time PCR assay for carcinogenic human papillomavirus (HPV) detection and simultaneous HPV genotype 16 (HPV16) and HPV18 genotyping. J Clin Microbiol. 2009 October; 47(10):3344-7. High-throughput two-step LNA real time PCR assay for the quantitative detection and genotyping of HPV prognostic-risk groups. J Clin Virol. 2009 August; 45(4):304-10. Study comparing human papillomavirus (HPV) real-time multiplex PCR and Hybrid Capture II INNO-LiPA v2 HPV genotyping PCR assays. J Clin Microbiol. 2009 July; 47(7):2106-13. Detection and differentiation of human papillomavirus genotypes HPV-6 and HPV-11 by FRET-based real-time PCR. J Virol Methods. 2008 November; 153(2):245-9.

Molecular beacon-based real-time PCR method for detection of 15 high-risk and 5 low-risk HPV types. J Virol Methods. 2008 April; 149(1):153-62. Real-time PCR assays using internal controls for quantitation of HPV-16 and beta-globin DNA in cervicovaginal lavages. J Virol Methods. 2003 December; 114(2):135-44.

Detection of Nucleic Acid Chains can be Conducted on Different Biological Probes and Samples, e.g. Stool, Swabs, Urine, Lung Secretions.

Comparison of microscopy, two xenic culture techniques, conventional and real-time PCR for the detection of Dientamoeba fragilis in clinical stool samples. Eur J Clin Microbiol Infect Dis. 2010 April; 29(4):411-6. Epub 2010 Feb. 14. Freezing of stool samples improves real-time PCR detection of *Entamoeba dispar* and *Entamoeba histolytica*. J Microbiol Methods. 2010 March; 80(3):310-2. Epub 2010 Jan. 18. Detection of Clonorchis sinensis in stool samples using real-time PCR. Ann Trop Med Parasitol. 2009 September; 103(6): 513-8. Rapid and sensitive detection of Shiga toxin-producing *Escherichia coli* from nonenriched stool specimens by real-time PCR in comparison to enzyme immunoassay and culture. J Clin Microbiol, 2009 July; 47(7):2008-12. Epub 2009 May 13. Direct detection of *Campylobacter jejuni* in human stool samples by real-time PCR. Can J Microbiol. 2008 September; 54(9):742-7. Enhancement of detection and quantification of rotavirus in stool using a modified real-time RT-PCR assay. J Med Virol, 2008 August; 80(8):1489-96. Detection of methicillin-resistant *Staphylococcus aureus* directly from nasal swab specimens by a real-time PCR assay. J Clin Microbiol. 2004 December; 42(12):5578-81 Detection and quantitation of HPV in genital and oral tissues and fluids by real time PCR. Virol J. 2010 Aug. 19; 7:194. Study comparing human papillomavirus (HPV) real-time multiplex PCR and Hybrid Capture II INNO-LiPA v2 HPV genotyping PCR assays. J Clin Microbiol. 2009 July; 47(7):2106-13. Epub 2009 May 6. Detection and differentiation of human papillomavirus genotypes HPV-6 and HPV-11 by FRET-based real-time PCR. J Virol Methods. 2008 November; 153

(2):245-9. Epub 2008 Sep. 4. Molecular beacon-based real-time PCR method for detection of 15 high-risk and 5 low-risk HPV types. J Virol Methods. 2008 April; 149(1):153-62. Epub 2008 Feb. 20. Diagnosis of amebic liver abscess and amebic colitis by detection of *Entamoeba histolytica* DNA in blood, urine, and saliva by a real-time PCR assay. J Clin Microbiol. 2010 August; 48(8):2798-801. Epub 2010 Jun. 9. Validation of a laboratory-developed real-time PCR protocol for detection of *Chlamydia trachomatis* and *Neisseria gonorrhoeae* in urine. Sex Transm Infect. 2010 June; 86(3):207-11. Detection of dengue virus in saliva and urine by real time RT-PCR. Virol 3. 2010 Jan. 27; 7:22. Endocervical swabs transported in first void urine as combined specimens in the detection of *Mycoplasma genitalium* by real-time PCR.

J Med Microbiol. 2009 January; 58(Pt 1):117-20. Detection of *Leishmania infantum* DNA by fret-based real-time PCR in urine from dogs with natural clinical leishmaniosis. Vet Parasitol. 2007 Jul. 20; 147(3-4):315-9. Epub 2007 May 25. Real-time PCR assay using specimens on filter disks as a template for detection of cytomegalovirus in urine. J Clin Microbiol. 2007 April; 45(4):1305-7. Epub 2007 Feb. 7. Real-time PCR assay for detection of quinolone-resistant *Neisseria gonorrhoeae* in urine samples. J Clin Microbiol. 2007 April; 45(4):1250-4. Epub 2007 Jan. 31. Human papillomavirus quantification in urine and cervical samples by using the Mx4000 and LightCycler general real-time PCR systems. J Clin Microbiol. 2007 March; 45(3):897-901. Epub 2007 Jan. 17. A novel real-time PCR to detect *Chlamydia trachomatis* in first-void urine or genital swabs. J Med Microbiol. 2006 December; 55(Pt 12):1667-74. Quantitative detection of *Escherichia coli* from urine of patients with bacteriuria by real-time PCR. Mol. Diagn. 2004; 8(3):179-84. Use of the Roche LightCycler instrument in a real-time PCR for *Trichomonas vaginalis* in urine samples from females and males. J Clin Microbiol. 2003 December; 41(12):5619-22. Isolation and detection of *Borrelia burgdorferi* DNA from cerebral spinal fluid, synovial fluid, blood, urine, and ticks using the Roche MagNA Pure system and real-time PCR. Diagn Microbiol Infect Dis. 2003 August; 46(4):235-40. Quantitative detection of *Mycoplasma genitalium* from first-pass urine of men with urethritis and asymptomatic men by real-time PCR. J Clin Microbiol. 2002 April; 40(4):1451-5. Rapid detection and quantification of CMV DNA in urine using LightCycler-based real-time PCR. J Clin Virol. 2002 February; 24(1-2):131-4. Direct detection of *Pseudomonas aeruginosa* from patients with healthcare associated pneumonia by real time PCR. Infect Genet Evol. 2010 Aug. 20. Quadruplex real-time quantitative PCR assay for the detection of pathogens related to late-onset ventilator-associated pneumonia: a preliminary report. J Microbiol Methods. 2010 June; 81(3):232-4. Epub 2010 Mar. 28. Usefulness of real-time PCR for lytA, ply, and Spn9802 on plasma samples for the diagnosis of pneumococcal pneumonia. Clin Microbiol Infect. 2010 August; 16(8):1135-41. Epub 2009 Oct. 14. Real-time PCR is more specific than conventional PCR for induced sputum diagnosis of *Pneumocystis* pneumonia in immunocompromised patients without HIV infection. Respirology. 2009 March; 14(2):203-9. Epub 2008 Dec. 11. Comprehensive detection of causative pathogens using real-time PCR to diagnose pediatric community-acquired pneumonia. J Infect Chemother. 2008 December; 14(6):424-32. Epub 2008 Dec. 17. Simultaneous detection of pathogens in clinical samples from patients with community-acquired pneumonia by real-time PCR with pathogen-specific molecular beacon probes. J Clin Microbiol. 2006 April; 44(4):1440-6.

Assessment of real-time PCR for diagnosis of *Mycoplasma pneumoniae* pneumonia in pediatric patients. Can J Microbiol. 2006 February; 52(2):125-9.

Nucleic Acid Chains Isolated from Food can be Detected

Total and pathogenic *Vibrio parahaemolyticus* in shrimp: Fast and reliable quantification by real-time PCR. Int J Food Microbiol. 2010 Aug. 25. Quadruplex real-time PCR assay for detection and identification of *Vibrio cholerae* O1 and O139 strains and determination of their toxigenic potential. Appl Environ Microbiol. 2009 November; 75(22):6981-5. Evaluation of a real-time PCR assay for the detection and quantification of *Bacillus cereus* group spores in food. J Food Prot. 2010 August; 73(8):1480-5. Pentaplexed quantitative real-time PCR assay for the simultaneous detection and quantification of botulinum neurotoxin-producing clostridia in food and clinical samples. Appl Environ Microbiol. 2010 July; 76(13):4387-95. Design of a new universal real-time PCR system targeting the tuf gene for the enumeration of bacterial counts in food. J Food Prot. 2010 April; 73(4):670-9.

Rapid detection and differentiation of *Campylobacter jejuni*, *Campylobacter coli*, and *Campylobacter lari* in food, using multiplex real-time PCR. J Food Prot. 2010 February; 73(2):241-50. Validation of a newly developed hexaplex real-time PCR assay for screening for presence of GMOs in food, feed and seed. Anal Bioanal Chem. 2010 March; 396(6): 2103-12. Multiplex real-time PCR using SYBR((R)) GreenER for the detection of DNA allergens in food. Anal Bioanal Chem. 2010 Jan. 20. A real-time PCR method for the detection of *Salmonella enterica* from food using a target sequence identified by comparative genomic analysis. Int J Food Microbiol. 2010 Feb. 28; 137(2-3):168-74. Detection of allergen walnut component in food by an improved real-time PCR method. J Food Prot. 2009 November; 72(11):2433-5. Real-time FRET PCR assay for *Salmonella enterica* serotype detection in food. Mil Med. 2009 September; 174(9):983-90.

Development and validation of a duplex real-time PCR method to simultaneously detect potentially allergenic sesame and hazelnut in food. J Agric Food Chem. 2009 Mar. 25; 57(6):2126-34. Real-time PCR method using capturing oligo-immobilized PCR tubes to determine the specific gene for soybean and genetically modified soybean in food matrices. Biosci Biotechnol Biochem. 2008 November; 72(11): 2953-8. TaqMan-based real-time PCR method for detection of *Yersinia pseudotuberculosis* in food. Appl Environ Microbiol. 2008 October; 74(20):6465-9 Real-time PCR for quantitative detection of bovine tissues in food and feed. J Food Prot. 2008 March; 71(3):564-72. Development of a real-time PCR method to detect potentially allergenic sesame (*Sesamum indicum*) in food. J Agric Food Chem. 2007 Dec. 26; 55(26):10540-7. A novel real-time PCR-based method for the detection of *Listeria monocytogenes* in food. Lett Appl Microbiol. 2007 November; 45(5):568-73.

A real-time PCR assay for the detection of *Salmonella* in a wide variety of food and food-animal matricest. J Food Prot. 2007 May; 70(5):1080-7.

Genes Coding for Toxins or Resistance can be Detected

Quantification of Shiga toxin-converting bacteriophages in wastewater and in fecal samples by real-time quantitative PCR.

Appl Environ Microbiol. 2010 September; 76(17):5693-701. Genetic diagnosis of community-acquired MRSA: a multiplex real-time PCR method for Staphylococcal cassette chromosome mec typing and detecting toxin genes. Tohoku J Exp Med. 2010; 220(2):165-70. A quadruplex real-time PCR assay for rapid detection and differentiation of the *Clostridium botulinum* toxin genes A, B, E and F. J Med Microbiol. 2010 January; 59(Pt 1):55-64. Epub. Rapid and sensitive detection of Shiga toxin-producing *Escherichia coli* from nonenriched stool specimens by real-time PCR in comparison to enzyme immunoassay and culture. J Clin Microbiol. 2009 July; 47(7):2008-12. Epub 2009 May 13. Development of a real-time PCR assay with an internal amplification control for the screening of Shiga toxin-producing *Escherichia coli* in foods. Lett Appl Microbiol. 2009 May; 48(5):554-9. Epub 2009 Feb. 9. Detection of *Mycobacterium tuberculosis* resistance mutations to rifampin and isoniazid by real-time PCR. Indian J Med Microbiol. 2010 July-September; 28(3):211-6. Rapid detection of influenza A pandemic (H1N1) 2009 virus neuraminidase resistance mutation H275Y by real-time reverse transcriptase PCR. J Clin Microbiol. 2010 May; 48(5):1884-7. Novel mixed-format real-time PCR assay to detect mutations conferring resistance to triazoles in *Aspergillus fumigatus* and prevalence of multi-triazole resistance among clinical isolates in the Netherlands. J Antimicrob Chemother. 2010 May; 65(5):901-5 Detection of fluoroquinolone resistance level in clinical canine and feline *Escherichia coli* pathogens using rapid real-time PCR assay. Vet Microbiol. 2009 Nov. 18; 139(3-4):379-85. Real-time PCR assays for monitoring benzimidazole resistance-associated mutations in *Ancylostoma* caninum. Exp Parasitol. 2009 May; 122(1):6-10.

Quantification of genes encoding resistance to aminoglycosides, beta-lactams and tetracyclines in wastewater environments by real-time PCR. Int J Environ Health Res. 2009 June; 19(3):219-30. Rapid detection of *Staphylococcus aureus* bacteremia and methicillin resistance by real-time PCR in whole blood samples. Eur J Clin Microbiol Infect Dis. 2009 August; 28(8):1001-5. Quadruplex real-time PCR assay using allele-specific scorpion primers for detection of mutations conferring clarithromycin resistance to *Helicobacter pylori*. J Clin Microbiol. 2008 July; 46(7):2320-6. Rapid identification of penicillin and macrolide resistance genes and simultaneous quantification of *Streptococcus pneumoniae* in purulent sputum samples by use of a novel real-time multiplex PCR assay. J Clin Microbiol. 2008 July; 46(7): 2384-8. Routine use of real-time PCR for detection of *Helicobacter pylori* and of clarithromycin resistance mutations. Gastroenterol Clin Biol. 2007 October; 31(10):792-5. Detection of azithromycin resistance in *Treponema pallidum* by real-time PCR. Antimicrob Agents Chemother. 2007 September; 51(9):3425-30 Detection of meticillin-resistant *staphylococcus aureus* (MRSA) colonization in newborn infants using real-time polymerase chain reaction (PCR). Acta Paediatr. 2010 Jun. 2. Detection limits of a rapid MRSA detection assay based on multiplex real-time PCR. J Infect Chemother. 2010 June; 16(3):223.

1.5.15.7 Labeling of Target Sequences with Solid-Phase-Bound Nuc Macromolecules

This reaction was performed in a manner similar to that detailed in Example 1.5.15.1. The target sequence (template 2, M2) was hybridized with a primer and nuc macromolecule (dU-PEG(8)-[T1,A1]-TAMRA) and then specifically bound to the solid phase via the anchor domain of the nuc macromolecule. This nuc macromolecule had dUTP as nuc component, a target domain which can bind to the target sequence, an anchor domain (dA25), and a fluorescent dye (TAMRA) at the 3' end of the anchor domain, which serves as a signal domain. A solid phase which was capable of binding these anchor domains (dT48 magnetic beads, preparation see section 1.5.15.5) was used. After binding, the solid phase was washed and suspended in incorporation buffer 1.

Natural nucleotides (dATP, dCTP, dGTP, each 100 µmol/l) were added to this solid phase with bound reaction components. The dTTP was omitted in reaction 1 (Lane 1) and added to reaction 2 (Lane 2) up to 100 µmol/l concentration. The reaction was started by adding Klenow fragment exo minus (1:50) and conducted at RT for 30 min. After the reaction, the solid phase was directly loaded onto the gel and products were separated by denaturing electrophoresis under 85° C.

Figure 30:
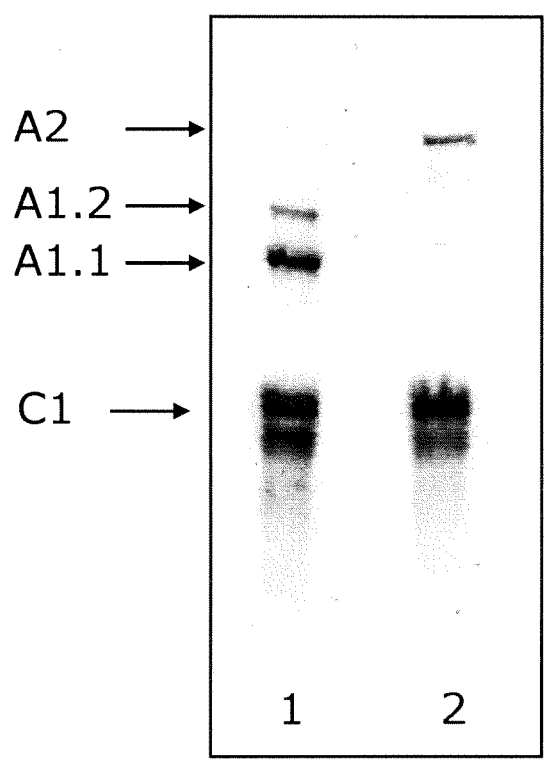
FIG. 30 shows a gel electrophoresis of labeled target sequences with solid-phase-bound nuc macromolecules (example 1.5.15.7).

The result is depicted in FIG. 30.

An incorporation of nuc macromolecules into the extended primer can be observed, wherein no complete synthesis of the complementary strand was achieved in the absence of dTTP (Arrow A1.1 and A1.2, Lane 1). In the presence of dTTP, Klenow fragment exo minus could conduct the strand synthesis in full length (Arrow A 2, Lane 2). Since in this experiment the nuc macromolecule carried a fluorescent dye, unused nucleotide can also be seen (arrow C1). The incompleteness of the consumption of nuc macromolecules is attributed to the steric effects of the surface.

List of Sequences Used:

```
Name, modification, sequence
Primer and probes/anchor
SEQ ID NO. 1 Primer T7-19:
5'- taatacgactcactatagg SEQ ID NO. 2 Primer T7-19-Cy3:
5'-Cy3- taatacgactcactatagg SEQ ID NO. 3 Primer dA50-T7-19:
5'- aaaaaaaaaa aaaaaaaaaa aaaaaaaaaa aaaaaaaaaa aaaaaaaaaa taatacgactcactatagg SEQ ID NO. 4 U19 Primer:
5' - GTT TTC CCA GTC ACG ACG SEQ ID NO. 5 Primer forward:
5'-tcc tac ggg agg cag cagt SEQ ID NO. 6 Primer reverse:
5'-gga cta cca ggg tat cta atc ctg tt SEQ ID NO. 7 Probe (FAM/TAMRA):
5' FAM-cgt att acc gcg gct gct gg cac-TAMRA SEQ ID NO. 8 dT48-Biotin (Binding partner for
anchor domain 1):
5'tttttttttt tttttttttt tttttttttt tttttttttt
tttttttt-Biotin SEQ ID NO. 9 B1-Biotin-Anchor (Binding partner
for anchor domain 2)
5'-Biotin- agtgaattcgagctcggtaC Oligonucleotide component of the nuc
macromolecules SEQ ID NO. 10 [T1, A1]-TAMRA:
Target-Domain-1, Anchor-Domain-1, TAMRA
5'NH2-cgt att acc gcg gct gct gg cac AAAAAAAAAA
AAAAAAAAAA AAAAA -TAMRA SEQ ID NO. 11 [T2, A2]-TAMRA:
Target-Domain-2, Anchor-Domain-2, TAMRA,
5'NH2-CGAGACGAAATGGGAtttttttttttttttttttttt-3'TAMRA SEQ ID NO. 12 [T3, A3]-TAMRA:
Target-Domain-3, Anchor-Domain-3, Fluorescein,
5'NH2-AAA AAA ACT gcg gct gct gg cac
Gtaccgagctcgaattcact -FAM Templates used:
SEQ ID NO. 13 Template 1 (M1):
5' GTT TTC CCA GTC ACG ACG GGAG gtg cc agc agc
cgc ggt aat acg ACCA cctatagtgagtcgtatta
```

-continued

SEQ ID NO. 14 Template 2 (M2):
5' GTT TTC CCA GTC ACG ACG GGAG gtg cc agc agc
cgc ggt aat acg AGT CTT CTCA cctatagtgagtcgtatta SEQ ID NO. 15 Template 3 (M3):
5' GTT TTC CCA GTC ACG ACG GGAG gtg cc agc agc
ggt aat acg AGT CTT CTGA cctatagtgagtcgtatta SEQ ID NO. 16 Template 4 (M4):
5' GTT TTC CCA GTC ACG ACG GGAG gtg cc agc ggt
aat acg AGT CTT CTGA cctatagtgagtcgtatta SEQ ID NO. 17 Template 5 (M5):
5' GTT TTC CCA GTC ACG ACG GGAG gtg cc agc agc
AAA AAA aat acg AGT CTT CTGA cctatagtgagtcgtatta SEQ ID NO. 18 Template 6 (M6):
5' GTT TTC CCA GTC ACG ACG GGAG gtg Ac agc Agc
cgc Agt aat Acg AGT CTT CTGA cctatagtgagtcgtatta SEQ ID NO. 19 Template 7 (M7):
5' GTT TTC CCA GTC ACG ACG GGAG gtg cc agc agc
cgc AAA AAA AAA AGT CTT CTGA cctatagtgagtcgtatta SEQ ID NO. 20 Template 8 (M8):
5' GTT TTC CCA GTC ACG ACG GGAG gtg cc agc agc
cgc AGT TTT TTT AGT CTT CTGA cctatagtgagtcgtatta SEQ ID NO. 21 Template 9 (M9):
5' GTT TTC CCA GTC ACG ACG GGAG cgc ggt aat acg
AGT CTT CTCA cctatagtgagtcgtatta SEQ ID NO. 22 Template 10 (M10)
5'-(A)$_{48}$TCC CAT TTC GTC TCG TTC CGC TTT
GTcctatagtgagtcgtatta All publications, patents, and patent applications that have been cited herein are incorporated into this application at full extent (even if it was not explicitly noted for a respective publication) and are subject to regulations in accordance with the USPTO for "incorporated by reference" for all purposes in the United States.

Individual embodiments are intended to illustrate the invention and can be further combined with each other by persons skilled in the area. Combinations of various embodiments also constitute the subject of the present invention.

Figure 26:
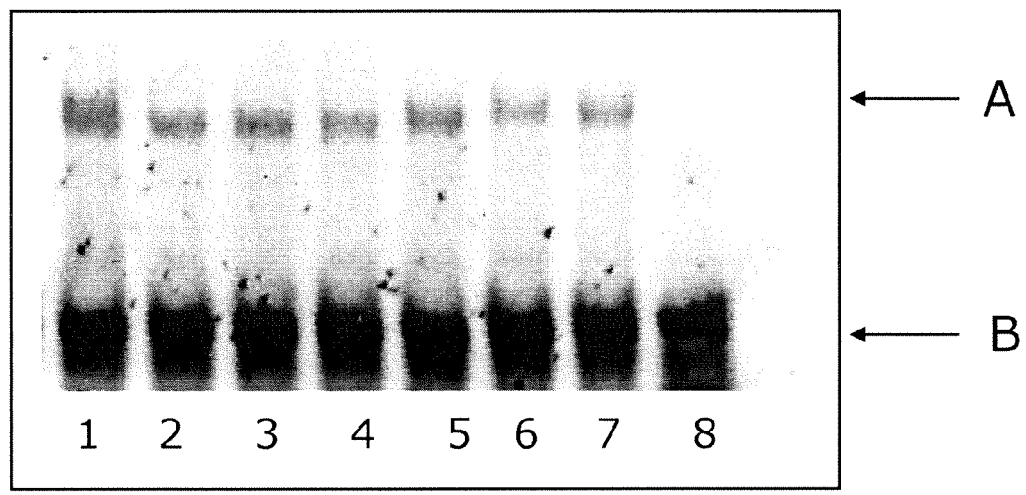
FIG. 26 shows separation of reaction products by gel electrophoresis after incorporation reaction described in example 1.5.15.1.

Legends for Figures:

FIG. 26, Example 1.5.15.1, Incorporation in Presence of Competing Nucleotides

Image of a gel after electrophoretic separation of the reaction products.

The following components were added into individual reactions in addition to the template, primer and polymerase. Individual lanes correspond to individual reactions.
1. +dU-PEG(8)-[T1,A1]-TAMRA
2. +dU-PEG(8)-[T1,A1]-TAMRA+dTTP 10 µmol/l
3. +dU-PEG(8)-[T1,A1]-TAMRA+dTTP 100 µmol/l
4. +dU-PEG(8)-[T1,A1]-TAMRA+dTTP 1 mmol/l
5. +dU-PEG(8)-[T1,A1]-TAMRA+dTTP 100 µmol/l+ dGTP 100 µmol/l
6. +dU-PEG(8)-[T1,A1]-TAMRA+dTTP 1 mmol/l+dGTP 100 µmol/l
7. +dU-PEG(8)-[T1,A1]-TAMRA+dTTP+dATP+dCTP+ dGTP je 100 µmol/l
8. Control: only dU-PEG(8)-[T1,A1]-TAMRA, no Polymerase Position of the extended primer with the incorporated dU-PEG(8)-[T1,A1]-TAMRA (arrow A), Position of the dU-PEG(8)-[T1,A1]-TAMRA in gel (arrow B).

FIG. 27, Example 1.5.15.2 Competition with 10 mmol/l dTTP

Image of a gel after electrophoretic separation of the reaction products.

The following components were included into individual reactions in addition to the template, primers, dATP, dGTP, dCTP (each 100 µmol/l), and polymerase (individual concentrations see below). Individual lanes correspond to individual reactions. An estimation of observed incorporation is given.

| Klenow 1:10 | |
|---|---|
| 1. + dU-PEG(8)-[T1,A1]-TAMRA | incorporation |
| 2. + dU-PEG(8)-[T1,A1]-TAMRA + dTTP 100 µmol/l | incorporation |
| 3. + dU-PEG(8)-[T1,A1]-TAMRA + dTTP 10 mmol/l | incorporation |
| Klenow 1:100 | |
| 4. + dU-PEG(8)-[T1,A1]-TAMRA | incorporation |
| 5. + dU-PEG(8)-[T1,A1]-TAMRA + dTTP 100 µmol/l | incorporation |
| 6. + dU-PEG(8)-[T1,A1]-TAMRA + dTTP 10 mmol/l | yield about 50% |
| Klenow 1:1000 | |
| 7. + dU-PEG(8)-[T1,A1]-TAMRA | incorporation |
| 8. + dU-PEG(8)-[T1,A1]-TAMRA + dTTP 100 µmol/l | incorporation |
| 9. + dU-PEG(8)-[T1,A1]-TAMRA + dTTP 10 mmol/l | low yield |
| Taq 1:100 | |
| 10. + dU-PEG(8)-[T1,A1]-TAMRA | incorporation |
| 11. + dU-PEG(8)-[T1,A1]-TAMRA + dTTP 100 µmol/l | incorporation |
| 12. + dU-PEG(8)-[T1,A1]-TAMRA + dTTP 10 mmol/l | low yield |
| Vent exo - 1:100 | |
| 13. + dU-PEG(8)-[T1,A1]-TAMRA + dTTP 10 mmol/l | no incorporation |
| 14. + dU-PEG(8)-[T1,A1]-TAMRA + dTTP 100 µmol/l | incorporation |
| 15. + dU-PEG(8)-[T1,A1]-TAMRA | incorporation |

Position of the extended primer with the incorporated dU-PEG(8)-[T1,A1]-TAMRA (arrow A1). Position of the partially extended primer with incorporated dU-PEG(8)-[T1, A1]-TAMRA in gel (arrow A2). Position of the dU-PEG(8)-[T1,A1]-TAMRA in gel (arrow B).

FIG. 28, Example 1.5.15.4, Cyclic Labeling Reaction, Different Target Sequences, Different Temperatures Image of a gel after electrophoretic separation of the reaction products. Individual lanes correspond to individual reactions.

FIG. 28, M2

(reactions with template 2, M2)
1. Cyclic primer extension (20 cycles) with Taq polymerase and the following components: M2, primer, four dNTPs, dU-PEG(4)-[T1,A1]-TAMRA;
2. Primer extension with Taq polymerase and the following components: M2, primer, four dNTPs, no dU-PEG(4)-[T1, A1]-TAMRA;
3. ladder: dU-PEG(4)-[T1,A1]-TAMRA, labeled primer Arrow A1: primer extension product labeled with the dU-PEG(4)-[T1,A1]-TAMRA (incomplete strand extension)

Arrow B1: primer extension product without dU-PEG(4)-[T1,A1]-TAMRA (labeling by primer Cy3)

Arrow C1: dU-PEG(4)-[T1,A1]-TAMRA (nuc macromolecule)

Arrow D1: degradation of dU-PEG(4)-[T1,A1]-TAMRA by 5-3 exonuclease activity of the Taq polymerase Arrow E1: labeled primer (T7-19-Cy3)

FIG. 28, M4

(reactions with template 4, M4)
1. Cyclic primer extension (20 cycles) with Taq polymerase, 35° C., the following components: M4, primer, four dNTPs, dU-PEG(4)-[T1,A1]-TAMRA;
2. Cyclic primer extension (20 cycles) with Taq polymerase, 45° C., the following components: M4, primer, four dNTPs, dU-PEG(4)-[T1,A1]-TAMRA;

3. Cyclic primer extension (20 cycles) with Taq polymerase, 55° C., the following components: M4, primer, four dNTPs, dU-PEG(4)-[T1,A1]-TAMRA;
4. Primer extension with Taq polymerase and the following components: M4, primer, four dNTPs, no dU-PEG(4)-[T1, A1]-TAMRA;
5. ladder: dU-PEG(4)-[T1,A1]-TAMRA, labeled primer
  Arrow A2: primer extension product labeled with the dU-PEG(4)-[T1,A1]-TAMRA (complete strand extension)
  Arrow B1: primer extension product without dU-PEG(4)-[T1,A1]-TAMRA (labeling by primer Cy3)
  Arrow C1: dU-PEG(4)-[T1,A1]-TAMRA (nuc macromolecule)
  Arrow E1: labeled primer (T7-19-Cy3)
  FIG. 28, M8
  (reactions with template 8, M8)
1. ladder: dU-PEG(4)-[T1,A1]-TAMRA, labeled primer
2. Cyclic primer extension (20 cycles) with Taq polymerase, 35° C., the following components: M8, primer, four dNTPs, dU-PEG(4)-[T1,A1]-TAMRA;
3. Cyclic primer extension (20 cycles) with Taq polymerase, 45° C., the following components: M8, primer, four dNTPs, dU-PEG(4)-[T1,A1]-TAMRA;
4. Cyclic primer extension (20 cycles) with Taq polymerase, 55° C., the following components: M8, primer, four dNTPs, dU-PEG(4)-[T1,A1]-TAMRA;
5. Primer extension with Taq polymerase and the following components: M8, primer, four dNTPs, no dU-PEG(4)-[T1, A1]-TAMRA;
  Arrow A2: primer extension product labeled with the dU-PEG(4)-[T1,A1]-TAMRA (complete strand extension)
  Arrow B1: primer extension product without dU-PEG(4)-[T1,A1]-TAMRA (labeling by primer Cy3)
  Arrow C1: dU-PEG(4)-[T1,A1]-TAMRA (nuc macromolecule)
  Arrow D1: degradation of dU-PEG(4)-[T1,A1]-TAMRA by 5-3 exonuclease activity of the Taq polymerase
  Arrow E1: labeled primer (T7-19-Cy3)
  FIG. 28, M9
  (reactions with template 8, M8)
1. Cyclic primer extension (20 cycles) with Taq polymerase, 35° C., the following components: M9, primer, four dNTPs, dU-PEG(4)-[T1,A1]-TAMRA;
2. Cyclic primer extension (20 cycles) with Taq polymerase, 45° C., the following components: M9, primer, four dNTPs, dU-PEG(4)-[T1,A1]-TAMRA;
3. Cyclic primer extension (20 cycles) with Taq polymerase, 55° C., the following components: M9, primer, four dNTPs, dU-PEG(4)-[T1,A1]-TAMRA;
4. Primer extension with Taq polymerase and the following components: M4, primer, four dNTPs, no dU-PEG(4)-[T1, A1]-TAMRA;
  Arrow B1: primer extension product without dU-PEG(4)-[T1,A1]-TAMRA (labeling by primer Cy3)
  Arrow C1: dU-PEG(4)-[T1,A1]-TAMRA (nuc macromolecule)
  Arrow E1: labeled primer (T7-19-Cy3)
  FIG. 29, Example 1.5.153, Labeling During PCR
  Image of a gel after electrophoretic separation of the reaction products.
  FIG. 29 part A
  Result of PCR reactions with a labeled primer. Individual lanes correspond to individual reactions. The components of the reactions are shown below. Template 2 (M2) was used as the target sequence.
1. PCR (20 cycles) with Taq polymerase, M2, both PCR-primer, four dNTPs, dU-PEG(4)-[T1,A1]-TAMRA;
2. PCR (20 cycles) with Vent exo minus polymerase, M2, both PCR-primer, four dNTPs, dU-PEG(4)-[T1,A1]-TAMRA;
3. ladder: dU-PEG(4)-[T1,A1]-TAMRA, labeled primer
4. PCR (20 cycles) with Taq polymerase, M2, both PCR-primer, four dNTPs, dU-PEG(8)-[T1,A1]-TAMRA;
5. PCR (20 cycles) with Vent exo minus polymerase, M2, both PCR-primer, four dNTPs, dU-PEG(8)-[T1,A1]-TAMRA;
6. PCR (20 cycles) with Taq polymerase, M2, both PCR-primer, four dNTPs, no dU-PEG(8)-[T1,A1]-TAMRA (control);
7. PCR (20 cycles) with Vent exo minus polymerase, M2, both PCR-primer, four dNTPs, no dU-PEG(8)-[T1,A1]-TAMRA (control);
  Arrow A1: PCR product labeled with the dU-PEG(4)-[T1,A1]-TAMRA or with dU-PEG(8)-[T1,A1]-TAMRA (incomplete strand extension)
  Arrow A2: PCR product labeled with the dU-PEG(4)-[T1,A1]-TAMRA or with dU-PEG(8)-[T1,A11]-TAMRA (complete strand extension)
  Arrow B1: PCR product without dU-PEG(4)-[T1,A1]-TAMRA or dU-PEG(8)-[T1,A1]-TAMRA (labeling by primer Cy3)
  Arrow C1: dU-PEG(4)-[T1,A1]-TAMRA (nuc macromolecule)
  Arrow D1: degradation of dU-PEG(4)-[T1,A1]-TAMRA or dU-PEG(8)-[T1,A1]-TAMRA by 5-3 exonuclease activity of the Taq polymerase
  Arrow E1: labeled primer (T7-19-Cy3)
  FIG. 29 Part B
  Comparison of PCR products with and without specific isolation by solid phase (dT48-anchor beads). Individual lanes correspond to individual reactions. The components of the reactions are shown below.
1. PCR (20 cycles) with Taq polymerase, M2, both PCR primers, four dNTPs, dU-PEG(4)-[T1,A1]-TAMRA;
2. PCR (20 cycles) with Taq polymerase, M2, both PCR primers, four dNTPs, no dU-PEG(4)-[T1,A1]-TAMRA (control);
3. Labeled PCR product (corresponding to PCR reaction in lane 1) isolated by binding to the solid phase via anchor domain of the incorporated nuc-macromolecule (residues of unused nuc macromolecules and nuc-macromolecules degraded by the exonuclease but still having an anchor domain are also visible)
4. No isolated PCR product without labeling by nuc macromolecule (corresponding PCR reaction in lane 2). The product did not bind to the solid phase because it had no anchor domain.
  The reactants purified with beads were detached from the beads by the temperature increase during electrophoresis. This event has occuried with a delay so that the migration distance in the gel is slightly less than that of the PCR products loaded directly onto the gel. Arrows on the left indicate the positions for Lane 1 and 2, arrows on the right for Lanes 3 and 4.
  Arrow A1: PCR product labeled with the dU-PEG(4)-[T1,A1]-TAMRA (incomplete strand extension)
  Arrow A2: PCR product labeled with the dU-PEG(4)-[T1,A1]-TAMRA (complete strand extension)
  Arrow B1: PCR product without dU-PEG(4)-[T1,A1]-TAMRA (labeling by primer Cy3)
  Arrow C1: dU-PEG(4)-[T1,A1]-TAMRA (nuc macromolecule)
  Arrow D1: degradation of dU-PEG(4)-[T1,A1]-TAMRA by 5-3 exonuclease activity of the Taq polymerase
  Arrow E1: labeled primer (T7-19-Cy3)

FIG. 31, Example 1.5.15.6, PCR and Labeling of the Bacterial DNA

Image of a gel after electrophoretic separation of the reaction products.

FIG. 31, Part A and B (first, imaging of fluorescence signals from nuc macromolecules was conducted (Part B), then the gel was stained with ethidium bromide and a further image was made (A)). Electrophoresis at 85-90° C.
1. ladder 100 bp
2. dU-PEG(4)-[T1,A1]-TAMRA, +T7-19-Cy3 Primer, +PCR-Produkt (from Lane 3, diluted 1:10)
3. PCR Reaktion without Probe and without nuc macromolecule
4. PCR Reaktion with Probe (FAM/TAMRA) but without nuc macromolecule
5. PCR Reaktion with nuc macromolecule dU-PEG(4)-[T1,A1]-TAMRA
6. PCR Reaktion with nuc macromolecule dU-PEG(4)-[T1,A1]-TAMRA+DMSO 5%
7. PCR as in Lane 4, PCR-Product purified with ultrafiltration MWCO 100 kDa
8. PCR as in Lane 5, PCR-Product purified with ultrafiltration MWCO 100 kDa
9. PCR as in Lane 4, incubation with dT48-Beads, washed with incorporation buffer 1
10. PCR and purification as in lane 7, then incubation with dT48-Beads, washed with incorporation buffer 1
11. PCR as in Lane 5, then binding to dT48-Beads, washed with incorporation buffer 1
12. PCR as in Lane 8, then binding to dT48-Beads, washed with incorporation buffer 1

Arrow A1: PCR product labeled with the dU-PEG(4)-[T1,A1]-TAMRA (complete and incomplete strand extension)

Arrow C1: dU-PEG(4)-[T1,A1]-TAMRA (nuc macromolecule)

Arrow D1: degradation of dU-PEG(4)-[T1,A1]-TAMRA by 5-3 exonuclease activity of the Taq polymerase Arrow F1: probe (FAM/TAMRA), lane 4

Arrow G1: degradation of probe (FAM/TAMRA) by 5-3 exonuclease, lane 4

The invention claimed is:

1. A method for enzymatic synthesis of one or more nucleic acid chains, comprising the step of enzymatic incorporation of nucleotides into the complementary strand of at least one target sequence or equivalents thereof, wherein at least one of the nucleotides is a nucleotide-conjugate having the structure:

(Nuc-linker)n- marker wherein:

Nuc is a nucleotide (nuc-component);

Linker is a linker component, wherein the linker links the nuc-component to a macromolecular marker component;

Marker is a macromolecular marker component which comprises at least one target domain having an oligonucleotide sequence complementary to a portion of the target sequence or equivalents thereof; and n is a positive integer from 1 to 1000; and wherein binding of the at least one target domain of the nucleotide-conjugate to the complementary portion of the target sequence facilitates selective incorporation of the said nucleotide-conjugate into the synthesized strand of the one or more nucleic acid chains.

2. The method for enzymatic synthesis of one or more nucleic acid chains according to claim 1, wherein the nuc-component of the nucleotide conjugate comprises at least one base selected independently from the group consisting of purine nucleobases, pyrimidine nucleobases and analogs of purine or pyrimidine nucleobases each of which is capable of forming Watson-Crick-base pairing.

3. The method for enzymatic synthesis of one or more nucleic acid chains according to claim 1, wherein the nuc-component of the nucleotide conjugate comprises at least one ribose moiety, wherein the 2'-position of the ribose moiety comprises a chemical group selected independently from the group consisting of H, OH, halogen, $NH_2$ and SH.

4. The method for enzymatic synthesis of one or more nucleic acid chains according to claim 1, wherein the nuc-component of the nucleotide conjugate comprises at least one ribose moiety, wherein the 3'-position of the ribose moiety comprises a chemical group is selected independently from the group consisting of H, OH, halogen, $—O—PO_3H$, SH, $N_3$, $NH_2$, $O—CH_3$, $O—CH_2—O—CH_3$ and $O—CH_2—CH=CH_2$.

5. The method for enzymatic synthesis of one or more nucleic acid chains according to claim 1, wherein the nuc-component of the nucleotide conjugate comprises at least one ribose moiety, wherein the 5'-position of the ribose moiety comprises a chemical group selected independently from the group consisting of triphosphate group, tetraphosphate group, alpha thiotriphosphate group and pharmaceutically acceptable salts thereof.

6. The method for enzymatic synthesis of one or more nucleic acid chains according to claim 1, wherein the marker of the at least one said nucleotide conjugate comprises at least one moiety selected from the group consisting of dye, fluorescent dye, quencher, antigen, hapten, biotin, oligonucleotide, protein, sugar moiety, hormone, nanocrystals, nanoparticles, microparticles and water soluble polymers.

7. The method for enzymatic synthesis of one or more nucleic acid chains according to claim 6, wherein at least two nucleotide conjugates are used simultaneously in the synthesis and the marker of each of the nucleotide conjugates comprises at least one characteristic moiety that is distinguishable from each other moiety by a characteristic moiety.

8. The method for enzymatic synthesis of one or more nucleic acid chains according to claim 6, wherein at least two nucleotide conjugates each comprising a distinct nuc-component are used simultaneously in the synthesis and the marker of each of the nucleotide conjugates comprises at least one moiety specific for a particular nuc-component of the nucleotide conjugate and wherein the marker of each of the nucleotide conjugates is distinguishable from each other by their specific moieties.

9. The method for enzymatic synthesis of one or more nucleic acid chains according to claim 6, wherein at least two nucleotide conjugates each having a characteristic and distinct target-domain are used simultaneously in the synthesis and the marker of each of the nucleotide conjugate comprises at least one characteristic moiety for a particular target-domain of the nucleotide conjugate and each of the markers is distinguishable from each other of the markers by the characteristic moieties.

10. A method for analysis of nucleic acid chains comprising the following steps:
   a) synthesizing at least one complementary strand to at least one target sequence or its equivalents, in accordance with the method of claim 6;
   b) providing a solid phase which can specifically bind the respective nucleic acids synthesized in step (a);
   c) incubating the nucleic acid strands synthesized in step (a) with the solid phase provided in step (b) under conditions which permit specific binding of the respective synthesized nucleic acid to the solid phase; and
   d) detection of the binding event in the nucleic acid strands in step (c).

11. The method for analysis of nucleic acid chains according to claim 10, wherein at least two nucleotide conjugates with characteristic and distinct target domains are used in the step (a) and the provided solid phase is capable of binding to each synthesized nucleic acid chain at a specific area of the solid phase.

12. The method for the analysis of nucleic acid chains according to claim 10, wherein the binding of the synthesized nucleic acid to the solid phase is conducted by one of the methods selected from the group consisting of: binding via hybridization to the newly synthesized labeled strand of the respective nucleic acid attached to the solid phase, binding via the characteristic moiety of the incorporated nucleotide conjugate to an appropriate binding partner attached to the solid phase, binding via the characteristic moiety of the primer to an appropriate binding partner attached to the solid phase, binding via the characteristic moiety of the probe to an appropriate binding partner attached to the solid phase.

13. A method for the detection of nucleic acid chains comprising the following steps:
   a) synthesizing at least one complementary strand to at least one target sequence or its equivalents, in accordance with the method of claim 6;
   b) providing a detector which can specifically detect a signal from the respective characteristic moiety of the marker of the nucleotide conjugates used in step (a); and
   c) detecting the signal from nucleotide conjugates incorporated into the nucleic acid strands in step (a).

14. The method for the synthesis of one or more nucleic acid chains in accordance with claim 1, wherein at least one primer is used in the synthesis.

15. The method for the synthesis of nucleic acid chains in accordance with claim 14, wherein at least one primer is capable of specific binding to the target sequence.

16. The method for the synthesis of nucleic acid chains in accordance with claim 14, wherein at least one primer is having at least one characteristic moiety selected from the group consisting of dye, fluorescent dye, quencher, antigen, hapten, biotin, oligonucleotide, protein, sugar moiety, hormones, nanocrystals, nanoparticles, microparticles and water soluble polymers.

17. The method for the synthesis of nucleic acid chains in accordance with claim 14, wherein the target domain of at least one nucleotide conjugate is capable of specific hybridizing to the target sequence downstream from the 3" position of at least one primer.

18. The method for the synthesis of nucleic acid chains in accordance with claim 1, comprising at least one oligonucleotide probe capable of specific hybridization to the synthesized one or more nucleic acid chains.

19. A method for the synthesis of nucleic acid chains in accordance with claim 18, wherein the at least one oligonucleotide probe comprises at least one characteristic moiety selected from the group consisting of dye, fluorescent dye, quencher, antigen, hapten, biotin, oligonucleotide, protein, sugar moiety, hormones, nanocrystals, nanoparticles, microparticles and water soluble polymers.

20. The method for the synthesis of nucleic acid chains in accordance with claim 19, wherein the at least one oligonucleotide probe is capable of specifically hybridizing to the target sequence downstream from the 3" position of at least one primer.

21. The method for the synthesis of nucleic acid chains in accordance with claim 1, wherein the synthesis step comprises use of at least one further kind of nucleotide.

22. The method in accordance with claim 21, wherein the one further kind of nucleotide is selected from the group consisting of nucleoside triphosphates (ATP, GTP, CTP, and UTP) and analogs thereof, 2'-deoxynucleoside triphosphates (dATP, dGTP, dCTP, dTTP, dUTP) and analogs thereof, and modified nucleotides.

23. The method for the synthesis of nucleic acid chains in accordance with claim 1, wherein the method is an amplification method of at least one target sequence or a portion thereof.

24. The method for the synthesis of nucleic acid chains in accordance with claim 1, comprising the following steps:
   a) synthesizing a complementary strand to at least one target sequence or its equivalents;
   b) detaching the extended complementary strand from the target sequence or its equivalents; and
   c) optionally repeating the steps a) to b).

25. The method in accordance with claim 1, wherein the primer and/or the nucleotide conjugate and/or the hybridization probe comprises a detectable reporter selected from the group consisting of dye, fluorescent dye, quencher, antigen, hapten, biotin, oligonucleotide, protein, sugar moiety, hormones, nanocrystals, nanoparticles, microparticles and corresponding signal carrying moieties thereof.

26. The method in accordance with claim 25, wherein the signal intensity of the detectable reporter is measured after the incorporation of the nucleotide conjugate into the growing strand.

27. A method in accordance with claim 26, wherein the amount of the target sequence in the mixture is quantified by measuring the signal from said detectable reporter.

28. A method in accordance with claim 1, wherein said nucleic acid chain (target sequence) is provided in single-stranded form.

29. A method in accordance with claim 1, wherein said nucleic acid chain (target sequence) is provided in double-stranded form.

30. The method in accordance with claim 1, wherein said nucleic acid chain (target sequence) originates from a biological sample.

31. The method in accordance with claim 1, wherein detection of the presence or absence or quantification of said nucleic acid chain (target sequence) is used for diagnostic purposes.

32. The method in accordance with claim 1, wherein the method is employed under conditions, which allow for selective binding/hybridization of said target domain to the portion of the target sequence.

33. The method in accordance with claim 1, wherein the method is conducted under conditions which allow for predominantly selective binding of said (target domain) to the target sequence.

34. A method in accordance with claim 1, wherein the method is used to amplify at least one nucleic acid chain from a sample.

35. The method in accordance with claim 1, wherein the method is used to label at least one nucleic acid chain.

36. The method in accordance with claim 1, wherein the method is used to detect at least one nucleic acid chain in a sample.

37. The method for synthesis in accordance with claim 1, wherein the synthesis is conducted as amplification of at least one target nucleic acid via Polymerase Chain Reaction (PCR).

38. The method according to the claim 37 comprising the following steps:
(1) conducting PCR for at least one nucleic acid chain (the target sequence) from a sample, with at least one polymerase, at least two PCR primers that are capable of binding to the specific target sequence, and at least one nucleotide conjugate;
wherein said nucleotide conjugate comprises at least one nucleoside triphosphate or an analog thereof, which is a substrate for the polymerase, and wherein the marker comprises at least one oligonucleotide capable of specifically hybridizing to at least one strand of the target sequence between the two PCR primers;
(2) providing oligonucleotide primers, wherein at least one primer has a complementary sequence to one strand of the target sequence and can start an extension reaction and at least one primer has a complementary sequence to the other strand of the target sequence and can start an extension reaction, wherein at least two primers are selected so that their binding sites within the target sequence are located on either side of the binding site of at least one target domain of said nucleotide conjugate;
(3) amplifying the target sequence, if present in the sample, using a polymerase and conditions of a PCR: (a) hybridization of the primers and of the nucleotide conjugate to the target sequence, (b) extension of the primers and incorporation of nucleotide conjugates (c) where appropriate, separation of the synthesized double strands of the target sequence, (d) where appropriate, repeating steps (a) to (c) multiple times; and
(4) detecting the incorporation event of the nucleotide conjugate.

39. The method in accordance with claim 1, wherein the synthesis is conducted as a method for amplification at isothermal conditions.

40. The method in accordance with claim 1, wherein the method is suitable for quantification of at least one amplified nucleic acid chain in the sample.

41. The method in accordance with claim 40 for quantification of an unknown amount of one target sequence in the sample, wherein a control experiment is carried out with a known amount of an identical or a different target sequence, and the results of measurement of the signal intensity from both experiments are compared to each other.

42. The method in accordance with claim 1, wherein said nucleotide conjugate comprises at least one nucleoside triphosphate which is coupled via a linker to the 5'-end of said oligonucleotide of the marker (target domain).

43. The method in accordance with claim 1, wherein oligonucleotide of the marker of the said nucleotide conjugate comprises a sequence of at least six nucleotides complementary to a portion of the target sequence.

44. The method in accordance with claim 1, wherein the oligonucleotide of the marker of the said nucleotide conjugate comprises at least one segment of a sequence which is not complementary to the target sequence.

45. A method in accordance with claim 1, wherein said oligonucleotide of the marker of the said nucleotide conjugate is not extendable by a polymerase.

46. The method for the enzymatic synthesis of one or more nucleic acid chains in accordance with claim 1, wherein at least one polymerase for enzymatic incorporation of nucleotides is used in the synthesis.

47. A method in accordance with claim 46, wherein said polymerase is a thermostable polymerase.

48. A method in accordance with claim 46, wherein said polymerase is a thermolabile polymerase.

49. A method in accordance with claim 46, wherein said polymerase is a reversibly inactivated thermostable polymerase.

50. A method in accordance with claim 46, wherein said polymerase has a strand displacement activity.

51. A method for processing of nucleic acid chains synthesized by the method of claim 1, wherein the nuc-component of the nucleotide conjugates has terminating properties for the synthesis of the nucleic acid chains by a polymerase and the target-domain of the nucleotide conjugates is capable of specific binding to at least one target nucleic acid sequence.

* * * * *

```
                        SEQUENCE LISTING

<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: Chemically synthesized

<400> SEQUENCE: 1
taatacgact cactatagg                                                  19

<210> SEQ ID NO 2
<211> LENGTH: 19
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Cy3 dye added to 5' end

<400> SEQUENCE: 2
taatacgact cactatagg                                                  19

<210> SEQ ID NO 3
<211> LENGTH: 69
<212> TYPE: DNA
<213> ORGANISM: Artificial Sequence
<220> FEATURE:
<223> OTHER INFORMATION: Chemically Synthesized

<400> SEQUENCE: 3
aaaaaaaaaa aaaaaaaaaa aaaaaaaaaa aaaaaaaaaa aaaaaaaaaa taatacgact     60
cactatagg                                                             69

<210> SEQ ID NO 4
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 4
```
gttttcccag tcacgacg                                                    18

<210> SEQ ID NO 5
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 5
tcctacggga ggcagcagt                                                   19

<210> SEQ ID NO 6
<211> LENGTH: 26
<212> TYPE: DNA
<213> ORGANISM: Artificial Sequence
<220> FEATURE:
<223> OTHER INFORMATION: Chemically synthesized

<400> SEQUENCE: 6
ggactaccag ggtatctaat cctgtt                                           26

<210> SEQ ID NO 7
<211> LENGTH: 23
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: 6-carboxyfluorescein on 5' end
<220> FEATURE:
<221> NAME/KEY: misc_feature
<222> LOCATION: (23)..(23)
<223> OTHER INFORMATION: tetramethylrhodamine on 3' end

<400> SEQUENCE: 7
cgtattaccg cggctgctgg cac                                              23

<210> SEQ ID NO 8
<211> LENGTH: 48
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (48)..(48)
<223> OTHER INFORMATION: Biotin on 3' end

<400> SEQUENCE: 8
tttttttttt tttttttttt tttttttttt tttttttttt tttttttt                   48

<210> SEQ ID NO 9
<211> LENGTH: 20
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: Biotin added to 5' end

<400> SEQUENCE: 9
agtgaattcg agctcggtac                                                  20

-continued

```
<210> SEQ ID NO 10
<211> LENGTH: 48
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: NH2 on 5' end
<220> FEATURE:
<221> NAME/KEY: misc_feature
<223> OTHER INFORMATION: tetramethylrhodamine on 3' end

<400> SEQUENCE: 10
cgtattaccg cggctgctgg cacaaaaaaa aaaaaaaaa aaaaaaaa        48

<210> SEQ ID NO 11
<211> LENGTH: 35
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: NH2 on 5' end
<220> FEATURE:
<221> NAME/KEY: misc_feature
<223> OTHER INFORMATION: tetramethylrhodamine on 3' end

<400> SEQUENCE: 11
cgagacgaaa tgggattttt tttttttttt ttttt                    35

<210> SEQ ID NO 12
<211> LENGTH: 43
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<223> OTHER INFORMATION: NH2 on 5' end
<220> FEATURE:
<221> NAME/KEY: misc_feature
<223> OTHER INFORMATION: 6-carboxyfluorescein on 3' end

<400> SEQUENCE: 12
aaaaaaactg cggctgctgg cacgtaccga gctcgaattc act           43

<210> SEQ ID NO 13
<211> LENGTH: 68
<212> TYPE: DNA
<213> ORGANISM: Artificial Sequence
<220> FEATURE:
<223> OTHER INFORMATION: Chemically syntheszed

<400> SEQUENCE: 13
gttttcccag tcacgacggg aggtgccagc agccgcggta atacgaccac ctatagtgag   60
tcgtatta                                                            68

<210> SEQ ID NO 14
<211> LENGTH: 74
<212> TYPE: DNA
<213> ORGANISM: Artificial Sequence
<220> FEATURE:
<223> OTHER INFORMATION: Chemically synthesized

<400> SEQUENCE: 14
gttttcccag tcacgacggg aggtgccagc agccgcggta atacgagtct tctcacctat   60
```
agtgagtcgt atta                                                       74

<210> SEQ ID NO 15
<211> LENGTH: 71
<212> TYPE: DNA
<213> ORGANISM: Artificial Sequence
<220> FEATURE:
<223> OTHER INFORMATION: Chemically synthesized

<400> SEQUENCE: 15
gttttcccag tcacgacggg aggtgccagc agcggtaata cgagtcttct gacctatagt     60
gagtcgtatt a                                                          71

<210> SEQ ID NO 16
<211> LENGTH: 68
<212> TYPE: DNA
<213> ORGANISM: Artificial Sequence
<220> FEATURE:
<223> OTHER INFORMATION: Chemically synthesized

<400> SEQUENCE: 16
gttttcccag tcacgacggg aggtgccagc ggtaatacga gtcttctgac ctatagtgag     60
tcgtatta                                                              68

<210> SEQ ID NO 17
<211> LENGTH: 74
<212> TYPE: DNA
<213> ORGANISM: Artificial Sequence
<220> FEATURE:
<223> OTHER INFORMATION: Chemically synthesized

<400> SEQUENCE: 17
gttttcccag tcacgacggg aggtgccagc agcaaaaaaa atacgagtct tctgacctat     60
agtgagtcgt atta                                                       74

<210> SEQ ID NO 18
<211> LENGTH: 74
<212> TYPE: DNA
<213> ORGANISM: Artificial Sequence
<220> FEATURE:
<223> OTHER INFORMATION: Chemically synthesized

<400> SEQUENCE: 18
gttttcccag tcacgacggg aggtgacagc agccgcagta atacgagtct tctgacctat     60
agtgagtcgt atta                                                       74

<210> SEQ ID NO 19
<211> LENGTH: 74
<212> TYPE: DNA
<213> ORGANISM: Artificial Sequence
<220> FEATURE:
<223> OTHER INFORMATION: Chemically synthesized

<400> SEQUENCE: 19
gttttcccag tcacgacggg aggtgccagc agccgcaaaa aaaaagtct tctgacctat      60 agtgagtcgt atta                                                       74

<210> SEQ ID NO 20
<211> LENGTH: 74
<212> TYPE: DNA
<213> ORGANISM: Artificial Sequence
<220> FEATURE:
<223> OTHER INFORMATION: Chemically synthesized

```
<400> SEQUENCE: 20
gttttcccag tcacgacggg aggtgccagc agccgcagtt tttttagtct tctgacctat        60
agtgagtcgt atta                                                          74

<210> SEQ ID NO 21
<211> LENGTH: 63
<212> TYPE: DNA
<213> ORGANISM: Artificial Sequence
<220> FEATURE:
<223> OTHER INFORMATION: Chemicallh synthesized

<400> SEQUENCE: 21
gttttcccag tcacgacggg agcgcggtaa tacgagtctt ctcacctata gtgagtcgta        60
tta                                                                      63

<210> SEQ ID NO 22
<211> LENGTH: 45
<212> TYPE: DNA
<213> ORGANISM: Artificial Sequence
<220> FEATURE:
<223> OTHER INFORMATION: Chemicallh synthesized

<400> SEQUENCE: 22
tcccatttcg tctcgttccg ctttgtccta tagtgagtcg tatta                        45
```